(12) United States Patent
Arya et al.

(10) Patent No.: US 9,492,554 B2
(45) Date of Patent: Nov. 15, 2016

(54) METHODS AND COMPOSITIONS RELATED TO VIRAL INHIBITION

(71) Applicant: Clemson University Research Foundation (CURF), Anderson, SC (US)

(72) Inventors: Dev P. Arya, Greenville, SC (US); Nihar Ranjan, Clemson, SC (US); Sunil Kumar, Clemson, SC (US)

(73) Assignee: Clemson University, Clemson, SC (US)

( * ) Notice: Subject to any disclaimer, the term of this patent is extended or adjusted under 35 U.S.C. 154(b) by 0 days.

(21) Appl. No.: 14/703,549

(22) Filed: May 4, 2015

(65) Prior Publication Data

US 2016/0263231 A1    Sep. 15, 2016

Related U.S. Application Data

(62) Division of application No. 12/857,425, filed on Aug. 16, 2010, now Pat. No. 9,072,761.

(60) Provisional application No. 61/234,260, filed on Aug. 14, 2009, provisional application No. 61/234,603, filed on Aug. 17, 2009.

(51) Int. Cl.
*A01N 43/04*    (2006.01)
*A61K 31/70*    (2006.01)
*A61K 47/48*    (2006.01)

(52) U.S. Cl.
CPC .............................. *A61K 47/48061* (2013.01)

(58) Field of Classification Search
None
See application file for complete search history.

(56) References Cited

PUBLICATIONS

Kirk et al., J. Am. Chem. Soc. (2000), vol. 122, pp. 980-981.
Willis et al., Biochemistry (2006), vol. 45, pp. 10217-10232.

*Primary Examiner* — Patrick Lewis
(74) *Attorney, Agent, or Firm* — Joseph T. Guy; Perkins Law Firm, LLC

(57) ABSTRACT

Disclosed herein are compounds, compositions and methods related to viral inhibition. In some forms, the compounds, compositions and methods are related to binding RNA.

17 Claims, 48 Drawing Sheets

Hoechst 33258 amino/aromatic resonance number

Fig. 10D

TABLE 1. Assignment of $^1$H NMR spectr of Hoechst 3358 in acidified 9.96% D2O

| Chemical Shift ppm downfield of TSP | Integration | Assignment |
|---|---|---|
| 2.85 | 4 | $CH_3N-(CH_2)_2$ |
| 2.90 | 3 | $NCH_3$ |
| 3.45 | 4 | $ArN-(CH_3)_2$ |
| 6.20 | 2 | H-1,5 |
| 6.50 | 1 | H-16 |
| 6.80 | 1 | H-18 |
| 6.95 | 2 | H-2,4 |
| 6.99 | 1 | H-9 |
| 7.08 | 1 | H-19 |
| 7.15 | 1 | H-11 |
| 7.20 | 1 | H-12 |

| ΔTm TAR RNA with and without the presence of ligands. |||
| --- | --- | --- |
| TAR with | Tm (°C) | ΔTm (°C) |
| None | 68 | N/A |
| Neomycin | 70 | 2 |
| Benzimidazole | 67 | -1 |
| Neo-Benzimidazole | 74 | 6 |

FIG. 19A
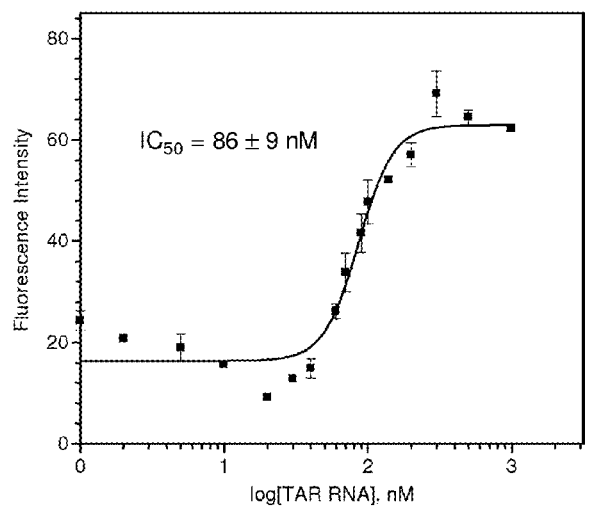
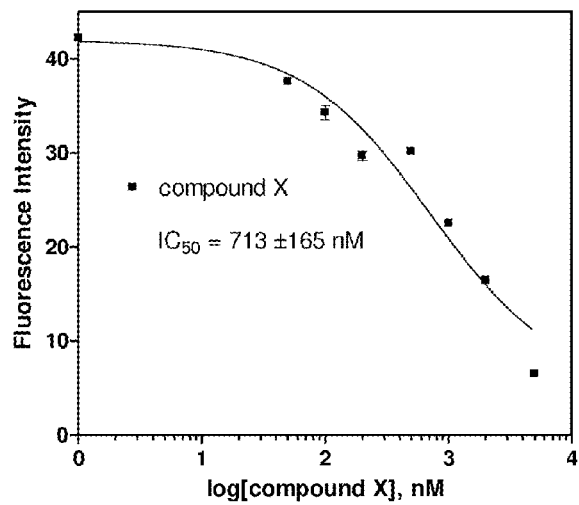
FIG. 19B

FIG. 19E
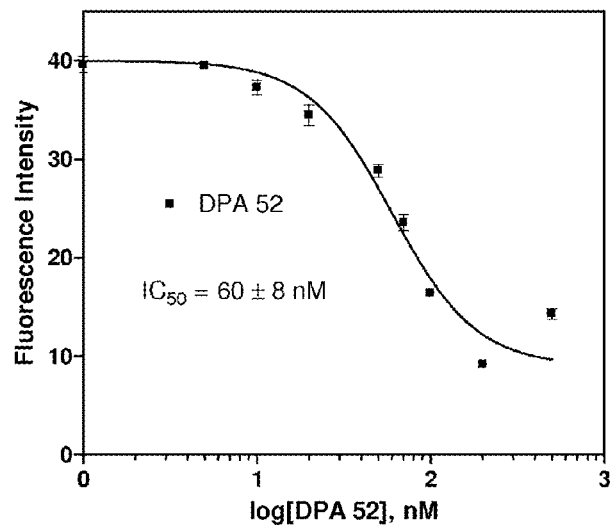
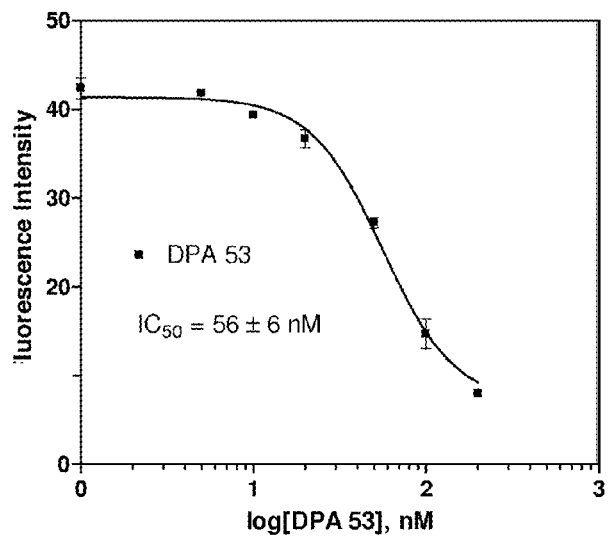
FIG. 19F

FIG. 19G
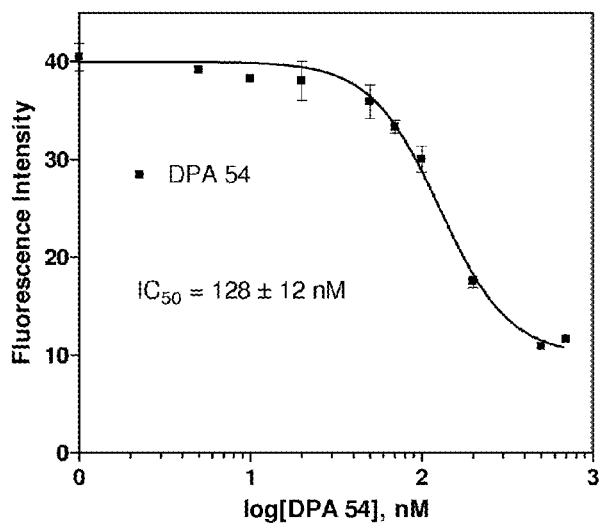
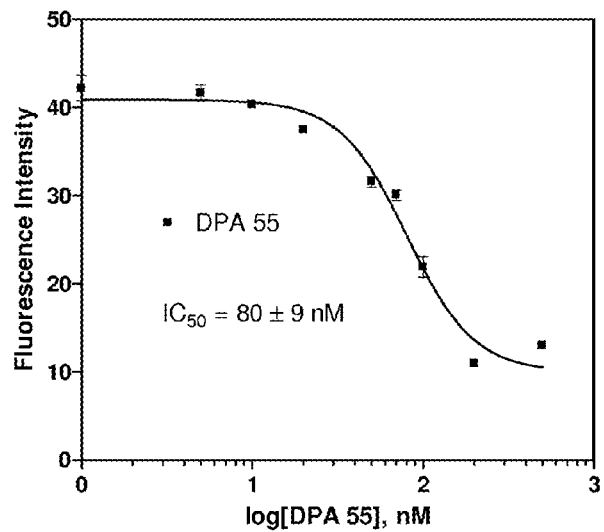
FIG. 19H

FIG. 19I
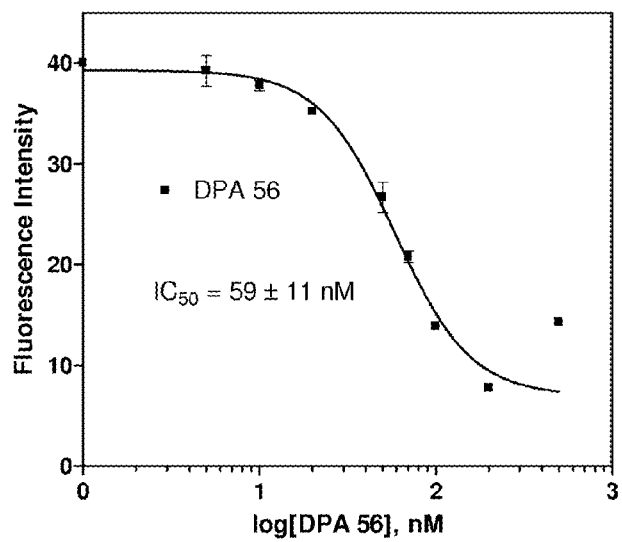
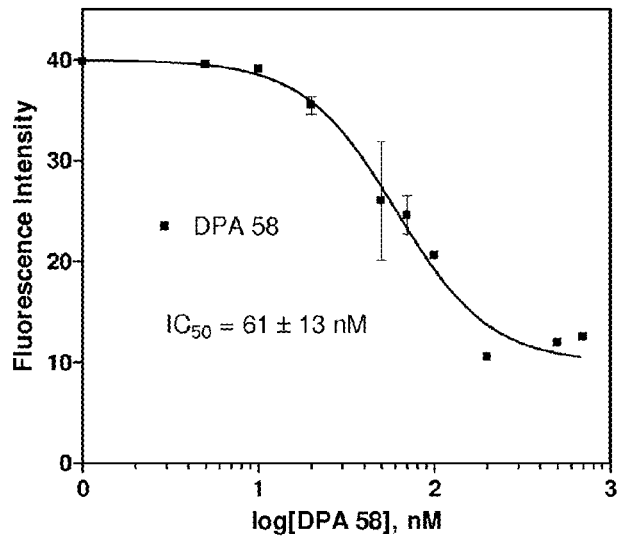
FIG. 19J

FIG. 19K
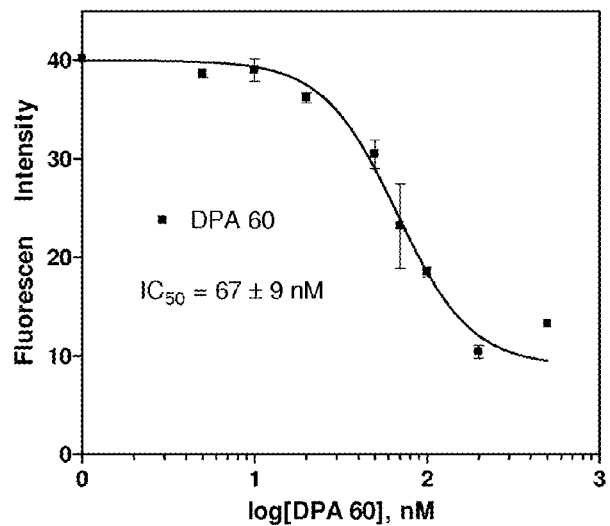
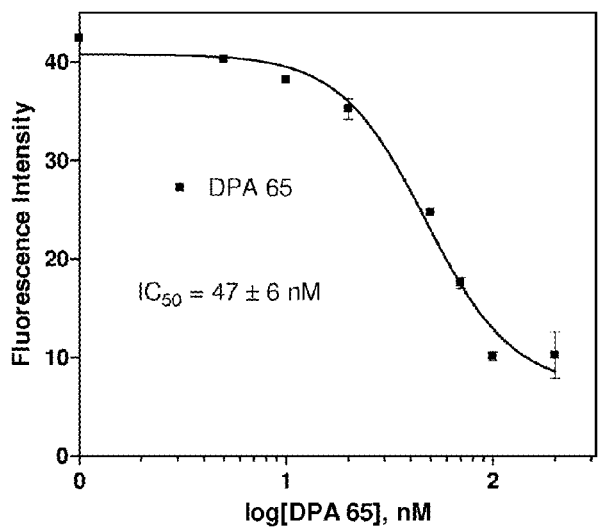
FIG. 19L

FIG. 19M
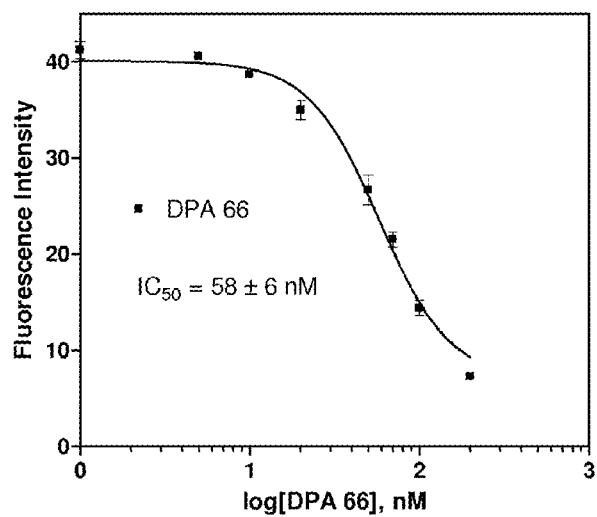
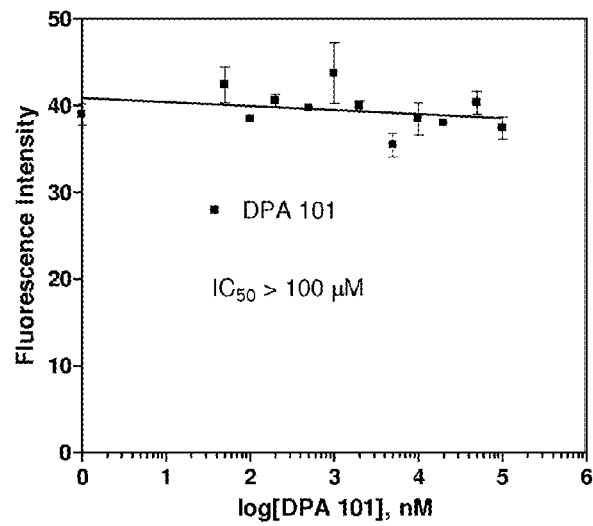
FIG.19N

FIG. 19Q
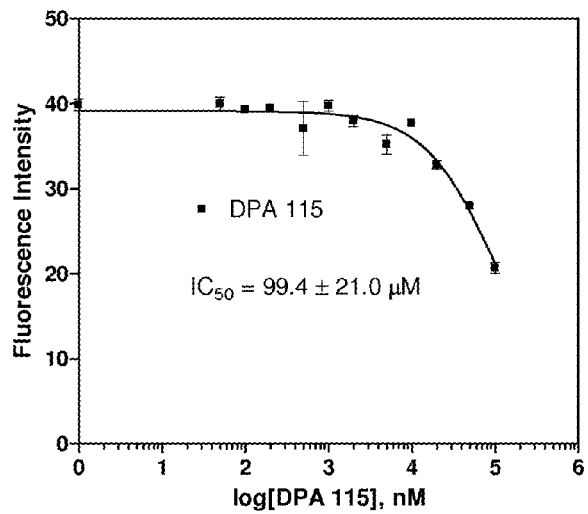
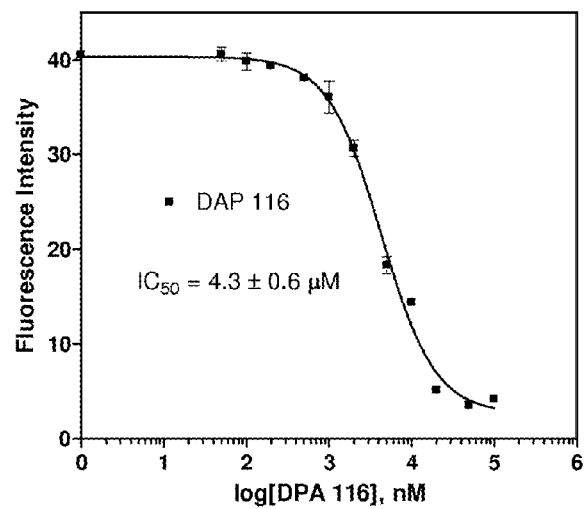
FIG. 19R

FIG. 19S
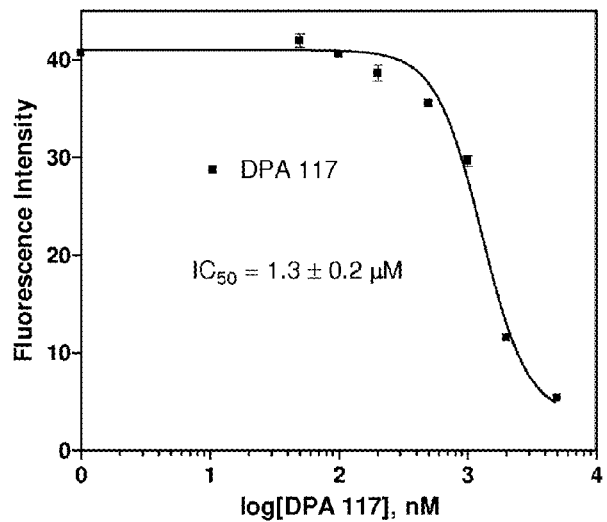
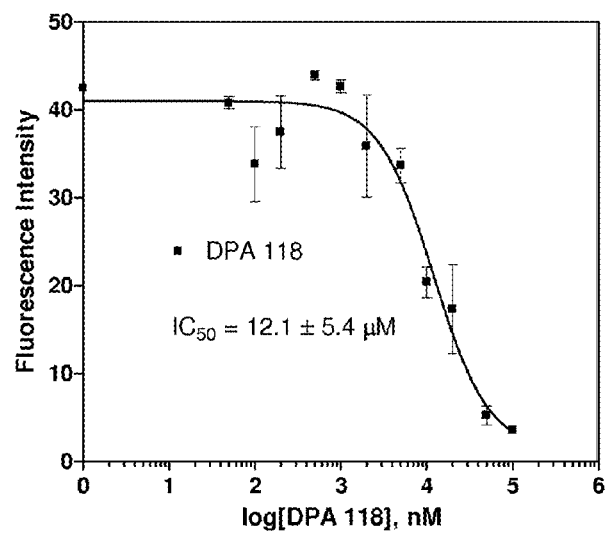
FIG. 19T

FIG. 19U
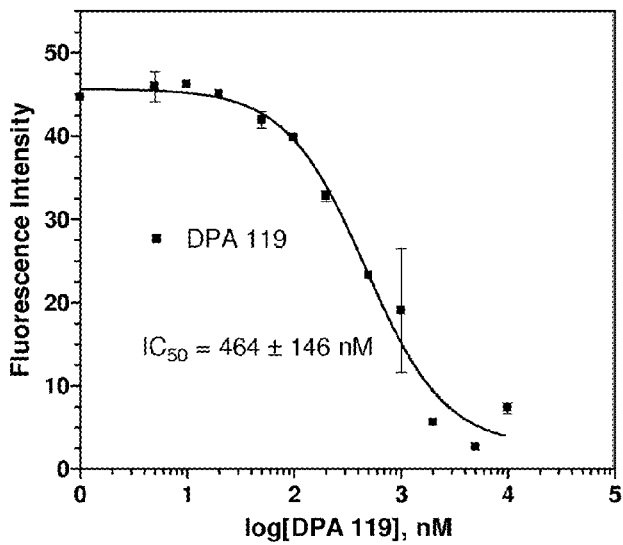
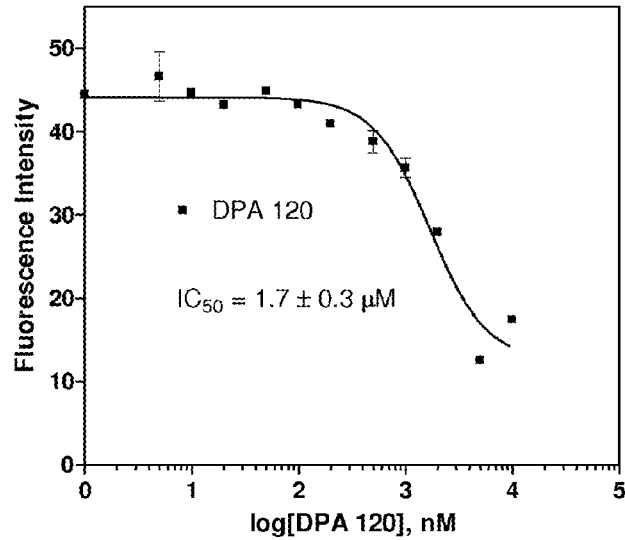
FIG. 19V

FIG. 19W
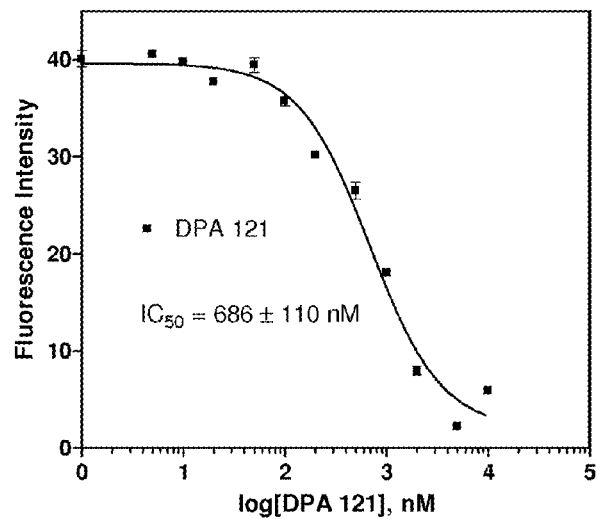
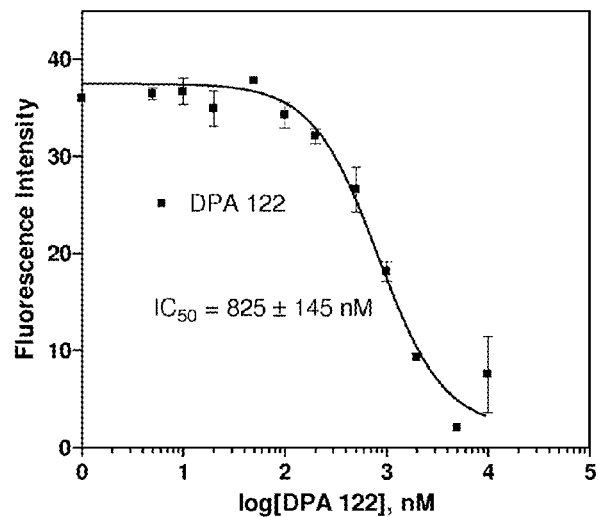
FIG. 19X

FIG. 19Y
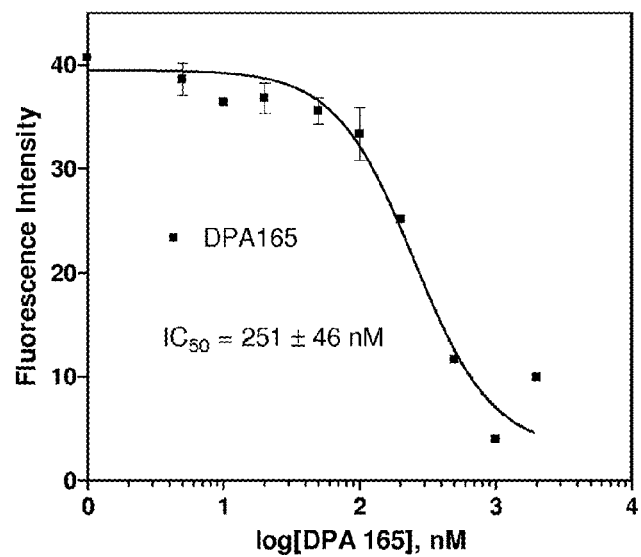
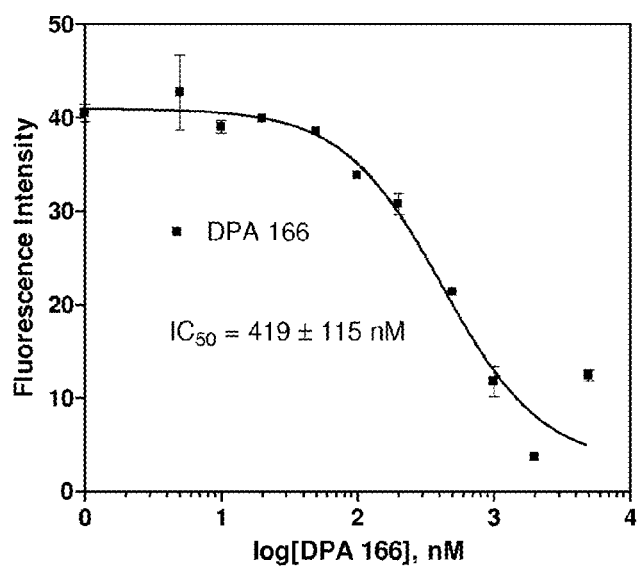
FIG. 19Z

FIG. 19AA
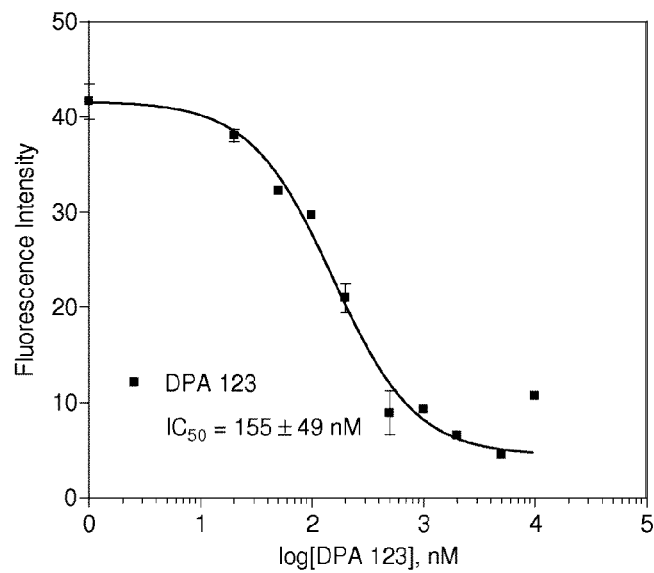
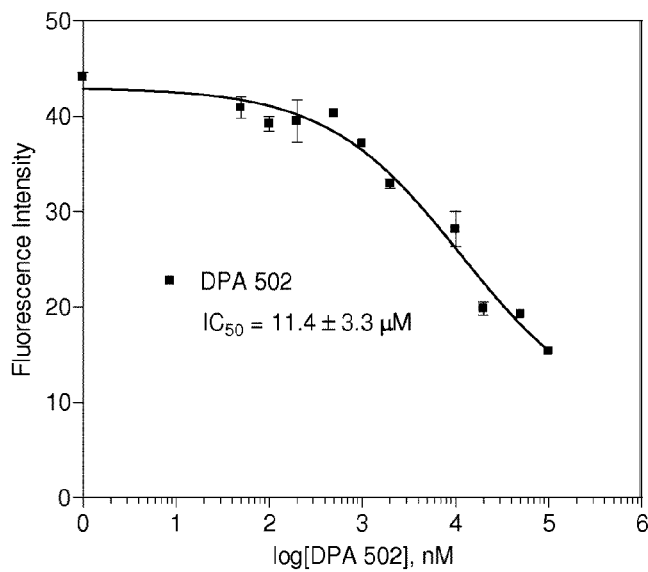
FIG. 19BB

FIG. 19CC
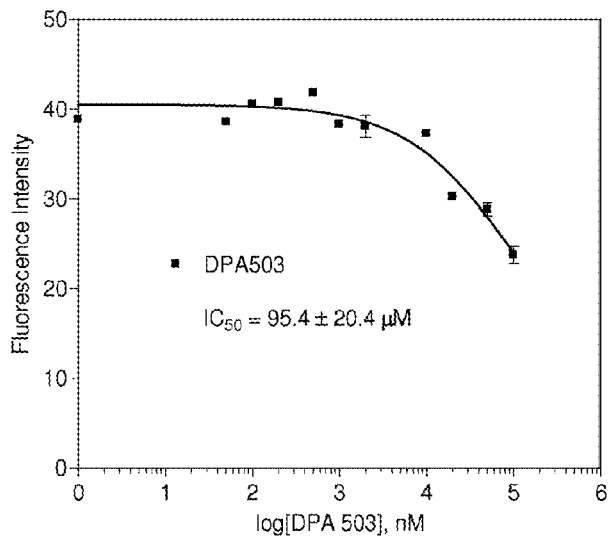
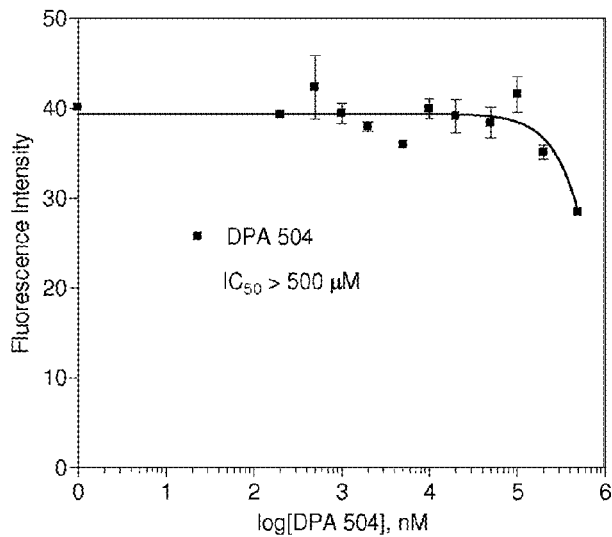
FIG. 19DD

FIG. 19EE
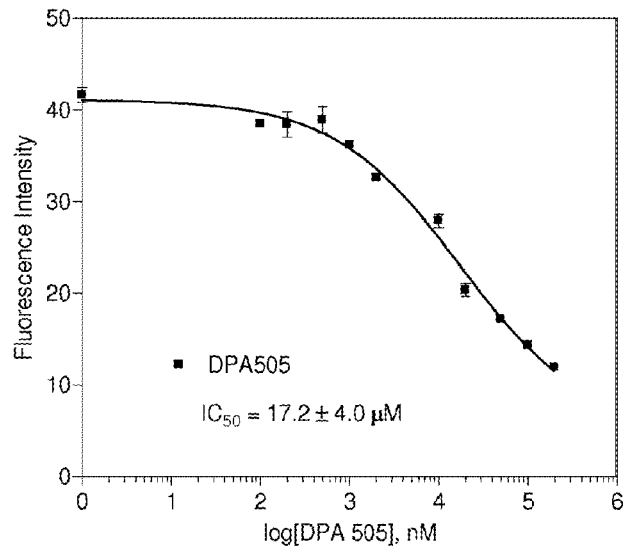
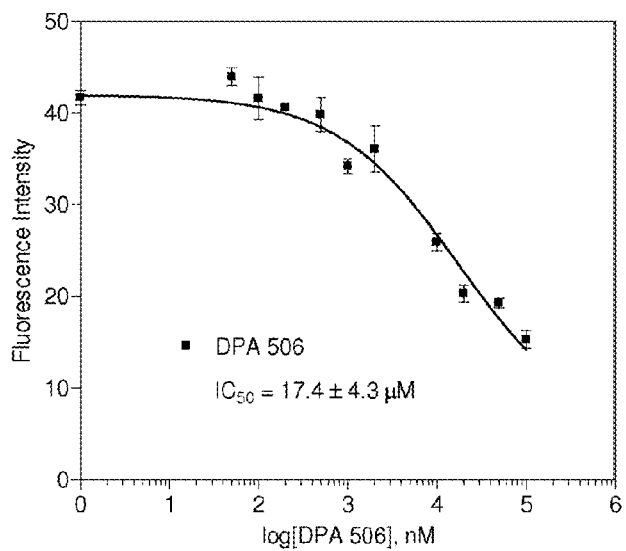
FIG. 19FF

FIG. 19GG
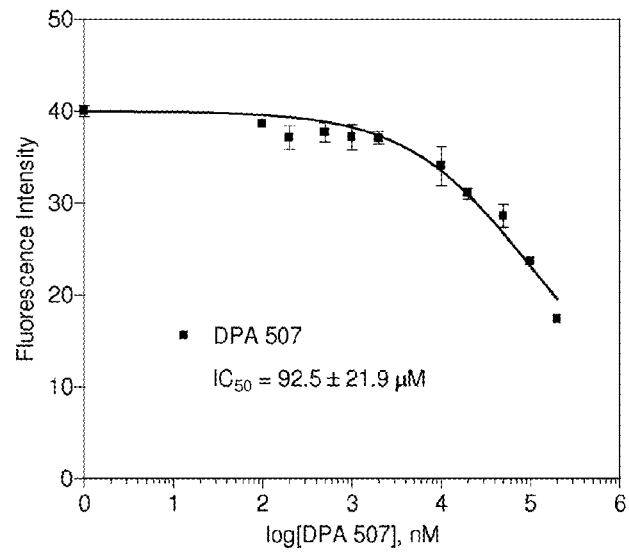
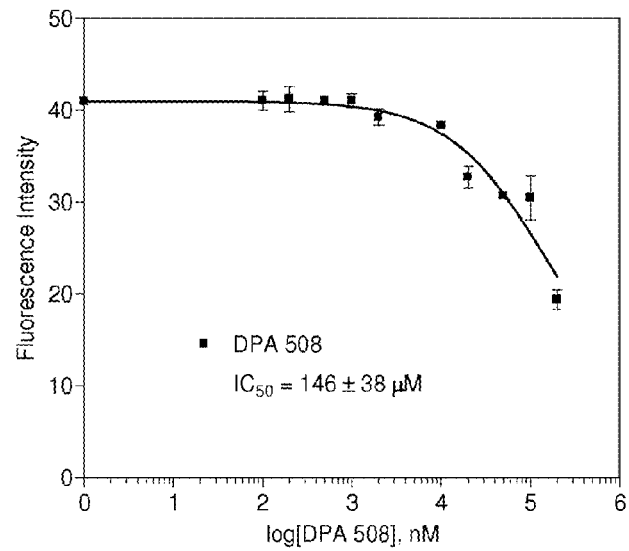
FIG. 19HH

DPA54- 1ANR

DPA55- 1ANR

DPA65 1ANR

Neomycin B- 1ANR

METHODS AND COMPOSITIONS RELATED TO VIRAL INHIBITION

CROSS REFERENCE TO RELATED APPLICATIONS

This application is a divisional application of pending U.S. patent Ser. No. 12/857,425 filed Aug. 16, 2010 which, in turn, claims the benefit of U.S. Provisional Application Ser. No. 61/234,260, filed on Aug. 14, 2009, and U.S. Provisional Application Ser. No. 61/234,603, filed on Aug. 17, 2009, both of which are incorporated herein by reference in their entireties.

ACKNOWLEDGEMENTS

This invention was made with government support under grant numbers NSF (0134972) (0134932) awarded by the National Science Foundation; NIH (CA125724) awarded by the National Institute of Health; and NIH (GM100607), also awarded by the National Institute of Health. The US government has certain rights in the invention.

BACKGROUND

The Human Immunodeficiency virus (HIV) is the causative agent of the Acquired Immunodeficiency Syndrome (AIDS). Like all retroviruses the genome of the virus encodes the Gag, Pol and Env proteins. In addition, the viral genome encodes further regulatory proteins, i.e. Tat and Rev, as well as accessory proteins, i.e. Vpr, Vpx, Vpu, Vif and Nef.

Despite public health efforts to control the spread of the AIDS epidemic, the number of new infections is still increasing. The World Health Organization estimated the global epidemic at 36.1 million infected individuals at the end of the year 2000, 50% higher than what was predicted on the basis of the data a decade ago (WHO & UNAIDS. UNAIDS, 2000). Globally, the number of new HIV-1 infections in 2000 is estimated at 5.3 million.

New therapies for fighting HIV infection and AIDS are needed. Disclosed are compositions with higher binding affinity and specificity to viral RNA, such as HIV RNA, such as TAR RNA, by conjugation to other small molecules. One example is the neomycin—Hoechst 33258 conjugates, and derivatives, as high affinity small molecule inhibitors of the Tat/TAR interaction. Conjugation of the aminoglycoside (neomycin) and Hoechst 33258 (benzimidazole) with an alkyl linker can provide a high affinity binding ligand, capable of binding to TAR with $IC_{50}$ in nanomolar concentrations. The disclosed TAR binding ligands, with improved affinity and specificity over currently known molecules can aid in the fight against HIV. Quick and efficient synthesis of the disclosed compositions can be done. (Arya and Coffee 2000; Arya, Coffee et al. 2001; Arya, Coffee et al. 2001; Arya, Micovic et al. 2003; Arya and Willis 2003; Arya, Xue et al. 2003; Arya, Xue et al. 2003; Arya, Coffee et al. 2004; Arya 2005; Willis and Arya 2006; Willis and Arya 2006).

SUMMARY

Disclosed are nucleic acid targeted drugs, a specific example being the development of aminoglycoside based molecules, as effective TAR binders for inhibition of Tat/TAR interaction.

Also disclosed methods and compositions provide ligands with a high level of specificity and affinity for TAR RNA for the use as an HIV treatment.

BRIEF DESCRIPTION OF THE DRAWINGS

FIGS. 10A-10D show the NMR identification of a Hoescht binding domain within TAR. The positively charged 6-membered ring is likely to interact electrostatically with backbone phosphate(s)

DETAILED DESCRIPTION OF THE INVENTION

Figure 1:
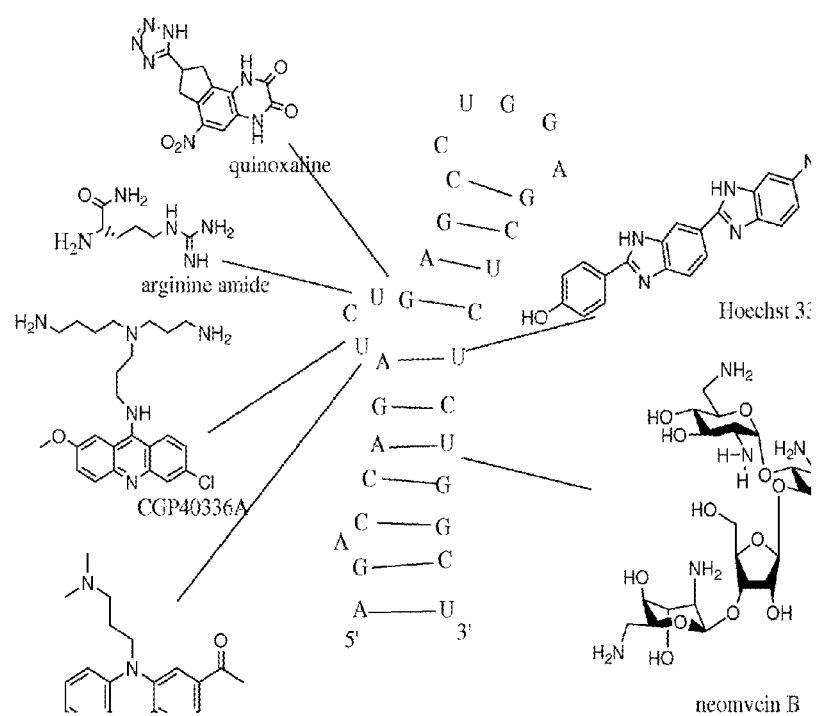
FIG. 1 shows the binding sites of different TAR ligands.

Throughout this application, various publications are referenced. The disclosures of these publications in their entireties are hereby incorporated by reference into this application in order to more fully describe the state of the an to which this pertains. The references disclosed are also individually and specifically incorporated by reference herein for the material contained in them that is discussed in the sentence in which the reference is relied upon.

Disclosed are materials, compounds, compositions, and components that can be used for, can be used in conjunction with, can be used in preparation for, or are products of the disclosed method and compositions. These and other materials are disclosed herein, and it is understood that when combinations, subsets, interactions, groups, etc. of these materials are disclosed that while specific reference of each various individual and collective combinations and permutation of these compounds may not be explicitly disclosed, each is specifically contemplated and described herein. For example, if an inhibitor is disclosed and discussed and a number of modifications that can be made to a number of R groups are discussed, each and every combination and permutation of the inhibitor and the modifications to its R group that are possible are specifically contemplated unless specifically indicated to the contrary. Thus, if a class of substituents A, B, and C are disclosed as well as a class of substituents D, E, and F and an example of a combination molecule, A-D is disclosed, then even if each is not individually recited, each is individually and collectively contemplated. Thus, in this example, each of the combinations A-E, A-F, B-D, B-E, B-F, C-D, C-E, and C-F are specifically contemplated and should be considered disclosed from disclosure of A, B, and C; D, E, and F; and the example combination A-D. Likewise, any subset or combination of these is also specifically contemplated and disclosed. Thus, for example, the sub-group of A-E, B-F, and C-E are specifically contemplated and should be considered disclosed from disclosure of A, B, and C; D, E, and F; and the example combination A-D. This concept applies to all aspects of this disclosure including, but not limited to, steps in methods of making and using the disclosed compositions. Thus, if there are a variety of additional steps that can be performed it is understood that each of these additional steps can be performed with any specific embodiment or combination of embodiments of the disclosed methods, and that each such combination is specifically contemplated and should be considered disclosed.

A. DEFINITIONS

1. A, An, The

As used in the specification and the appended claims, the singular forms "a," "an" and "the" include plural referents unless the context clearly dictates otherwise. Thus, for example, reference to "a pharmaceutical carrier" includes mixtures of two or more such carriers, and the like.

2. Activity

As used herein, the term "activity" refers to a biological activity.

3. Cell

The term "cell" as used herein also refers to individual cells, cell lines, or cultures derived from such cells. A "culture" refers to a composition comprising isolated cells of the same or a different type. The term co-culture is used to designate when more than one type of cell are cultured together in the same dish with either full or partial contact with each other.

4. Compound

For the purposes of the present disclosure the terms "compound," "analog," and "composition of matter" stand equally well for the chemical entities described herein, including all enantiomeric forms, diastereomeric forms, salts, and the like, and the terms "compound," "analog," and "composition of matter" are used interchangeably throughout the present specification.

5. Comprise

Throughout the description and claims of this specification, the word "comprise" and variations of the word, such as "comprising" and "comprises," means "including but not limited to," and is not intended to exclude, for example, other additives, components, integers or steps.

6. Chemistry a) Aldehyde

The term "aldehyde" as used herein is represented by the formula —C(O)H.

b) Alkyl

The term "alkyl" as used herein is a branched or unbranched saturated hydrocarbon moiety. "Unbranched" or "Branched" alkyls comprise a non-cyclic, saturated, straight or branched chain hydrocarbon moiety having from 1 to 24 carbons, 1 to 12, carbons, 1 to 6 carbons, or 1 to 4 carbon atoms. Examples of such alkyl radicals include methyl, ethyl, propyl, butyl, pentyl, hexyl, heptyl, octyl, n-propyl, iso-propyl, butyl, n-butyl, sec-butyl, t-butyl, amyl, t-amyl, n-pentyl and the like. Lower alkyls comprise a noncyclic, saturated, straight or branched chain hydrocarbon residue having from 1 to 4 carbon atoms, i.e., $C_1$-$C_4$ alkyl.

Moreover, the term "alkyl" as used throughout the specification and claims is intended to include both "unsubstituted alkyls" and "substituted alkyls", the later denotes an alkyl radical analogous to the above definition that is further substituted with one, two, or more additional organic or inorganic substituent groups. Suitable substituent groups include but are not limited to hydroxyl, cycloalkyl, amino, mono-substituted amino, di-substituted amino, unsubstituted or substituted amido, carbonyl, halogen, sulfhydryl, sulfonyl, sulfonato, sulfamoyl, sulfonamide, azido, acyloxy, nitro, cyano, carboxy, carboalkoxy, alkylcarboxamido, substituted alkylcarboxamido, dialkylcarboxamido, substituted dialkylcarboxamido, alkylsulfonyl, alkylsulfinyl, thioalkyl, thiohaloalkyl, alkoxy, substituted alkoxy, haloalkoxy, heteroaryl, substituted heteroaryl, aryl or substituted aryl. It will be understood by those skilled in the art that an "alkoxy" can be a substituted of a carbonyl substituted "alkyl" forming an ester. When more than one substituent group is present then they can be the same or different. The organic substituent moieties can comprise from 1 to 12 carbon atoms, or from 1 to 6 carbon atoms, or from 1 to 4 carbon atoms. It will be understood by those skilled in the art that the moieties substituted on the "alkyl" chain can themselves be substituted, as described above, if appropriate.

c) Alkenyl

The term "alkenyl" as used herein is an alkyl residue as defined above that also comprises at least one carbon-carbon double bond in the backbone of the hydrocarbon chain. Examples include but are not limited to vinyl, allyl, 2-butenyl, 3-butenyl, 2-pentenyl, 3-pentenyl, 4-pentenyl, 2-hexenyl, 3-hexenyl, 4-hexenyl, 5-hexanyl, 2-heptenyl, 3-heptenyl, 4-heptenyl, 5-heptenyl, 6-heptenyl and the like. The term "alkenyl" includes dienes and trienes of straight and branch chains.

d) Alkynyl

The term "alkynyl" as used herein is an alkyl residue as defined above that comprises at least one carbon-carbon triple bond in the backbone of the hydrocarbon chain. Examples include but are not limited ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, 5-hexynyl and the like. The term "alkynyl" includes di- and tri-ynes.

e) Alkoxy

The term "alkoxy" as used herein is an alkyl residue, as defined above, bonded directly to an oxygen atom, which is then bonded to another moiety. Examples include methoxy, ethoxy, n-propoxy, iso-propoxy, n-butoxy, t-butoxy, iso-butoxy and the like f) Aryl

The term "aryl" as used herein is a ring radical containing 6 to 18 carbons, or preferably 6 to 12 carbons, comprising at least one aromatic residue therein. Examples of such aryl radicals include phenyl, naphthyl, and ischroman radicals. Moreover, the term "aryl" as used throughout the specification and claims is intended to include both "unsubstituted alkyls" and "substituted alkyls", the later denotes an aryl ring radical as defined above that is substituted with one or more, preferably 1, 2, or 3 organic or inorganic substituent groups, which include but are not limited to a halogen, alkyl, alkenyl, alkynyl, hydroxyl, cycloalkyl, amino, mono-substituted amino, di-substituted amino, unsubstituted or substituted amido, carbonyl, halogen, sulfhydryl, sulfonyl, sulfonato, sulfamoyl, sulfonamide, azido acyloxy, nitro, cyano, carboxy, carboalkoxy, alkylcarboxamido, substituted alkylcarboxamido, dialkylcarboxamido, substituted dialkylcarboxamido, alkylsulfonyl, alkylsulfinyl, thioalkyl, thiohaloalkyl, alkoxy, substituted alkoxy or haloalkoxy, aryl, substituted aryl, heteroaryl, heterocyclic ring, ring wherein the terms are defined herein. The organic substituent groups can comprise from 1 to 12 carbon atoms, or from 1 to 6 carbon atoms, or from 1 to 4 carbon atoms. It will be understood by those skilled in the art that the moieties substituted on the "aryl" can themselves be substituted, as described above, if appropriate.

g) Acyl

The term "acyl" as used herein is a R—C(O)— residue having an R group containing 1 to 8 carbons. Examples include but are not limited to formyl, acetyl, propionyl, butanoyl, iso-butanoyl, pentanoyl, hexanoyl, heptanoyl, benzoyl and the like, and natural or un-natural amino acids.

h) Azide

As used herein, the term "azide", "azido" and their variants refer to any moiety or compound comprising the monovalent group —$N_3$ or the monovalent ion—$N_3$.

i) Acyloxy

The term "acyloxy" as used herein is an acyl radical as defined above directly attached to an oxygen to form an R—C(O)O— residue. Examples include but are not limited to acetyloxy, propionyloxy, butanoyloxy, iso-butanoyloxy, benzoyloxy and the like.

j) Backbone Atom

The term backbone atom when used herein with respect to a linker refers to an atom in the shortest direct path of covalent bonding between the two chief moieties that are linked by the linker.

k) Carbonate Group

The term "carbonate group" as used herein is represented by the formula —OC(O)OR, where R can be hydrogen, an alkyl, alkenyl, alkynyl, aryl, aralkyl, cycloalkyl, halogenated alkyl, or heterocycloalkyl group described above.

l) Carboxylic Acid

The term "carboxylic acid" as used herein is represented by the formula —C(O)OH.

m) Carbonyl Group

The term "carbonyl group" as used herein is represented by the formula C=O.

n) Cycloalkyl

The term "cycloalkyl" as used herein is a saturated hydrocarbon structure wherein the structure is closed to form at least one ring. Cycloalkyls typically comprise a cyclic radical containing 3 to 8 ring carbons, such as cyclopropyl, cyclobutyl, cyclopentyl, cyclopenyl, cyclohexyl, cycloheptyl and the like. Cycloalkyl radicals can be multicyclic and can contain a total of 3 to 18 carbons, or preferably 4 to 12 carbons, or 5 to 8 carbons. Examples of multicyclic cycloalkyls include decahydronapthyl, adamantyl, and like radicals.

Moreover, the term "cycloalkyl" as used throughout the specification and claims is intended to include both "unsubstituted cycloalkyls" and "substituted cycloalkyls", the later denotes an cycloalkyl radical analogous to the above definition that is further substituted with one, two, or more additional organic or inorganic substituent groups that can include but are not limited to hydroxyl, cycloalkyl, amino, mono-substituted amino, di-substituted amino, unsubstituted or substituted amido, carbonyl, halogen, sulfhydryl, sulfonyl, sulfonato, sulfamoyl, sulfonamide, azido, acyloxy, nitro, cyano, carboxy, carboalkoxy, alkylcarboxamido, substituted alkylcarboxamido, dialkylcarboxamido, substituted dialkylcarboxamido, alkylsulfonyl, alkylsulfinyl, thioalkyl, thiohaloalkyl, alkoxy, substituted alkoxy, haloalkoxy, heteroaryl, substituted heteroaryl, aryl or substituted aryl. When the cycloalkyl is substituted with more than one substituent group, they can be the same or different. The organic substituent groups can comprise from 1 to 12 carbon atoms, or from 1 to 6 carbon atoms, or from 1 to 4 carbon atoms.

o) Cycloalkenyl

The term "cycloalkenyl" as used herein is a cycloalkyl radical as defined above that comprises at least one carbon-carbon double bond. Examples include but are not limited to cyclopropenyl, 1-cyclobutenyl, 2-cyclobutenyl, 1-cyclopentenyl, 2-cyclopentenyl, 3-cyclopentenyl, 1-cyclohexyl, 2-cyclohexyl, 3-cyclohexyl and the like.

p) Di-Substituted Amino

The term "di-substituted amino" as used herein is a moiety comprising a nitrogen atom substituted with two organic radicals that can be the same or different, which can be selected from but are not limited to aryl, substituted aryl, alkyl, substituted alkyl or arylalkyl, wherein the terms have the same definitions found throughout. Some examples include dimethylamino, methylethylamino, diethylamino and the like.

q) Ether

The term "ether" as used herein is represented by the formula $AOA^1$, where A and $A^1$ can be, independently, an alkyl, halogenated alkyl, alkenyl, alkynyl, aryl, heteroaryl, cycloalkyl, cycloalkenyl, heterocycloalkyl, or heterocycloalkenyl group described above.

r) Ester

The term "ester" as used herein is represented by the formula —C(O)OA, where A can be an alkyl, halogenated alkyl, alkenyl, alkynyl, aryl, heteroaryl, cycloalkyl, cycloalkenyl, heterocycloalkyl, or heterocycloalkenyl group described above.

s) Haloalkyl

The term "haloalkyl" as used herein an alkyl residue as defined above, substituted with one or more halogens, preferably fluorine, such as a trifluoromethyl, pentafluoroethyl and the like.

t) Haloalkoxy

The term "haloalkoxy" as used herein a haloalkyl residue as defined above that is directly attached to an oxygen to form trifluoromethoxy, pentafluoroethoxy and the like.

u) Halo, Halogen

The term "halo" or "halogen" refers to a fluoro, chloro, bromo or iodo group.

v) Heteroaryl

The term "heteroaryl" as used herein is an aryl ring radical as defined above, wherein at least one of the ring carbons, or preferably 1, 2, or 3 carbons of the aryl aromatic ring has been replaced with a heteroatom, which include but are not limited to nitrogen, oxygen, and sulfur atoms. Examples of heteroaryl residues include pyridyl, bipyridyl, furanyl, and thiofuranyl residues. Substituted "heteroaryl" residues can have one or more organic or inorganic substituent groups, or preferably 1, 2, or 3 such groups, as referred to herein-above for aryl groups, bound to the carbon atoms of the heteroaromatic rings. The organic substituent groups can comprise from 1 to 12 carbon atoms, or from 1 to 6 carbon atoms, or from 1 to 4 carbon atoms.

w) Heterocyclyl

The term "heterocyclyl" or "heterocyclic group" as used herein is a non-aromatic mono- or multi ring radical structure having 3 to 16 members, preferably 4 to 10 members, in which at least one ring structure include 1 to 4 heteroatoms (e.g. O, N, S, P, and the like). Heterocyclyl groups include, for example, pyrrolidine, oxolane, thiolane, imidazole, oxazole, piperidine, piperizine, morpholine, lactones, lactams, such as azetidiones, and pyrrolidiones, sultams, sultones, and the like. Moreover, the term "heterocyclyl" as used throughout the specification and claims is intended to include both "unsubstituted alkyls" and "substituted alkyls", the later denotes an aryl ring radical as defined above that is substituted with one or more, preferably 1, 2, or 3 organic or inorganic substituent groups, which include but are not limited to a halogen, alkyl, alkenyl, alkynyl, hydroxyl, cycloalkyl, amino, mono-substituted amino, di-substituted amino, unsubstituted or substituted amido, carbonyl, halogen, sulfhydryl, sulfonyl, sulfonato, sulfamoyl, sulfonamide, azido acyloxy, nitro, cyano, carboxy, carboalkoxy, alkylcarboxamido, substituted alkylcarboxamido, dialkylcarboxamido, substituted dialkylcarboxamido, alkylsulfonyl, alkylsulfinyl, thioalkyl, thiohaloalkyl, alkoxy, substituted alkoxy or haloalkoxy, aryl, substituted aryl, heteroaryl, heterocyclic ring, ring wherein the terms are defined herein. The organic substituent groups can comprise from 1 to 12 carbon atoms, or from 1 to 6 carbon atoms, or from 1 to 4 carbon atoms. It will be understood by those skilled in the art that the moieties substituted on the "heterocyclyl" can themselves be substituted, as described above, if appropriate.

x) Hoeschst 33258 Derived Benzimidazoles or Benzimidazole Derivatives

"Hoeschst 33258 derived benzimidazoles or benzimidazole derivatives" or the like terms are herein referred to any compound or moiety that includes a benzimidazole group. For example, a "Hoeschst 33258 derived benzimidazoles or benzimidazole derivatives" can have the structure $1_n$-$2_n$-$3_n$-$4_n$-$5_n$-$6_n$-$7_n$-$8_n$-$9_n$, wherein each n can independently be 0 or 1, wherein 1-9 can independently be H, O, N, S, alkyl, alkenyl, alkynyl, aryl, heteroaryl, cycloalkyl, cycloalkenyl, heterocyclyl, benzimidazole, amino, mono-substituted amino, di-substituted amino, unsubstituted or substituted amido, carbonyl, halogen, sulfhydryl, sulfonyl, sulfonato, sulfamoyl, sulfonamide, azido, acyloxy, nitro, cyano, carboxy, carboalkoxy, alkylcarboxamido, substituted alkylcarboxamido, dialkylcarboxamido, substituted dialkylcarboxamido, alkylsulfonyl, alkylsulfinyl, thioalkyl, thiohaloalkyl, alkoxy, substituted alkoxy, haloalkoxy, wherein at least one sub group is substituted or unsubstituted benzimidazole, for example $3_n$ can be substituted or unsubstituted benzimidazole. It is understood by those skilled in the art that each individual subgroup can be further substituted, for example, an aryl in position $2_n$ can be further substituted as defined elsewhere herein. Furthermore, $1_n$-$2_n$-$3_n$-$4_n$-$5_n$-$6_n$-$7_n$-$8_n$ can be attached to any other compound or moiety at any position, for example, position 1 can be further attached to a linker which can be further attached to a glycoside, aminoglycoside, or sugar. It is understood that any and all of these modifications can be made alone or in any combination. A non-limiting example of a "Hoeschst 33258 derived benzimidazole or benzimidazole derivative" is

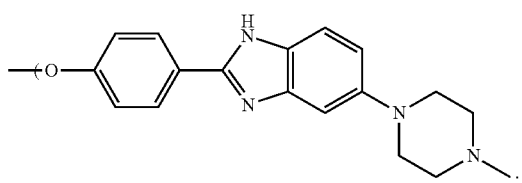

Another set of more specific benzimidazoles are shown in compound 8. odifications

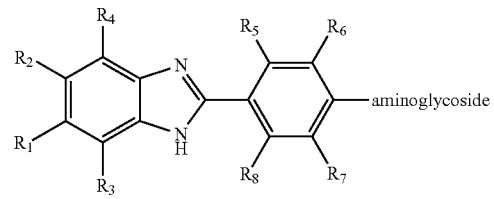

Compound 8

R2-R8=OH, Halogen, Cl, Br, F, I, $NH_2$, Alkyl, OR (R=alkyl), $NO_2$, H

R1=OH, Halogen, Cl, Br, F, I, $NH_2$, Alkyl, OR (R=alkyl), $NO_2$, H, N-methyl piperazine, piperazine.

Modifications of benzimidazoles can be found in Kamal A. et al., Medicinal Bioorganic & Chemistry Letters 14 (2004) 4791-4794; Synthetic Communications1, 39: 175-188, 2009, Helvetica Chimica Acta, 83, 2000, 2197-2213, Tanada, M., et al., J. Org. Chem., 2006, 71 (1), 125-134, Rajur S B, et al. J. Org. Chem., 1997, 62 (3), pp 523-529 which are herein incorporated by reference at least for material related to structure and synthesis of benzimidazole derivatives.

y) Keto Group

The term "keto group" as used herein is represented by the formula —C(O)R, where R is an alkyl, alkenyl, alkynyl, aryl, aralkyl, cycloalkyl, halogenated alkyl, or heterocycloalkyl group described above.

z) Linked

As used herein, the terms "linked", "operably linked" and "operably bound" and variants thereof mean, for purposes of the specification and claims, to refer to fusion, bond, adherence or association of sufficient stability to withstand conditions encountered in single molecule applications and/or the methods and systems disclosed herein, between a combination of different molecules such as, but not limited to: between a detectable label and nucleotide, between a detectable label and a linker, between a nucleotide and a linker, between a protein and a functionalized nanocrystal; between a linker and a protein; and the like. For example, in a labeled polymerase, the label is operably linked to the polymerase in such a way that the resultant labeled polymerase can readily participate in a polymerization reaction. See, for example, Hermanson, G., 2008, Bioconjugate Techniques, Second Edition. Such operable linkage or binding may comprise any sort of fusion, bond, adherence or association, including, but not limited to, covalent, ionic, hydrogen, hydrophilic, hydrophobic or affinity bonding, affinity bonding, van der Waals forces, mechanical bonding, etc.

aa) Linker

The term "linker" and its variants, as used herein, include any compound or moiety that can act as a molecular bridge that operably links two different molecules. There are many different linkers and types disclosed herein, such as those designated with a -B-.

bb) Metabolite

The term "metabolite" refers to active derivatives produced upon introduction of a compound into a biological milieu, such as a patient.

cc) Urethane

The term "urethane" as used herein is represented by the formula —OC(O)NRR', where R and R' can be, independently, hydrogen, an alkyl, alkenyl, alkynyl, aryl, aralkyl, cycloalkyl, halogenated alkyl, or heterocycloalkyl group described above.

dd) Monosubstituted Amino

The term "mono-substituted amino" as used herein is a moiety comprising an NH radical substituted with one organic substituent group, which include but are not limited to alkyls, substituted alkyls, cycloalkyls, aryls, or arylalkyls. Examples of mono-substituted amino groups include methylamino (—NH—CH$_3$); ethylamino (—NHCH$_2$CH$_3$), hydroxyethylamino (—NH—CH$_2$CH$_2$OH), and the like.

ee) Moiety

A "moiety" is part of a molecule (or compound, or analog, etc.). A "functional group" is a specific group of atoms in a molecule. A moiety can be a functional group or can include one or functional groups.

ff) Silyl Group

The term "silyl group" as used herein is represented by the formula —SiRR'R", where R, R', and R" can be, independently, hydrogen, an alkyl, alkenyl, alkynyl, aryl, aralkyl, cycloalkyl, halogenated alkyl, alkoxy, or heterocycloalkyl group described above.

gg) Stable

When used with respect to pharmaceutical compositions, the term "stable" is generally understood in the art as meaning less than a certain amount, usually 10%, loss of the active ingredient under specified storage conditions for a stated period of time. The time required for a composition to be considered stable is relative to the use of each product and is dictated by the commercial practicalities of producing the product, holding it for quality control and inspection, shipping it to a wholesaler or direct to a customer where it is held again in storage before its eventual use. Including a safety factor of a few months time, the minimum product life for pharmaceuticals is usually one year, and preferably more than 18 months. As used herein, the term "stable" references these market realities and the ability to store and transport the product at readily attainable environmental conditions such as refrigerated conditions, 2° C. to 8° C.

hh) Sulfo-Oxo Group

The term "sulfo-oxo group" as used herein is represented by the formulas —S(O)$_2$R, —OS(O)$_2$R, or, —OS(O)$_2$OR, where R can be hydrogen, an alkyl, alkenyl, alkynyl, aryl, aralkyl, cycloalkyl, halogenated alkyl, or heterocycloalkyl group described above.

7. Detection Agent

A "detection agent" or like terms refers to any molecule or moiety which can be detected by, such as flourescence, radioactivity, phosphorescence, or the like.

8. Higher

The terms "higher," "increases," "elevates," or "elevation" or variants of these terms, refer to increases above basal levels, e.g., as compared to a control. The terms "low," "lower," "reduces," or "reduction" or variation of these terms, refer to decreases below basal levels, e.g., as compared to a control. For example, basal levels are normal in vivo levels prior to, or in the absence of, or addition of an agent such as an agonist or antagonist to activity.

9. Inhibit

By "inhibit" or other forms of inhibit means to hinder or restrain a particular characteristic. It is understood that this is typically in relation to some standard or expected value, in other words it is relative, but that it is not always necessary for the standard or relative value to be referred to. For example, "inhibits phosphorylation" means hindering or restraining the amount of phosphorylation that takes place relative to a standard or a control.

a) Weight/%

References in the specification and concluding claims to parts by weight, of a particular element or component in a composition or article, denotes the weight relationship between the element or component and any other elements or components in the composition or article for which a part by weight is expressed. Thus, in a compound containing 2 parts by weight of component X and 5 parts by weight component Y, X and Y are present at a weight ratio of 2:5, and are present in such ratio regardless of whether additional components are contained in the compound.

A weight percent of a component, unless specifically stated to the contrary, is based on the total weight of the formulation or composition in which the component is included.

10. Labeled RNA Binder

A "labeled RNA binder" or like terms refers to a molecule comprising a detection agent.

11. Optionally

"Optional" or "optionally" means that the subsequently described event or circumstance may or may not occur, and that the description includes instances where said event or circumstance occurs and instances where it does not.

12. Pharmacological Activity

As used herein, the term "pharmacological activity" refers to the inherent physical properties of a peptide or polypeptide. These properties include but are not limited to half-life, solubility, and stability and other pharmacokinetic properties.

13. Primers

"Primers" are a subset of probes which are capable of supporting some type of enzymatic manipulation and which can hybridize with a target nucleic acid such that the enzymatic manipulation can occur. A primer can be made from any combination of nucleotides or nucleotide derivatives or analogs available in the art which do not interfere with the enzymatic manipulation.

14. Probes

"Probes" are molecules capable of interacting with a target nucleic acid, typically in a sequence specific manner, for example through hybridization. The hybridization of nucleic acids is well understood in the art and discussed herein. Typically a probe can be made from any combination of nucleotides or nucleotide derivatives or analogs available in the art.

15. Prevent

By "prevent" or other forms of prevent means to stop a particular characteristic or condition. Prevent does not require comparison to a control as it is typically more absolute than, for example, reduce or inhibit. As used herein, something could be reduced but not inhibited or prevented, but something that is reduced could also be inhibited or prevented. It is understood that where reduce, inhibit or prevent are used, unless specifically indicated otherwise, the use of the other two words is also expressly disclosed. Thus, if inhibits phosphorylation is disclosed, then reduces and prevents phosphorylation are also disclosed.

16. Pro-Drug

The term "pro-drug or prodrug" is intended to encompass compounds which, under physiologic conditions, are converted into therapeutically active agents. A common method for making a prodrug is to include selected moieties which are hydrolyzed under physiologic conditions to reveal the desired molecule. In other embodiments, the prodrug is converted by an enzymatic activity of the host animal.

17. Ranges

Ranges can be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that when a value is disclosed that "less than or equal to" the value, "greater than or equal to the value" and possible ranges between values are also disclosed, as appropriately understood by the skilled artisan. For example, if the value "10" is disclosed the "less than or equal to 10" as well as "greater than or equal to 10" is also disclosed. It is also understood that the throughout the application, data are provided in a number of different formats, and that this data, represents endpoints and starting points, and ranges for any combination of the data points. For example, if a particular datum point "10" and a particular datum point 15 are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

18. Reduce

By "reduce" or other forms of reduce means lowering of an event or characteristic. It is understood that this is typically in relation to some standard or expected value, in other words it is relative, but that it is not always necessary for the standard or relative value to be referred to. For example, "reduces phosphorylation" means lowering the amount of phosphorylation that takes place relative to a standard or a control.

19. Subject

As used throughout, by a "subject" is meant an individual. Thus, the "subject" can include, for example, domesticated animals, such as cats, dogs, etc., livestock (e.g., cattle, horses, pigs, sheep, goats, etc.), laboratory animals (e.g., mouse, rabbit, rat, guinea pig, etc.) mammals, non-human mammals, primates, non-human primates, rodents, birds, reptiles, amphibians, fish, and any other animal. The subject can be a mammal such as a primate or a human.

20. Treatment

"Treating" or "treatment" does not mean a complete cure. It means that the symptoms of the underlying disease are reduced, and/or that one or more of the underlying cellular, physiological, or biochemical causes or mechanisms causing the symptoms are reduced. It is understood that reduced, as used in this context, means relative to the state of the disease, including the molecular state of the disease, not just the physiological state of the disease.

21. Therapeutic Effective

The term "therapeutically effective" means that the amount of the composition used is of sufficient quantity to ameliorate one or more causes or symptoms of a disease or disorder. Such amelioration only requires a reduction or alteration, not necessarily elimination. The term "carrier" means a compound, composition, substance, or structure that, when in combination with a compound or composition, aids or facilitates preparation, storage, administration, delivery, effectiveness, selectivity, or any other feature of the compound or composition for its intended use or purpose. For example, a carrier can be selected to minimize any degradation of the active ingredient and to minimize any adverse side effects in the subject.

B. COMPOSITIONS AND METHODS

1. HIV

Given the steady spread of the HIV epidemic, there is still a need to bring an effective vaccine or therapy to the clinic. A number of different HIV-1 vaccine delivery strategies such as novel vectors or adjuvant systems have now been developed and evaluated in different pre-clinical settings as well as in clinical trials. The first vaccine candidate that entered a phase III clinical trial is based on envelope gp 120 protein in alum (Francis et al., AIDS Res. Hum. Retroviruses 1998; 14 (Suppl 3)(5): S325-31). The phase III trials have been started although the vaccine did not prove to be too successful in the earlier phase II trial.

Infection of the CD4+ subclass of T-lymphocytes with the HIV-1 virus leads to depletion of this essential lymphocyte subclass which inevitably leads to opportunistic infections, neurological disease, neoplastic growth and eventually death. HIV-1 infection and HIV-1 associated diseases represent a major health problem and considerable attention is currently being directed towards the successful design of effective therapeutics.

(1) HIV

HIV-1 is a member of the lentivirus family of retroviruses (Teich, N. et al., 1984 In RNA Tumor Viruses ed. R. Weiss, N. Teich, H. Varmus, J. Coffin CSH Press, pp. 949-56). The life cycle of HIV-1 is characterized by a period of proviral latency followed by active replication of the virus. The primary cellular target for the infectious HIV-1 virus is the CD4+ subset of human T-lymphocytes. Targeting of the virus to the CD4+ subset of cells is due to the fact that the CD4+ cell surface protein acts as the cellular receptor for the HIV-1 virus (Dalgleish, A. et al., 1984, Nature 312:763-67; Klatzmann et al. 1984, Nature 312:767-68; Maddon et al. 1986 Cell 47:333-48).

Figure 2:
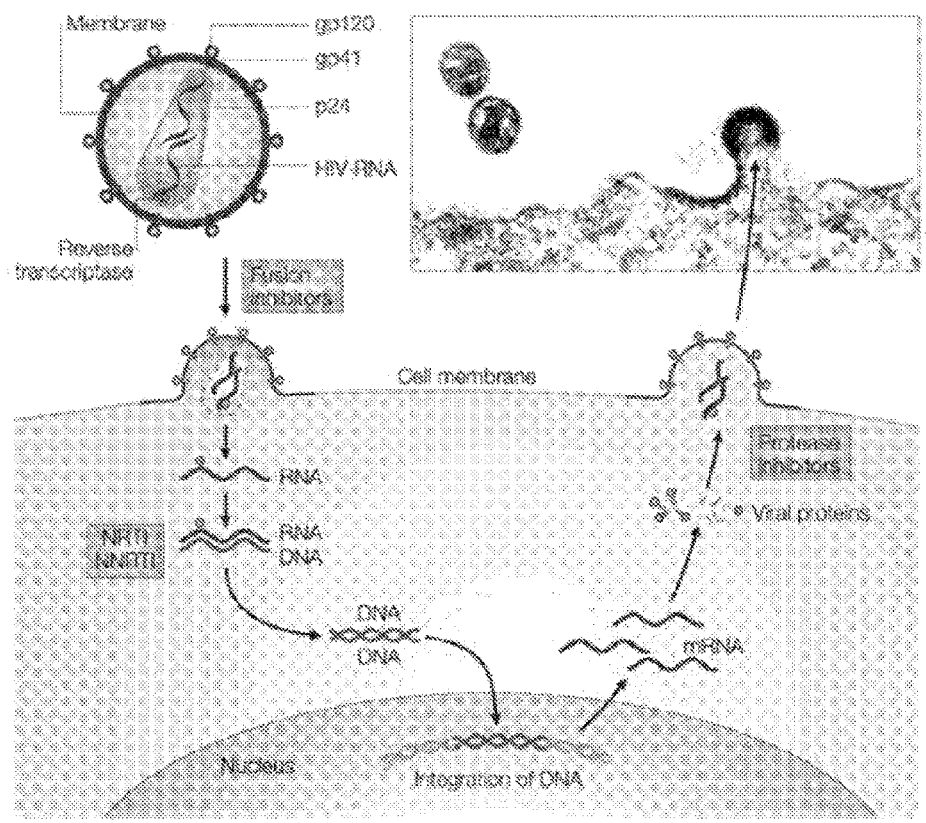
FIG. 2 shows the HIV replication cycle. First virus attaches to receptor (CD4) & co-receptor (chemokine receptor CCR5 or CXCR4); The virus enters through fusion with target cell membrane; The viral RNA genome undergoes reverse transcription; The proviral DNA integrates into the host chromosome; The viral proteins are translated; The viral proteins assemble at the cell membrane; The immature virus particle containing the RNA genome egresses the cell; The maturation of the viral particle: the virion buds & capsid proteins are processed, leading to a structural rearrangement of the virion
Figure 3:
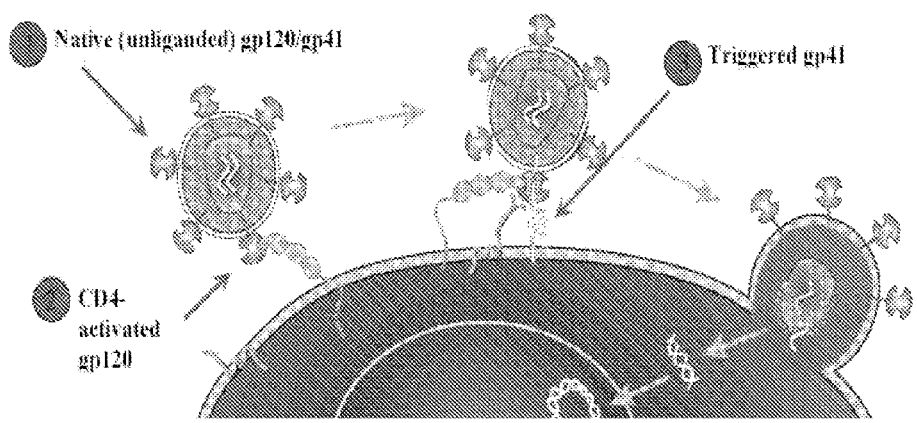
FIG. 3 shows the initial binding of HIV to the cell surface. Phase 1 represents the native envelope glycoproteins on the surface of the virus. Phase 2 represents the "activation" of glycoprotein gp120 upon binding to the CD4 cell surface molecule. Phase 3 represents the conformation change in the envelope glycoproteins to provide a stronger binding to the cell surface. Lastly, the virus fuses with the cell which allows entry of the viral DNA into the host cell.

The HIV life cycle is shown in FIG. 2. HIV-1 infection of susceptible cells is initiated via interactions between the virus envelope glycoprotein (gp120) and the CD4+ cell surface receptor (FIG. 3). Fusion of the viral and cell membranes then proceeds through subsequent interaction of this complex with a specific chemokine receptor, primarily the CCR5 or the CXCR4 chemokine receptor (Bieniasz & Cullen, 1998, Front. Biosci. 3:D44-D58; Moore et al., 1997, Curr. Opin. Immunol. 9:551-562). HIV-1 isolates that can infect T-cell lines and induce syncytia (SI) use the CXCR4 receptor and are termed X4 HIV-1. Such isolates are typically recovered late in the course of HIV progression and differ from the non-syncytia inducing (NSI) strains which predominate in the early stages of HIV infection. NSI strains gain entry to target cells through use of the CCR5 receptor and are referred to as R5 HIV-1.

After binding to the cell surface and fusion of the virus and cell membrane, the HIV-1 virion becomes internalized and the virus's RNA genome is reverse transcribed into linear double-stranded DNA molecules. This process is dependent on the action of the virally encoded reverse transcriptase. Following replication of the viral genome, the linear DNA molecule integrates into the host genome through the action of the viral integrase protein, thus establishing the proviral form of HIV-1. During the early phase of proviral expression, transcription of the viral genome results in expression of regulatory proteins such as Tat, Nef and Rev. Transcriptional activation of the proviral DNA is mediated through the viral 5' LTR sequences (long terminal repeats). The initial low level of viral transcription is dramatically increased by the HIV encoded transactivator protein termed tat (transactivator protein) (Cullen, B. R. et al. 1989, Cell 58:423-26). The Rev protein promotes the transition from the early phase expression of regulatory proteins to late phase expression of structural proteins. Upon translation of the new viral proteins, the proteins assemble at the cell membrane in the form of newly synthesized viral particles. This is followed by budding of virus particles from the cell membrane allowing the virus to infect new cells.

Figure 4:
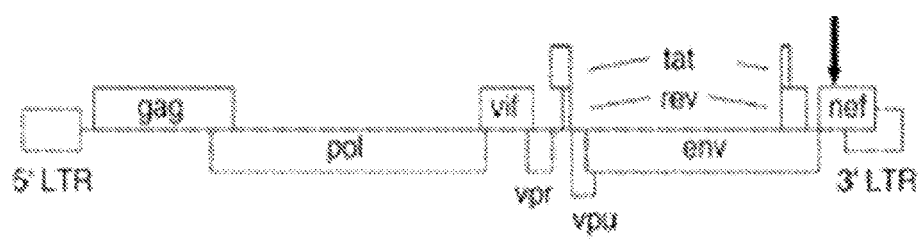
FIG. 4 shows a general depiction of the HIV genome.

The general outline of the HIV genome is depicted in FIG. 4. Currently, there are several strategies for inhibiting HIV. Protease inhibitors can block replication at the end of the replication cycle by disallowing cleavage of nascent proteins necessary for assembly of daughter virions. Fusion inhibitors prevent conformational changes between viral envelope proteins and cell surface chemokine receptors therefore inhibiting the fusion of the cell membrane and the virus thus preventing the viral DNA from entering the cell. Nucleoside- and non-nucleoside reverse transcriptase inhibitors (NRTI & NNRTIs) bind reverse transcriptase and prevent reverse transcription and thus replication of the viral genome. The main problem with these therapeutic approaches is that single point mutations in the viral genome often result in emergence of resistant viral strains.

b) TAR

Human Immunodeficiency Virus (HIV) is a devastating disease that has reached near epidemic proportions in some countries, while continuing to prove almost impossible to treat. Currently, only four targets have been clinically implemented for the treatment of HIV all of which are proteins. However, recent advance in medicinal chemistry have shown that RNA can provide a suitable target in the cell. This discovery has resulted in the examination, and validation, of the trans-activation responsive (TAR) region of HIV mRNA as a potential therapeutic target. The inhibition of the Tat/TAR interaction, which facilitates HIV RNA transcription subsequently arrests HIV replication. The possibility of neomycin, considered a promiscuous RNA binder, displacing the Tat protein from the TAR RNA have opened up new possibilities for the use of TAR as a target for HIV treatment. Since this discovery, numerous other TAR binding compounds have been identified, and current efforts are being made to conjugate these molecules to neomycin in order to create a high affinity TAR binding ligand, with increased specificity. However few high affinity molecules that can specifically bind TAR at nanomolar concentrations have been identified. Therefore, there is a critical need to identify new synthetic approaches to further develop high affinity and TAR specific ligands.

Figure 5:
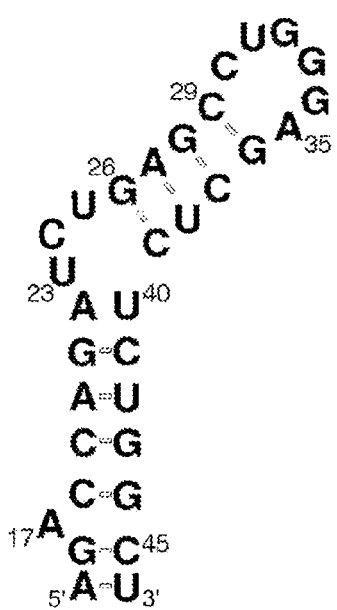
FIG. 5 shows the stem loop structure for the transactivation response element (TAR). TAR also comprises nt 1-59 of HIV-1 mRNA and both this sequence and the stem loop are essential for transactivation. The stem loop sequence, shown, is specifically recognized by the Tat protein, and recruits RNA polymerase II to the HIV-I mRNA transcripts for transcription.

The transactivator of transcription (Tat) is a non-structural viral protein (a protein encoded by the virus genome that is not actually part of the virus itself). Tat is a variable RNA binding peptide of 86 to 110 amino acids in length that is encoded on two separate exons of the HIV genome. Tat is highly conserved among all human lentiviruses and is essential for viral replication. When lentivirus Tat binds to the transactivation responsive RNA region, transcription levels increase significantly. The transactivation response element (TAR) comprises nt 1-59 of HIV-1 mRNA, and contains a stem loop structure essential for transactivation. The stem loop sequence, shown in FIG. 5, is specifically recognized by the Tat protein, and recruits RNA polymerase II to the HIV-I mRNA transcripts for transcription.

The two helical regions of the TAR are separated by a three nucleotide bulge; this pyrimidine bulge is responsible for Tat recognition, while the loop on the end of the TAR is necessary for trans activation. The binding of the Tat protein to TAR involves interactions in the major groove of the RNA, specifically between U23 and the peptide backbone, and non-specific electrostatic interactions between the arginine-rich region of Tat and the phosphate backbone of the RNA (Loret, Georgel et al. 1992). In order to develop an effective inhibitor of the Tat-TAR interaction, a molecule must have high affinity and specificity for the bulge, or a site adjacent to the bulge that is able to induce a conformational change in the bulge (Krebs, Ludwig et al. 2003).

The use of interactions which are highly specific to the virus and unseen within the human body are most promising in terms of both efficacy and flexibility. With respect to RNA transcription, two key protein/RNA interactions have been identified as promising areas for intervention; these being RRE/Rev and TAR/Tat. The RRE/Rev interaction is critical in exporting and protecting viral RNA in its journey from the cell nucleus. Though this interaction has been reduced to a minimal construct allowing efficient study, the complex 3-D structure of RRE RNA leaves many unanswered questions in the search for compounds which can inhibit this interaction. The TAR/Tat interaction facilitates full length viral RNA transcription (Marciniak, Calnan et al. 1990). Primarily, the conservation of sequence and structure of the TAR region in both SIV and HIV is remarkably conserved (Berkhout 1992). This conservation of RNA together with the slow mutation rate in both RNA and DNA is expected to yield a low chance of mutation with the discovery of an effective inhibitory agent. The Tat/TAR interaction is also a positive feedback loop within the HIV life cycle (trans-activation results in the synthesis of more Tat), while Tat has also been proven to have multi-faceted roles within the HIV life cycle (Andersen, Contera et al. 2004). Therefore, it is most evident that the addition of low mutability of the target, along with the inhibition of a positive-feedback loop within the life cycle effectively inhibits this protein/RNA interaction. This inhibition in turn results in an extremely effective therapeutic intervention of the life cycle of the HIV virus.

There are several advantages for targeting TAR. One advantage is that it targets replication inhibition at the transcriptional level which is an unused target in the replication cycle. Another advantage is the fact that the TAR sequence is well-conserved within HIV-1 strains and therefore identifying compounds that target TAR will provide inhibition of a variety of HIV strains, not just one or two.

The only resistant strains will be those that contain mutations within the TAR stem-loop sequence that arise simultaneously with a compensatory mutation(s) within the Tat gene. These mutants are extremely rare.

Evidence shows that blocking the Tat/TAR interaction in infected cells prevents replication (Sharp & Marciniak, (1989) Cell 59: 229, Johnston & Hoth, (1993) Science 260: 1286). Therefore, disrupting the Tat/TAR interaction is an effective way to prevent HIV replication and thus, inhibit the virus.

The Tat/TAR interaction can be mimicked by argininamide. Binding of Tat to TAR is mediated by a single arginine residue. Free arginine can bind in the same manner, and argininamide can be used to substitute for this amino acid. Argininamide binding occurs within the 3-nt bulge region of the TAR stem-loop (Calnan et al., (1991) Science 252: 1167; Tao & Frankel (1992) PNAS, 89: 2723; Puglisi, et al., (1992) Science. 257: 5066: 76-80).

Virtually all strategies to date center around targeting the argininamide binding site and thus creating a competitive inhibitor for Tat. This approach is difficult considering argininamide is highly specific, and has a binding constant of ~1 nM.

Figure 6:
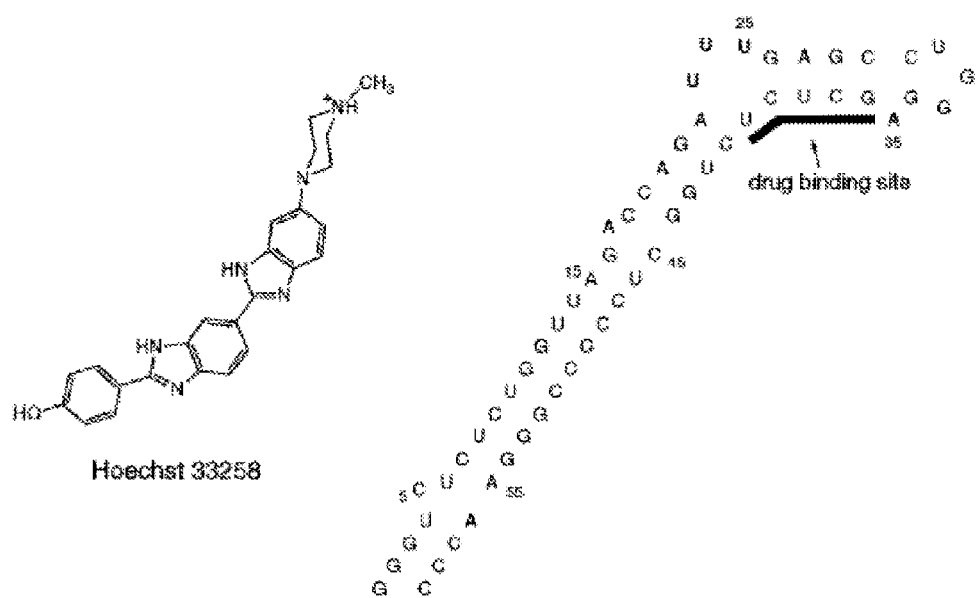
FIG. 6 shows Hoechst 33258 binds HIV-1 TAR in a single relatively high affinity site, localized by foot-printing to the upper region of the bulge/lower region of the upper stem (AT selective DNA minor groove binder, and is also a nucleic acid intercalator), although it will bind non-specifically when present in excess over TAR.

Another compound that can bind TAR is Hoescht 33258 (FIG. 6). Hoechst binds HIV-1 TAR in a single relatively high affinity site, yet to be specified precisely, but has been localized by foot-printing to the upper region of the bulge/lower region of the upper stem (AT selective DNA minor groove binder, and is also a nucleic acid intercalator), although it will bind non-specifically when present in excess over TAR (Dassonneville, et al., (1997) Nucleic Acids Research, 25: 4487-4492).

Disclosed herein are aminoglycosides as RNA binders. They are promiscuous binders due to the electrostatic nature of their binding and their conformational flexibility. Neomycin, an aminoglycoside, binds TAR with only ~6 micromolar affinity (Faber et al. (2000) J Biol Chem 275:20660-20666).

Figure 7A:
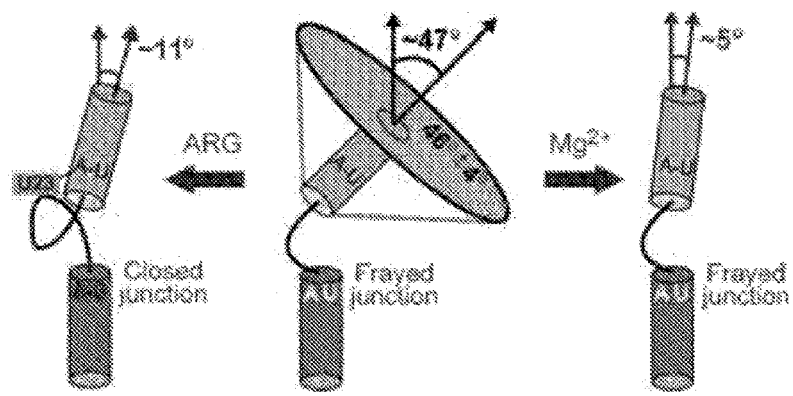
FIG. 7A shows the experimental design to arrest TAR motion by trapping it in a non-recognizable bent conformation.
Figure 7B:
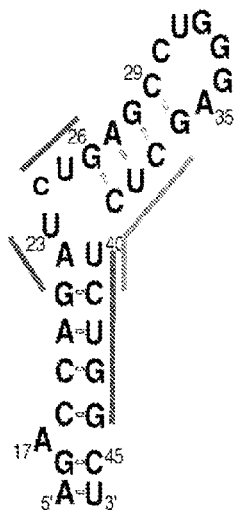
FIG. 7B The inherent flexibility of TAR's 3-nt bulge region.

TAR has inherent flexibility about its 3-nt bulge region. Argininamide (Tat, and the RNA pol II complex/) binds via near-linear conformation of TAR. FIG. 6 shows the conformational changes of TAR. It is not necessary to compete for the Tat binding site, but instead, arresting TAR motion, trapping it in a non-recognizable bent conformation, can have a deleterious effect on conformational change upon ligand binding (FIGS. 7A and 7B).

Conjugates can be designed that take advantage of two modes of binding, increasing specificity and affinity, and ideally binding the two different helices of TAR as well.

If a ligand molecule A and ligand molecule B bind to a receptor, ligands A-B are expected to bind so that binding constant of A-B equals the product of two individual binding constants. The product of the $K_d$ values for Hoechst 33258 (benzimidazole) and neomycin conjugates (in addition to neomycin-neomycin linked conjugates) to TAR will lead to a $K_d$ in the nM-pM range. The key in such studies is to identify the linker that maximizes binding and minimizes any entropic penalties of conjugation. Though certain aminoglycoside derivatives and conjugates have been studied as possible TAR binders, none approach the levels of affinity or specificity necessary for effective drug development (Lapidot, Vijayabaskar et al. 2004; Riguet and Bailly 2004; Riguet, Tripathi et al. 2004; Riguet, Desire et al. 2005; Yajima, Shionoya et al. 2006) (Hamma and Miller 2003; Hamma, Saleh et al. 2003). The disclosed compositions can overcome these difficulties in RNA targeted HIV drug development.

2. Methods of Binding and Inhibiting TAR

The disclosed compositions can be used to inhibit TAR function. The disclosed compositions can also be administered to a subject who has or is at risk of having a lentiviral infection, such as an HIV infection or has AIDS. The compositions can be administered as disclosed herein.

In addition, the compositions can be used as reagents in assays for identifying lentiviruses, such as HIV. For example, the compositions can be labeled, with for example, fluorescent molecules and administered in vivo, in vitro, or ex vivo. Then using standard assay procedures for the cognate label the virus can be identified by the location (binding) of the labeled composition.

Also disclosed, the compositions can be used as controls in any screening assay for binding to TAR or for inhibiting TAR activity. Thus, disclosed are complexes comprising the disclosed compositions and TAR in isolated and unisolated form. The methods comprise performing a TAR screening assay and during some point, binding one of the compositions disclosed herein with TAR or in an activity assay, producing a control. The output of the control can then be compared to other outputs from the assay. The data from this type of control can also be used as a standard, where it is not run in parallel to the rest of the assay, but rather is performed at an earlier or later date.

3. Aminoglycosides

PCT/US2006/029675 by Dev Pyra filed on Jul. 31, 2006 is herein incorporated by reference in its entirety, but at least for material related to aminoglycosides, nucleic acids, and conjugates of these, as well as structural information of nucleic acids.

Aminoglycoside antibiotics are bactericidal drags that have been at the forefront of antimicrobial therapy for almost five decades. The past decade (1990-2000) saw a resurgence in aminoglycoside-based drag development as their chemistry/mechanism of action became better understood. This work, however, had almost exclusively focused on targeting RNA.

Aminoglycoside antibiotics are bactericidal agents that are comprised of two or more amino sugars joined in glycosidic linkage to a hexose nucleus (Chow C S, et al (1997) Chem Rev 97:1489). Though they exhibit a narrow toxic/therapeutic ratio, their broad antimicrobial spectrum, rapid bactericidal action, and ability to act synergistically with other drags makes them highly effective in the treatment of nosocomial (hospital acquired) infections (Kotra L P, et al (2000) J Urol 163:1076). They are clinically useful in the treatment of urinary tract infections (Santucci R, et al (2000) J Urol 163:1076), lower respiratory infections, bacteremias, and other superinfections by resistant organisms (Forge A, et al (2000) Audio Neurootol 5:3). Their greatest potential has been in combination drug regimens for the treatment of infections that are difficult to cure with single agents and for use in patients who are allergic to other classes of drugs (Gerding D (2000) Infect Control Hosp Epidemiol 21: S12). Aminoglycosides (FIGS. 1 and 2) contain a unique polyamine/carbohydrate structure, and have attracted considerable attention because of their specific interactions with RNA (Kaul M, et al (2003) J Mol Biol 326:1373). The bactericidal action of aminoglycosides is attributed to the irreversible inhibition of protein synthesis following their binding to the 30S subunit of the bacterial ribosome and thus interfering with the mRNA translation process. The miscoding causes membrane damage, which eventually disrupts the cell integrity, leading to bacterial cell death (Moazed D, et al (1987) Nature 327:389; Purohit P, et al (1994) Nature 370:659; Recht M I, et al D (1996) J Mol Biol 262:421; Miyaguchi H, et al (1996) Nucleic Acids Res 24:3700).

Aminoglycosides are a group of antibiotics that are effective against certain types of bacteria. Those which are derived from *Streptomyces* species are named with the suffix—mycin, while those which are derived from *micromonospora* are named with the suffix—micin. The aminoglycosides are polar-cations which consist of two or more amino sugars joined in a glycosidic linkage to a hexose nucleus, which is usually in a central position.

Aminoglycosides include: amikacin, apramycin, arbekacin, bambermycins, butirosin, dibekacin, dibekacin, dihydrostreptomycin, fortimicin, geneticin, gentamicins (e.g., gentamicin Cl, gentamicin CIa, gentamicin C2, and analogs and derivatives thereof), isepamicin, kanamycins (e.g. kanamycin A, kanamycin B, kanamycin C, and analogs and derivatives thereof), lividomycin, micronomicin, neamine, neomycins (e.g. neomycin B and analogs and derivatives thereof), netilmicin, paromomycin, ribostamycin, sisomicin, spectinomycin, streptomycin, streptonicozid, tobramycin, trospectomycin, and viomycin.

Examples of such aminoglycoside antibiotics include kanamycin (Merck Index 9th ed. #5132), gentamicin (Merck Index 9th ed. #4224), amikacin (Merck Index 9th ed. #A1), dibekacin (Merck Index 9th ed. #2969), tobramycin (Merck Index 9th ed. #9193), streptomycin (Merck Index 9th ed. #8611/8612), paromomycin (Merck Index 9th ed. #6844), sisomicin (Merck Index 9th ed. #8292), isepamicin and netilmicin, all known in the art. The useful antibiotics include the several structural variants of the above compounds (e.g. kanamycin A, B and C; gentamicin A, Cl, CIa, C2 and D; neomycin B and C and the like). The free bases, as well as pharmaceutically acceptable acid addition salts of these aminoglycoside antibiotics, can be employed.

Aminoglycosides can be modified for further modification at several positions, for example, azido groups can be incorporated which can be used for further modifications. The following references provide non-limiting examples of incorporation of reactive functionalities on aminoglycosides and are hereby fully incorporated by reference (Nunns et al, Tetrahedron Letters, 40(52):9341-9345, 1999; Greenberg et al. J Am Chem Soc, 121(28):6527-6541, 1999; Haddad et al. J Am Chem Soc, 124(13):3229-3237, 2002; Francois et al. Angew. Chem. Int. Ed. 2004, 43:6735-6738; Ding et al. Angew Chem Int Ed 2003, 42: 3409-3412; Alper et al. J Am Chem Soc 1998, 12:1965-1978; Michael et al. Bioorg Med Chem 1999, 7:1361-1371; Quader et al. J. Org. Chem. 2007, 72:1962-1979).

Described in Scheme 17 are non-limiting positions that have and can been modified in Paromomycin, Neomycin and Neamine.

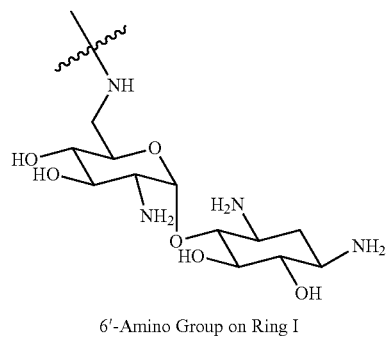

6'-Amino Group on Ring I

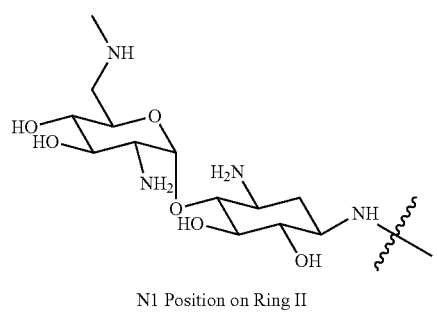

N1 Position on Ring II

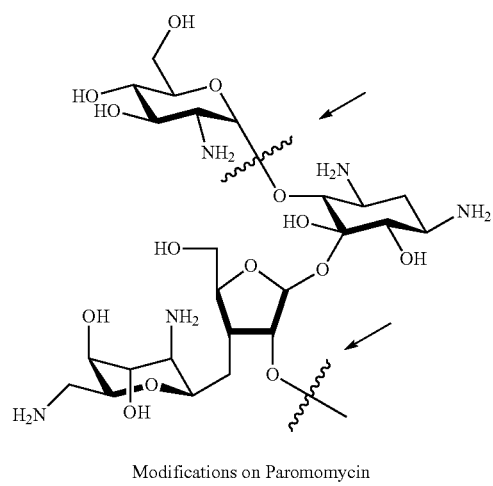

Modifications on Paromomycin

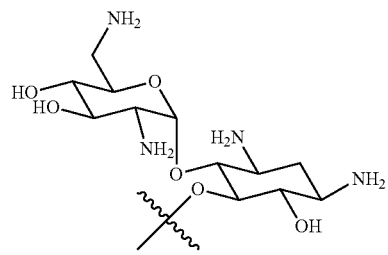

5-O- Position on Ring II

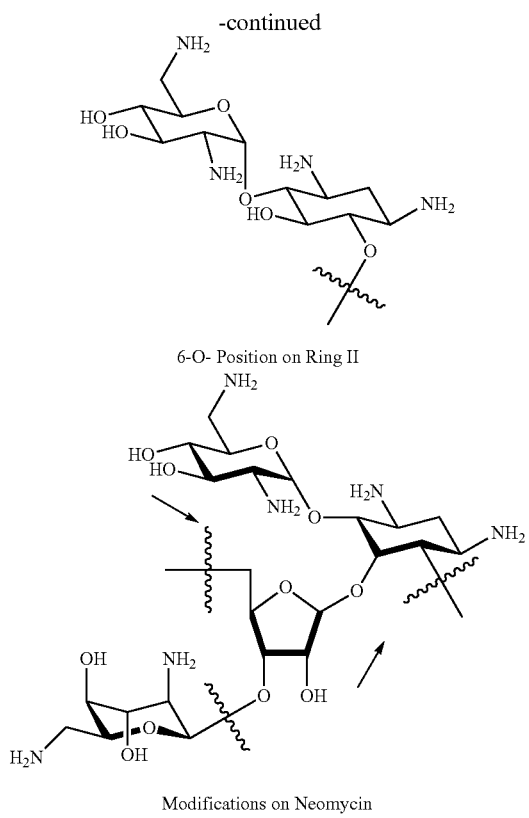

6-O- Position on Ring II

Modifications on Neomycin

Scheme 17.

Shown are non-limiting examples of possible positions for modifications of aminoglycosides. The squiggly lines represent non-limiting positions available for modification and incorporation of reactive groups.

a) Neomycin.

In 1995, Mei and co-workers discovered that aminoglycoside antibiotics were able to inhibit Tat peptide binding to the TAR RNA (Mei 1995). They discovered the $IC_{50}$ values for neomycin, streptomycin, and gentamicin to be 0.92±0.09 µM, 9.5±0.8 µM, and 45±4 µM, respectively. Their study also determined that the aminoglycosides were bound to the duplex region of the RNA, directly below the bulge used for identification by Tat, and that neomycin B was able to form higher order complexes with the TAR. Further studies on the interactions of neomycin with TAR have since been completed, with up to three binding sites identified (Krebs, Ludwig et al. 2003), suggesting that dimeric and trimeric aminoglycosides could provide better specificity to TAR. From further studies (CD spectroscopy), it appears that the binding by neomycin induces a conformational change in the RNA, which is different from the usual architecture that Tat recognizes, acting as a noncompetitive inhibitor of the Tat-TAR interaction and increasing the rate constant ($k_{off}$) for the dissociation of the peptide (Wang, Huber et al. 1998). Wang et. al. also determined that the aminoglycoside binds TAR in the minor groove, opposite to the major groove binding normally seen. Recently NMR was used to examine the structural changes that neomycin induces in the TAR RNA; it was found that the neamine core is covered with the bulge, thereby reducing the volume of the major groove in which Tat is normally bound (Faber, Sticht et al. 2000).

4. Major Groove Binders

A major groove binder is a composition or compound which can bind the major groove of duplex nucleic acid. It is understood that there are B-major groove binders which bind B-form duplex and A-major groove binders which binder A-form duplex.

It is understood that the disclosed compositions can have any major groove binder conjugated to it, as disclosed herein. The major groove binders disclosed are exemplary only.

5. Minor Groove Binders

A minor groove binder is a composition or compound which can bind the minor groove of duplex DNA. It is understood that there are B-minor groove binders which bind the minor groove of b-form duplex and A-minor groove binders which bind the minor groove of A-form duplex.

It is understood that the disclosed compositions can have any minor groove binder conjugated to it, as disclosed herein. The minor groove binders disclosed below are exemplary only.

Minor groove recognition relies on van der Waals' contacts, hydrogen bonds, Coulombic attraction and intrinsic properties of the DNA such as flexibility, hydration and electrostatic potential. Successful minor groove binding ligands typically consist of heterocyclic units such as pyrrole or imidazole groups linked by amides. The flexibility of the single bonds between the heterocyclic groups and the amide linkages is crucial to successful minor groove recognition since the ligand is able to adopt a twist that matches the helical winding of the DNA, thereby permitting the ligand to maintain contact with the DNA over the foil length of its recognition site.

Two thoroughly studied minor groove binders (MGBs) are Hoechst 33258 (Hoechst) and DAPI, which bind preferentially at AT-rich regions of B-DNA. Also disclosed are minor groove binders, such as polyamides, that preferentially bind GC-rich regions.

a) DNA-Selective Hoechst Dyes

The bisbenzimide dyes—Hoechst 33258, Hoechst 33342 and Hoechst 34580 are cell membrane-permeant, minor groove-binding DNA stains that fluoresce bright blue upon binding to DNA. Hoechst 33342 has slightly higher membrane permeability than Hoechst 33258, but both dyes are quite soluble in water (up to 2% solutions can be prepared) and relatively nontoxic. Hoechst 34580 has somewhat longer-wavelength spectra than the other Hoechst dyes when bound to nucleic acids. These Hoechst dyes, which can be excited with the UV spectral lines of the argon-ion laser and by most conventional fluorescence excitation sources, exhibit relatively large Stokes shifts (spectra) (excitation/emission maxima—350/460 nm), making them suitable for multicolor labeling experiments. The Hoechst 33258 and Hoechst 33342 dyes have complex, pH-dependent spectra when not bound to nucleic acids, with a much higher fluorescence quantum' yield a'fpH 5 than at pH 8. Their fluorescence is also enhanced by surfactants such as sodium dodecyl sulfate (SDS). These dyes appear to show a wide spectrum of sequence-dependent DNA affinities and bind with sufficient strength to poly(d(A-T)) sequences that they can displace several known DNA intercalators. They also exhibit multiple binding modes and distinct fluorescence emission spectra that are dependent on dye:base pair ratios. Hoechst dyes are used in many cellular applications, including cell-cycle and apoptosis studies (Section 15.4, Section 15.5) and they are common nuclear counterstains (Section 8.6). Hoechst 33258, which is selectively toxic to malaria parasites, is also useful for flow-cytometric screening of blood samples for malaria parasites and for assessing their susceptibility to drugs; however, some of the SYTO dyes disclosed herein are likely to provide superior performance in these assays.

Since the discovery of neomycin as a small molecule inhibitor of the TAR RNA, a number of small molecules have been proven to inhibit the Tat-TAR interaction with structures and binding sites quite different from aminoglycosides or known intercalators (FIG. 1) (Krebs, Ludwig et al. 2003). Of specific interest is the Hoechst 33258 compound. Hoechst 33258 was initially synthesized as an AT-specific minor groove binder, and is currently used to visualize as well as provide quantitative measurements of DNA concentrations. Studies in the early 1990's showed that in addition to attachment to DNA through minor groove interactions, Hoechst 33258 is capable of intercalation into GC rich areas of DNA (Loontiens, Regenfuss et al. 1990; Loontiens, McLaughlin et al. 1991; Bailly, Colson et al. 1993). It was determined that the 2-amino group prevents minor groove binding in GC rich sequences, and electronic linear dichroism in combination with competition experiments with known intercalators confirmed that intercalation is a binding mode for Hoechst (Bailly, Colson et al. 1993).

After the discovery that Hoechst is capable of intercalation, Hoechst was also found to use this mode of binding for intercalation into the TAR region of HIV RNA. Hoechst was screened with several other minor groove DNA binding molecules and known intercalators. From this study, using ELD, it was determined that Hoechst was indeed capable of intercalating into the TAR RNA, despite its bulky groups flanking the bisbenzimidazole chromophore (Bailly, Colson et al. 1996). Later studies determined that the Hoechst had a strong stabilizing affect on the TAR, and that the most likely occurrence of the intercalation of Hoechst is between bases U40 and C39, due to the weak stacking interactions between them (Dassonneville, Hamy et al. 1997). Though the specific orientation or binding constant has yet to be published, it is hypothesized that the Hoechst intercalates perpendicular to the helical axis of the TAR. Of recent note is that Hoechst has similarly been shown to intercalate in the CC bubble of site 1 thymidylate synthetase RNA with a binding constant below 100 nM (Cho and Rando 2000). Our preliminary NMR work has identified portions of Hoechst 33258 that are critical in binding TAR we have begun to synthesize benzimidazole conjugates for identifying high affinity TAR binders.

The Hoechst 33258 and Hoechst 33342 dyes are available as solids (H1398, H1399), as guaranteed high-purity solids (FluoroPure Grade; H21491, H21492) and, for ease of handling, as 10 mg/mL aqueous solutions (H3569, H3570). The Hoechst 34580 dye is available as a solid (H21486).

6. DNA Vs RNA Recognition

RNA recognition has proven to be more challenging than DNA recognition by small molecules. Recognition of DNA-RNA hybrids by small molecules was virtually unexplored at the beginning of this century (Ren J, et al (2001)). DNA-based intercalators and groove binders were the first to be examined for RNA recognition. These approaches met with limited success, due in large part to the different 3-D structures of functional RNA molecules. Sequence-specific RNA recognition has more similarities to recognition principles used in targeting proteins than to DNA duplexes. As with proteins, a distribution of charged pockets can provide a 3-D pattern that can be targeted specifically by compounds exhibiting structural electrostatic complementarity. Aminoglycosides have been shown to provide complementary scaffolds where the positively charged ammonium groups displace several $Mg^{2+}$ ions from their RNA binding sites (Tor Y, et al (1998) Chem Biol 5: 8277; Hermann T (2000) Angew Chem Int Ed Engl 39:1890; Hermann T, et al (1998) Biopolymers 48:155; Hermann T, et al (1998) J Mol Biol 276:903; Hermann T, et al (1998) Curr Opin Biotechnol 9:66; Hermann T, et al (1999) J Med Chem 42:1250; Henry C M (2000) Chem Eng News 78:41).

7. DNA and RNA Binding Compounds

Disclosed herein are compound and compositions, comprising DNA and RNA binders. It has been discovered that a class of compounds, referred to herein as DNA and RNA binders, are useful for inhibiting the HIV cell cycle replication process. For example, DNA and RNA binder compounds can have the structure of formula I

A-B-C or a pharmaceutically acceptable salt or acid form thereof, wherein A is a glycoside, aminoglycoside, or sugar, wherein B is a linker, and wherein C is a glycoside, aminoglycoside, sugar, aryl, heteroaryl, heterocyclyl, Hoechst 33258, or Hoechst 33258 derived benzimidazoles.

In some forms A can be an aminoglycoside. In some forms A can be neomycin.

In some forms B can be -$(L_1)_n$-$(L_2)_m$-$(L_3)_o$-$(L_4)_p$-$(L_5)_q$-$(L_6)_r$-$(L_7)_s$-$(L_8)_t$-$(L_9)_u$-, wherein n, m, o, p, q, r, s, t, u are independently 0 or 1, wherein $(L_1)$, $(L_2)$, $(L_3)$, $(L_4)$, $(L_5)$, $(L_6)$, $(L_7)$, $(L_8)$, and $(L_9)$ are independently O, N, S, $C_1$-$C_8$ alkyl, $C_2$-$C_8$ alkenyl, $C_2$-$C_8$ alkoxy, aryl, heteroaryl, heterocyclyl,

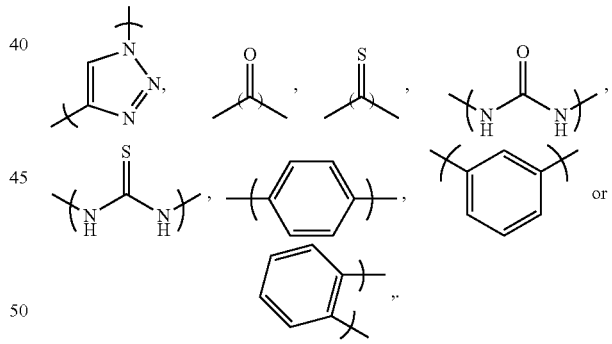

In some forms C can be an aminoglycoside. In some forms C can be neomycin. In some forms C can be Hoechst 33258. In some forms C can be a Hoechst 33258 derived benzimidazoles. In some forms C can be

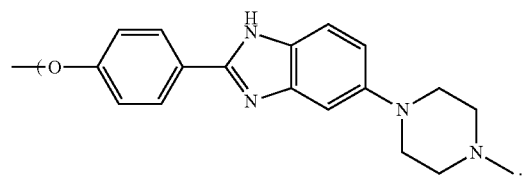

In some forms A (bonded to B and C) can be

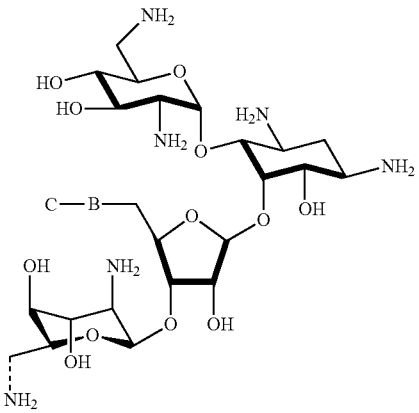

wherein B is a linker,
wherein C is a glycoside, aminoglycoside, sugar, aryl, heteroaryl, heterocyclyl, benzimidazole derivatives, Hoechst 33258, or Hoeschst 33258 derived benzimidazoles.

In some forms B can be -$(L_1)_n$-$(L_2)_m$-$(L_3)_o$-$(L_4)_p$-$(L_5)_q$-$(L_6)_r$-$(L_7)_s$-$(L_8)_t$-$(L_9)_u$-, wherein n, m, o, p, q, r, s, t, u are independently 0 or 1,
wherein $(L_1)$, $(L_2)$, $(L_3)$, $(L_4)$, $(L_5)$, $(L_6)$, $(L_7)$, $(L_8)$, and $(L_9)$ are independently O, N, S, $C_1$-$C_8$ alkyl, $C_2$-$C_8$ alkenyl, $C_2$-$C_8$ alkoxy, aryl, heteroaryl, heterocyclyl,

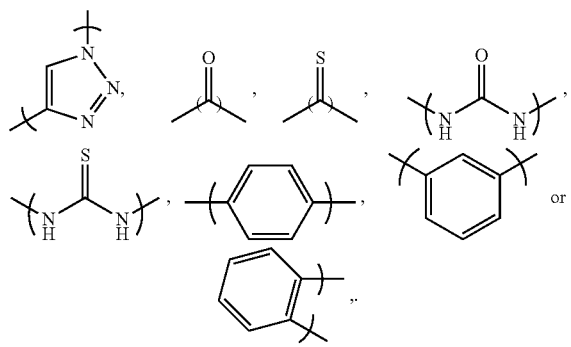

In some forms C can be an aminoglycoside. In some forms C can be neomycin. In some forms C can be Hoechst 33258 derived benzimidazoles. In some forms C can be

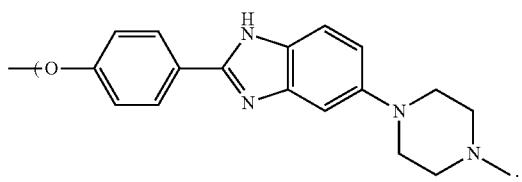

In some forms B (bonded to A and C) can be
A-$(L_1)_n$-$(L_2)_m$-$(L_3)_o$-$(L_4)_p$-$(L_5)_q$-$(L_6)_r$-$(L_7)_s$-$(L_8)_t$-$(L_9)_u$-C,
wherein n, m, o, p, q, r, s, t, u are independently 0 or 1,
wherein $(L_1)$, $(L_2)$, $(L_3)$, $(L_4)$, $(L_5)$, $(L_6)$, $(L_7)$, $(L_8)$, and $(L_9)$ are independently O, N, S, $C_1$-$C_8$ alkyl, $C_2$-$C_8$ alkenyl, $C_2$-$C_8$ alkoxy, aryl, heteroaryl, heterocyclyl,

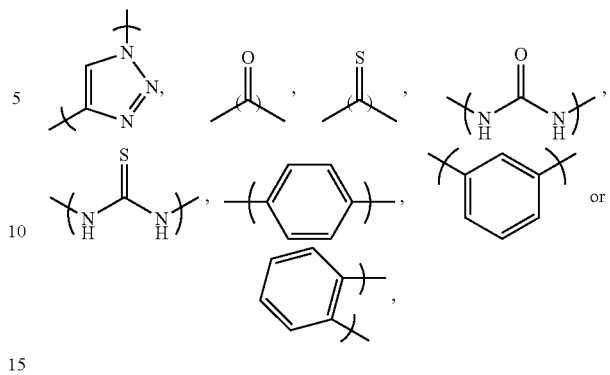

wherein A can be a glycoside, aminoglycoside, or sugar, wherein C can be glycoside, aminoglycoside, sugar, aryl, heteroaryl, heterocyclyl, Hoechst 33258, Hoeschst 33258 derived benzimidazoles.

In some forms A can be an aminoglycoside. In some forms A can be neomycin.

In some forms C can be an aminoglycoside. In some forms C can be neomycin. In some forms C can be Hoechst 33258 derived benzimidazoles. In some forms C can be

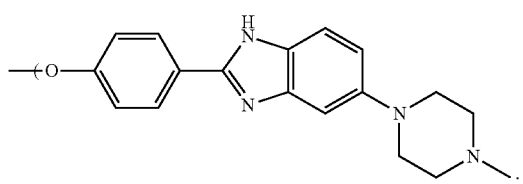

In some forms C (bonded to B and A) can be

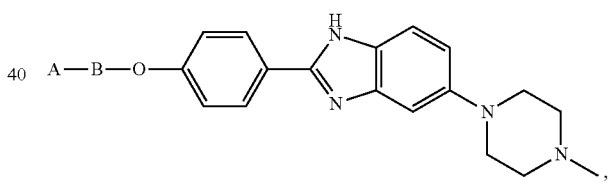

Wherein A is a glycoside, aminoglycoside, or sugar, and wherein B is a linker.

In some forms A can be an aminoglycoside. In some forms A can be neomycin.

In some forms B can be -$(L_1)_n$-$(L_2)_m$-$(L_3)_o$-$(L_4)_p$-$(L_5)_q$-$(L_6)_r$-$(L_7)_s$-$(L_8)_t$-$(L_9)_u$-, wherein n, m, o, p, q, r, s, t, u are independently 0 or 1,
wherein $(L_1)$, $(L_2)$, $(L_3)$, $(L_4)$, $(L_5)$, $(L_6)$, $(L_7)$, $(L_8)$, and $(L_9)$ are independently O, N, S, $C_1$-$C_8$ alkyl, $C_2$-$C_8$ alkenyl, $C_2$-$C_8$ alkoxy, aryl, heteroaryl, heterocyclyl,

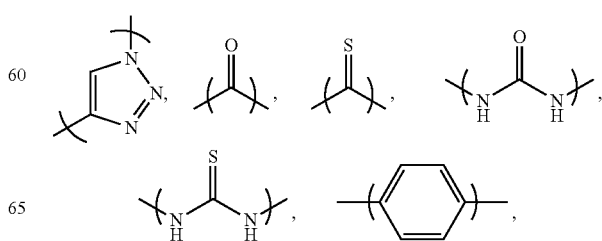

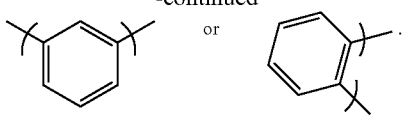

In some forms C (bonded to B and A) can be

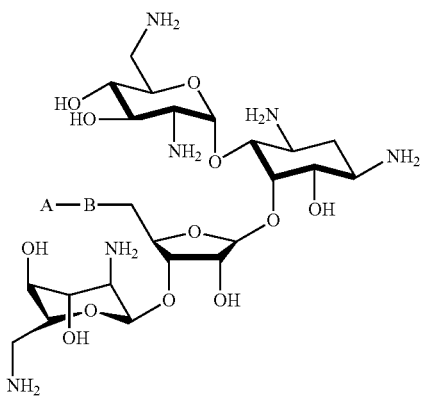

wherein A is a glycoside, aminoglycoside, or sugar, and wherein B is a linker.

In some forms A can be an aminoglycoside. In some forms A can be neomycin.

In some forms B can be -$(L_1)_n$-$(L_2)_m$-$(L_3)_o$-$(L_4)_p$-$(L_5)_q$-$(L_6)_r$-$(L_7)_s$-$(L_8)_t$-$(L_9)_u$-, wherein n, m, o, p, q, r, s, t, u are independently 0 or 1,
wherein $(L_1)$, $(L_2)$, $(L_3)$, $(L_4)$, $(L_5)$, $(L_6)$, $(L_7)$, $(L_8)$, and $(L_9)$ are independently O, N, S, $C_1$-$C_8$ alkyl, $C_2$-$C_8$ alkenyl, $C_2$-$C_8$ alkoxy, aryl, heteroaryl, heterocyclyl,

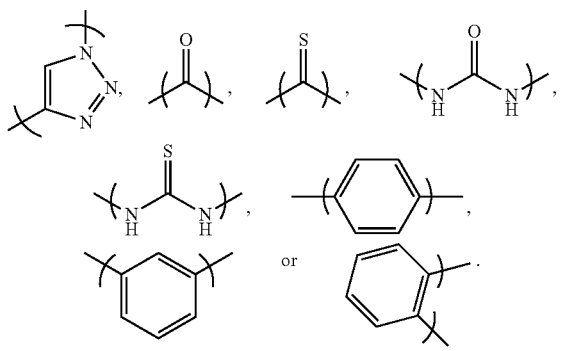

8. Specific Exemplary Embodiments

Disclosed are compounds comprising the structure

A-B-C or a pharmaceutically acceptable salt or acid form thereof, wherein A is a glycoside, aminoglycoside, or sugar, wherein B is a linker, and
wherein C is a glycoside, aminoglycoside, sugar, aryl, heteroaryl, heterocyclyl, Hoechst 33258, or Hoeschst 33258 derived benzimidazoles.

Also disclosed are compounds, wherein A is an aminoglycoside, wherein A comprises neomycin, wherein B comprises a backbone of less than 50, wherein B comprises a backbone of less than 40, wherein B comprises a backbone of less than 30, wherein B comprises a backbone of less than 20, and/or alone or in any combination with any other limitation or characteristic disclosed herein.

Also disclosed are compounds, wherein B is -$(L_1)_v$-, wherein v is independently 1-20,
wherein each $(L_1)$ is independently O, N, S, $C_1$-$C_8$ alkyl, $C_2$-$C_8$ alkenyl, $C_2$-$C_8$ alkoxy, aryl, heteroaryl, heterocyclyl,

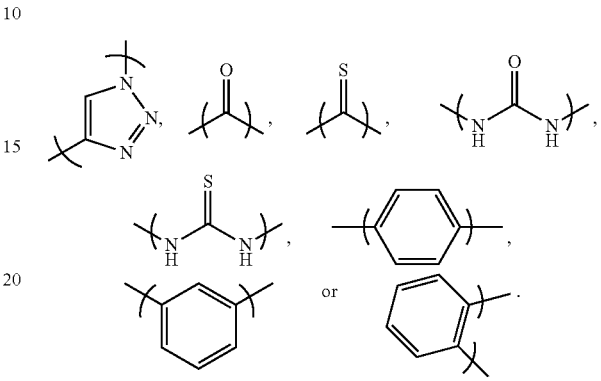

wherein each $(L_1)$ is can be the same or different, and/or alone or in any combination with any other limitation or characteristic disclosed herein.

Also disclosed are compounds, wherein B is -$(L_1)_n$-$(L_2)_m$-$(L_3)_o$-$(L_4)_p$-$(L_5)_q$-$(L_6)_r$-$(L_7)_s$-$(L_8)_t$-$(L_9)_u$-,
wherein n, m, o, p, q, r, s, t, u are independently 0 or 1,
wherein $(L_1)$, $(L_2)$, $(L_3)$, $(L_4)$, $(L_5)$, $(L_6)$, $(L_7)$, $(L_8)$, and $(L_9)$ are independently O, N, S, $C_1$-$C_8$ alkyl, $C_2$-$C_8$ alkenyl, $C_2$-$C_8$ alkoxy, aryl, heteroaryl, heterocyclyl,

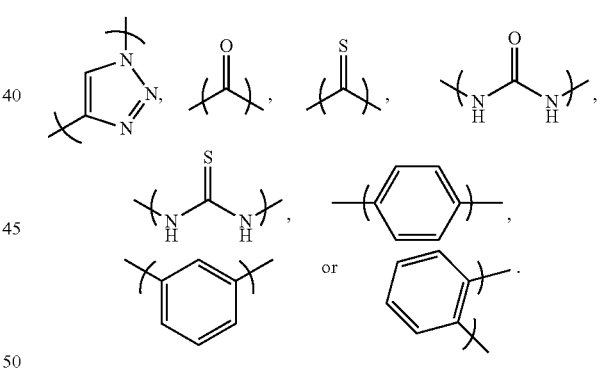

and/or alone or in any combination with any other limitation or characteristic disclosed herein Also disclosed are compounds, wherein B is O, N, S, $C_1$-$C_8$ alkyl, $C_2$-$C_8$ alkenyl, $C_2$-$C_8$ alkoxy,

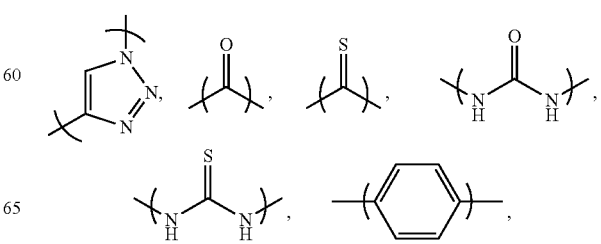

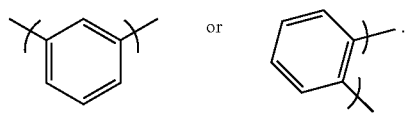

and/or alone or in any combination with any other limitation or characteristic disclosed herein Also disclosed are compounds, wherein C comprises an aminoglycoside, wherein the aminoglycoside comprises neomycin, wherein C comprises a Hoechst 33258 derived benzimidazole, wherein C comprises Hoechst 33258, and/or alone or in any combination with any other limitation or characteristic disclosed herein.

Also disclosed are compounds, wherein C is

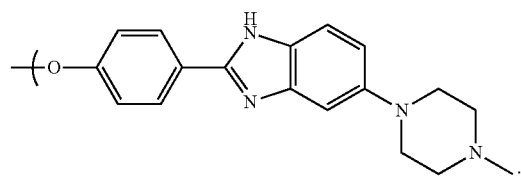

and/or wherein A (bonded to B and C) comprises

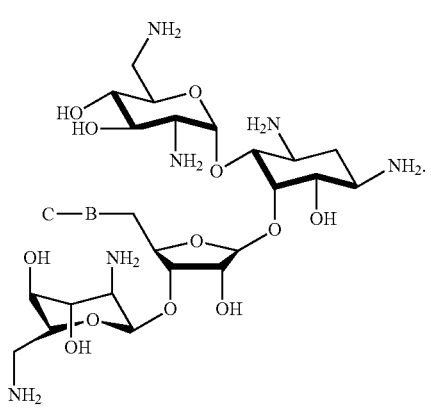

and/or alone or in any combination with any other limitation or characteristic disclosed herein Also disclosed are compounds, wherein n, m, o, p, q, r, are 1 and s, t, u are 0, wherein ($L_1$) is

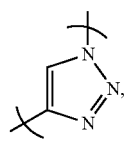

wherein ($L_2$) is $C_1$-$C_8$ alkyl, wherein ($L_3$) is

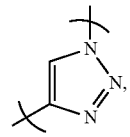

wherein ($L_4$) is $C_1$-$C_8$ alkyl, wherein ($L_5$) is

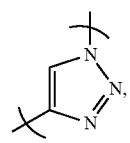

and wherein ($L_6$) is $C_1$-$C_8$ alkyl, and/or alone or in any combination with any other limitation or characteristic disclosed herein.

Also disclosed are compounds, wherein n, m, o, p, q, r, are 1 and s, t, u are 0, wherein ($L_1$) is

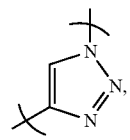

wherein ($L_2$) is $C_4$ alkyl, wherein ($L_3$) is

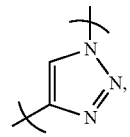

wherein ($L_4$) is $C_2$ alkyl, wherein ($L_5$) is

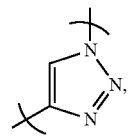

and wherein ($L_6$) is $C_1$ alkyl, and/or alone or in any combination with any other limitation or characteristic disclosed herein.

Also disclosed are compounds, wherein wherein n, m, o, p, q, r, are 1 and s, t, u are 0, wherein (L$_1$) is

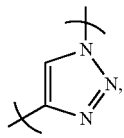

wherein (L$_2$) is C$_4$ alkyl,
wherein (L$_3$) is

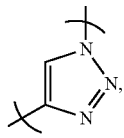

wherein (L$_4$) is C$_5$ alkyl,
wherein (L$_5$) is

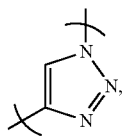

and
wherein (L$_6$) is C$_1$ alkyl, and/or alone or in any combination with any other limitation or characteristic disclosed herein.

Also disclosed are compounds, wherein n, m, o, p, q, r, are 1 and s, t, u are 0,
wherein (L$_1$) is

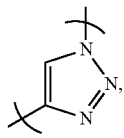

wherein (L$_2$) is C$_4$ alkyl,
wherein (L$_3$) is

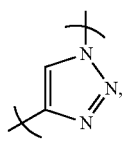

wherein (L$_4$) is C$_6$ alkyl,
wherein (L$_5$) is

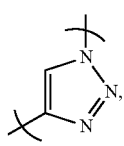

wherein (L$_6$) is C$_1$ alkyl, and/or alone or in any combination with any other limitation or characteristic disclosed herein.

Also disclosed are compounds, wherein n, m, o, p, q, r, are 1 and s, t, u are 0,
wherein (L$_1$) is

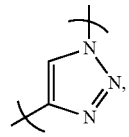

wherein (L$_2$) is C$_4$ alkyl,
wherein (L$_3$) is

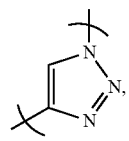

wherein (L$_4$) is C$_8$ alkyl,
wherein (L$_5$) is

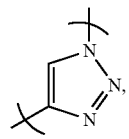

and
wherein (L$_6$) is C$_1$ alkyl, and/or alone or in any combination with any other limitation or characteristic disclosed herein.

Also disclosed are compounds, wherein n, m, o, p, q, r, s are 1 and t, u are 0,
wherein (L$_1$) is

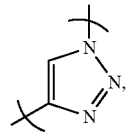

wherein (L$_2$) is C$_4$ alkyl,
wherein (L$_3$) is

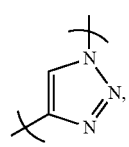

wherein (L$_4$) is C$_8$ alkyl,
wherein (L$_5$) is C$_2$ alkyl, wherein ($L_6$) is

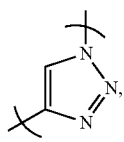

and
   wherein ($L_7$) is $C_1$ alkyl, and/or alone or in any combination with any other limitation or characteristic disclosed herein.

Also disclosed are compounds, wherein n, m, o, p, are 1 and q, r, s, t, u are 0,
   wherein ($L_1$) is

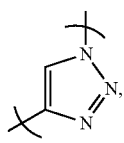

wherein ($L_2$) is,

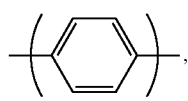

wherein ($L_3$) is

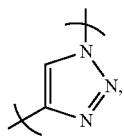

and
   wherein ($L_4$) is $C_2$ alkyl, and/or alone or in any combination with any other limitation or characteristic disclosed herein.

Also disclosed are compounds, wherein n, m, o, p, q, r, are 1 and s, t, u are 0,
   wherein ($L_1$) is

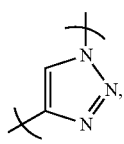

wherein ($L_2$) is $C_1$ alkyl,
wherein ($L_3$) is O,
wherein ($L_4$) is $C_1$ alkyl, wherein ($L_5$) is

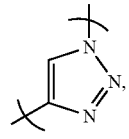

and
   wherein ($L_6$) is $C_2$ alkyl, and/or alone or in any combination with any other limitation or characteristic disclosed herein.

Also disclosed are compounds, wherein n, m, o, p, are 1 and q, r, s, t, u are 0,
   wherein ($L_1$) is

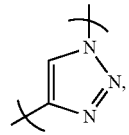

wherein ($L_2$) is $C_3$ alkyl,
wherein ($L_3$) is

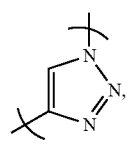

and
   wherein ($L_4$) is $C_2$ alkyl, and/or alone or in any combination with any other limitation or characteristic disclosed herein.

Also disclosed are compounds, wherein n, m, o, p, are 1 and q, r, s, t, u are 0,
   wherein ($L_1$) is

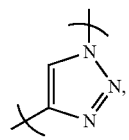

wherein ($L_2$) is $C_4$ alkyl,
wherein ($L_3$) is

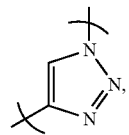

and
   wherein ($L_4$) is $C_2$ alkyl, and/or alone or in any combination with any other limitation or characteristic disclosed herein.

Also disclosed are compounds, wherein n, m, o, p, are 1 and q, r, s, t, u are 0, wherein (L₁) is

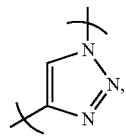

wherein (L₂) is C₆ alkyl,
wherein (L₃) is

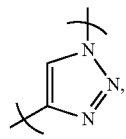

and
wherein (L₄) is C₂ alkyl, and/or alone or in any combination with any other limitation or characteristic disclosed herein.

Also disclosed are compounds, wherein n, m, are 1 and o, p, q, r, s, t, u are 0,
wherein (L₁) is

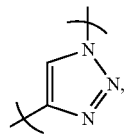

and
wherein (L₂) is C₁ alkyl, and/or alone or in any combination with any other limitation or characteristic disclosed herein.

Also disclosed are compounds, wherein v is 6,
wherein (L₁)₁ is

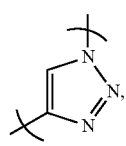

Wherein (L₁)₂ is C₁-C₈ alkyl,
Wherein (L₁)₃ is

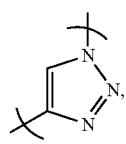

Wherein (L₁)₄ is C₁-C₈ alkyl,

Wherein (L₁)₅ is

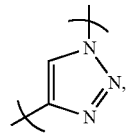

and
Wherein (L₁)₆ is C₁-C₈ alkyl, and/or alone or in any combination with any other limitation or characteristic disclosed herein.

Also disclosed are compounds, wherein v is 6,
wherein (L₁)₁ is

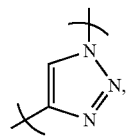

wherein (L₁)₂ is C₄ alkyl,
wherein (L₁)₃ is

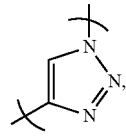

wherein (L₁)₄ is C₂ alkyl,
wherein (L₁)₅ is

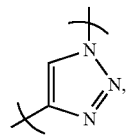

and
wherein (L₁)₆ is C₁ alkyl, and/or alone or in any combination with any other limitation or characteristic disclosed herein.

Also disclosed are compounds, wherein v is 6,
wherein (L₁)₁ is

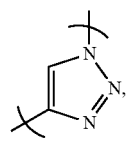

wherein (L₁)₂ is C₄ alkyl, wherein $(L_1)_3$ is

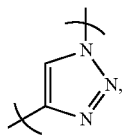

wherein $(L_1)_4$ is $C_5$ alkyl,
wherein $(L_1)_5$ is

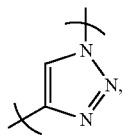

and
wherein $(L_1)_6$ is $C_1$ alkyl, and/or alone or in any combination with any other limitation or characteristic disclosed herein.

Also disclosed are compounds, wherein v is 6,
wherein $(L_1)_1$ is

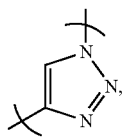

wherein $(L_1)_2$ is $C_4$ alkyl,
wherein $(L_1)_3$ is

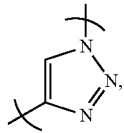

wherein $(L_1)_4$ is $C_6$ alkyl,
wherein $(L_1)_5$ is

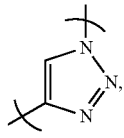

and
wherein $(L_1)_6$ is $C_1$ alkyl, and/or alone or in any combination with any other limitation or characteristic disclosed herein.

Also disclosed are compounds, wherein v is 6,
wherein $(L_1)_1$ is

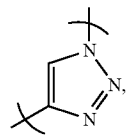

wherein $(L_1)_2$ is $C_4$ alkyl,
wherein $(L_1)_3$ is

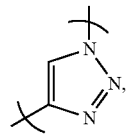

wherein $(L_1)_4$ is $C_8$ alkyl,
wherein $(L_1)_5$ is

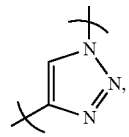

and
wherein $(L_1)_6$ is $C_1$ alkyl, and/or alone or in any combination with any other limitation or characteristic disclosed herein.

Also disclosed are compounds, wherein v is 7,
wherein $(L_1)_1$ is

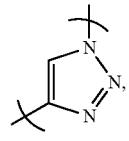

wherein $(L_1)_2$ is $C_4$ alkyl,
wherein $(L_1)_3$ is

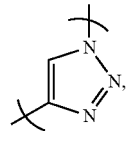

wherein $(L_1)_4$ is $C_8$ alkyl,
wherein $(L_1)_5$ is $C_2$ alkyl,
wherein $(L_1)_6$ is

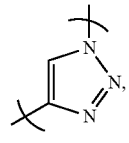

and wherein $(L_1)_7$ is $C_1$ alkyl, and/or alone or in any combination with any other limitation or characteristic disclosed herein.

Also disclosed are compounds, wherein v is 4,
wherein $(L_1)_1$ is

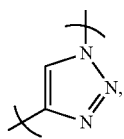

wherein $(L_1)_2$ is,

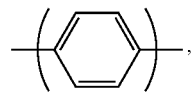

wherein $(L_1)_3$ is

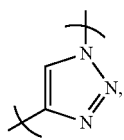

and
wherein $(L_1)_4$ is $C_2$ alkyl, and/or alone or in any combination with any other limitation or characteristic disclosed herein.

Also disclosed are compounds, wherein v is 6,
wherein $(L_1)_1$ is

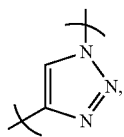

wherein $(L_1)_2$ is $C_1$ alkyl,
wherein $(L_1)_3$ is O,
wherein $(L_1)_4$ is $C_1$ alkyl,
wherein $(L_1)_5$ is

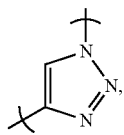

and
wherein $(L_1)_6$ is $C_2$ alkyl, and/or alone or in any combination with any other limitation or characteristic disclosed herein.

Also disclosed are compounds, wherein v is 4,
wherein $(L_1)_1$ is

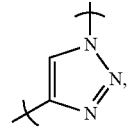

wherein $(L_1)_2$ is $C_3$ alkyl,
wherein $(L_1)_3$ is

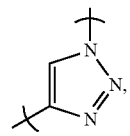

and
wherein $(L_1)_4$ is $C_2$ alkyl, and/or alone or in any combination with any other limitation or characteristic disclosed herein.

Also disclosed are compounds, wherein v is 4,
wherein $(L_1)_1$ is

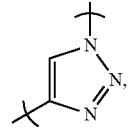

wherein $(L_1)_2$ is $C_4$ alkyl,
wherein $(L_1)_3$ is

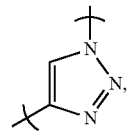

and
wherein $(L_1)_4$ is $C_2$ alkyl, and/or alone or in any combination with any other limitation or characteristic disclosed herein.

Also disclosed are compounds, wherein v is 4,
wherein $(L_1)_1$ is

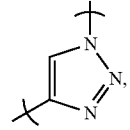

wherein $(L_1)_2$ is $C_6$ alkyl,
wherein $(L_1)_3$ is

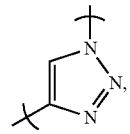

and
wherein $(L_1)_4$ is $C_2$ alkyl, and/or alone or in any combination with any other limitation or characteristic disclosed herein.

Also disclosed are compounds, wherein v is 2, wherein $(L_1)_1$ is

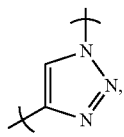

and
wherein $(L_1)_2$ is $C_1$ alkyl, and/or alone or in any combination with any other limitation or characteristic disclosed herein.

Also disclosed are compositions comprising any of the compounds disclosed herein.

Also disclosed are compositions, wherein the compound binds RNA, wherein the RNA comprises viral RNA, wherein the viral RNA comprises lentiviral RNA, wherein the lentiviral RNA comprises HIV RNA, wherein the HIV viral RNA comprises TAR, and/or alone or in any combination with any other limitation or characteristic disclosed herein.

Disclosed are methods of binding RNA, comprising incubating a any of the compositions or compounds disclosed with RNA and/or alone or in any combination with any other limitation or characteristic disclosed herein.

Also disclosed are methods of inhibiting a viral life cycle, comprising incubating any disclosed composition or compound with a virus, and/or alone or in any combination with any other limitation or characteristic disclosed herein.

Also disclosed are methods of treating a disease, comprising administering any composition or compound disclosed herein to a subject, and/or alone or in any combination with any other limitation or characteristic disclosed herein.

Also disclosed are methods, wherein the disease is a viral disease, wherein the composition inhibits a viral life cycle, wherein the composition inhibits viral replication, and/or alone or in any combination with any other limitation or characteristic disclosed herein.

Also disclosed are methods of protecting cells from HIV cytopathic effects, comprising contacting the compositions and compounds disclosed herein with a cell, or wherein the cell is in vivo in a subject, and/or alone or in any combination with any other limitation or characteristic disclosed herein.

Also disclosed are methods of detecting a lentivirus in a sample, comprising the steps of labeling any composition or compound disclosed herein, with a detection agent, producing a labeled RNA binder, incubating the labeled RNA binder with a sample from a subject producing binding data, detecting the labeled RNA binder, producing a detection record.

Also disclosed are methods, further comprising determining that the presence of a lentivirus if the labeled RNA binder is detected in the sample above background producing a positive output, further comprising the step of instructing a treatment to be performed on the subject if a positive output is produced, further comprising the step of performing a treatment on the subject, where one or more steps is performed on a machine, wherein the method is a computer implemented method, further comprising the step of outputting results from the sample analysis, and/or alone or in any combination with any other limitation or characteristic disclosed herein.

Also disclosed are methods of analyzing a subject's sample comprising; receiving a detection record, wherein the record contains sample data; measuring binding between a labeled RNA binder and a sample and outputting results from the sample analysis.

Disclosed are methods, wherein the method is a computer implemented method, wherein receiving the detection record comprises receiving the detection record from a storage medium, wherein receiving the detection record comprises receiving the record from a computer system, wherein receiving the detection record comprises receiving the detection record via a computer network, and/or alone or in any combination with any other limitation or characteristic disclosed herein.

Also disclosed are methods of analyzing sample of a subject comprising, recommending the performance of any method disclosed herein, to be performed, and/or alone or in any combination with any other limitation or characteristic disclosed herein.

Also disclosed are methods comprising the steps of receiving an output from any method disclosed herein and recommending a treatment be performed on the subject, and/or alone or in any combination with any other limitation or characteristic disclosed herein.

Disclosed are one or more computer readable media storing program code that, upon execution by one or more computer systems, causes the computer systems to perform one or more steps of the methods disclosed herein, and/or alone or in any combination with any other limitation or characteristic disclosed herein.

Disclosed are computer program products comprising a computer usable memory adapted to be executed to implement the methods disclosed herein.

Disclosed are computer products, comprising a logic processing module, a configuration file processing module, a data organization module, and data display organization module, that are embodied upon a computer readable medium, and/or alone or in any combination with any other limitation or characteristic disclosed herein.

Also disclosed are computer program products, comprising a computer usable medium having a computer readable program code embodied therein, said computer readable program code adapted to be executed to implement a method for generating the sample analysis of any method disclosed herein, said method further comprising: providing a system, wherein the system comprises distinct software modules, and wherein the distinct software modules comprise a logic processing module, a configuration file processing module, a data organization module, and a data display organization module, and/or alone or in any combination with any other limitation or characteristic disclosed herein.

Disclosed are methods, further comprising a computerized system configured for performing the method, further comprising the outputting of the results from the sample analysis, and/or alone or in any combination with any other limitation or characteristic disclosed herein.

Disclosed are computer-readable medium having stored thereon instructions that, when executed on a programmed processor perform the methods disclosed herein, and/or alone or in any combination with any other limitation or characteristic disclosed herein.

Also disclosed are sample analysis systems, the system comprising: a data store capable of storing detection data; a system processor comprising one or more processing elements, the one or more processing elements programmed or adapted to: receive binding data comprising data of a labeled RNA binding to a sample; store the binding data in the data store; compare the binding data to a control; and output a determination of the presence of an RNA bound by the labeled RNA binder based upon the comparison of the binding data with the control, and/or alone or in any combination with any other limitation or characteristic disclosed herein 1.

Also disclosed are systems, wherein the system receives the binding data from a storage system, wherein the system receives the binding data via a computer network, further comprising a label detection system, and/or alone or in any combination with any other limitation or characteristic disclosed herein.

Disclosed are methods, wherein maximum protection is achieved in 3-44% of cells, wherein the compositions provide maximum protection and have only 5% or less toxicity to the cells, further comprising inhibiting HIV antigen synthesis, wherein less than 15% of cells produce HIV antigens, wherein less than 50% of cells produce HIV antigens, wherein 80% of cells or less produce HIV antigens, wherein the method of inhibiting HIV antigen synthesis wherein 90% of cells or less produce HIV antigens, wherein the method of inhibiting the release of reverse transcriptase from a cell comprising administering the composition of claim 1 to the cell, wherein control treated cells produce about 1,000,000 cpm/l and composition treated cells produce about 500,000 cpm/l or less, and/or alone or in any combination with any other limitation or characteristic disclosed herein.

Claim KKK. The method of claim III, wherein control treated cells produce about 900,000 cpm/l and composition treated cells produce about 200,000 cpm/l or less.

Claim LLL. The method of claim III, wherein control treated cells produce about 50,000 cpm/l and composition treated cells produce about 20,000 cpm/l or less.

9. Computers a) Computer Readable Media, Computer Program Product, Processors. Computer Usable Memory, Computer Systems In some embodiments, instructions stored on one or more computer readable media that, when executed by a system processor, cause the system processor to perform the methods described above, and in greater detail below. Further, some embodiments may include systems implementing such methods in hardware and/or software. A typical system may include a system processor comprising one or more processing elements in communication with a system data store (SDS) comprising one or more storage elements. The system processor may be programmed and/or adapted to perform the functionality described herein. The system may include one or more input devices for receiving input from users and/or software applications. The system may include one or more output devices for presenting output to users and/or software applications. In some embodiments, the output devices may include a monitor capable of displaying to a user graphical representation of the described analytic functionality.

The described functionality may be supported using a computer including a suitable system processor including one or more processing elements such as a CELERON, PENTIUM, XEON, CORE 2 DUO or CORE 2 QUAD class microprocessor (Intel Corp., Santa Clara, Calif.) or SEMPRON, PHENOM, OPTERON, ATHLON X2 or ATHLON 64 X2 (AMD Corp., Sunnyvale, Calif.), although other general purpose processors could be used. In some embodiments, the functionality, as further described below, may be distributed across multiple processing elements. The term processing element may refer to (1) a process running on a particular piece, or across particular pieces, of hardware, (2) a particular piece of hardware, or either (1) or (2) as the context allows. Some implementations can include one or more limited special purpose processors such as a digital signal processor (DSP), application specific integrated circuits (ASIC) or a field programmable gate arrays (FPGA). Further, some implementations can use combinations of general purpose and special purpose processors.

The environment further includes a system data store (SDS) that could include a variety of primary and secondary storage elements. In one preferred implementation, the SDS would include registers and RAM as part of the primary storage. The primary storage may in some implementations include other forms of memory such as cache memory, non-volatile memory (e.g., FLASH, ROM, EPROM, etc.), etc. The SDS may also include secondary storage including single, multiple and/or varied servers and storage elements. For example, the SDS may use internal storage devices connected to the system processor. In implementations where a single processing element supports all of the functionality a local hard disk drive may serve as the secondary storage of the SDS, and a disk operating system executing on such a single processing element may act as a data server receiving and servicing data requests.

It will be understood by those skilled in the art that the different information used in the systems and methods for respiratory analysis as disclosed herein may be logically or physically segregated within a single device serving as secondary storage for the SDS; multiple related data stores accessible through a unified management system, which together serve as the SDS; or multiple independent data stores individually accessible through disparate management systems, which may in some implementations be collectively viewed as the SDS. The various storage elements that comprise the physical architecture of the SDS may be centrally located or distributed across a variety of diverse locations.

b) Computer Network

A computer network or like terms are one or more computers in operable communication with each other.

c) Computer Implemented

Computer implemented or like terms refers to one or more steps being actions being performed by a computer, computer system, or computer network.

d) Computer Program Product

A computer program product or like terms refers to product which can be implemented and used on a computer, such as software.

e) Sample Analysis

A sample analysis is any analysis involving a sample from a subject.

f) Obtaining

Obtaining as used in the context of data or values, such as detection data or values refers to acquiring this data or values. It can be acquired, by for example, collection, such as through a machine, such as an a label detection machine. It can also be acquired by downloading or getting data that has already been collected, and for example, stored in a way in which it can be retrieved at a later time.

g) Outputting Results

Outputting or like terms means an analytical result after processing data by an algorithm.

h) Detection Record

A detection record or like terms is any collection of detection data.

i) Detection Data

A detection data or like terms refers to any collection of data out put by a detection device.

j) A Detection Device

A "detection device" or like terms refers to and device that is capable of detecting a detection agent.

k) Systems

Disclosed herein are machines, apparati, and systems, which are designed to perform the various methods disclosed herein. It is understood that these can be multipurpose machines having modules and/or components dedicated to the performance of the disclosed methods. For example, a label detection device can be modified as described herein so that it contains a module and/or component which for example, a) produces a detection record, which identifies one or more cells which are labeled, and/or performs a sample analysis, such as a sample analysis alone or in any combination. In particular, the modules and components within the label detection device responsible for determining when to begin assisting a breath, can be linked to the modules and/or components responsible for identifying and/or manipulating a detection record.

Thus, the methods and systems herein can have the data, in any form uploaded by a person operating a device capable of performing the methods disclosed herein. The methods can also be associated with the computers and systems as described herein, either incorporated into these systems or being on device which is connected to them.

l) Computer Readable Medium

In addition, or instead, the functionality and approaches discussed above, or portions thereof, can be embodied in instructions executable by a computer, where such instructions are stored in and/or on one or more computer readable storage media. Such media can include primary storage and/or secondary storage integrated with and/or within the computer such as RAM and/or a magnetic disk, and/or separable from the computer such as on a solid state device or removable magnetic or optical disk. The media can use any technology as would be known to those skilled in the art, including, without limitation, ROM, RAM, magnetic, optical, paper, and/or solid state media technology.

10. Methods and Assays for Identifying any Form of Nucleic Acid Binding a) Competition Dialysis of Neomycin-Acridine Conjugate with Nucleic Acid Forms In addition to stabilizing DNA, RNA, and hybrid triple helices, neomycin also induces the stabilization of hybrid duplexes as well as hybrid triple helices (Arya D P, et al (2001) J Am Chem Soc 123:11093). This significantly adds to the number of nucleic acids (other than RNA) that aminoglycosides can target. A rapid technique has been established for a quantitative assay to determine the relative binding affinities for host triplex, duplex DNA, singlestranded (SS) DNA/RNA and other possible nucleic acid targets (tetraplex) for a given aminoglycoside ligand using a thermodynamically rigorous competitive equilibrium dialysis method that exploits therapeutically useful drug concentrations (Ren J, et al (2000) J Am Chem Soc 122:424; Ren J, et al (2001) Methods Enzymol, vol 34O. Academic, New York, p 99). In the assay, solutions consisting of identical concentrations of different nucleic acid structures were dialysed simultaneously against a common ligand dissolved in appropriately buffered conditions. After equilibration, the amount of ligand bound to each DNA was measured by spectrophotometry. More ligand accumulated in the dialysis tube containing the structural form of highest binding affinity and, since all of the DNA samples were in equilibrium with the same free ligand concentration, the amount of ligand bound was directly proportional to the binding constant for each conformational form. Thus, comparison among the DNA samples gave a rapid and thermodynamically reliable indication of structural selectivity for any given ligand.

Figure 11:
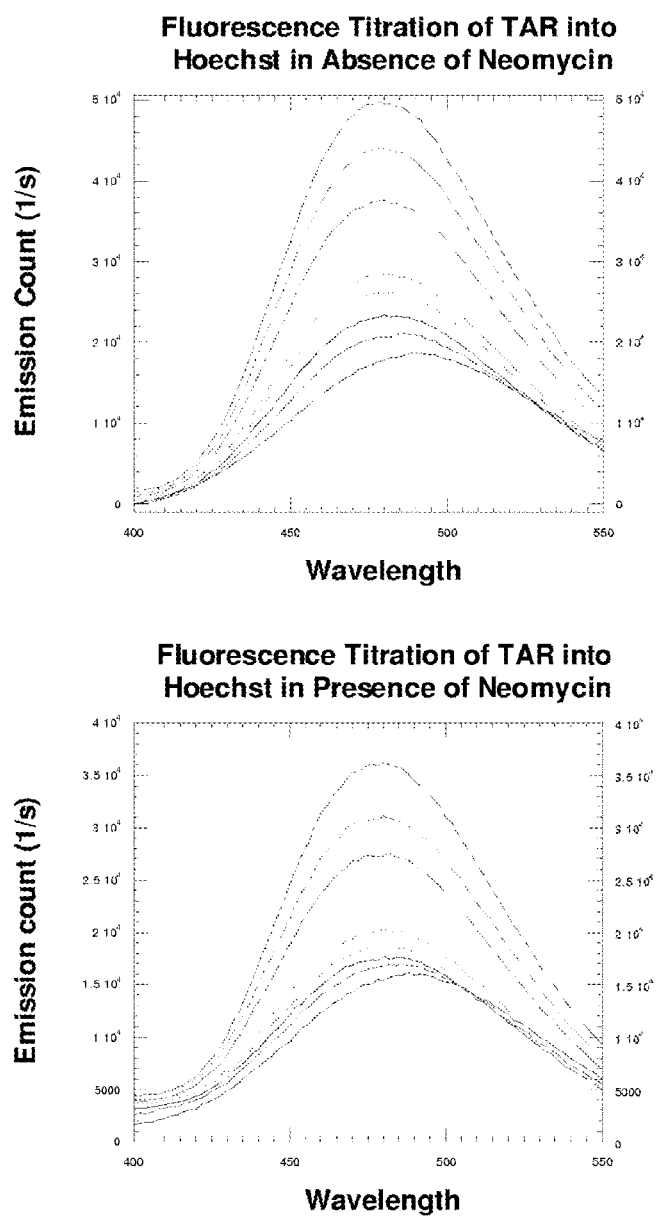
FIG. 11 shows fluorescence titration results demonstrating that Neomycin does not displace the binding of Hoechst in TAR. The titration of concentrated RNA or 1:1 RNA: neomycin solution (100 µM) into 1.8 mL of 2 µM Hoescht 22358 (up to 4 molar equivalents) was performed. The titration was done in a 100 mM NaCl, 10 mM cacodylate pH 6.8 buffer and was excited at 338 nm.

Since aminoglycosides do not have a chromophore for spectrophotometric analysis, competition dialysis of three acridines with increasing positive charge was used to decipher aminoglycoside specificity (FIG. 11). Competition dialysis studies were carried out using 9-aminoacridine, quinacrine, and a neomycin-acridine (neo-acridine) conjugate (Kirk S R, et al (2000) J Am Chem Soc 122:980) against 14 different nucleic acids. Going from acridine to neo-acridine, the effect of neomycin conjugated to the acridine chromophore was evaluated. At • first sight, dialysis of neo-acridine (FIG. 12) showed highly promiscuous binding with little preference for any specific nucleic acid structure, except for a clear preference for RNA triplex. Among comparable single strand, duplex, and triplex structures, maximum binding was always observed with the triplexes. This seemingly promiscuous binding yielded a different picture upon careful analysis of the dialysis data. All three drugs showed comparable binding to one nucleic acid: calf thymus DNA. Calf thymus DNA also represents a standard duplex DNA. This observation was used to replot the dialysis results to emphasize differences relative to that standard. These results, shown in FIG. 13, better illustrate the change in specificity of the different acridines toward different nucleic acids. While 9-aminoacridine and quinacrine showed a clear preference for DNA triplex, neo-acridine binding to RNA triplex is much greater than DNA triplex and even better than the natural aminoglycoside RNA target: eubacterial 16S A-site. Drug binding was also observed with DNA as well as RNA duplex, and even with DNA tetraplex. The binding to DNA tetraplex was still lower than to the RNA triplex. RNA>>DNA duplexes were better targets than DNA homoduplexes; poly(dA)>>poly(rU) hybrid duplex being comparable in binding to the tetraplexes. Also observed was the significant binding with the poly(dG)>>poly(dC) duplex.

A competition 'dialysis assay using tenfold (100 riM) and 100-fold (10 nM) lower concentrations (nanomolar range)

was also carried out. Results from dialysis under 100 nM drug concentration (FIG. 14) showed that neo-acridine favors nucleic acid forms that can adopt an A-type conformation. However, reliable results could not be obtained at 1 nM and 10 nM concentrations due to the low fluorescence intensity of the neo-acridine conjugate.

Neo-acridine binding to RNA triplex was also investigated by UV thermal melts, ITC, viscometric and CD titrations. Thermal denaturation in the presence of neo-acridine showed an increase in $T_{m3 \to 2}$ at low drug concentrations. At higher drug concentrations, the duplex was stabilized as well. Neomycin is one of the best stabilizers, of an RNA triple helix (Arya D P, et al (2001) J Am Chem Soc 123:538.5). Viscosity measurements showed a clear groove binding (as seen by shortening of RNA triplex length) upon titration of neomycin as well as neoacridine into the triplex (Arya D P, et al (2003) J Am Chem Soc 125:10148).

11. DNA and/or RNA Binding Compounds

Disclosed in Table 1 are neomycin-benzimidazole conjugates and neomycin-hoescht conjugates.

TABLE 1

Neomycin-Benzimidazole and Neomycin-Hoescht Conjugates

| Name | | Linker Length | Mol Wt |
|---|---|---|---|
| DPA113 | 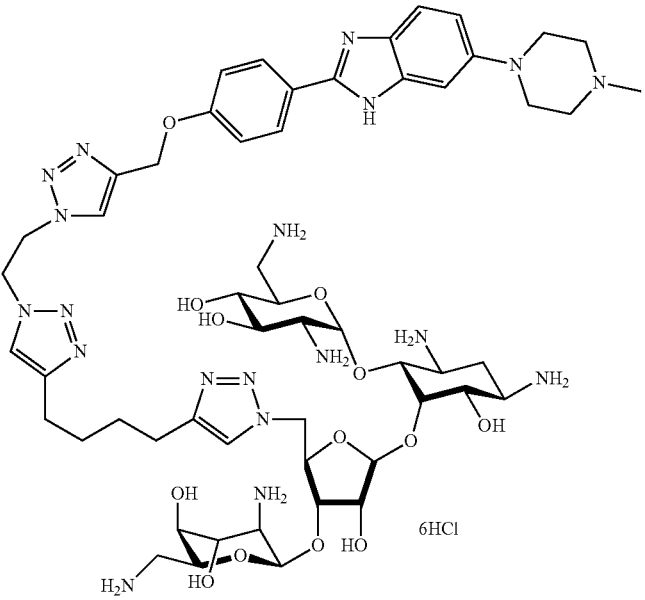 | 16 | 1423.11 |
| DPA114 | 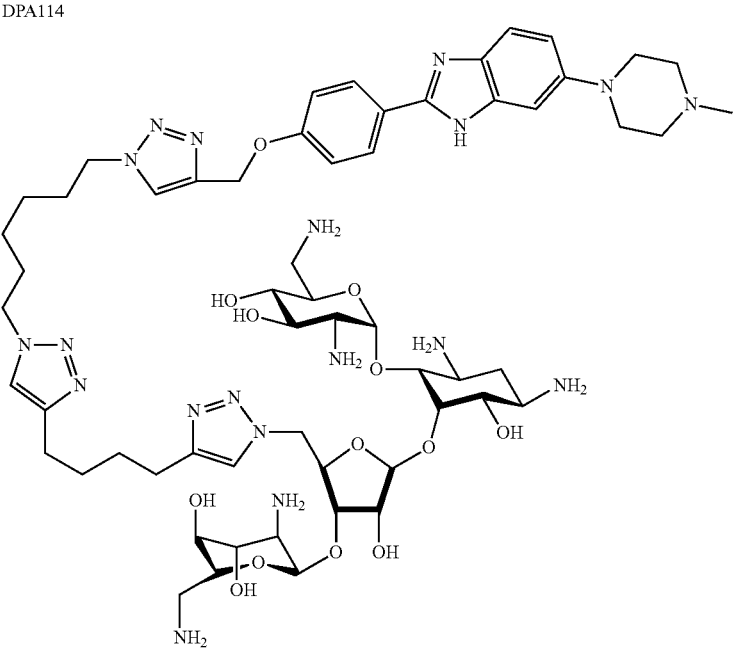 | 19 | 1433.50 |

TABLE 1-continued
Neomycin-Benzimidazole and Neomycin-Hoescht Conjugates
| Name | Linker Length | Mol Wt |
|---|---|---|
| DPA115 | 20 | 1465.19 |
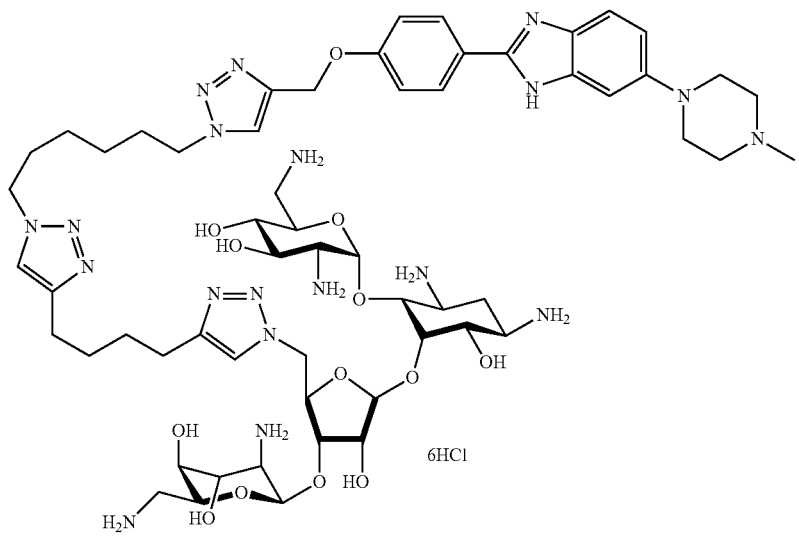
| DPA116 | 22 | 1503.58 |
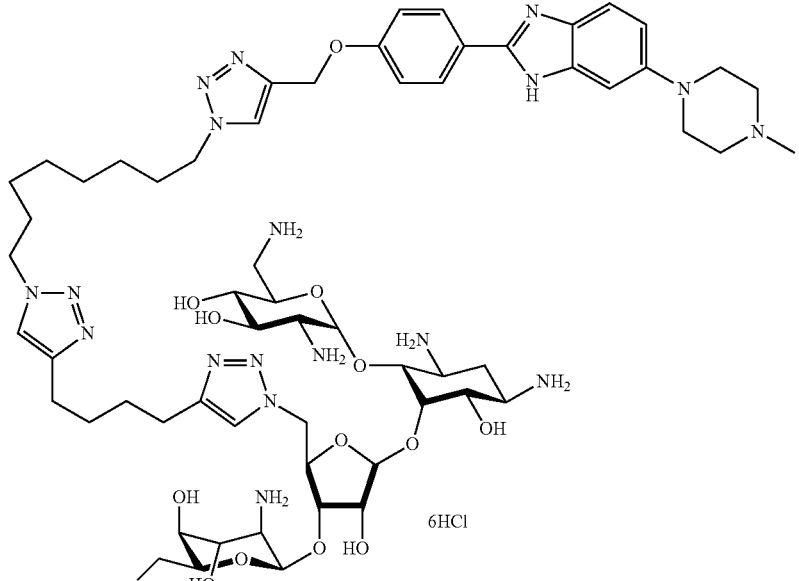

TABLE 1-continued

Neomycin-Benzimidazole and Neomycin-Hoescht Conjugates

| Name | Linker Length | Mol Wt |
|---|---|---|
| DPA117 | 24 | 1535.32 |
| DPA118 | 12 | 1358.42 |
| DPA119 | 11 | 1329.98 |

TABLE 1-continued
Neomycin-Benzimidazole and Neomycin-Hoescht Conjugates
| Name | Linker Length | Mol Wt |
|---|---|---|
| DPA120 | 11 | 1328.00 |
| DPA121 | 12 | 1342.43 |
| DPA122 | 14 | 1370.08 |
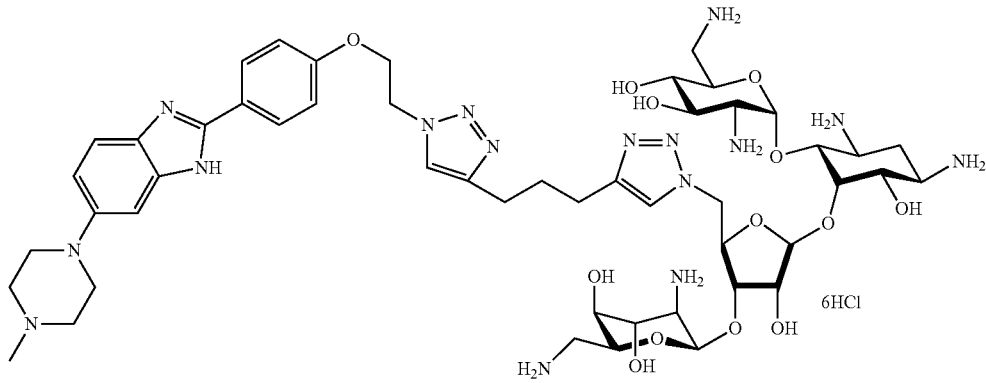
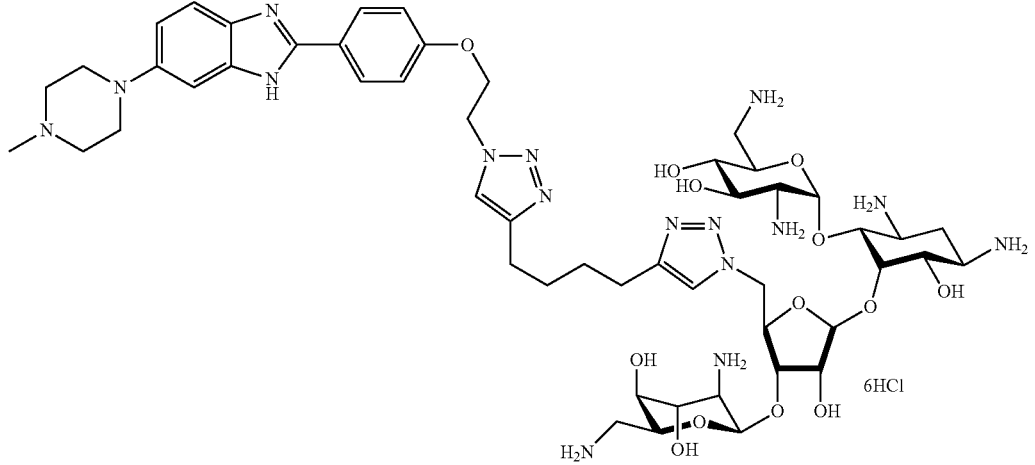
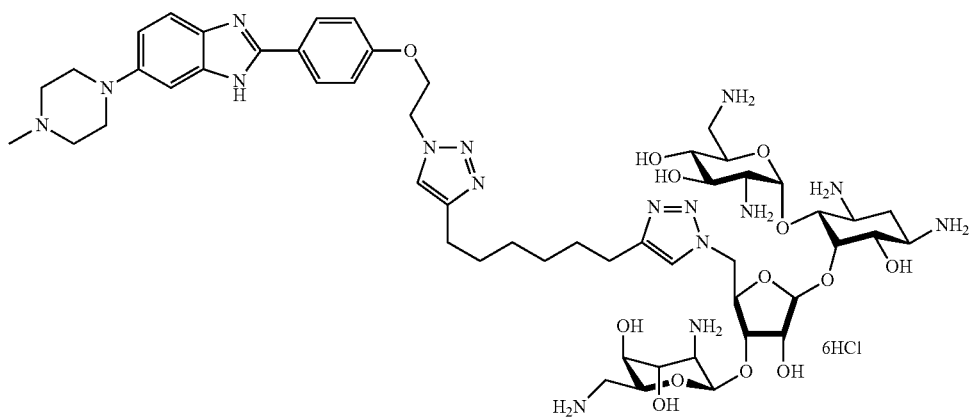

TABLE 1-continued

Neomycin-Benzimidazole and Neomycin-Hoescht Conjugates

| Name | Linker Length | Mol Wt |
|---|---|---|
| DPA123 | 4 | 1204.85 |
| DPA165 | 4 | 1320.96 |
| DPA166 | 9 | 1363.05 |

Table 2 discloses another group of RNA binding compounds, neomycin-neomycin conjugates.
TABLE 2
Neomycin Neomycin Dimer Conjugates
| Mol. Wt. | Linker length | Name |
|---|---|---|
| 1810.96 | 7 | DPA 51 |
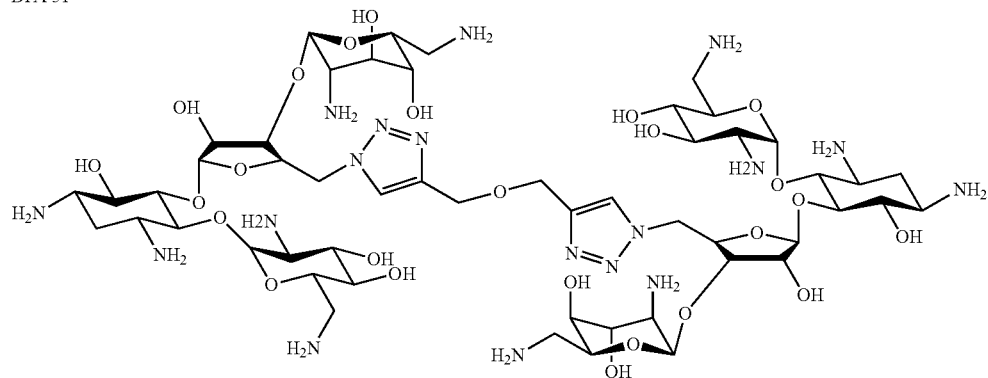
Chemical Formula: $C_{52}H_{108}Cl_{12}N_{18}O_{25}$
Exact Mass: 1804.40
Molecular Weight: 1810.96
| 1808.98 | 7 | DPA 52 |
|---|---|---|
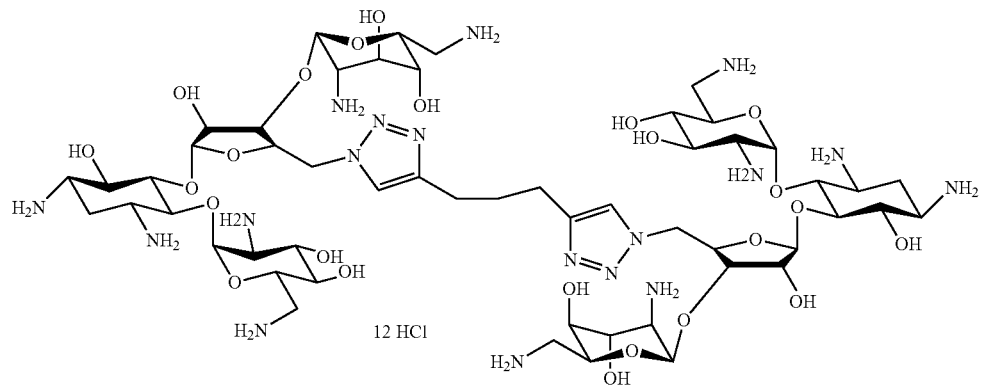
Chemical Formula: $C_{53}H_{110}Cl_{12}N_{18}O_{24}$
Exact Mass: 1802.42
Molecular Weight: 1808.98

TABLE 2-continued
Neomycin Neomycin Dimer Conjugates
| Mol. Wt. | Linker length | Name |
|---|---|---|
| 1843.00 | 8 | DPA 53 |
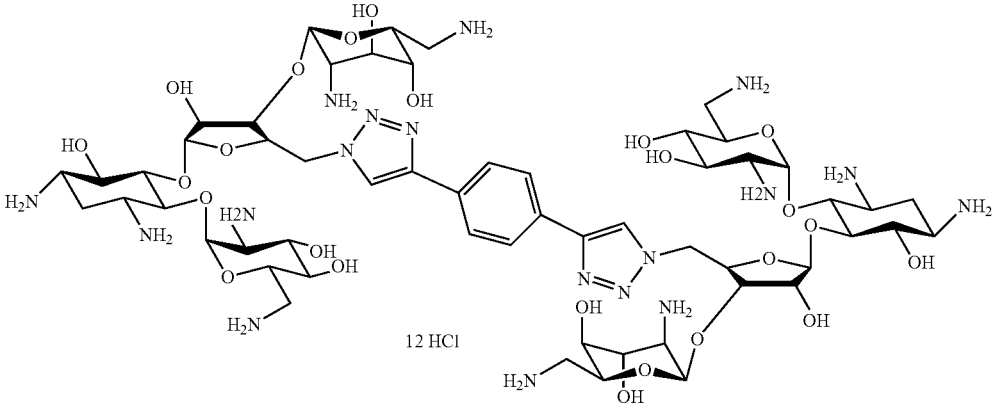
Chemical Formula: $C_{53}H_{108}Cl_{12}N_{18}O_{24}$
Exact Mass: 1836.40
Molecular Weight: 1843.00
| | | |
|---|---|---|
| 1823.01 | 9 | DPA 54 |
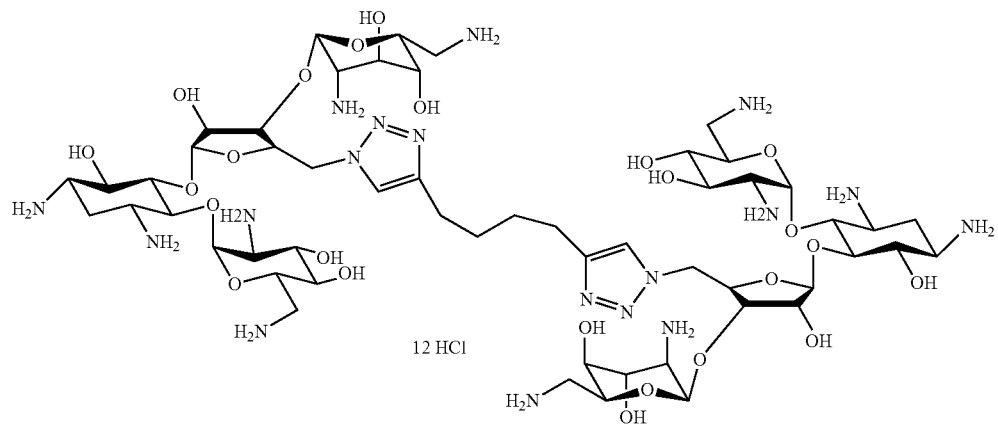
Chemical Formula: $C_{54}H_{112}Cl_{12}N_{18}O_{24}$
Exact Mass: 1816.44
Molecular Weight: 1823.01

TABLE 2-continued
Neomycin Neomycin Dimer Conjugates
| Mol. Wt. | Linker length | Name |
|---|---|---|
| 1877.10 | 11 | DPA 55 |
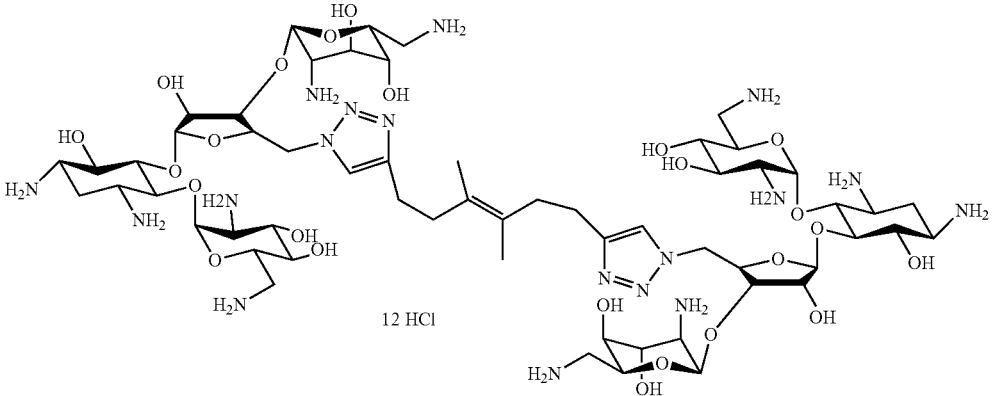
Chemical Formula: $C_{58}H_{118}Cl_{12}N_{18}O_{24}$
Exact Mass: 1870.48
Molecular Weight: 1877.10
| | | |
|---|---|---|
| 1851.06 | 11 | DPA 56 |
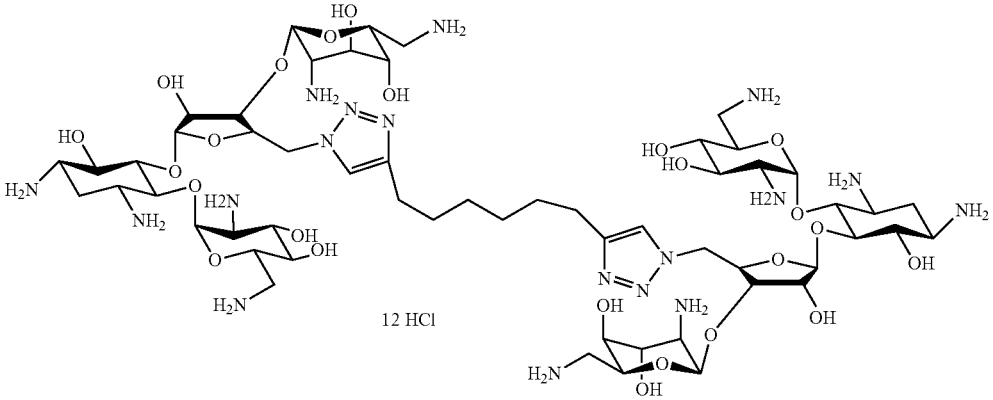
Chemical Formula: $C_{56}H_{116}Cl_{12}N_{18}O_{24}$
Exact Mass: 1844.47
Molecular Weight: 1851.06
| | | |
|---|---|---|
| 1939.27 | 16 | DPA 58 |
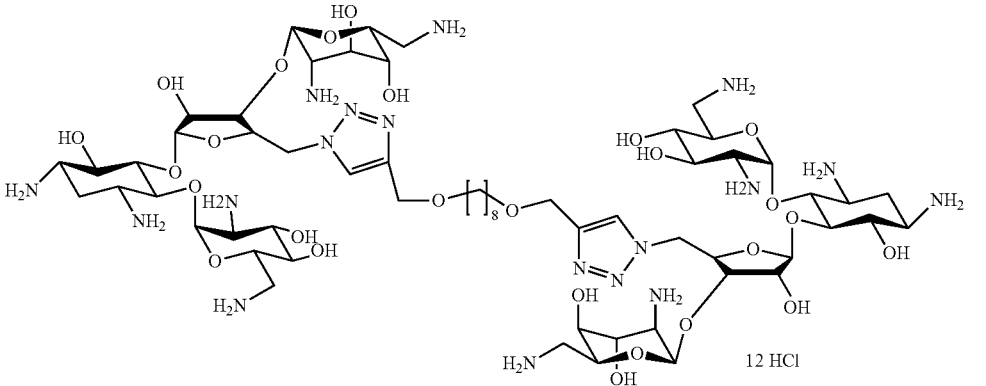

TABLE 2-continued
Neomycin Neomycin Dimer Conjugates
| Mol. Wt. | Linker length | Name |
|---|---|---|
| 1995.27 | 20 | DPA 60 |
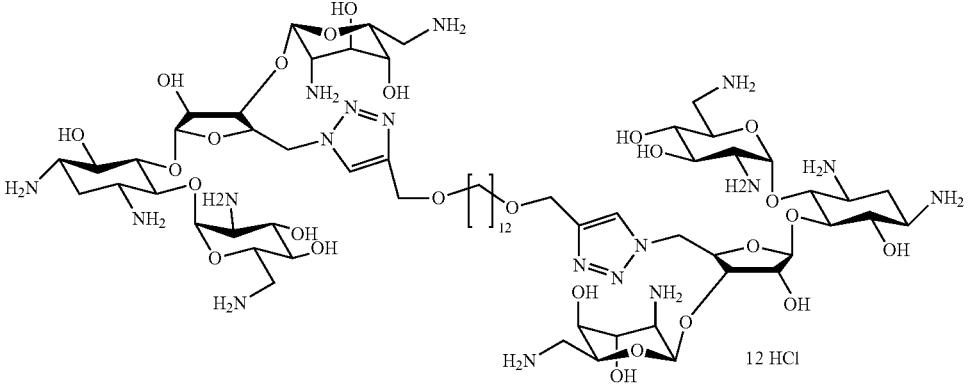
| 1843.00 | 7 | DPA 65 |
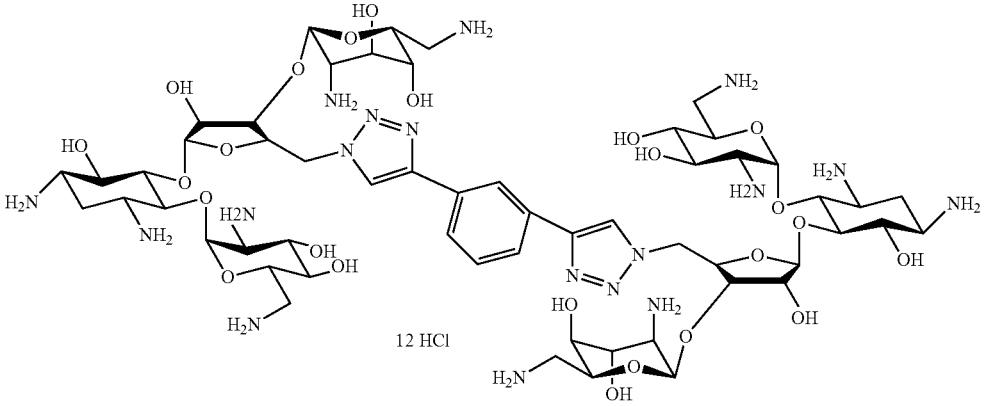
Chemical Formula: $C_{56}H_{108}Cl_{12}N_{18}O_{24}$
Exact Mass: 1836.40
Molecular Weight: 1843.00
| 1706.91 | 1 | DPA 71 |
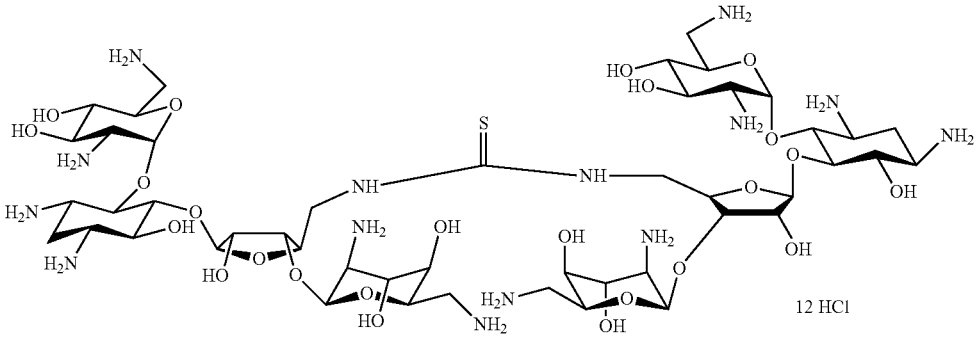
Chemical Formula: $C_{47}H_{104}Cl_{12}N_{14}O_{24}S$
Molecular Weight: 1706.91

TABLE 2-continued
Neomycin Neomycin Dimer Conjugates
| Mol. Wt. | Linker length | Name |
|---|---|---|
| 1824.98 | 7 | DPA 72 |
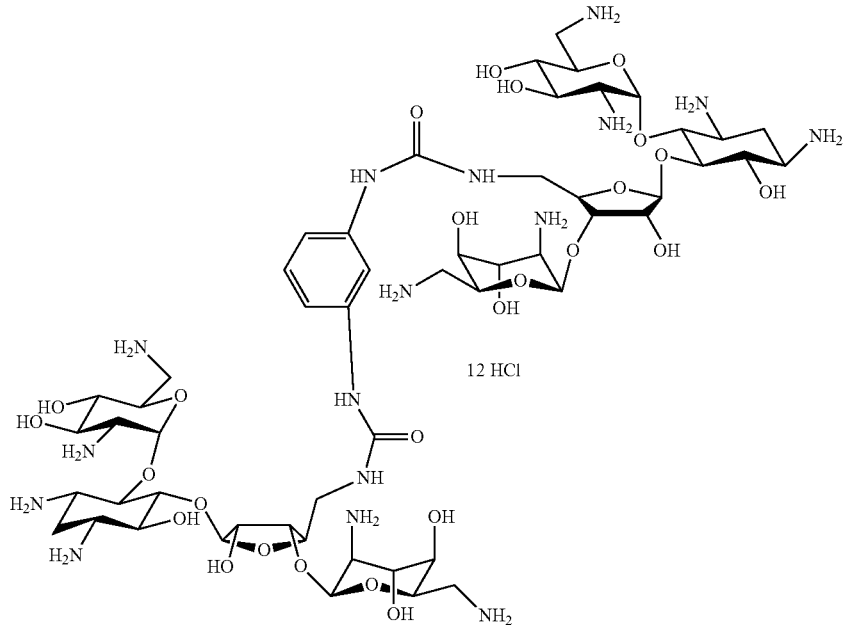
Chemical Formula: $C_{54}H_{110}Cl_{12}N_{16}O_{26}$
Molecular Weight: 1824.98
| 1823.09 | 7 | DPA 73 |
|---|---|---|
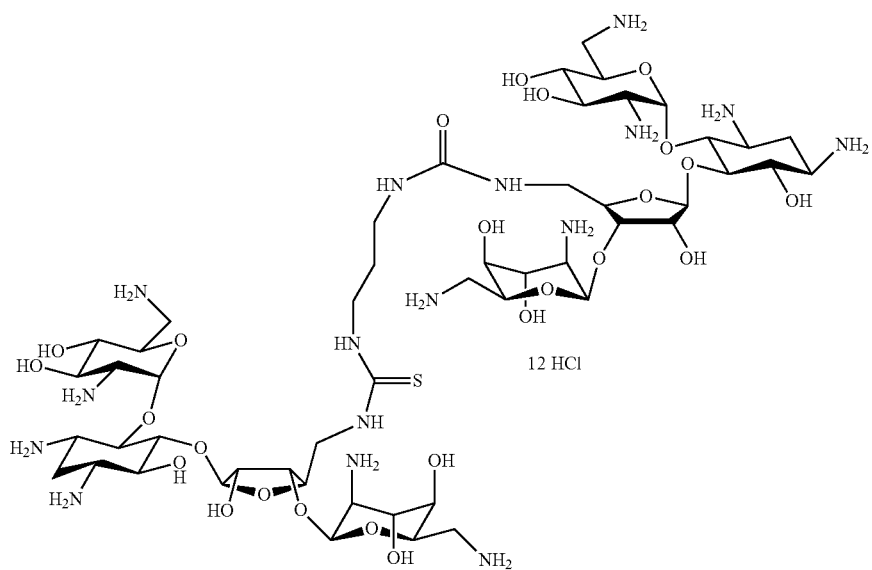
Chemical Formula: $C_{51}H_{112}Cl_{12}N_{16}O_{24}S_2$
Molecular Weight: 1823.09

TABLE 2-continued
Neomycin Neomycin Dimer Conjugates
| Mol. Wt. | Linker length | Name |
|---|---|---|
| 1824.98 | 8 | DPA 74 |
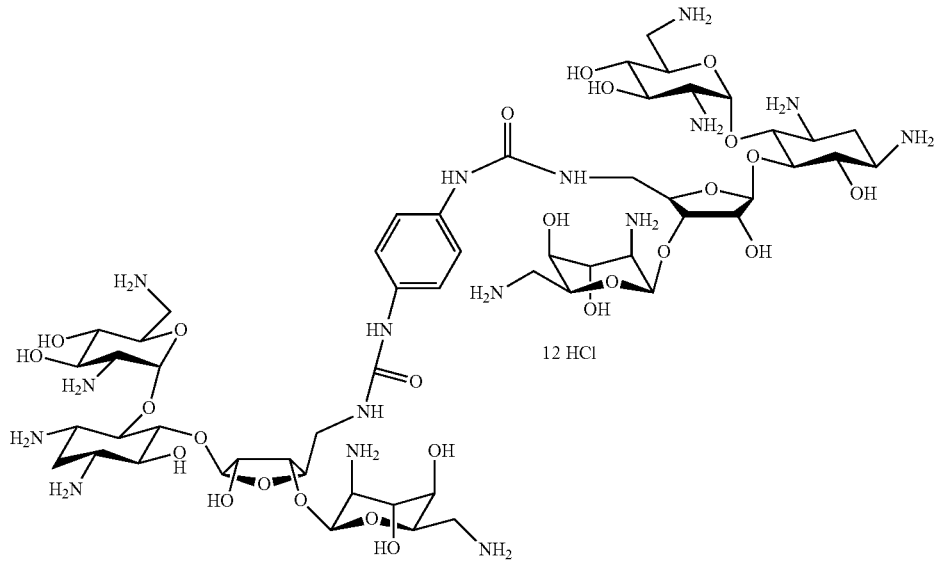
Chemical Formula: $C_{54}H_{110}Cl_{12}N_{16}O_{26}$
Molecular Weight: 1824.98
| | | |
|---|---|---|
| 1833.04 | 10 | DPA 75 |
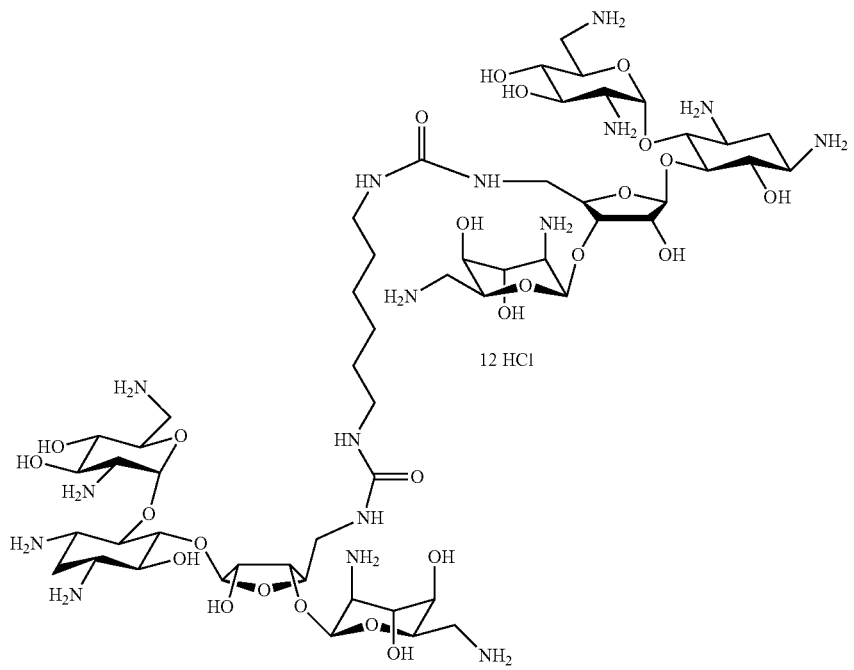
Chemical Formula: $C_{54}H_{118}Cl_{12}N_{16}O_{26}$
Molecular Weight: 1833.04

TABLE 2-continued
Neomycin Neomycin Dimer Conjugates
| Mol. Wt. | Linker length | Name |
|---|---|---|
1897.17    12    DPA 76
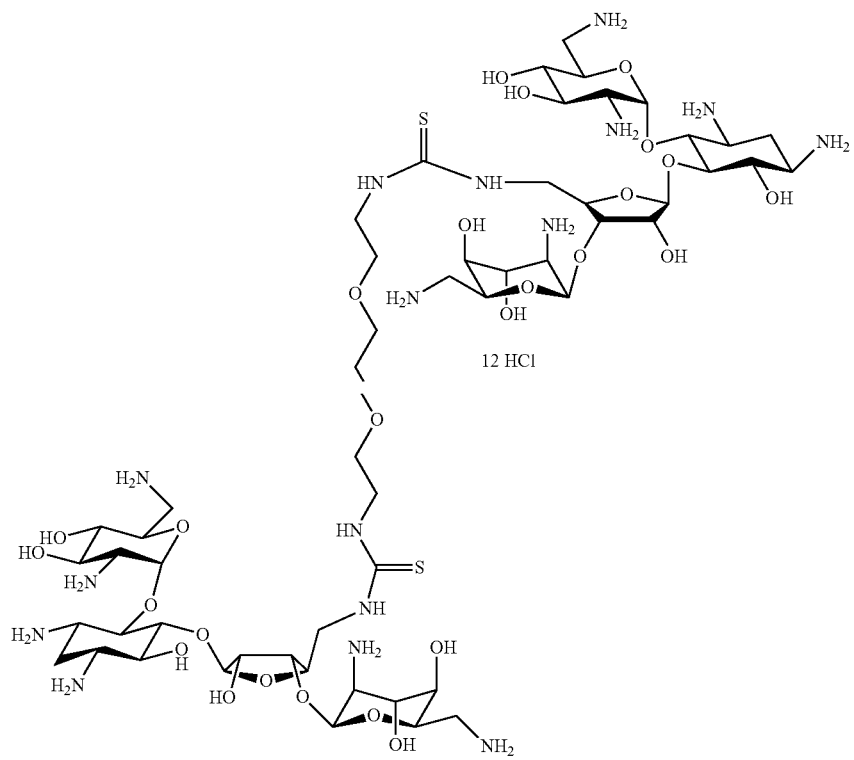
12 HCl
Chemical Formula: $C_{54}H_{118}Cl_{12}N_{16}O_{26}S_2$
Molecular Weight: 1897.17
1917.20    16    DPA 77
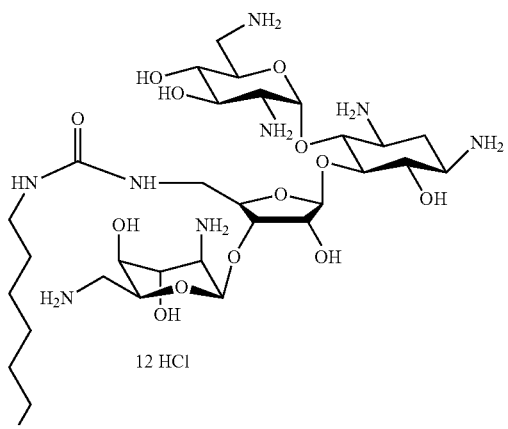
12 HCl

TABLE 2-continued
Neomycin Neomycin Dimer Conjugates
| Mol. Wt. | Linker length | Name |
|---|---|---|
| | | |
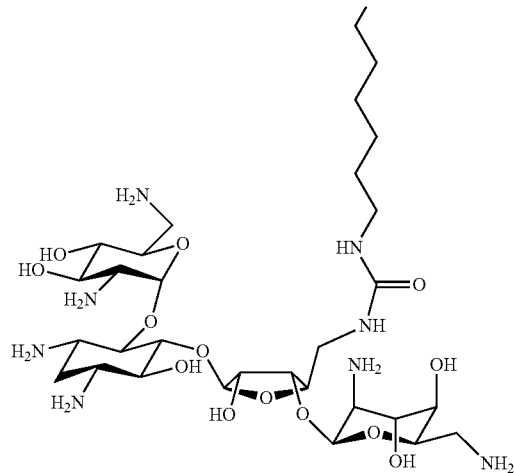
Chemical Formula: $C_{60}H_{130}Cl_{12}N_{16}O_{26}$
Molecular Weight: 1917.20
| 1953.28 | 16 | DPA 78 |
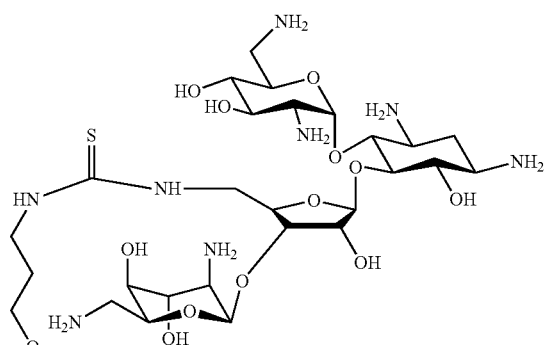
12 HCl
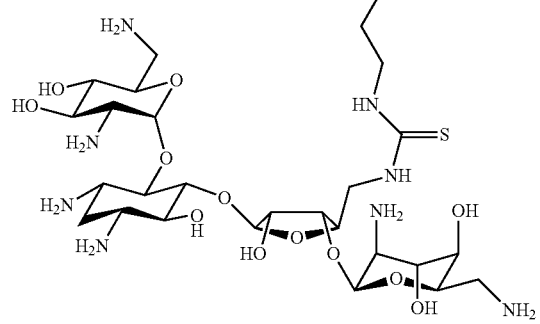
Chemical Formula: $C_{58}H_{126}Cl_{12}N_{16}O_{26}S_2$
Molecular Weight: 1953.28

TABLE 2-continued
Neomycin Neomycin Dimer Conjugates
| Mol. Wt. | Linker length | Name |
|---|---|---|
| 2017.41 | 18 | DPA 79 |
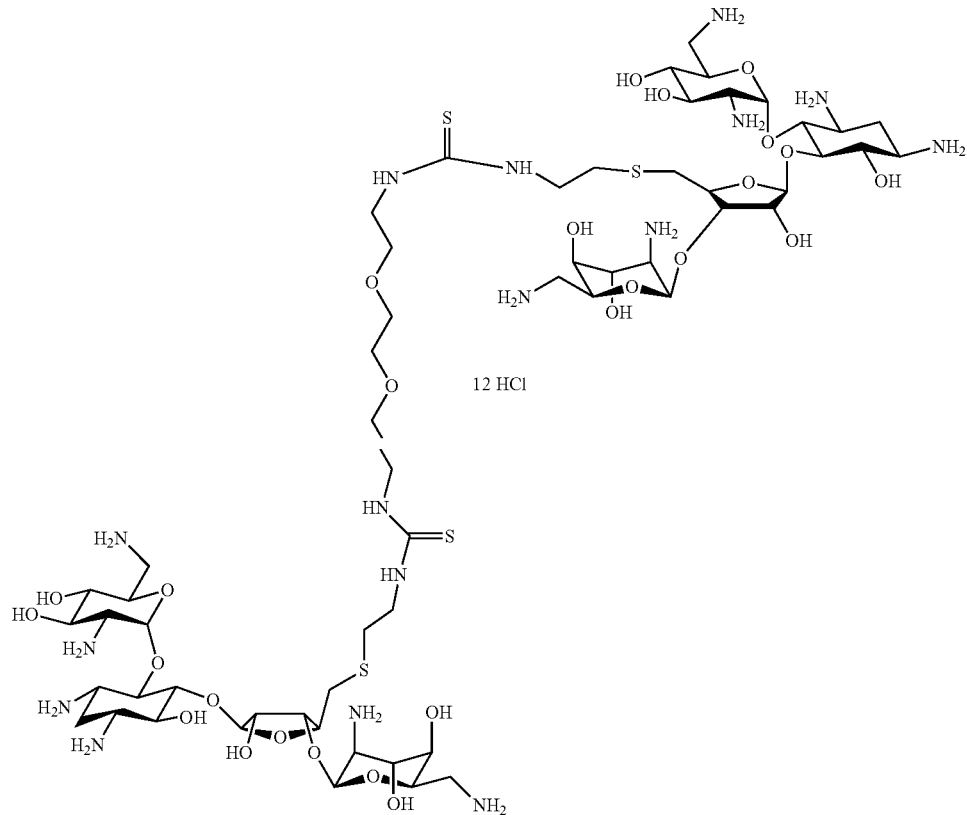
Chemical Formula: $C_{58}H_{126}Cl_{12}N_{16}O_{26}S_4$
Molecular Weight: 2017.41
| 2037.44 | 22 | DPA 80 |
|---|---|---|
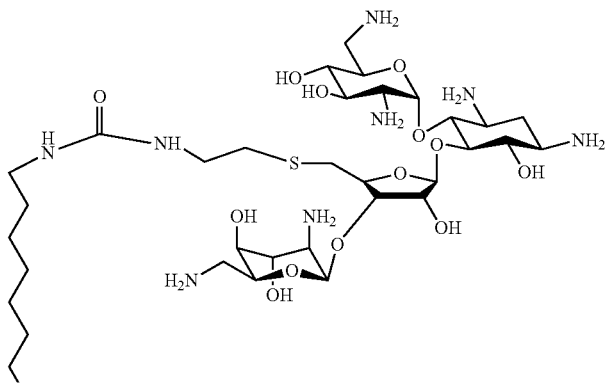

TABLE 2-continued

Neomycin Neomycin Dimer Conjugates

| Mol. Wt. | Linker length | Name |
|---|---|---|

Chemical Formula: $C_{64}H_{138}Cl_{12}N_{16}O_{26}S_2$
Molecular Weight: 2037.44

1857.11

Chemical Formula: $C_{54}H_{110}Cl_{12}N_{16}O_{24}S_2$
Exact Mass: 1850.36
Molecular Weight: 1857.11

12. Pharmaceutical Carriers/Delivery of Pharmaceutical Products

As described above, the compositions can also be administered in vivo in a pharmaceutically acceptable carrier. By "pharmaceutically acceptable" is meant a material that is not biologically or otherwise undesirable, i.e., the material may be administered to a subject, along with the nucleic acid or vector, without causing any undesirable biological effects or interacting in a deleterious manner with any of the other components of the pharmaceutical composition in which it is contained. The carrier would naturally be selected to minimize any degradation of the active ingredient and to minimize any adverse side effects in the subject, as would be well known to one of skill in the art.

The compositions may be administered orally, parenterally (e.g., intravenously), by intramuscular injection, by intraperitoneal injection, transdermally, extracorporeally, topically or the like, including topical intranasal administration or administration by inhalant. As used herein, "topical intranasal administration" means delivery of the compositions into the nose and nasal passages through one or both of the nares and can comprise delivery by a spraying mechanism or droplet mechanism, or through aerosolization of the nucleic acid or vector. Administration of the compositions by inhalant can be through the nose or mouth via delivery by a spraying or droplet mechanism. Delivery can also be directly to any area of the respiratory system (e.g., lungs) via intubation. The exact amount of the compositions required will vary from subject to subject, depending on the species, age, weight and general condition of the subject, the severity of the allergic disorder being treated, the particular nucleic acid or vector used, its mode of administration and the like. Thus, it is not possible to specify an exact amount for every composition. However, an appropriate amount can be determined by one of ordinary skill in the art using only routine experimentation given the teachings herein.

Parenteral administration of the composition, if used, is generally characterized by injection. Injectables can be prepared in conventional forms, either as liquid solutions or suspensions, solid forms suitable for solution of suspension in liquid prior to injection, or as emulsions. A more recently revised approach for parenteral administration involves use of a slow release or sustained release system such that a constant dosage is maintained. See, e.g., U.S. Pat. No. 3,610,795, which is incorporated by reference herein.

The materials may be in solution, suspension (for example, incorporated into microparticles, liposomes, or cells). These may be targeted to a particular cell type via antibodies, receptors, or receptor ligands. The following references are examples of the use of this technology to target specific proteins to tumor tissue (Senter, et al., Bioconjugate Chem., 2:447-451, (1991); Bagshawe, K. D., Br. J. Cancer, 60:275-281, (1989); Bagshawe, et al., Br. J. Cancer, 58:700-703, (1988); Senter, et al., Bioconjugate Chem., 4:3-9, (1993); Battelli, et al., Cancer Immunol. Immunother., 35:421-425, (1992); Pietersz and McKenzie, Immunolog. Reviews, 129:57-80, (1992); and Roffler, et al., Biochem. Pharmacol, 42:2062-2065, (1991)). Vehicles such as "stealth" and other antibody conjugated liposomes (including lipid mediated drug targeting to colonic carcinoma), receptor mediated targeting of DNA through cell specific ligands, lymphocyte directed tumor targeting, and highly specific therapeutic retroviral targeting of murine glioma cells in vivo. The following references are examples of the use of this technology to target specific proteins to tumor tissue (Hughes et al., Cancer Research, 49:6214-6220, (1989); and Litzinger and Huang, Biochimica et Biophysica Acta, 1104:179-187, (1992)). In general, receptors are involved in pathways of endocytosis, either constitutive or ligand induced. These receptors cluster in clathrin-coated pits, enter the cell via clathrin-coated vesicles, pass through an acidified endosome in which the receptors are sorted, and then either recycle to the cell surface, become stored intracellularly, or are degraded in lysosomes. The internalization pathways serve a variety of functions, such as nutrient uptake, removal of activated proteins, clearance of macromolecules, opportunistic entry of viruses and toxins, dissociation and degradation of ligand, and receptor-level regulation. Many receptors follow more than one intracellular pathway, depending on the cell type, receptor concentration, type of ligand, ligand valency, and ligand concentration. Molecular and cellular mechanisms of receptor-mediated endocytosis has been reviewed (Brown and Greene, DNA and Cell Biology 10:6, 399-409 (1991)).

a) Pharmaceutically Acceptable Carriers

The compositions, including antibodies, can be used therapeutically in combination with a pharmaceutically acceptable carrier.

Suitable carriers and their formulations are described in Remington: The Science and Practice of Pharmacy (19th ed.) ed. A. R. Gennaro, Mack Publishing Company, Easton, Pa. 1995. Typically, an appropriate amount of a pharmaceutically-acceptable salt is used in the formulation to render the formulation isotonic. Examples of the pharmaceutically-acceptable carrier include, but are not limited to, saline, Ringer's solution and dextrose solution. The pH of the solution is preferably from about 5 to about 8, and more preferably from about 7 to about 7.5. Further carriers include sustained release preparations such as semipermeable matrices of solid hydrophobic polymers containing the antibody, which matrices are in the form of shaped articles, e.g., films, liposomes or microparticles. It will be apparent to those persons skilled in the art that certain carriers maybe more preferable depending upon, for instance, the route of administration and concentration of composition being administered.

Pharmaceutical carriers are known to those skilled in the art. These most typically would be standard carriers for administration of drugs to humans, including solutions such as sterile water, saline, and buffered solutions at physiological pH. The compositions can be administered intramuscularly or subcutaneously. Other compounds will be administered according to standard procedures used by those skilled in the art.

Pharmaceutical compositions may include carriers, thickeners, diluents, buffers, preservatives, surface active agents and the like in addition to the molecule of choice. Pharmaceutical compositions may also include one or more active ingredients such as antimicrobial agents, antiinflammatory agents, anesthetics, and the like.

The pharmaceutical composition may be administered in a number of ways depending on whether local or systemic treatment is desired, and on the area to be treated. Administration maybe topically (including ophthalmically, vaginally, rectally, intranasally), orally, by inhalation, or parenterally, for example by intravenous drip, subcutaneous, intraperitoneal or intramuscular injection. The disclosed antibodies can be administered intravenously, intraperitoneally, intramuscularly, subcutaneously, intracavity, or transdermally.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like.

Formulations for topical administration may include ointments, lotions, creams, gels, drops, suppositories, sprays, liquids and powders. Conventional pharmaceutical carriers, aqueous, powder or oily bases, thickeners and the like may be necessary or desirable.

Compositions Tor oral administration include powders or granules, suspensions or solutions in water or non-aqueous media, capsules, sachets, or tablets. Thickeners, flavorings, diluents, emulsifiers, dispersing aids or binders maybe desirable.

Some of the compositions may potentially be administered as a pharmaceutically acceptable acid- or base-addition salt, formed by reaction with inorganic acids such as hydrochloric acid, hydrobromic acid, perchloric acid, nitric acid, thiocyanic acid, sulfuric acid, and phosphoric acid, and organic acids such as formic acid, acetic acid, propionic acid, glycolic acid, lactic acid, pyruvic acid, oxalic acid, malonic acid, succinic acid, maleic acid, and fumaric acid, or by reaction with an inorganic base such as sodium hydroxide, ammonium hydroxide, potassium hydroxide, and organic bases such as mono-, di-, trialkyl and aryl amines and substituted ethanolamines.

b) Therapeutic Uses

Effective dosages and schedules for administering the compositions may be determined empirically, and. making such determinations is within the skill in the art. The dosage ranges for the administration of the compositions are those large enough to produce the desired effect in which the symptoms disorder are effected. The dosage should not be so large as to cause adverse side effects, such as unwanted cross-reactions, anaphylactic reactions, and the like. Generally, the dosage will vary with the age, condition, sex and extent of the disease in the patient, route of administration, or whether other drugs are included in the regimen, and can be determined by one of skill in the art. The dosage can be adjusted by the individual physician in the event of any counterindications. Dosage can vary, and can be administered in one or more dose administrations daily, for one or several days. Guidance can be found in the literature for appropriate dosages for given classes of pharmaceutical products. For example, guidance in selecting appropriate doses for antibodies can be found in the literature on therapeutic uses of antibodies, e.g., Handbook of Monoclonal Antibodies, Ferrone et al., eds., Noges Publications, Park Ridge, N.J., (1985) ch. 22 and pp. 303-357; Smith et al., Antibodies in Human Diagnosis and Therapy, Haber et al., eds., Raven Press, New York (1977) pp. 365-389. A typical daily dosage of the antibody used alone might range from about 1 µg/kg to up to 100 mg/kg of body weight or more per day, depending on the factors mentioned above.

Following administration of a disclosed composition for treating, inhibiting, or preventing a condition or disease, the efficacy of the therapeutic composition can be assessed in various ways well known to the skilled practitioner. For instance, one of ordinary skill in the art will understand that a composition disclosed herein is efficacious in treating or inhibiting an a disease of "condition iri" a" subject by observing that the composition reduces or prevents one or more symptoms or characteristics of the disease or condition.

13. Computer Readable Mediums

It is understood that the disclosed nucleic acids and proteins can be represented as a sequence consisting of the nucleotides of amino acids. There are a variety of ways to display these sequences, for example the nucleotide guanosine can be represented by G or g. Likewise the amino acid valine can be represented by Val or V. Those of skill in the art understand how to display and express any nucleic acid or protein sequence in any of the variety of ways that exist, each of which is considered herein disclosed. Specifically contemplated herein is the display of these sequences on computer readable mediums, such as, commercially available floppy disks, tapes, chips, hard drives, compact disks, and video disks, or other computer readable mediums. Also disclosed are the binary code representations of the disclosed sequences. Those of skill in the art understand what computer readable mediums are. Thus, computer readable mediums on which the nucleic acids or protein sequences are recorded, stored, or saved.

Disclosed are computer readable mediums comprising the sequences and information regarding the sequences set forth herein.

14. Kits

Disclosed herein are kits that are drawn to reagents that can be used in practicing the methods disclosed herein. The kits can include any reagent or combination of reagent discussed herein or that would be understood to be required or beneficial in the practice of the disclosed methods. For example, the kits could include primers to perform the amplification reactions discussed in certain embodiments of the methods, as well as the buffers and enzymes required to use the primers as intended.

15. Compositions with Similar Functions

It is understood that the compositions disclosed herein have certain functions. Disclosed herein are certain structural requirements for performing the disclosed functions, and it is understood that there are a variety of structures which can perform the same function which are related to the disclosed structures, and that these structures will ultimately achieve the same result.

C. METHODS OF MAKING THE COMPOSITIONS

The compositions disclosed herein and the compositions necessary to perform the disclosed methods can be made using any method known to those of skill in the art for that particular reagent or compound unless otherwise specifically noted.

1. Nucleic Acid Synthesis

For example, the nucleic acids, such as, the oligonucleotides to be used as primers can be made using standard chemical synthesis methods or can be produced using enzymatic methods or any other known method. Such methods can range from standard enzymatic digestion followed by nucleotide fragment isolation (see for example, Sambrook et al., Molecular Cloning: A Laboratory Manual, 2nd Edition (Cold Spring Harbor Laboratory Press, Cold Spring Harbor, N. Y., 1989) Chapters 5, 6) to purely synthetic methods, for example, by the cyanoethyl phosphoramidite method using a Milligen or Beckman System lPlus DNA synthesizer (for example, Model 8700 automated synthesizer of Milligen-Biosearch, Burlington, Mass. or ABI Model 380B). Synthetic methods useful for making oligonucleotides are also described by Baita et al., Ann. Rev. Biochem. 53:323-356 (1984), (phosphotriester and phosphite-triester methods)*, and Narang et al., Methods Enzymol., 65:610-620 (1980), (phosphotriester method). Protein nucleic acid molecules can be made using known methods such as those described by Nielsen et al., Bioconjug. Chem. 5:3-7 (1994).

2. Peptide Synthesis

One method of producing the disclosed proteins is to link two or more peptides, or polypeptides together by protein chemistry techniques. For example, peptides or polypeptides can be chemically synthesized using currently available laboratory equipment using either Fmoc (9-fluorenylrnethyloxycarbonyl) or Boc (tert-butyloxycarbonoyl) chemistry. (Applied Biosystems, Inc., Foster City, Calif.). One skilled in the art can readily appreciate that a peptide or polypeptide corresponding to the disclosed proteins, for example, can be synthesized by standard chemical reactions. For example, a peptide or polypeptide can be synthesized and not cleaved from its synthesis resin whereas the other fragment of a peptide or protein can be synthesized and subsequently cleaved from the resin, thereby exposing a terminal group which is functionally blocked on the other fragment. By peptide condensation reactions, these two fragments can be co valently joined via a peptide bond at their carboxyl and amino termini, respectively, to form an antibody, or fragment thereof. (Grant G A (1992) Synthetic Peptides: A User Guide. W.H. Freeman and Co., N.Y. (1992); Bodansky M and Trost B., Ed. (1993) Principles of Peptide Synthesis. Springer-Verlag Inc., NY (which is herein incorporated by reference at least for material related to peptide synthesis). Alternatively, the peptide or polypeptide is independently synthesized in vivo as described herein. Once isolated, these independent peptides or polypeptides may be linked to form a peptide or fragment thereof via similar peptide condensation reactions.

For example, enzymatic ligation of cloned or synthetic peptide segments allow relatively short peptide fragments to be joined to produce larger peptide fragments, polypeptides or whole protein domains (Abrahmsen L et al., Biochemistry, 30:4151 (1991)). Alternatively, native chemical ligation of synthetic peptides can be utilized to synthetically construct large peptides or polypeptides from shorter peptide fragments. This method consists of a two step chemical reaction (Dawson et al. Synthesis of Proteins by Native Chemical Ligation. Science, 266:776-779 (1994)). The first step is the chemoselective reaction of an unprotected synthetic peptide—thioester with another unprotected peptide segment containing an amino-terminal Cys residue to give a thioester-linked intermediate as the initial covalent product. Without a change in the reaction conditions, this intermediate undergoes spontaneous, rapid intramolecular reaction to form a native peptide bond at the ligation site (Baggiolini M et al. (1992) FEBS Lett. 307:97-101; Clark-Lewis I et al., J. Biol. Chem., 269:16075 (1994); Clark-Lewis I et al., Biochemistry, 30:3128 (1991); Rajarathnam K et al., Biochemistry 33:6623-30 (1994)).

Alternatively, unprotected peptide segments are chemically linked where the bond formed between the peptide segments as a result of the chemical ligation is an unnatural (non-peptide) bond (Schnolzer, M et al. Science, 256:221 (1992)). This technique has been used to synthesize analogs of protein domains as well as large amounts of relatively pure proteins with full biological activity (deLisle Milton R C et al., Techniques in Protein Chemistry IV. Academic Press, New York, pp. 257-267 (1992)).

D. PROCESS CLAIMS FOR MAKING THE COMPOSITIONS

Disclosed are processes for making the compositions as well as making, the intermediates leading to the compositions. There are a variety of methods that can be used for making these compositions, such as synthetic chemical methods and standard molecular biology methods. It is understood that the methods of making these and the other disclosed compositions are specifically disclosed.

E. METHODS OF USING THE COMPOSITIONS

1. Methods of Using the Compositions as Research Tools

The disclosed compositions can be used in a variety of ways as research tools. For example, the disclosed compositions, can be used to study the interactions between aminoglycosides and nucleic acids, by for example acting as inhibitors of triplex binding.

The compositions can be used for example as targets in combinatorial chemistry protocols or other screening protocols to isolate molecules that possess desired functional properties related to their nucleic acid binding.

The disclosed compositions can be used as discussed herein as, either reagents in micro arrays or as reagents to probe or analyze existing microarrays. The disclosed compositions can be used in any known method for isolating or identifying single nucleotide polymorphisms. The compositions can also be used in any method for determining allelic analysis. The compositions can also be used in any known method of screening assays, related to chip/micro arrays. The compositions can also be used in any known way of using the computer readable embodiments of the disclosed compositions, for example, to study relatedness or to perform molecular modeling analysis related to the disclosed compositions.

F. METHODS

1. Click Chemistry

The term "click chemistry" comprises and identifies various groups of chemical reactions characterized by particular properties such as rapidity, regioselectivity and high yield and having a high thermodynamic driving force, generally greater than or equal to 20 kcal/mol.

"Click" reactions includes cycloaddition reactions such as Diels-Alder reactions, and Huisgen 1,3-dipolar cycloadditions. An example of a cycloaddition consists of a reaction in which two unsaturated molecules react to form a cyclic compound with the formation of two new $\sigma$ bonds using $\pi$ electrons.

Diels-Alder reactions (O. Diels, K. Alder, Ann. 1928, 460, 98; 0. Diels, K. Alder, Ann. 1929, 470, 62; 0. Diels, K. Alder, Ber. 1929, 62, 2081 2087) are cycloadditions [4+2] as they imply a system of 4 $\pi$ electrons (diene) and a system of 2 $\pi$ electrons (dienophile). The reaction products are substituted cyclohexanes. The dienophile can also contain double bonds between carbon and another atom (for example an oxygen), with the formation of heterocyclic rings.

The mechanism is almost certainly concerted and in a single step: both of the new carbon-carbon bonds are partially formed in the same transition state, even if not necessarily in the same extent. The Diels-Alder reaction is not only useful, because it forms a cyclic compound, but above all because it takes place with great facility on a wide range of reagents. The reaction is favored by the electron-attractor substituents in the dienophile, but simple alkenes can also react; the reaction often takes place with the production of heat by simple mixing of the reagents.

1,3-dipolar cycloadditions are cycloadditions which are thermodynamically permitted between a 1,3-dipole and a dipolarophile to form 5-atom aromatic heterocyclic rings, partially or totally saturated. 1,3-dipoles are compounds which can be described by octet or sextet zwitterionic forms and can be of the allyl type (angulated structure) or of the propargyl-allene type. 1,3-dipoles can have an N, O or S atom, as central atom. 1,3-dipoles with a nitrogen as central atom are the most common. Examples of nitrogen 1,3-dipoles of the propargyl (linear) type are azide, nitrilide, nitrilimine, nitriloxide, diazoalkane and nitrogen suboxide. The application of 1,3-dipolar cycloaddition reactions in the construction of isoxazole and pyrazole rings is particularly important due to their regioselectivity (generally total) and stereospecificity (G. A. Pagani, A. Abbotto, "Chimica Eterociclica", Ed. Piccin). Among these types of reactions, Huisgen [3+2] 1,3-dipolar cycloaddition reactions are common (R. Huisgen et al., Chem. Ber. 1967, 100, 2494-2507): these are condensation reactions between organic azides and species having terminal alkyne groups which lead to the formation of a single derivative, rapidly and with a high yield, characterized by a bisubstituted 1,2,3-triazole ring (R, Huisgen, Pure Appl. Chem. 1989, 61, 613-628). The above reaction generates a mixture of 1,4- and 1, 5-bisubstituted triazole rings. Various attempts were made for controlling the re-gioselectivity, until the discovery, in 2002, of the possibility of using copper (I) as reaction catalyst, which exclusively leads to the formation of the 1,4-bisubstituted 1, 2, 3-triazole ring (FIG. 2) (V. Rostovtsev, et al., Angew. Chem. Int. Ed., 2002, 41, 2596-2599; C W. Tor⊘e et al., J". Org. Chem., 2002, 67, 3057-3064; B. K. Sharpies et al., WO 03/101972).

In this type of reaction, substituted primary, secondary and tertiary azides and also aromatic azides are used. Numerous compounds having alkyne terminal groups can be used in said reaction, which is not impaired by the presence of various functional groups such as esters, acids, alkenes, alcohols and amines.

The same type of reaction between azides and alkynes takes place under bland conditions in an aqueous environment also in the absence of a catalyst, when the alkyne has electron-attractor substituents (Z. Li et al., Tetrahedron Letters, 2004, 45, 3143-3146).

The practical importance of this reaction, which is particularly relevant within the field of so-called "click chemistry", derives from the easy insertion of the terminal azide groups and alkyne groups in a wide variety of organic molecules. These groups subsequently react with each other also in the presence of other species with various possible functionalities. This prerogative has proved to be particularly advantageous in numerous sectors, from drug discovery to surface science, in which the formation of new bonds, and therefore new products, must be regioselective, rapid and must take place with high yields.

The Huisgen reaction, for example, has in fact been used in recent years for rapidly and effectively conjugating mono- and di-saccharides by means of bridges containing 1, 2, 3-triazole rings (S. Chittaboina et al., Tet-rahedron Letters, 2005, 46, 2331-2336), to link functional groups, which would otherwise be difficult to introduce, to linear β-glucanes with the same method, (T. Hasegawa et al., Carbohydrate Research, 2006, 341, 35-40), for the regioselective synthesis with high yields of a wide range of dendrimers (V. Fokin et al., WO 2006/005046), for the coupling of macromolecules such as oligonucleotides and proteins with other molecular entities (W. Pieken et al., WO 98/30575), for the crosslinking of polyvinyl alcohols by means of linkers containing triazole groups (J. Ossipov et al., Macromolecules, 2006, 39 (5), 1709-1718).

Although cycloaddition reactions are known as being common synthesis procedures for obtaining various types of chemical derivatives, the process according to the present invention envisages crosslinking by means of "click chemistry" reactions of polycarboxylated polysaccharides, in which at least one of the polysaccharide chains consists of suitably functionalized chains of hyaluronic acid or derivatives thereof—as also other uronanes and generic polycarboxylates—with the production of hydrogels with a known crosslinking degree which can be well modulated.

2. Neomycin-Benzomidazole and Neomycin-Hoescht Conjugates and their Synthesis a) Synthesis of Alkyne and Azido Ended Benzimidazole (Parent Molecules)

Benzimidazoles derived from Hoechst 33258 were synthesized using standard chemical procedures as outlined in Scheme 1. Commercially available 5-Chloro, 2-nitro Aniline was reacted with N-methyl Piperazine under basic conditions to give compound 2. Reduction of compound 2 under heterogeneous catalytic conditions afforded the corresponding diamine (3) which was then reacted using appropriate alkyne ended Benzaldehyde derivative (4) (prepared in one step using Mitsunobu Conditions) or Azido ended Benzaldehyde derivative (6) using freshly generated oxidants to yield desired Benzimidazoles (Scheme 1).

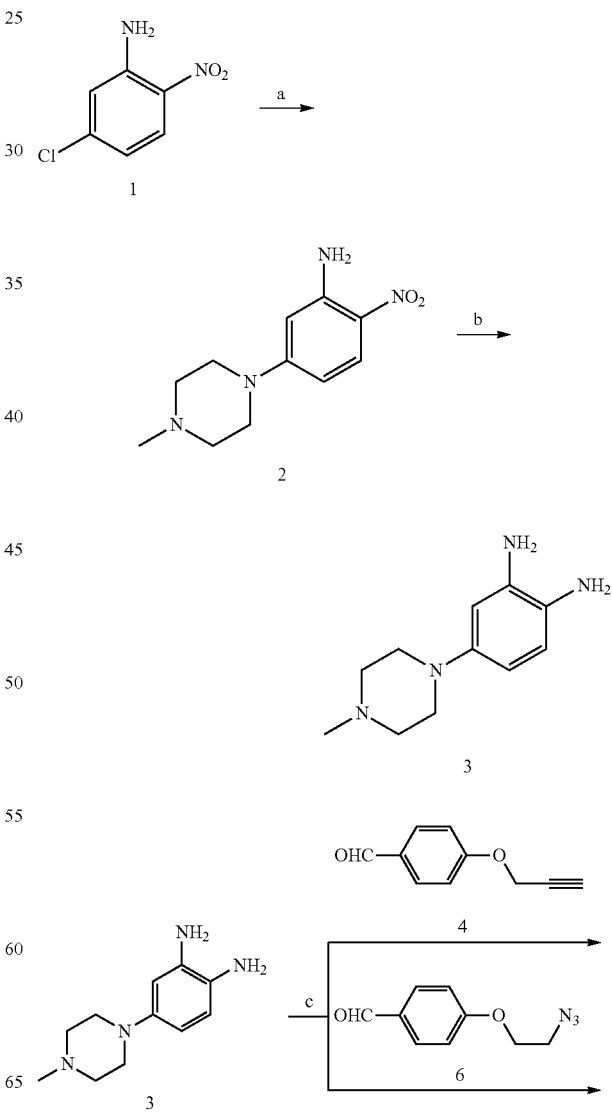

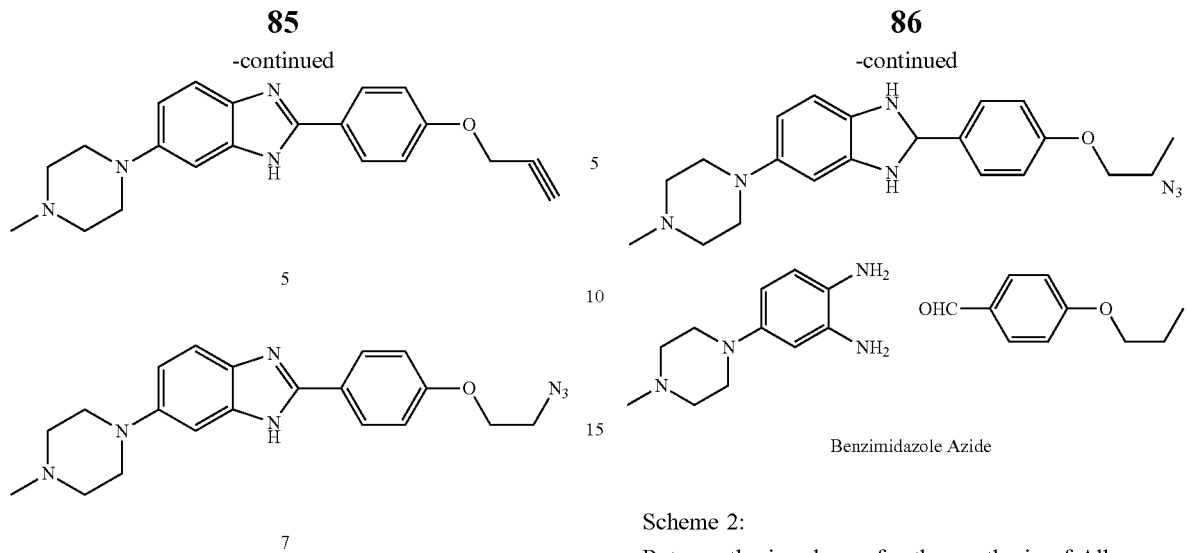

Reagents and Conditions: (a) DMF, N-methylpiperazine, 100° C., 5 h, 60% (b) Pd—C (10%), Ethanol, H$_2$, 6 h (c) Na$_2$S$_2$O$_5$, H$_2$O, Reflux, 5 h, 66-75%

Scheme 1:

Scheme of synthesis to afford Alkyne and Azido ended Hoechst 33258 derived Benzimidazoles for click chemistry based synthetic applications.

b) Retrosynthesis of Alkyne and Azido Ended Benzimidazole

To obtain alkyne and azido ended Benzimidazoles for applications in click chemistry, a divergent synthetic strategy was adopted as shown by retrosynthetic analysis in Scheme 2.

Scheme 2:

Retrosynthesis scheme for the synthesis of Alkyne and Azido ended Hoechst 33258 derived Benzimidazoles for click chemistry based synthetic applications.

c) Synthesis of Azido Ended Benzimidazole Linkers

To easily elongate the Benzimidazole linker lengths, a click chemistry approach was followed. Both alkyne and azido ended parent benzimidazole molecules, were synthesized and therefore had the flexibility to have either alkyne or azido ended linkers at the end. As outlined above (Scheme 3), an alkyne ended parent benzimidazole monomer was reacted with bis azides of varying linker lengths (prepared in one step from their corresponding dibromides).

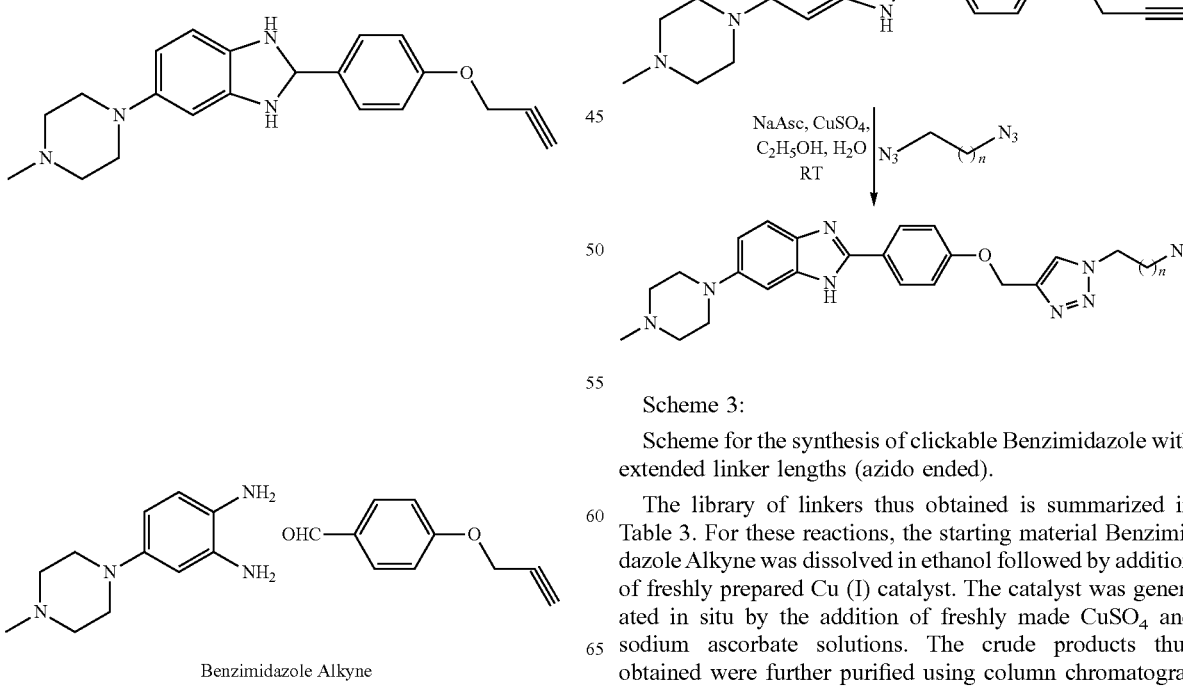

Scheme 3:

Scheme for the synthesis of clickable Benzimidazole with extended linker lengths (azido ended).

The library of linkers thus obtained is summarized in Table 3. For these reactions, the starting material Benzimidazole Alkyne was dissolved in ethanol followed by addition of freshly prepared Cu (I) catalyst. The catalyst was generated in situ by the addition of freshly made CuSO$_4$ and sodium ascorbate solutions. The crude products thus obtained were further purified using column chromatography on silica gel using dichloromethane-MeOH as eluent.

TABLE 3

Synthesized Benzimidazole Linkers from alkyne ended benzimidazoles
Structure

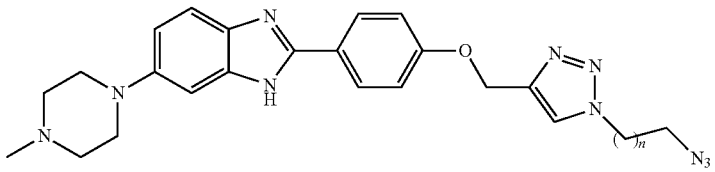

| Name | n | Linker Length | Mol. Wt. |
|---|---|---|---|
| DPA103 | 1 | 8 | 458.23 |
| DPA104 | 4 | 11 | 500.28 |
| DPA105 | 5 | 12 | 514.63 |
| DPA106 | 7 | 14 | 542.68 |
| DPA107 | 9 | 16 | 570.43 | d) Synthesis of Alkyne Ended Benzimidazole Linkers

To prepare alkyne ended Benzimidazole linkers lengths, a click chemistry approach similar to the used for the synthesis of azido ended linkers was followed as shown in Scheme 4. As outlined above, an azido ended parent benzimidazole monomer was reacted with bisalkyne of varying linker lengths (these alkynes were obtained from commercial suppliers).

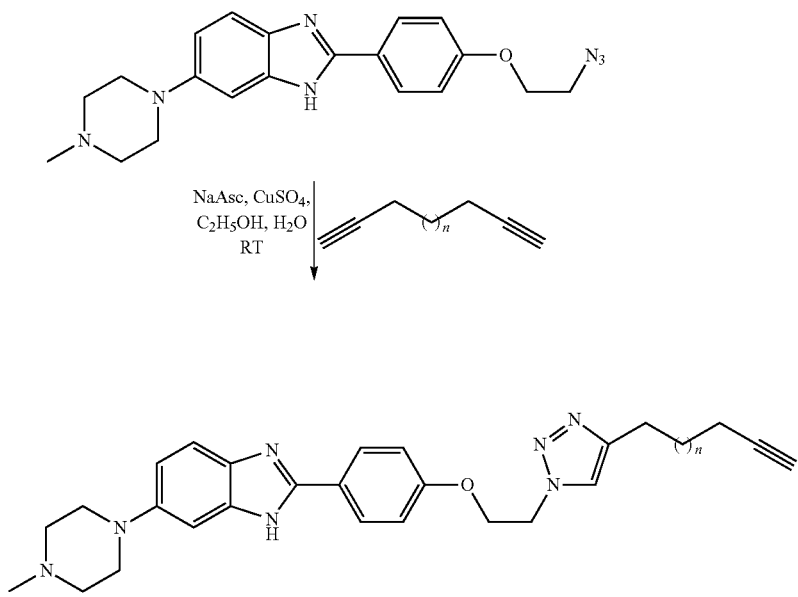

Scheme 4:
Scheme for the synthesis of clickable Benzimidazole with extended linker lengths (alkyne ended).

The library of linkers thus obtained is summarized in Table 4. For these reactions, the starting material Azido ended Benzimidazole was dissolved in ethanol followed by addition of excess bisalkyne and freshly prepared Cu (I) catalyst. The catalyst was generated in situ by the addition of freshly made $CuSO_4$ and sodium ascorbate solutions. The crude products thus obtained were further purified using column chromatography on silica gel using dichloromethane-MeOH as eluent to afford desired linkers.

TABLE 4

Synthesized Benzimidazole Linkers from azido ended benzimdazoles
Structure

| Name | n | Linker Length | Mol. Wt. |
|---|---|---|---|
| DPA108 | | 12 | 503.60 |
| DPA109 | | 11 | 471.55 |
| DPA110 | 0 | 11 | 469.58 |
| DPA111 | 2 | 12 | 483.61 |
| DPA112 | 4 | 14 | 511.66 | e) Synthesis of Protected Neomcyin with Azide/Alkyne End

Since the Benzimidazole linkers that were synthesized carry both Alkyne/azido ends on them, they were needed to have Neomycin partners with opposite functionalities i.e, azido/alkyne for click chemistry to be used as a means of conjugation. Syntheses of both azido and alkyne terminal Neomycin were carried out as displayed in Scheme 5. To synthesize the target compounds, Neomycin B Sulfate was reacted with di-tertiarybutyl dicarbonate to give Neomycin B with all the six amino groups protected on them. The protected Neomycin was reacted with triisopropyl sulfonyl chloride to afford a compound with a labile functionality on the 5"-OH of the ribose ring of the protected compound. Nucleophilic substitution of this labile group using NaN$_3$ afforded the azido ended protected Neomycin. Such azido ended protected Neomcyin can be reacted with excess bis alkyne (1,7 octadiyne in our case) to afford protected Neomycin with alkyne end.

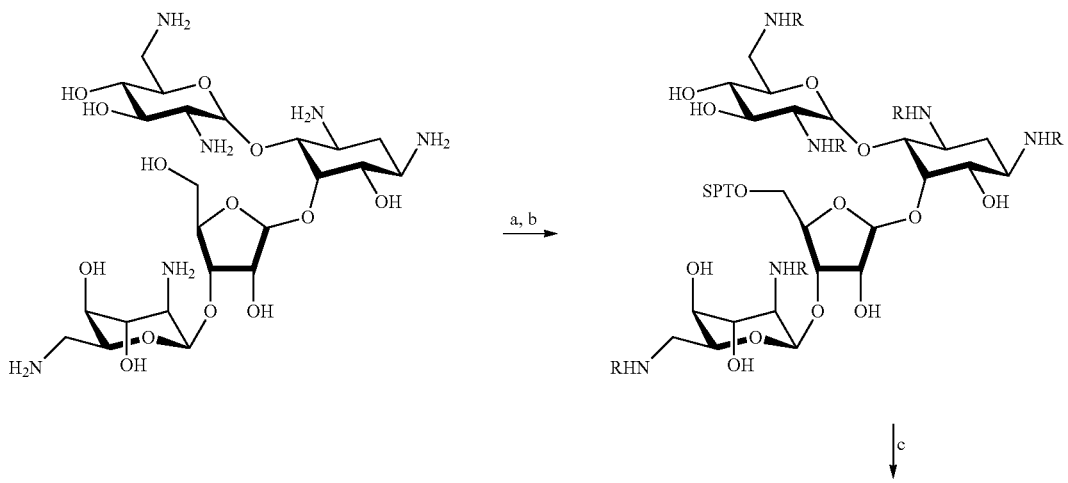

91 92

-continued

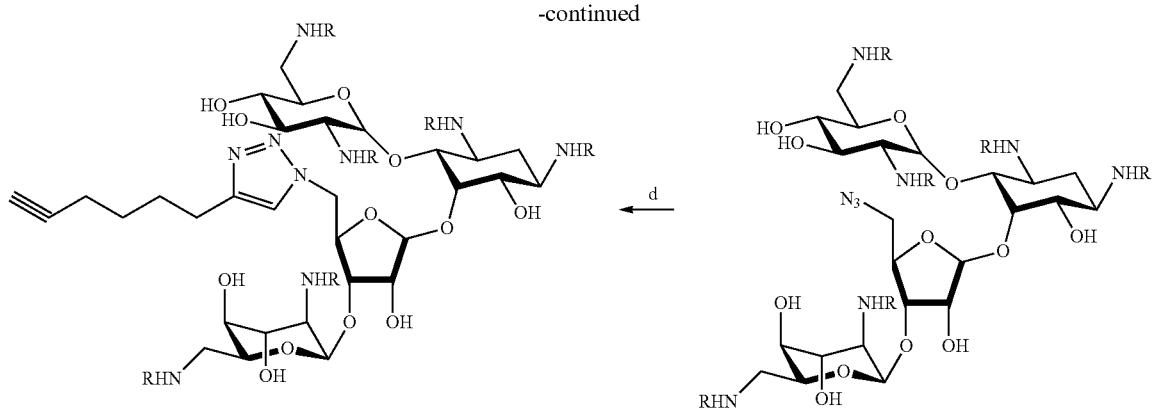

R = Boc

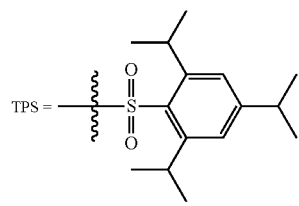

Reagents and Conditions: (a) Boc$_2$O, DMF, Et$_3$N, H$_2$O, 75° C., 18 h, 75% (b) 2,4,6 Triisopropylbenzenesulfonyl chloride, Pyridine, RT, 61% (c) NaN$_3$, DMF:H$_2$O (10:1), 100° C., 90% (d) 1,7 octadiyne, CuSO$_4$, Sodium Ascorbate, H$_2$O, C$_2$H$_5$OH, 90%

Scheme 5:

Synthesis scheme of Protected Neomycin Azide and Alkyne ended precursors for conjugate synthesis.

f) Synthesis of Protected Neomycin-Benzimidazole Conjugates

To synthesize protected Neomycin Benzimidazole compounds, two separate synthetic ways were used. In the first method, the azido ended benzimidazole linkers were reacted with the alkyne ended protected Neomycin under CuSO$_4$, Sodium Ascorbate click chemistry conditions Scheme 6A. In the second method, the alkyne ended benzimidazole was reacted with protected Neomycin Azide to form the desired conjugates (Scheme 6B). The formation of conjugates was monitored used thin layer chromatography. All the crude conjugates thus obtained were subjected to purification using column chromatography on a short path silica gel using dichloromethane-methanol mixture as eluent.

A

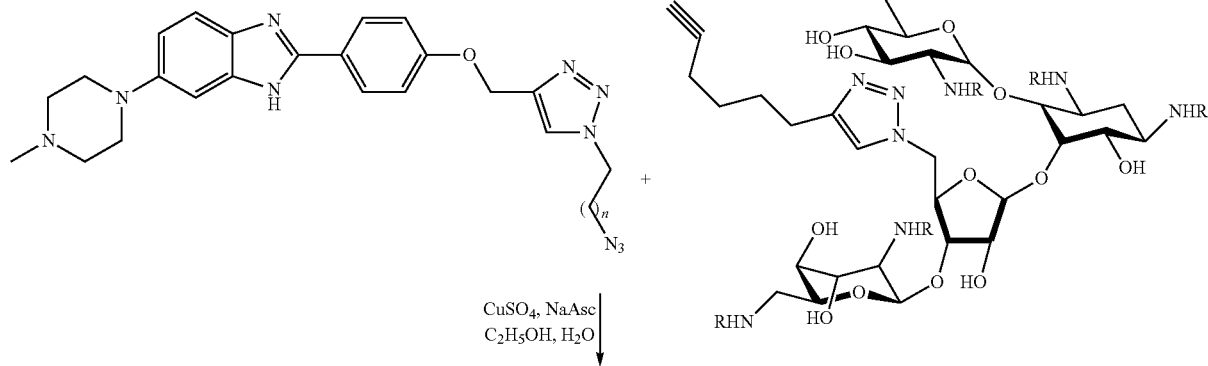

-continued
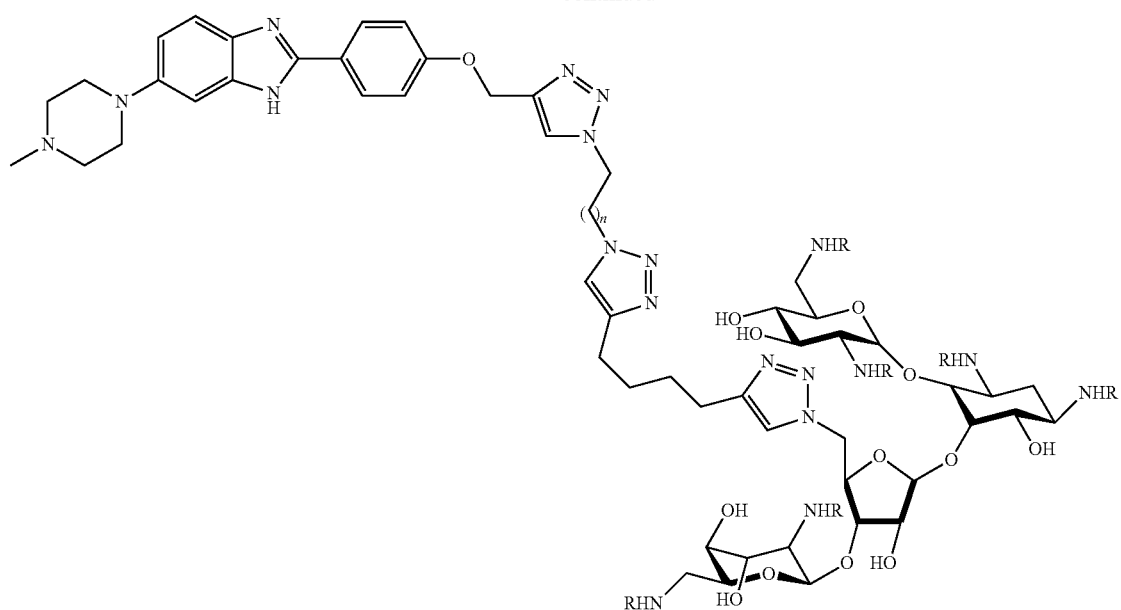
B
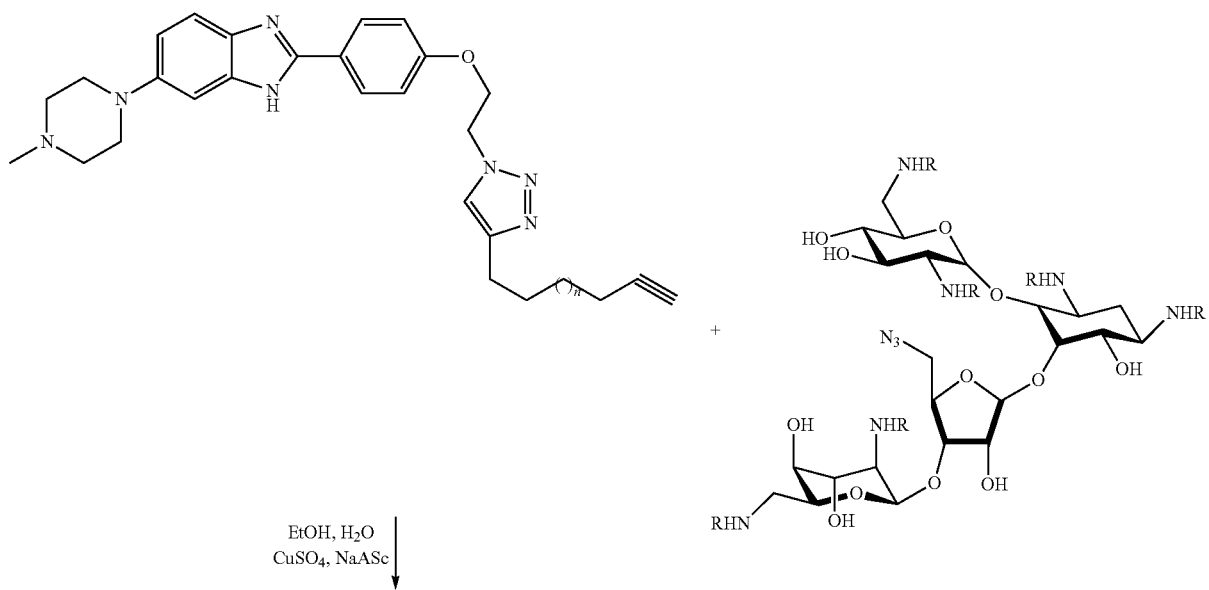
EtOH, H₂O
CuSO₄, NaASc

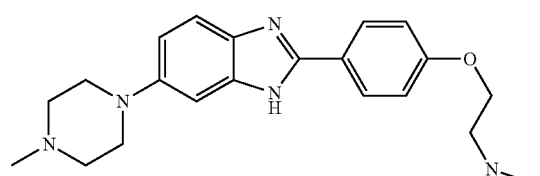
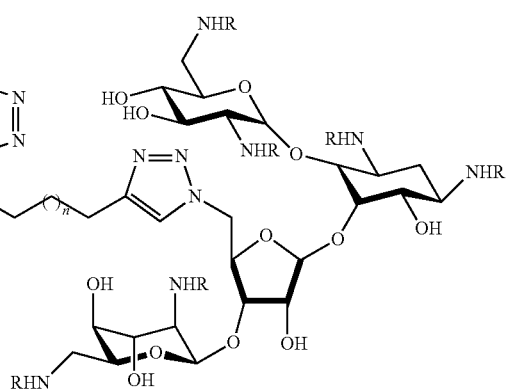

R = Boc

Scheme 6:
Scheme of Synthesis of Protected Neomycin-Benzimidazole Conjugates from A)alkyne B)azido ended benzimidazole linkers.

g) Synthesis of Neomycin-Benzimidazole Conjugates: Deprotection of the Protected Conjugates Protected Neomycin benzimidazole conjugates were dissolved in dioxane at room temperature followed by the addition of 4M HCl in dioxane. The mixture was swirled in hand for 15 mins. Diethyl ether was added and then centrifuged followed by two more additions of ether (2×1 mL). To the precipitated product cold Methanol was added and swirled followed by additions of diethyl ether and Hexane. The supernatant liquid was discarded and the precipitate was dried under reduced pressure to yield the desired compound as yellowish white solid (75-98% yield).

A

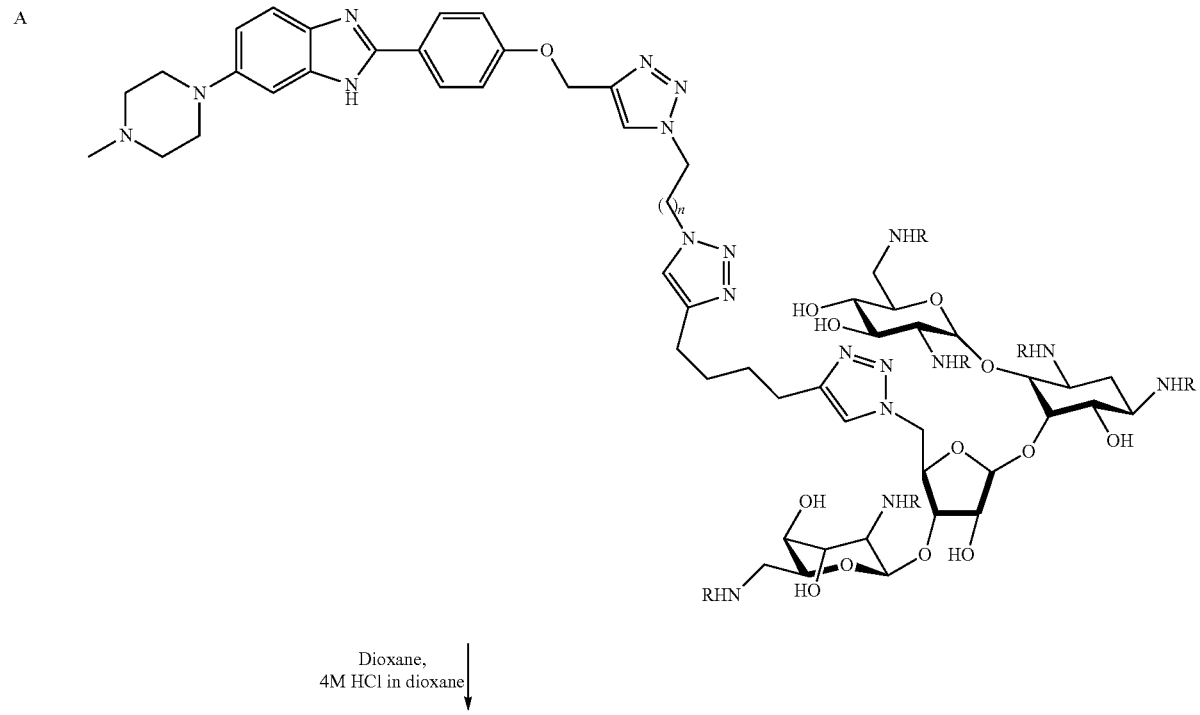

Dioxane,
4M HCl in dioxane

-continued
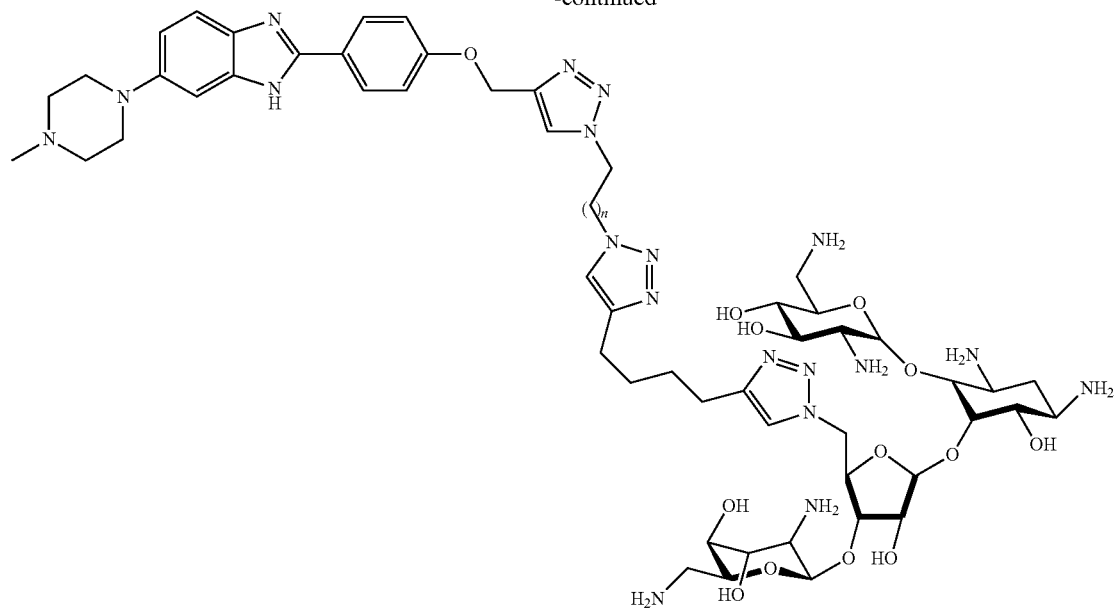
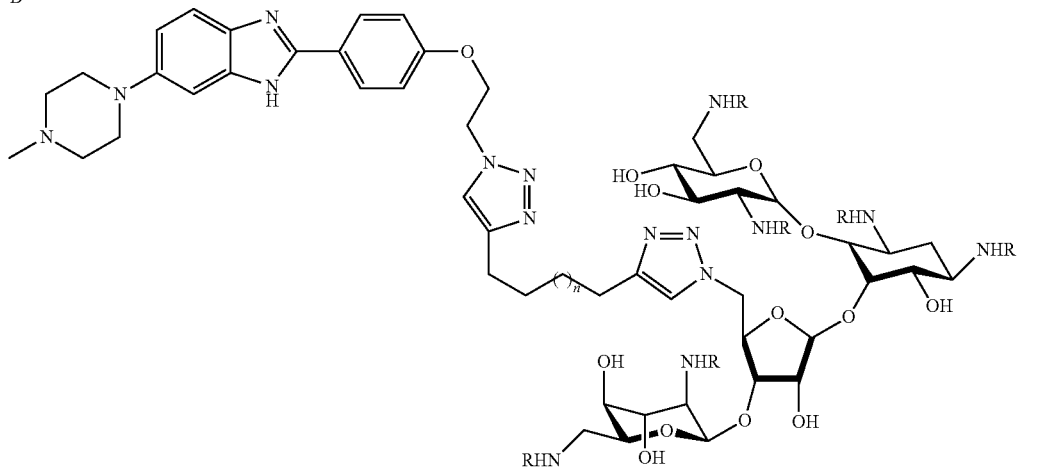
Dioxane,
4M HCl in dioxane
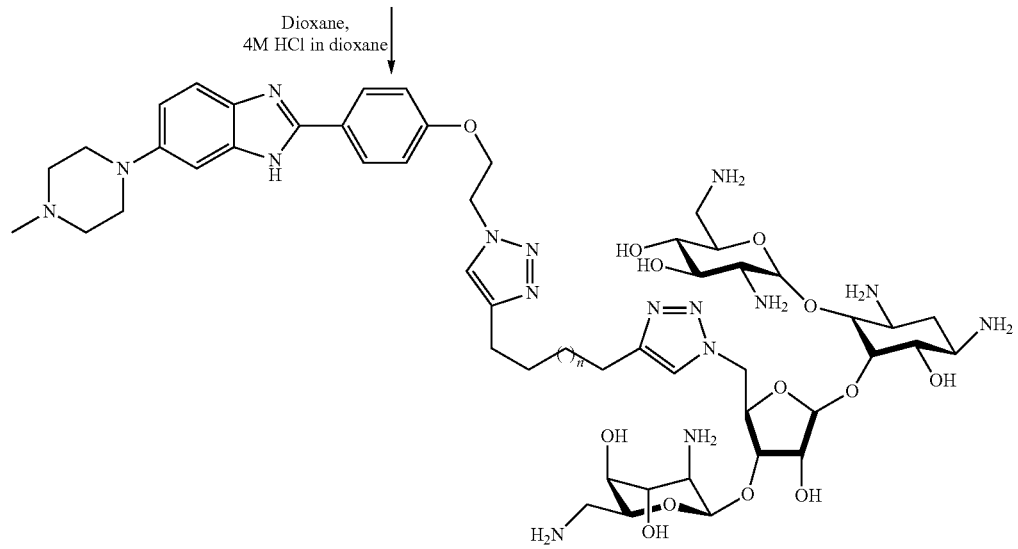
R = Boc Scheme 7:

Scheme of Synthesis of Neomycin-Benzimidazole Conjugates from their corresponding protected conjugates.

Tables 1 and 2 (this refers to the table that lists the neo-benz and neo-hoescht compounds) displays the list of conjugates made.

h) Synthesis of Alkyne Ended Hoechst 33258 Linkers

To synthesize alkyne ended Hoechst 33258 ligands, 3,4 dinitro Benzoic acid was converted to its wienreb amide Scheme 8 (Condition A). The wienreb amide was reduced to afford the diamine 2 which was condensed with an aldehyde with appropriate alkyne linker spacing to give benzimidazoles 4a,4b. The benzimidazoles were then reduced in the presence of metal hydride to give 6a,6b which bear aldehyde functionalities on them. These aldehydes were condensed with diamine 5b to give the desired clickable Hoechst 33258 ligands.

Reagents and Conditions: A) (i) SOCl$_2$, Reflux (ii) CH$_3$ONHCH$_3$.HCl, Pyridine, DCM B) Pd—C, H$_2$, EtOH C) Na$_2$S$_2$O$_5$, H$_2$O, C$_2$H$_5$OH, Reflux D) LiAlH$_4$, THF/Ether E) (i) N-Methyl piperazine, K$_2$CO$_3$, DMF, 80° C. (ii) Pd—C, H$_2$, C$_2$H$_5$OH Scheme 8:

Synthesis scheme of alkyne ended Hoechst 33258 ligands for conjugation to Neomycin.

i) Synthesis of Neomycin-Hoechst Conjugates

The alkyne ended Hoechst alkyne was reacted with protected Neomcyin Azide under click chemistry conditions as given in Scheme 9. The protected Neomycin conjugates obtained were then subjected to column chromatography purification. The purified protected Neomycin-Hoechst conjugate was dissolved in dioxane and deprotected under acidic conditions to afford the desired conjugates DPA165 and DPA166 (Tables 1 and 2).

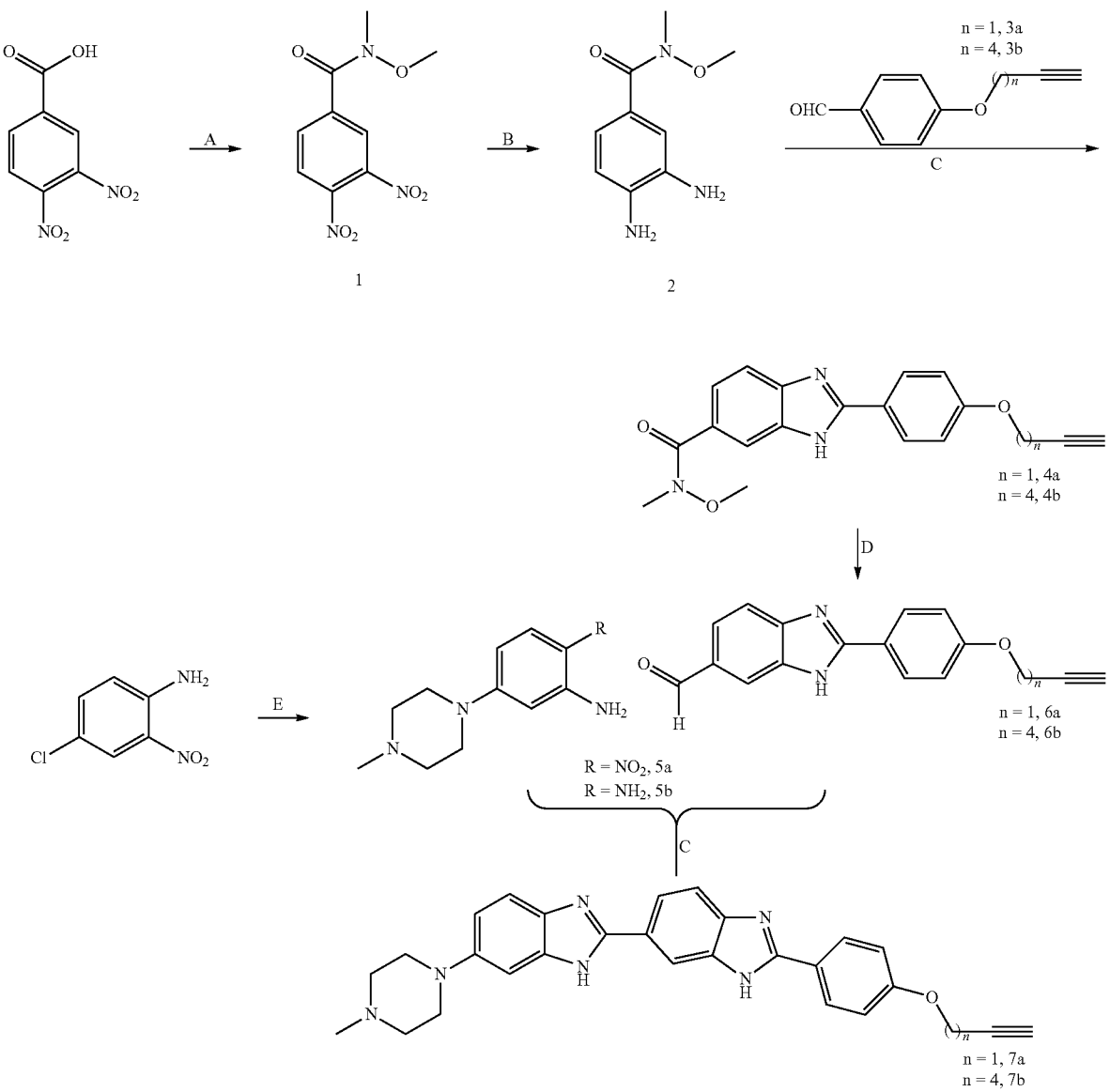

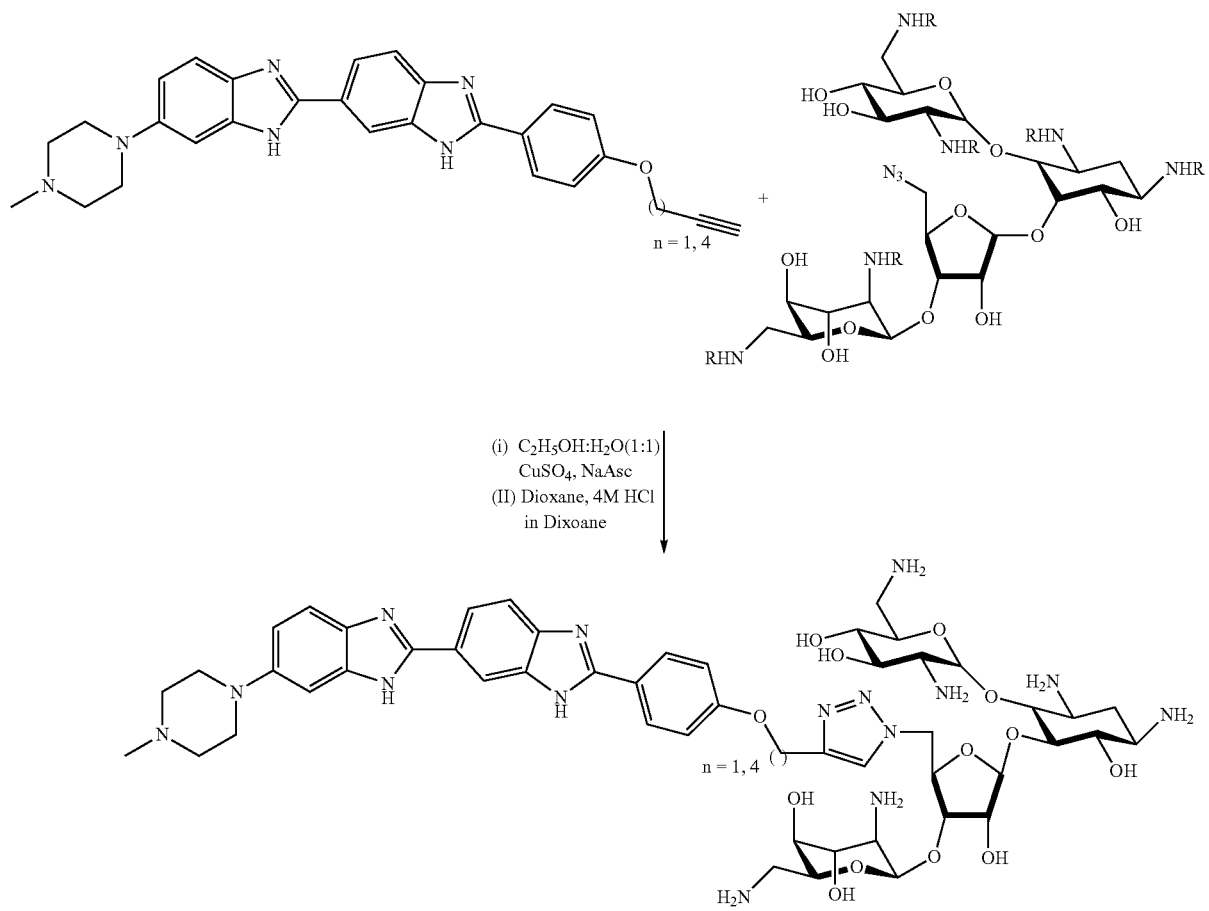

Scheme 9:
Synthesis of Neomycin-Hoechst conjugates using click chemistry j) Characterization Data of Deprotected Neomycin-Benzimidazole Conjugates The Neomycin-Benzimidamzole conjugates were characterized by NMR. All chemical shifts (δ) are reported in ppm.

DPA102:
1HNMR (Acetone-d6, 300 MHz): δ 8.15-8.13 (d, 2H, J=8.8 Hz), 7.87 (s1, 1H), 7.45 (br, 1H), 7.14-7.12 (d, 2H, 1H), 7.05 (br, 1H), 6.99-6.96 (dd, 1H, J1=8.6 Hz, J2=2.2 Hz), 4.34-4.33 (t, 2H, J=4.8 Hz), 3.74-3.72 (t, 2H, J=4.8 Hz), 2.55-2.53 (t, 4H, 4.7 Hz), 2.29 (s, 3H).

DPA 110:
1HNMR (Acetone-d6, 300 MHz): δ 8.15-8.12 (d2H, J=8.7 Hz), 7.87 (s1, 1H), 7.46-7.43 (d, 1H, J=8.7 Hz), 7.08-7.05 (br, 3H), 6.97-6.94 (dd, 1H, J1=8.7 Hz, J2=1.9 Hz), 4.84-4.81 (t, 2H, J=5.1 Hz), 4.54-4.51 (t, 2H, J=5.1 Hz), 3.20 (br, 4H), 2.82-2.77 (t, 2H, 7.0 Hz), 2.66 (br, 4H), 2.38-2.37 (4H), 2.27-2.22 (m, 2H), 1.91-1.82 (m, 2H)

DPA111:
1HNMR (Acetone-d6, 300 MHz): δ 8.13-8.10 (d, 2H, J=8.8 Hz), 7.84 (s1, 1H), 7.45-7.43 (d, 1H, J=8.7 Hz), 7.09-7.05 (br, 3H), 6.98-6.94 (dd, 1H, J1=8.7 Hz, J2=2.2 Hz), 4.84-4.81 (t, 2H, J=5.1 Hz), 4.55-4.52 (t, 2H, J=5.1 Hz), 3.20 3.17 (t, 4H, J=4.4 Hz), 2.73-2.68 (t, 2H, 7.0 Hz), 2.63-2.59 (br, 4H, 4.4 Hz), 2.34-2.33 (4H), 2.24-2.19 (m, 2H), 1.83-1.72 (m, 2H), 1.61-1.52 (m, 2H)

DPA 113
1HNMR (D2O, 300 MHz): δ 8.68 (1H), 8.53 (1H), 8.02-7.70 (3H), 7.59-7.38 (1H), 7.22-6.93 (4H), 5.97 (1H), 5.33 (1H), 5.21 (1H), 5.11 (1H), 4.84 (1H), 4.46 (1H), 4.24 (1H), 4.17-4.08 (2H), 4.07-3.82 (4H), 3.80-3.69 (3H), 3.66-3.01 (26H), 2.88 (3H), 2.83-2.69 (2H), 2.56-2.45 (2H), 2.43-2.32 (2H), 2.03-1.84 (2H), 1.82-1.63 (2H), 1.29-1.21 (2H).

DPA 115
1HNMR (D2O, 300 MHz): δ 8.58 (1H), 8.10 (1H), 7.92-7.64 (2H), 7.58-7.44 (1H), 7.37 (1H), 7.29-7.00 (4H), 5.97 (1H), 5.39-5.08 (3H), 4.55-4.37 (1H), 4.35-4.18 (1H), 4.16-3.68 (7H), 3.66-2.93 (16H), 2.91 (3H), 2.49-2.33 (1H), 1.92-1.32 (5H), 1.23-0.65 (9H)

DPA117
1HNMR (D2O, 300 MHz): δ 8.61 (1H), 8.44 (1H), 8.00 (1H), 7.83-7.72 (2H), 7.69-7.62 (1H), 7.60-7.48 (1H), 7.21-7.08 (4H), 5.99 (1H), 5.34 (1H), 5.12 (1H), 4.89-4.80 (1H), 4.73-4.52 (3H), 4.50-4.43 (1H), 4.41-4.34 (1H), 4.32-4.20 (4H), 4.18-4.01 (5H), 3.98-3.82 (6H), 3.79-3.67 (4H), 3.39-3.22 (8H), 3.20-2.96 (9H), 2.97-2.81 (7H), 2.80-2.69 (2H), 2.68-2.48 (3H), 2.46-2.33 (2H), 1.98 (1H), 1.95-1.74 (4H), 1.73-1.30 (8H), 1.29-1.03 (9H), 1.01-0.67 (14H)

DPA 118
1HNMR (D2O, 300 MHz): δ δ 8.28 (1H), 8.10 (1H), 7.74-7.48 (5H), 7.380-7.25 (2H), 7.14-6.79 (4H), 5.90-6.67 (1H), 5.42-5.17 (1H). 4.32-4.01 (3H), 3.93-3.39 (9H), 3.34-2.96 (13H), 2.91-2.47 (7H), 2.40-2.31 (2H), 1.95-1.72 (1H) 1.36-0.98 (4H)

DPA 119

1HNMR (D2O, 300 MHz): δ 8.09 (1H), 7.90 (1H), 7.69-7.66 (2H), 7.53-7.42 (1H), 7.22-7.08 (2H), 6.99-6.87 (2H), 5.82-5.81 (1H), 5.37-5.06 (3H), 4.60-4.31 (5H), 4.29-4.02 (6H), 3.99-3.81 (6H), 3.80-3.68 (5H), 3.65-3.22 (23H), 3.20-3.01 (16H), 3.00-2.80 (6H), 2.46-2.35 (2H), 1.96-1.74 (2H), 1.16-1.03 (2H)

DPA 122

1HNMR (D2O, 300 MHz): δ 8.16-7.19 (1H), 7.89-7.78 (1H), 7.76-7.59 (2H), 7.56-7.43 (1H), 7.22-7.05 (2H), 7.03-8.81 (2H), 6.06-5.92 (1H), 5.41-5.31 (1H), 5.29-5.19 (1H), 4.63-4.33 (1H), 4.31-4.18 (1H), 4.17-4.01 (2H), 3.98-3.80 (4H), 3.79-2.93 (25H), 2.92-2.79 (3H), 2.74-2.20 (5H), 1.96-1.74 (1H), 1.60-1.26 (4H), 1.24-0.94 (6H).

DPA 123

1HNMR (D2O, 300 MHz): δ 8.26 (1H), 7.87 (2H)), 7.55 (1H), 7.20 (4H), 6.03 (1H), 5.37 (1H), 5.30-5.17 (3H), 4.98-4.57 (3H), 4.51 (2H), 4.24 (2H), 4.13 (2H), 3.97-3.91 (5H), 3.86-3.70 (4H), 3.69-68 (2H), 3.66-3.25 (15H), 3.20-3.08 (5H), 2.87 (3H), 2.41 (1H), 1.85 (1H), 1.05 (3H).

k) Percent Yield of DPA113-DPA123

Disclosed in Table 5 are the percent yields for some of the disclosed neomycin-benzimidazole conjugates. The yields shown are cumulative yields of coupling and deprotections steps.

| Name | Linker Length | Isolated % Yield |
|---|---|---|
| DPA113 | 16 | 52 |
| DPA114 | 19 | 55 |
| DPA115 | 20 | 54 |
| DPA116 | 22 | 60 |
| DPA117 | 24 | 56 |
| DPA118 | 12 | 66 |
| DPA119 | 11 | 65 |
| DPA120 | 11 | 62 |
| DPA121 | 12 | 68 |
| DPA122 | 14 | 70 |
| DPA123 | 4 | 62 | l) Mass Spectral Characterization of Protected Neomycin-Benzimidazole Conjugates Table 6 discloses mass spectral characterization data of the protected Neomycin-Benzimidazole conjugates.

| Name | m/z Calcd | m/z observed |
|---|---|---|
| BocDPA113 | 1803.94 | 1814.24 |
| BocDPA115 | 1860.00 | 1882.12 [M + Na]+ |
| BocDPA116 | 1888.03 | 1910.23 [M + Na]+ |
| BocDPA118 | 1742.88 | 1745.16 |
| BocDPA119 | 1710.87 | 1707.05 |
| BocDPA120 | 1708.89 | 1711.92 |
| BocDPA121 | 1722.91 | 1721.71 |
| BocDPA122 | 1750.94 | 1750.64 |
| BocDPA123 | 1585.81 | 1585.19 | m) Characterization of Neomycin-Hoechst 33258 Conjugates

(1) Compound 1

A solution of 3, 4-dinitrobenzoic acid (1.00 g, 4.71 mmol) in thionyl chloride (3.0 mL) was heated at 80° C. under nitrogen atmosphere for 5 h. Thionyl chloride was the removed under reduced pressure. Co-evaporations with dry toluene were done to ensure complete removal of Thionyl chloride. It was then dissolved in dry DCM and placed in an ice bath. To this, an ice cold solution of dimethylhydroxylamine hydrochloride (0.57 g, 5.86 mmol) in dry $CH_2Cl_2$ (5.0 mL), dry Pyridine (1.0 mL) was added and the mixture was shaken at 0° C. for 15 mins. The mixture was then stirred overnight at room temperature under nitrogen and then diluted with $CH_2Cl_2$ and washed with $H_2O$ and brine. It was then extracted with dichloromethane (3×50 mL). The organic layers were combined and dried with $Na_2SO_4$. Dichloromethane was removed under vacuo. The yellow residue was then subjected to column chromatography on silica gel in EtOAc:Hexane (2:1-1:1) to afford pure compound as pale Yellow solid (Yield=90%).

$^1$HNMR (300 MHz, $CDCl_3$): 8.29 (d, 1H, 1.6 Hz), 8.13-8.11 (dd, 1H, $J_1$=9.0 Hz, $J_2$=2.3 Hz), 7.98-7.95 (d, 1H, J=8.3 Hz), 3.59 (s, 3H), δ 3.42 (s, 3H); $^{13}$CMR (75 MHz, $CDCl_3$); δ 164.8, 143.4, 142.2, 139.1, 133.5, 125.5, 124.7, 61.7, 33.1. MS (GC-MS) m/z for $C_9H_9N_3O_6$ [M]+ Calcd. 255.18. found 255.10.

(2) Compound 3a

To a solution of p-hydroxybenzaldehyde (2.0 g, 16.37 mmol) in dry DCM (30 mL) and 1, 4 dioxane (5 mL), Triphenyl phosphine (6.3 g, 24.2 mmol) was dissolved and the solution was ice cooled. To this, diisopropyl azodicarboxylate, DIAD, (4.8 mL, 24.2 mmol) was added drop wise over a period of 15 min at 0° C. The contents were initially stirred at 0° C. for 30 min and then at room temperature overnight. Progress of the reaction was monitored by thin layer chromatography. The solvents were removed under reduced pressure. Column chromatography on silica gel (Hexane-EtOAc, 100:0-70) afforded the desired compound as white solid (Yield=50%).

$^1$HNMR (500 MHz, $CDCl_3$): δ 9.91 (s, 1H), 7.88-7.86 (dd, 2H, $J_1$=8.82 Hz, $J_2$=1.94 Hz), 7.11-7.09 (dd, 2H, $J_1$=8.74 Hz, $J_2$=1.7 Hz), 4.80-4.95 (d, 2H, J=2.36 Hz), 2.60-2.59 (t, 1H, J=2.43 Hz). $^{13}$CMR (125 MHz, $CDCl_3$): δ 190.75, 162.38, 131.89, 130.62, 115.19, 77.87, 76.38, 55.96. MS (GC-MS) m/z for $C_{10}H_8O_2$ [M]+ Calcd. 160.05. found 160.15.

(3) Compound 3

To a solution of p-hydroxy benzaldehyde (1 g, 8.18 mmol) in dry dichloromethane (15 mL) and dioxane (5 mL), 5-Hexyn-1-ol (0.80 g, 8.18 mmol) and triphenyl phosphine (3.17 g, 12.1 mmol) were added. This reaction mixture was ice cooled. To this DIAD (2.4 mL, 12.1 mmol) was added dropwise. The reaction mixture was stirred at 0° C. for 1 h and then it was stirred at room temperature was 6 h. TLC showed complete consumption of the starting material. Solvent was evaporated and the crude mixture was loaded on a silica gel column and eluted with Hexane-Ethyl Acetate (0-25%) to yield the pure compound as yellow oil (Yield=85%).

$^1$HNMR (300 MHz, $CDCl_3$): δ 9.881 (s, 1H), 7.84-7.81 (dd, 2H, $J_1$=8.82 Hz, $J_2$=1.98 Hz), 7.01-6.98 (dd, 2H, $J_1$=8.71 Hz, $J_2$=1.75 Hz), 4.10-4.06 (d, 2H, J=6.25 Hz), 2.32-2.27 (m, 2H), 2.00-1.91 (m, 3H), 1.79-1.69 (m, 2H). $^{13}$CMR (125 MHz, $CDCl_3$): δ 190.78, 164.06, 131.98, 130.66, 114.73, 84.82, 68.85, 67.70, 28.04, 24.89, 18.11. MS (GC-MS) m/z for $C_{13}H_{14}O_2$ [M]+ Calcd. 202.10. found 202.25.

(4) Compound 4a

To solution of N-Methoxy, N-methyl 3, 4 dinitrobenzamide (500 mg, 1.96 mmol) in ethanol (20 mL), 100 mg of Pd—C (10%) was added. The flask was vacuumed and the atmosphere was made inert inside the reaction vessel. It was then hydrogenated for 5 h to afford compound 2 which was used without purification. 4-(prop-2-ynyloxy)benzaldehyde (313 mg, 1.96 mmol) and sodium pyrosulfite (188 mg, 0.98 mmol) in water (0.8 mL) were added into it and the reaction mixture was refluxed overnight. The catalyst was filtered off through the bed of celite and ethanol was evaporated under reduced pressure. Column chromatography on Silica Gel (DCM-2-Propanol) afforded the desired product as slightly yellow solid (Yield=45%).

$^1$HNMR (500 MHz, DMSO): δ13.1 (s, 1H), 8.16-8.14 (d, 2H, J=8.5 Hz), 7.91-7.79 (1H), 7.67-7.66 (d, 1H, J=8.5 Hz) 7.56-7.54 (d, 1H, J=8.0 Hz), 7.50-7.46 (m, 1H), 7.20-7.17 (dd, 2H, $J_1$=2.5 Hz, $J_2$=9.0 Hz), 4.92-4.91 (d, 2H), 4.36 (d, 1H) 3.58 (s, 3H), 3.35 (s, 3H)
$^{13}$CNMR (125 MHz, DMSO): δ70.15, 159.30, 153.13, 145.94, 137.01, 128.61, 123.09, 119.05, 115.79, 111.0779.02, 62.49, 56.08, 25.96 MS (MALDI-TOF) m/z for $C_{19}H_{17}N_3O_3$ [M]$^+$ Calcd. 335.13. found 336.34.

(5) Compound 4b

To solution of N-Methoxy, N-methyl 3, 4 dinitrobenzamide (1.00 g, 3.91 mmol) in ethanol (30 mL), Pd—C (10%) (100 mg) was added. It was then hydrogenated for 5 h. 4-(hex-5-ynyloxy)benzaldehyde (0.82 g, 4.10 mmol) and sodium pyrosulfite (389 mg, 2.05 mmol) in water (0.5 mL) was added into it and the reaction mixture was refluxed for 20 h. The catalyst was filtered off through the bed of celite and ethanol was evaporated under reduced pressure. Column chromatography on Silica Gel (DCM-2-Propanol 99:1-93:7) afforded the desired product as pale brown oil (Yield=74%, R=0.75 in DCM-2-Propanol 90:10).

$^1$HNMR (300 MHz, in DMSO): δ 8.15-8.12 (d, br, 2H, J=13.78 Hz), 7.93-7.80 (d, 1H, J=13.78 Hz), 7.68-7.56 (dd, 1H, $J_1$=8.27 Hz, $J_2$=8.36 Hz), 7.50-7.47 (d, 1H, J=8.62 Hz), 7.13-7.10 (d, br, 2H, J=8.87 Hz), 4.09-4.05 (t, 2H, J=4.64 Hz), 3.57 (s, 3H), 3.30 (s, 3H), 2.80-2.79 (t, 1H, J=2.64 Hz), 2.28-2.22 (m, 2H), 1.88-1.79 (m, 2H), 1.67-1.57 (m, 2H)
$^{13}$CNMR (75 MHz, in DMSO): δ 170.2, 160.7, 158.8, 146.0, 137.0, 134.8, 128.7, 123.0, 119.0, 115.3, 111.8, 84.7, 71.8, 67.6, 60.9, 34.1, 28.2, 25.0, 21.1, 17.9.
MS (MALDI-TOF) m/z for $C_{22}H_{23}N_3O_3$ [M]$^+$ Calcd. 377.17. found 336.34.

(6) Compound 5a

To a solution of 5-chloro-2-nitro-aniline (5.0 gm, 28.9 mmol) in DMF (16.0 mL), N-methyl piperazine 4800 mL, 44.7 mmol) and $K_2CO_3$ (6.0 gm, 44.7 mmol) was added and the mixture was heated at 110° C. for 5 h. It was then brought to room temperature. DMF was removed under reduced pressure. Water (100 mL) was then added to the yellow residue obtained. It was then extracted with ethyl acetate (3×100 mL). Organic layers were then collected together and dried over sodium sulfate. Solvent was then removed under reduced pressure. The yellow residue was obtained. It was then recrystallized in ethyl acetate to afford the pure compound as yellow solid. (Yield=55%)

$^1$HNMR (500 MHz, CDCl$_3$): δ 8.01-7.99 (d, 1H, J=9.68 Hz), 6.29-6.26 (dd, 1H, $J_1$=9.73 Hz, $J_2$=2.63 Hz), 6.21 (br, 2H), 5.97-5.96 (d, 1H, J=2.60 Hz), 3.38-3.36 (t, 4H, J=5.14 Hz), 2.53-2.50 (t, 4H, J=5.10 Hz), 2.34 (s, 3H). $^{13}$CNMR (125 MHz, CDCl$_3$): δ 155.50, 147.19, 128.19, 127.92, 124.70, 105.69, 98.31, 54.57, 46.81, 46.07. MS (GC-MS) m/z for $C_{11}H_{16}N_4O_2$ [M]$^+$ Calcd. 236.13. found 236.15.

(7) Compound 6a

To a stirred suspension of 4a (300 mg, 0.89 mmol) in THF-Ether (40 mL, 3:1), Lithium aluminum hydride (136 mg, 3.57 mmol) was added into portions at −70° C. under Argon and then the stirring was continued for 14 hrs at a 0° C. TLC used to monitor the progress of the reaction. The reaction mixture was quenched by the addition of saturated ammonium chloride solution (50 mL). It was then extracted with ethyl acetate (3×50 mL). Organic layers were combined and then dried over sodium sulfate. Solvent was removed under reduced pressure. Column Chromatography in Ethyl Acetate:Hexane (1:1-2:1) yielded the pure compound as a light yellow solid (Yield=73%).

$^1$HNMR (in DMSO, 500 MHz): δ 13.25 (s, br, 1H), 10.05 (s, 1H), 8.19-8.17 (d, 2H, J=8.50 Hz), 8.10 (br, 1H), 7.77 (br, 1H) 7.68 (br, 1H) 7.21-7.19 (d, 2H, J=9.0 Hz), 4.93-4.92 (t, 2H, J=2.0 Hz), 3.65 (s, 1H). $^{13}$CNMR (in DMSO, 125 MHz): 193, 60.22, 56.12. MS (MALDI-TOF) m/z for $C_{17}H_{12}N_2O_2$ [M]$^+$ Calcd. 276.09. found 278.27 [M+2H]$^+$.

(8) Compound 6b

To a stirred suspension of 2-(4-(hex-5-ynyloxy)phenyl)-N-methoxy-N-methyl-3H-benzoimidazole-5-carboxamide (771 mg, 2.04 mmol) in dry THF (40 mL), Lithium aluminum hydride (310.27 mg, 8.17 mmol) was added in small portions at −70° C. under Argon and then the stirring was continued for 12 hrs at a 0° C. TLC used monitor the progress of the reaction. The reaction mixture was quenched by the addition of saturated ammonium chloride solution (100 mL). It was then extracted with ethyl acetate (3×100 mL). Organic layers were combined and then dried over sodium sulfate. Solvent was removed under reduced pressure. Column Chromatography in Ethyl Acetate:Hexane (1:1-2:1) afforded the pure compound as light yellow liquid was obtained as (Yield=72%, R$_f$=0.66 in EtOAc:Hexane 60:40).

$^1$HNMR (in MeOD, 300 MHz): δ 9.89 (s, 1H), 7.96 (br, 1H) 7.89-7.86 (dd, 2H, $J_1$=8.89 Hz, $J_2$=2.01 Hz), 7.71-7.68 (dd, 1H, $J_1$=9.8 Hz, $J_2$=1.44 Hz), 7.57-7.55 (d, 1H, J=8.32 Hz), 6.93-6.90 (dd, 2H, $J_1$=8.92 Hz, $J_2$=2.02 Hz), 3.93-3.89 (t, 2H, J=5.91 Hz), 2.25-2.20 (m, 3H), 1.88-1.79 (m, 2H), 1.69-0.59 (m, 2H). $^{13}$CNMR (in DMSO, 75 MHz): δ 192.4, 161.5, 131.7, 128.3, 123.7, 121.0, 114.6, 83.3, 68.5, 27.9, 24.8, 17.4 MS (MALDI-TOF) m/z for $C_{20}H_{18}N_2O_2$ [M]$^+$ Calcd. 318.14. found 319.25.

(9) Compound 7a

To a solution of 5-(4-methylpiperazin-1-yl)-2-nitroaniline (65 mg, 0.27 mmol) in Ethanol (8 mL), Pd—C (40 mg) was added and then it was put under a hydrogen balloon for 6 hrs. TLC showed complete reduction of the starting material. To that, 2-(4-(prop-2-ynyloxy) phenyl)-3H-benzoimidazole-5-carbaldehyde (85.5 mg, 0.31 mmol) and a solution of $Na_2S_2O_5$ (30 mg, 0.16 mmol) in water (200 mL) was added and the mixture was refluxed for 14 h. The starting diamine was consumed completely. It was then let to come to the room temperature. Charcoal was filtered over celite and the resulting filtrate was evaporated under reduced pressure.

Column chromatography on silica gel in EtOAc-MeOH (0-30% with drops if TEA) afforded the pure product as yellowish red solid (70 mg).

$^1$HNMR (in MeOD, 300 MHz): δ 8.25 (br, 1H), 8.08-8.05 (d, 2H, J=8.84 Hz), 7.97-7.93 (dd, 1H, $J_1$=9.97 Hz, $J_2$=1.30 Hz), 7.70-7.68 (d, 1H, J=8.32 Hz), 7.53-7.50 (d, 1H, J=8.77 Hz), 7.17-7.14 (3H), 7.07-7.03 (1H), 4.83-4.82 (d, 2H, J=2.29 Hz), 3.26-3.23 (t, 4H, J=4.55 Hz), 3.04-3.03 (t, 1H, J=2.33 Hz), 2.74-2.71 (t, 4H, J=4.64 Hz), 2.42 (s, 3H) MS (MALDI-TOF) m/z for $C_{28}H_{26}N_6O$ [M]$^+$ Calcd. 462.22. found 462.29.

(10) Compound 7b

To a solution of 5-(4-methylpiperazin-1-yl)-2-nitroaniline (237 mg, 1.0 mmol) in Ethanol (40 mL), Pd—C (150 mg) was added and then it was put under a hydrogen balloon for 5 hrs. TLC showed complete reduction of the starting material. To that, 2-(4-(hex-5-ynyloxy)phenyl)-3H-benzoimidazole-5-carbaldehyde (355 mg, 1.1 mmol) and a solution of $Na_2S_2O_5$ (105 mg, 0.55 mmol) in water (0.2 mL) was added and the mixture was refluxed for 23 h. It was then let to come to the room temperature. Charcoal was filtered over celite and the resulting filtrate was evaporated under reduced pressure. Column chromatography on silica gel in EtOAc-MeOH (0-30% with drops if TEA) afforded the pure product as yellowish solid (360 mg, Yield=72%, R=0.15 in EtOAc:MeOH:TEA8:2:10 drops).

$^1$HNMR (in MeOD, 500 MHz): δ 8.21 (s, 1H), 8.01-7.99 (dd, 2H, $J_1$=8.60 Hz, $J_2$=2.06 Hz), 7.93-7.91 (dd, 1H, $J_1$=8.64 Hz, $J_2$=2.02 Hz) 7.67-7.65 (d, 1H, J=8.30 Hz), 7.51-7.50 (d, 1H, J=9.00 Hz), 7.13-7.12 (d, 1H, J=8.80 Hz), 7.05-7.04 (d, 1H, J=8.54 Hz), 7.03-7.01 (dd, dd, 2H, $J_1$=8.84 Hz, $J_2$=2.06 Hz), 4.03-3.99 (t, 2H, J=2.26 Hz), 3.25-3.23 (t, 4H, J=4.62 Hz), 3.21-3.18 (m, br, 2H) 2.76-2.74 (t, 4H, J=4.66 Hz), 2.53 (s, 1H), 2.44 (s, 3H), 2.28-2.24 (m, br, 3H), 2.02 (s, 1H), 1.93-1.86 (m, br, 2H), 1.70-1.77 (m br, 2H), 1.32-1.29 (m 2H). No good carbon spectra obtained. MS (MALDI-TOF) m/z for $C_{31}H_{32}N_6O$ [M]$^+$ Calcd. 504.26. found 504.10.

(11) Synthesis of Boc Protected DPA165

To a solution of compound 7a (12.1 mg, 26.3 mmol) and Neomycin Azide (45 mg, 36.0 mmol) in Ethanol (500 mL), Sodium Ascorbate (2.0 mg, 10.10 mmol) and $CuSO_4$ (1.0 mg, 6.2 mmol) in water (500 mL) was added and the mixture was stirred in dark for 31 h. The volatiles were evaporated under reduced pressure and the resulting residue was loaded on a silica gel column. Elution with EtOAC-MeOH with drops of TEA (2% gradient up to 30% MeOH) yielded the desired compound as pale yellow solid (yield=72%).

$^1$HNMR (in MeOD, 500 MHz): δ 8.31-8.30 (2H), 8.13-8.11 (2H), 8.00-7.98 (1H), 7.74-7.72 (1H), 7.55-7.53 (1H), 7.29-7.28 (2H), 7.17 (1H), 7.09-7.07 (2H), 6.66-6.59 (2H), 5.48-5.46 (1H), 5.40-5.35 (2H), 5.15 (1H), 4.97 (1H), 4.75-4.66 (1H), 4.35-4.34 (1H), 4.29 (1H), 4.22-4.19 (1H), 4.00-3.99 (1H), 3.93 (1H), 3.80-3.78 (2H), 3.70-3.62 (4H), 3.61-3.54 (3H), 3.53-3.51 (1H), 3.48-3.45 (1H), 3.43-3.37 (6H), 3.30-3.24 (6H), 3.23-3.14 (8H), 2.77-2.75 (4H), 2.45 (3H), 1.94-1.93 (3H), 1.50-1.37 (54H), 1.34-1.29 (12H), 1.14-1.09 (3H) MS (MALDI-TOF) m/z for $C_{81}H_{119}N_{15}O_{25}$ [M]$^+$ Calcd. 1701.85. found 1702.60.

(12) Synthesis of Boc Protected DPA166

To a solution of compound 7b (43.2 mg, 85.6 μmol) and Neomycin Azide (123 mg, 100 μmol) in Ethanol (1.0 mL), Sodium Ascorbate (8.0 mg, 40.0 μmol) and $CuSO_4$ (3.0 mg, 18.7 μmol) in water (500 μL) was added and the mixture was stirred in dark for 31 h. The volatiles were evaporated under reduced pressure and the resulting residue was loaded on a silica gel column. Elution with EtOAC-MeOH with drops of TEA (2% gradient up to 30% MeOH) yielded the desired compound as pale yellow solid (yield=57%).

$^1$HNMR (in MeOD, 500 MHz): δ 8.29 (1H), 8.09-8.06 (2H), 8.00-7.97 (2H), 7.72-7.71 (1H), 7.54-7.53 (1H), 7.17 (1H), 7.13-7.08 (3H), 5.44 (1H), 5.19 (1H), 4.98-4.96 (1H), 4.66-4.62 (1H), 4.36-4.35 (1H), 4.30 (1H), 4.15-4.07 (4H), 3.98-3.95 (1H), 3.93 (1H), 3.66-3.62 (2H), 3.59-3.55 (2H), 3.52-3.42 (3H), 3.41-3.35 (6H), 3.29-3.25 (5H), 3.23-3.20 (4H), 2.88-2.85 (2H), 2.78-2.77 (4H), 2.45 (3H), 2.03 (1H), 1.97-1.81 (6H), 1.60-1.45 (54H), 1.34-1.30 (4H), 1.14-1.11 (1H). MS (MALDI-TOF) m/z for $C_{84}H_{125}N_{15}O_{25}$ [M]$^+$ Calcd. 1743.90. found 1743.63.

(13) Synthesis of DPA165

To a solution of Boc-protected Neomycin-Hoechst 33258 Conjugate 1 (20 mg, 11.74 μmol) in Dioxane (500 μL), a solution of 4M HCl in Dioxane (0.9 mL) was added into it dropwise and then the mixture was stirred for 30 minutes at room temperature. Volatiles were removed under reduced pressure. A slight yellow solid (highly hygroscopic) was obtained (yield=90%).

$^1$HNMR (in $D_2O$, 500 MHz): δ 8.29 (1H), 8.02 (1H), 7.88-7.86 (3H), 7.82-7.80 (1H), 7.53-7.51 (1H), 7.20-7.17 (2H), 7.13-7.11 (1H), 7.06 (1H), 6.06-6.05 (1H), 5.38 (1H), 5.24 (1H), 5.21 (1H), 4.88 (1H), 4.84 (1H), 4.81-4.75 (4H), 4.56-4.54 (1H), 4.53-4.50 (1H), 4.27-4.25 (1H), 4.16-4.12 (2H), 4.04-3.81 (5H), 3.79-3.66 (6H), 3.60-3.49 (11H), 3.47-3.37 (3H), 3.36-3.29 (3H), 3.28-3.19 (3H), 3.11-3.05 (5H), 3.02-3.00 (5H), 2.89-2.81 (4H), 2.43-2.40 (1H), 1.92-1.88 (1H).

3. Neomycin-Neomycin Dimer Conjugates and their Synthesis a) Synthesis of Dialkyne Linkers for Click Chemistry of Neomycin Neomycin Dimer's Neomycin-neomycin dimer conjugates are disclosed herein as well as the synthesis of these conjugates via click chemistry. Click chemistry involves both dialkyne and azide linkers. Scheme 10 outlines the synthesis of dialkyne linkers and some of the commercially available dialkyne linkers used for the synthesis of neomycin-neomycin conjugates.

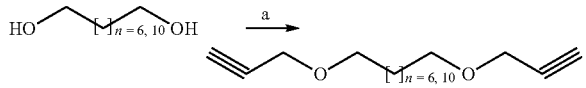

Reagents and conditions: (a) Propargyl bromide in toluene, THF, NaH, 0° C. to r.t. in 30 min., overnight, 30%.
Commercially Available Dialkyne Linkers Used in Neomycin Neomycin Dimer's Synthesis:

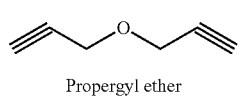

Propergyl ether

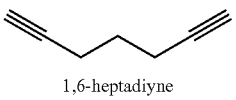

1,6-heptadiyne

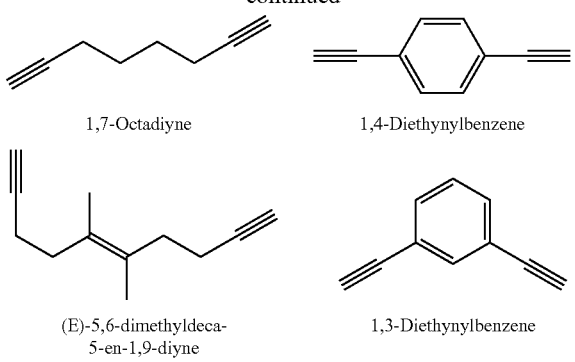

1,7-Octadiyne 1,4-Diethynylbenzene (E)-5,6-dimethyldeca-5-en-1,9-diyne 1,3-Diethynylbenzene Scheme 10:
Synthesis scheme of dialkynes used in the synthesis of Neomycin Neomycin dimer's.

b) Synthesis of Protected Neomycin-5"-Azide

When synthesizing a molecule with more than one functional group, it can be difficult to carry out a reaction with one group without unintentionally interfering or reacting with another group. Protecting groups help avoid unintentional reactions. The protecting group must be removed after the desired reaction is completed.

Disclosed is the synthesis of protected Neomycin with a functional azide group to allow for the future synthesis of neomycin-neomycin conjugates via click chemistry. In Scheme 11, the amine groups are protected while one of the —OH groups is replaced with an azide.

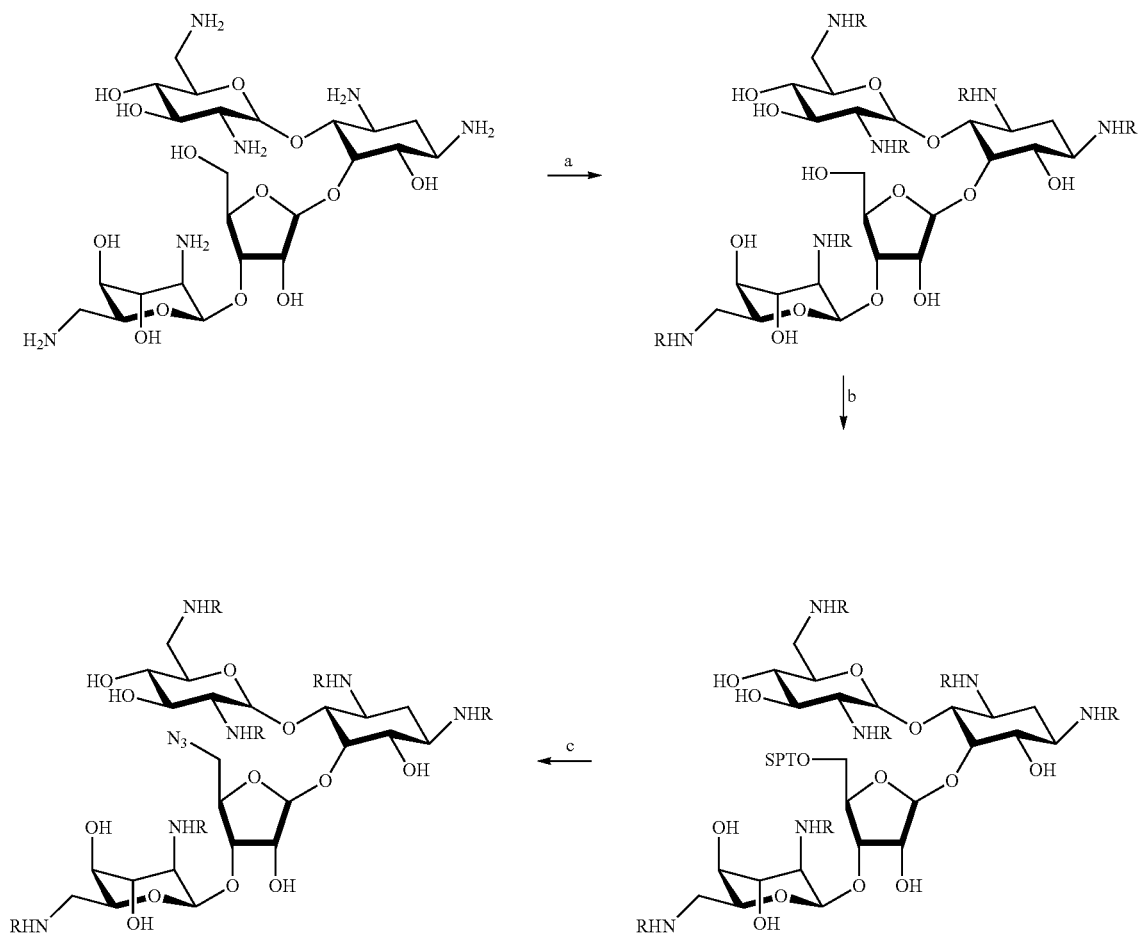

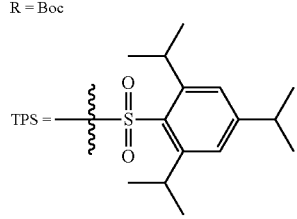

Reagents and Conditions: (a) Boc$_2$O, DMF, Et$_3$N, H$_2$O, 60° C., 12 h, 77% (b) 2,4,6 Triisopropylbenzenesulfonyl chloride, Pyridine, RT, 60% (c) NaN$_3$, DMF:H$_2$O (10:1), 90° C., 16 h, 90%.

Scheme 11:
Synthesis scheme of Protected Neomycin-5″-azide.

c) Synthesis of Protected Neomycin Neomycin Dimer Conjugates

To synthesize protected Neomycin Neomycin dimers, dialkyne linkers (both commercially available and synthesized) can be reacted in 0.5 mole equivalent stoichiometric ratio in the presence of CuI, DIPEA and toluene as shown in scheme 12. All the conjugates can be synthesized by click chemistry followed by purification through column chromatography (0 to 10% Et-OH in DCM).

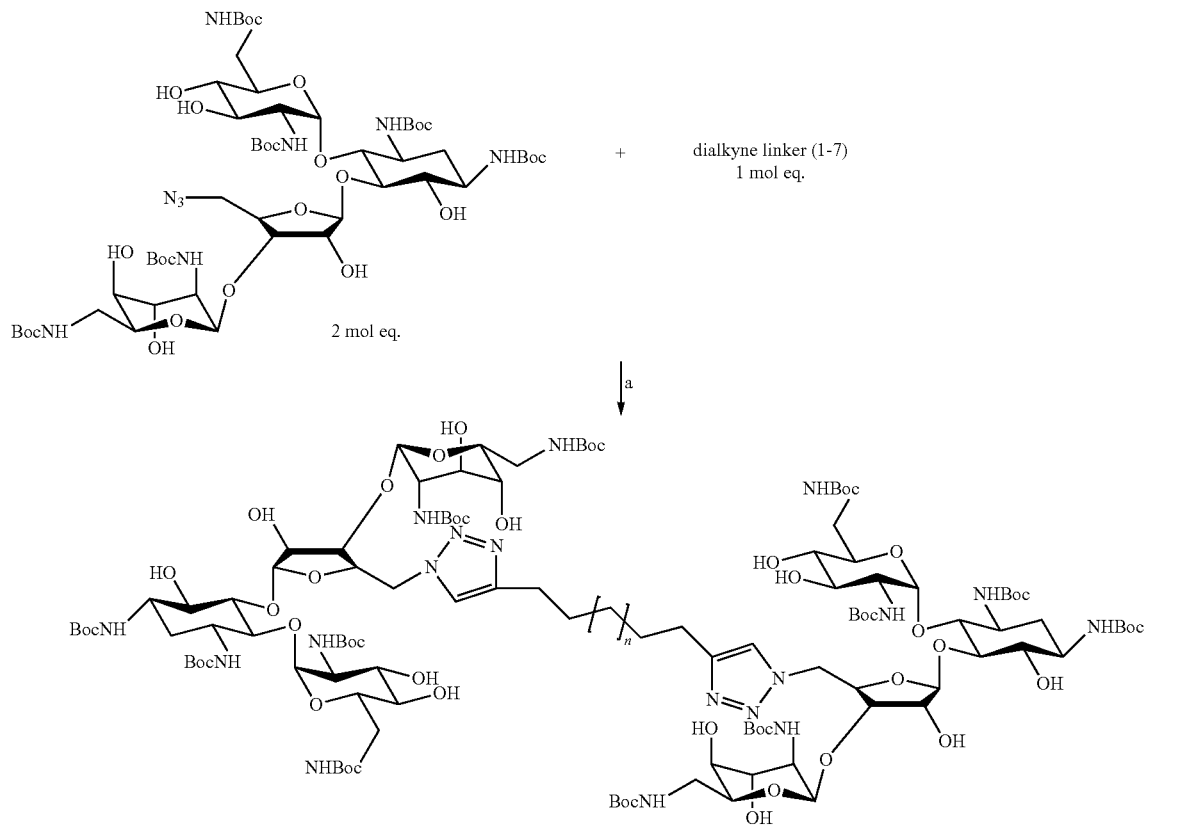

Reagents and conditions: (a) CuI, DIPEA, Toluene, r.t., 18 h.

Scheme 12:
Synthesis of Neomycin Neomycin conjugates by using click chemistry.

d) Synthesis of Neomycin Neomycin Conjugates by Using Thio-Coupling Chemistry

(a) Synthesis of Diisothiocyanate Linker's from Diamine

In one embodiment, the Neomycin-Neomycin dimer conjugates can be synthesized using thio-coupling chemistry. Thio-coupling chemistry can involve the use of diisothiocyanate linkers. Scheme 13 outlines the synthesis of diisothiocyanate linkers from diamine and some of the commercially available diisocyanate linkers used for the synthesis of neomycin-neomycin conjugates.

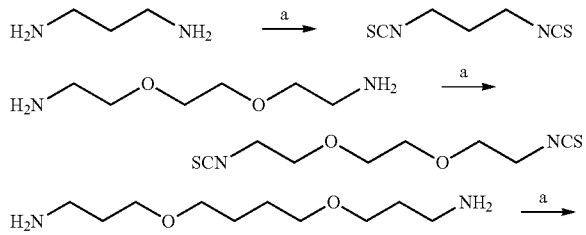

-continued

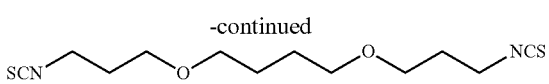

Reagents and conditions: (a) TCDP, DCM, r.t., 4 h.

Commercially Available Diisocyanate:

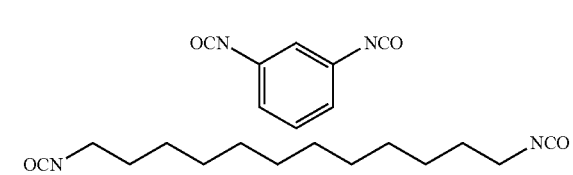

113

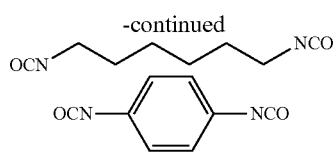

Scheme 13:
Scheme for the synthesis of diisothiocyanates and some commercially available diisocyanate.

114

(b) Synthesis of Protected Neomycin-5''-Amine and Neomycin-5''-Isothiocyanate

Both protected Neomycin-5''-amine and Neomycin-5''-isothiocyanate were synthesized to introduce nucleophilic and electrophilic ends on Neomycin (Scheme 14). Neomycin-5''-amine was synthesized by simply reducing Neomycin-5''-azide on charcoal surface in the atmosphere of $H_2$ gas. Neomycin-5''-amine then reacted with TCDP to introduce the isothiocyanate functional group on the 5''-position.

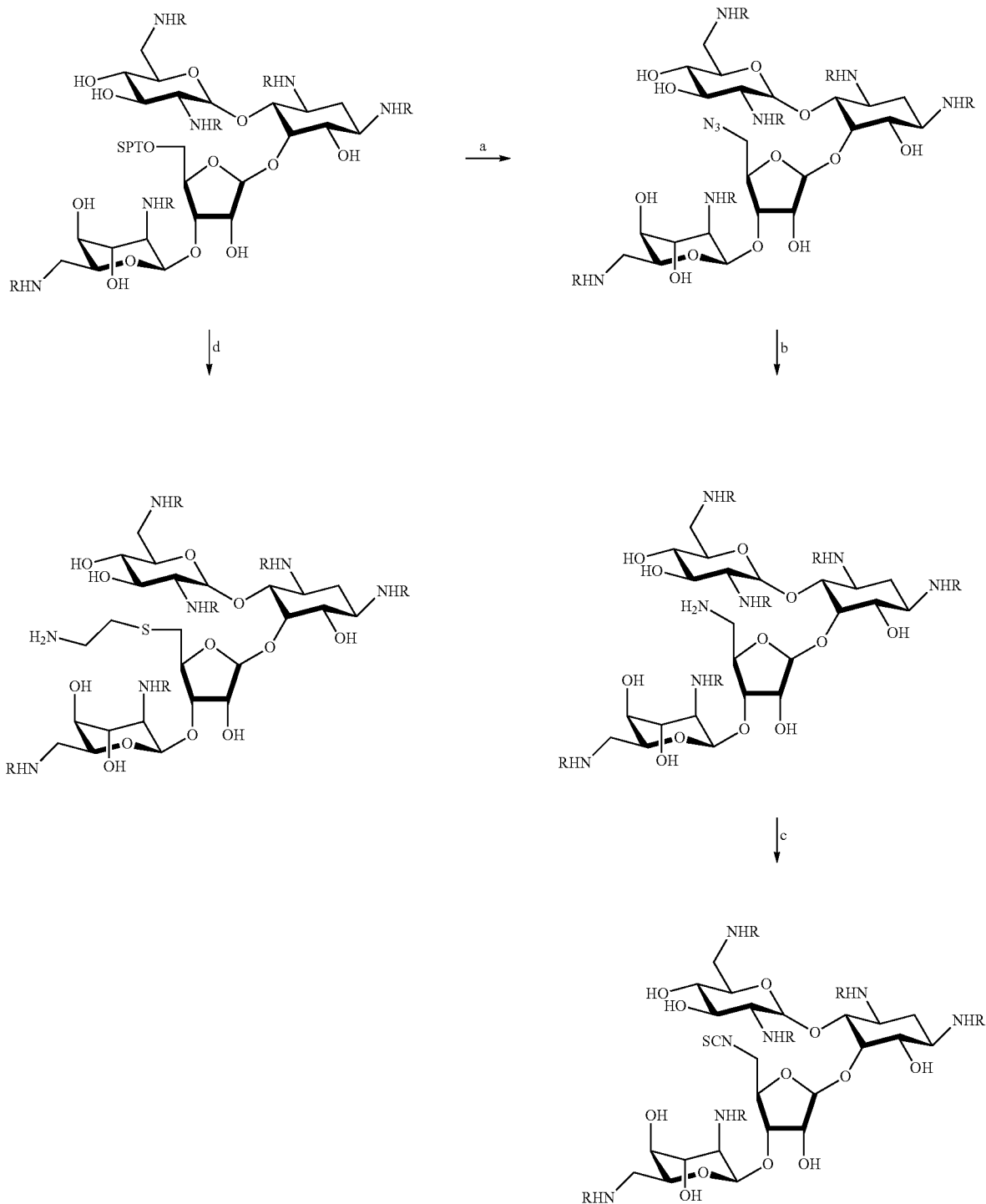

R = Boc

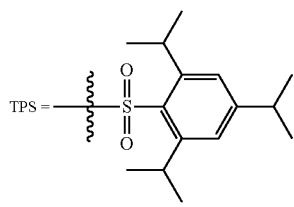

Reagents and Conditions: (a) NaN$_3$, DMF:H$_2$O (10:1), 90° C., 16 h, 90%. (b) Pd/C, H$_2$ gas, 5 h., quantitative. (c) TCDP, DCM, r.t., 4 h., 80%. (d) Na metal, Et-OH, aminothanethio.HCl, 4 h., r.t., 70%.

Scheme 14:
Synthesis of Neomycin-5"-amine and Neomycin-5"-isothiocyanate.

(c) Synthesis of Neomycin Neomycin Dimer Conjugates by Using Thio-Coupling Chemistry Nucleophilic Neomycin-5"-amine reacts with electrophilic diisothiocyanate and form the thio-urea linkage between two neomycin units as shown in Scheme 15. The crude compound is purified by using column chromatography (0 to 10% Et-OH in DCM).

Reagents and Conditions: (a) DMAP, pyridine, r.t., 18 h.

Scheme 15:
Synthesis scheme for Neomycin Neomycin dimers by thio-coupling.

4. Deprotection of Neomycin Neomycin Dimers

Disclosed herein are protected compounds in order to avoid unintentional reactions. Upon completion of the reaction, compounds can be deprotected.

A solution of Neo-Neo dimer was dissolved in dioxane, followed by addition of 4M HCl/dioxane and the reaction was stirred for 15 min. at r.t (Scheme 16). Removal of volatiles on roto-vap resulted in a yellowish powder which on subsequent washing with ether and drying under vacuum, was dissolved in deionized water and lyophilized to afford the compound as a brown solid. As shown in Scheme 16, conjugates made by both click chemistry and thio-coupling chemistry can be deprotected in a similar fashion.

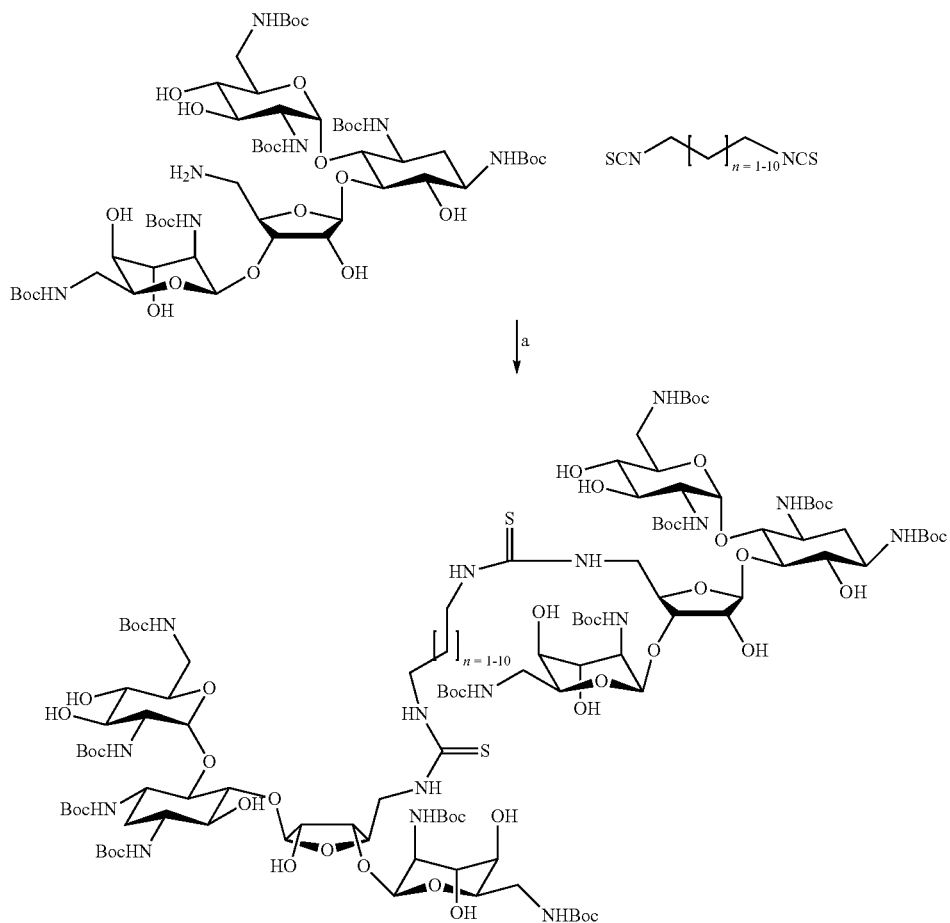

A
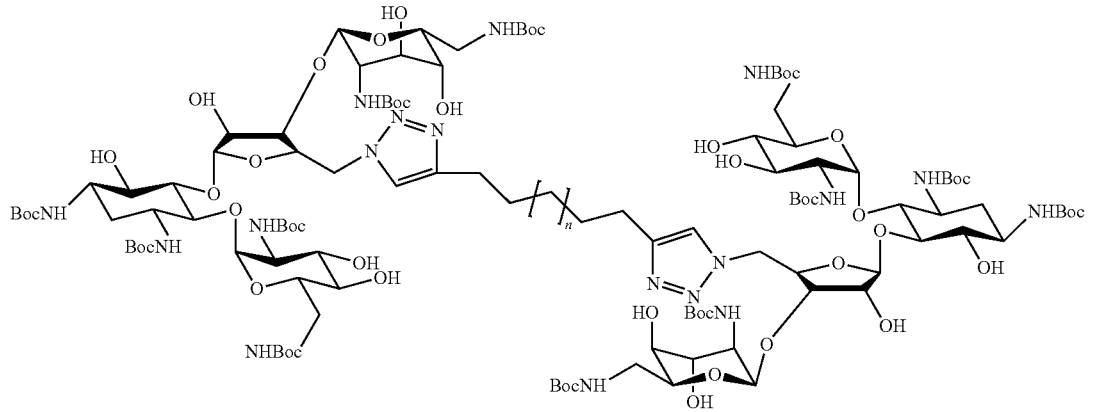
Dioxane, 4M HCl in dioxane, 15 min, r.t.
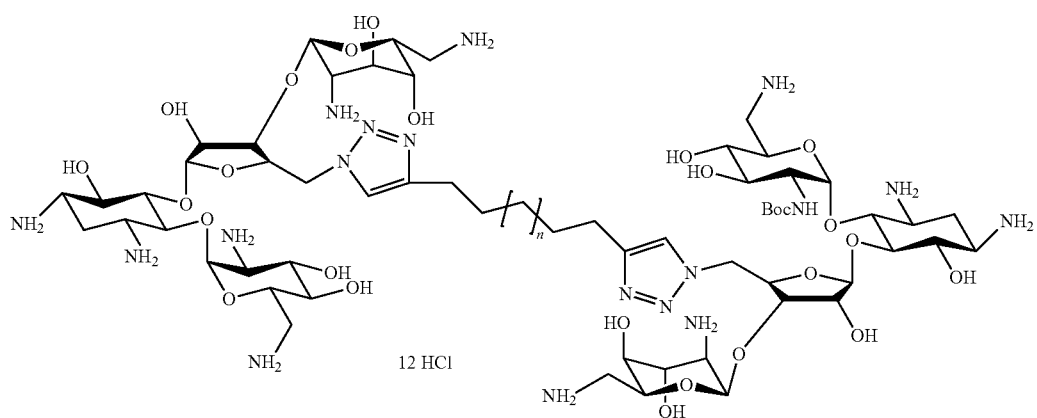
B
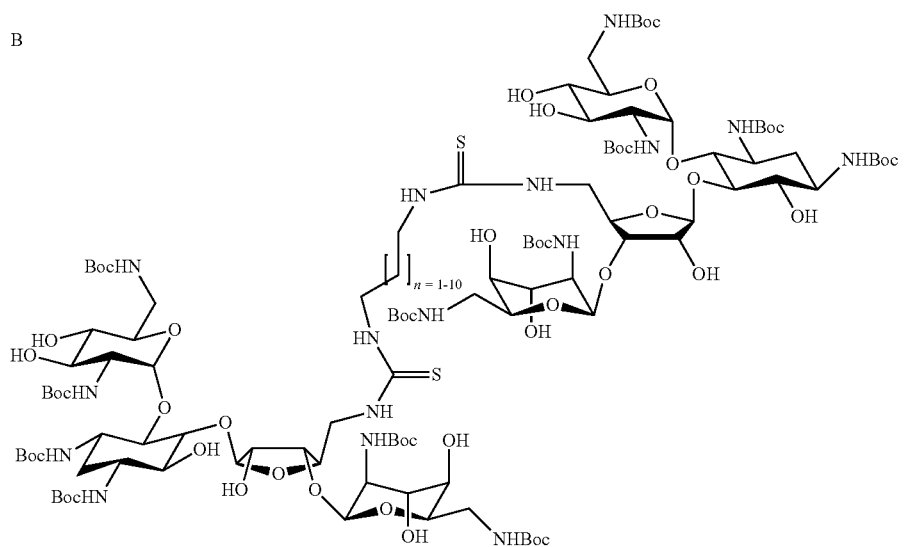
Dioxane, 4M HCl in dioxane, 15 min, r.t.

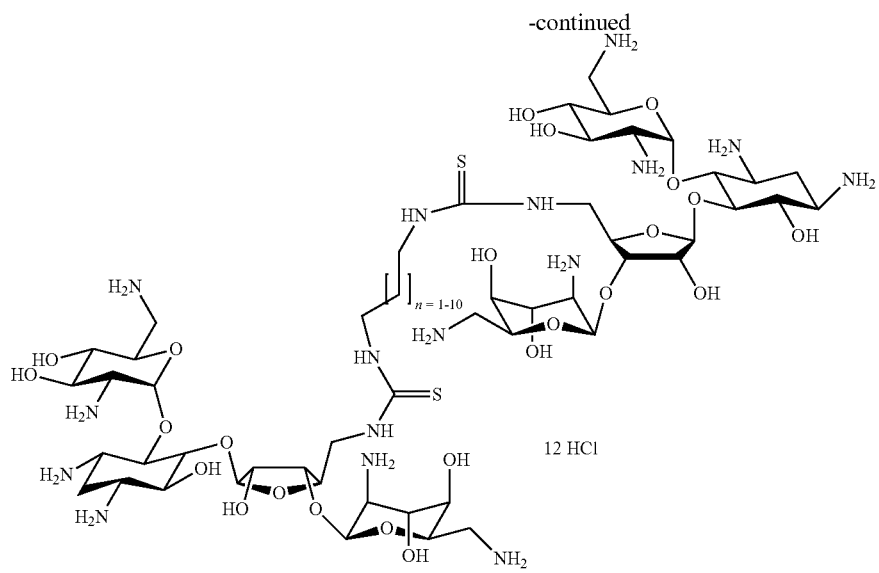

Scheme 16:
Scheme for the deprotection of Neomycin Neomycin dimer conjugates from their protected conjugates.

5. Characterization Data of Deprotected Neomycin Neomycin Dimer Conjugates

The Neomycin Neomycin dimer conjugates were characterized by NMR. All chemical shifts (δ) are reported in ppm.

DPA 51:
$^1$HNMR (300 MHz, D$_2$O, 25° C.): ∂ 7.85 (s, 2H, triazole peak), 5.40 (br, 2H), 5.37 (2H), 5.11 (2H), 4.9 (2H), 4.23 (2H), 4.09 (4H), 3.82 (8H), 3.76 (4H), 3.67 (4H), 3.44-3.56 (12H), 3.34 (4H), 3.0-3.3 (18H), 2.84-2.86 (8H), 2.7 (8H), 2.38 (4H), 2.03 (4H), 1.94 (2H).

DPA 52:
$^1$HNMR (300 MHz, D$_2$O, 25° C.): ∂ 7.83 (s, 2H, triazole peak), 5.40 (br, 2H), 5.37 (2H), 5.11 (2H), 4.9 (2H), 4.23 (2H), 4.09 (4H), 3.82 (8H), 3.76 (4H), 3.67 (4H), 3.44-3.56 (12H), 3.34 (4H), 3.0-3.3 (18H), 2.84-2.86 (8H), 2.7 (8H), 2.38 (4H), 2.03 (4H), 1.94 (2H), 1.78 (4H), DPA 53:
$^1$HNMR (300 MHz, D$_2$O, 25° C.): ∂ 8.50 (s, 2H, triazole peak), 7.95 (s, 4H), 5.40 (br, 2H), 5.37 (2H), 5.11 (2H), 4.9 (2H), 4.23 (2H), 4.09 (4H), 3.82 (8H), 3.76 (4H), 3.67 (4H), 3.44-3.56 (12H), 3.0-3.3 (18H), 2.84-2.86 (8H), 2.7 (8H), 2.38 (4H), 2.03 (4H), 1.94 (2H), DPA 54:
$^1$HNMR (300 MHz, D$_2$O, 25° C.): ∂ 7.75 (s, 2H, triazole peak), 5.40 (br, 2H), 5.37 (2H), 5.11 (2H), 4.9 (2H), 4.23 (2H), 4.09 (4H), 3.82 (8H), 3.76 (4H), 3.67 (4H), 3.44-3.56 (12H), 3.34 (4H), 3.0-3.3 (18H), 2.84-2.86 (8H), 2.7 (8H), 2.38 (4H), 2.03 (4H), 1.94 (2H), 1.78 (4H), DPA 55:
$^1$HNMR (300 MHz, D$_2$O, 25° C.): ∂ 7.86 (s, 2H, triazole peak), 5.40 (br, 2H), 5.37 (2H), 5.11 (2H), 4.9 (2H), 4.23 (2H), 4.09 (4H), 3.82 (8H), 3.76 (4H), 3.67 (4H), 3.44-3.56 (12H), 3.40 (6H) 3.34 (4H), 3.0-3.3 (18H), 2.84-2.86 (12H), 2.7 (8H), 2.38 (4H), 2.03 (4H), 1.94 (2H).

DPA 56:
$^1$HNMR (300 MHz, D$_2$O, 25° C.): ∂ 7.90 (s, 2H, triazole peak), 5.40 (br, 2H), 5.37 (2H), 5.11 (2H), 4.9 (2H), 4.23 (2H), 4.09 (4H), 3.82 (8H), 3.76 (4H), 3.67 (4H), 3.44-3.56 (12H), 3.34 (4H), 3.0-3.3 (18H), 2.84-2.86 (8H), 2.7 (8H), 2.38 (4H), 2.03 (4H), 1.94 (2H), 1.78 (4H), 1.56 (4H).

DPA 58:
$^1$HNMR (300 MHz, D$_2$O, 25° C.): ∂ 7.80 (s, 2H, triazole peak), 5.40 (br, 2H), 5.37 (2H), 5.11 (2H), 4.9 (2H), 4.23 (2H), 4.20 (4H), 4.09 (4H), 3.82 (8H), 3.76 (4H), 4H (3.75), 3.67 (4H), 3.44-3.56 (12H), 3.34 (4H), 3.0-3.3 (18H), 2.84-2.86 (8H), 2.7 (8H), 2.38 (4H), 2.03 (4H), 1.94 (2H), 1.78 (4H), 1.56 (8H).

DPA 60:
$^1$HNMR (300 MHz, D$_2$O, 25° C.): ∂ 7.79 (s, 2H, triazole peak), 5.40 (br, 2H), 5.37 (2H), 5.11 (2H), 4.9 (2H), 4.23 (2H), 4.20 (4H), 4.09 (4H), 3.82 (8H), 3.76 (4H), 4H (3.75), 3.67 (4H), 3.44-3.56 (12H), 3.34 (4H), 3.0-3.3 (18H), 2.84-2.86 (8H), 2.7 (8H), 2.38 (4H), 2.03 (4H), 1.94 (2H), 1.78 (4H), 1.56 (16H).

DPA 65:
$^1$HNMR (300 MHz, D$_2$O, 25° C.): ∂ 8.55 (s, 2H, triazole peak), 8.25 (s, 1H), 7.85 (s, 2H), 7.6 (s, 1H), 5.40 (br, 2H), 5.37 (2H), 5.11 (2H), 4.9 (2H), 4.23 (2H), 4.09 (4H), 3.82 (8H), 3.76 (4H), 3.67 (4H), 3.44-3.56 (12H), 3.0-3.3 (18H), 2.84-2.86 (8H), 2.7 (8H), 2.38 (4H), 2.03 (4H), 1.94 (2H), DPA 71:
$^1$HNMR (300 MHz, D$_2$O, 25° C.): ∂ 5.40 (br, 2H), 5.37 (2H), 5.11 (2H), 4.9 (2H), 4.23 (2H), 4.09 (4H), 3.82 (8H), 3.76 (4H), 3.67 (4H), 3.44-3.56 (12H), 3.0-3.3 (18H), 2.84-2.86 (8H), 2.7 (8H), 2.38 (4H), 2.03 (4H), 1.94 (2H).

DPA 72:
$^1$HNMR (300 MHz, D$_2$O, 25° C.): ∂ 7.10-7.45 (m, broad, 4H), 5.40 (br, 2H), 5.37 (2H), 5.11 (2H), 4.9 (2H), 4.23 (2H), 4.09 (4H), 3.82 (8H), 3.76 (4H), 3.67 (4H), 3.44-3.56 (12H), 3.0-3.3 (18H), 2.84-2.86 (8H), 2.7 (8H), 2.38 (4H), 2.03 (4H), 1.94 (2H).

DPA 73:
$^1$HNMR (300 MHz, D$_2$O, 25° C.): ∂ 5.40 (br, 2H), 5.37 (2H), 5.11 (2H), 4.9 (2H), 4.23 (2H), 4.09 (4H), 3.82 (8H), 3.76 (4H), 3.67 (4H), 3.44-3.56 (12H), 3.4 (4H) 3.0-3.3 (18H), 2.84-2.86 (8H), 2.7 (8H), 2.38 (4H), 2.03 (4H), 1.94 (2H), 1.80 (2H).

DPA 74:
$^1$HNMR (300 MHz, D$_2$O, 25° C.): ∂ 7.25 (s, broad, 4H), 5.40 (br, 2H), 5.37 (2H), 5.11 (2H), 4.9 (2H), 4.23 (2H), 4.09

(4H), 3.82 (8H), 3.76 (4H), 3.67 (4H), 3.44-3.56 (12H), 3.0-3.3 (18H), 2.84-2.86 (8H), 2.7 (8H), 2.38 (4H), 2.03 (4H), 1.94 (2H).

DPA 75:

$^1$HNMR (300 MHz, D$_2$O, 25° C.): ∂ 5.40 (br, 2H), 5.37 (2H), 5.11 (2H), 4.9 (2H), 4.23 (2H), 4.09 (4H), 3.82 (8H), 3.76 (4H), 3.67 (4H), 3.44-3.56 (12H), 3.34 (4H), 3.0-3.3 (18H), 2.84-2.86 (8H), 2.7 (8H), 2.38 (4H), 2.03 (4H), 1.94 (2H), 1.50 (4H), 1.38 (4H).

DPA 76:

$^1$HNMR (300 MHz, D$_2$O, 25° C.): ∂ 5.40 (br, 2H), 5.37 (2H), 5.11 (2H), 4.9 (2H), 4.23 (2H), 4.09 (4H), 3.82 (8H), 3.76 (4H), 3.67 (4H), 3.60 (12H), 3.44-3.56 (12H), 3.0-3.3 (18H), 2.84-2.86 (8H), 2.7 (8H), 2.38 (4H), 2.03 (4H), 1.94 (2H).

DPA 77:

$^1$HNMR (300 MHz, D$_2$O, 25° C.): ∂ 5.40 (br, 2H), 5.37 (2H), 5.11 (2H), 4.9 (2H), 4.23 (2H), 4.09 (4H), 3.82 (8H), 3.76 (4H), 3.67 (4H), 3.44-3.56 (12H), 3.34 (4H), 3.0-3.3 (18H), 2.84-2.86 (8H), 2.7 (8H), 2.38 (4H), 2.03 (4H), 1.94 (2H), 1.35 (8H), 1.15 (12H).

DPA 78:

$^1$HNMR (300 MHz, D$_2$O, 25° C.): ∂ 6.01 (br s, 2H), 5.89 (br s, 2H), 5.44 (br s, 2H), 5.39 (s, 2H), 5.30 (s, 2H), 4.95 (m, 8H), 4.56 (m, 8H), 4.46 (m, 4H), 4.39 (m, 4H), 4.34 (m, 4H), 4.25 (m, 4H), 4.02 (m, 20H), 3.82-3.83 (m, 4H), 3.80-3.81 (m, 16H), 3.64 (m, 4H), 3.682 (m, 4H), 3.58 (t, 4H), 3.55 (t, 4H), 3.38 (m, 4H), 1.871 (p, 4H), 1.62 (p, 4H), 1.6 (br s, 4H). MALDI-TOF: calcd for C$_{58}$H$_{114}$N$_{16}$O$_{26}$S$_2$ [M+H+Na]$^+$ 1547.75. found 1547.56.

DPA 79:

$^1$HNMR (300 MHz, D$_2$O, 25° C.): 5.40 (br, 2H), 5.37 (2H), 5.11 (2H), 4.9 (2H), 4.23 (2H), 4.09 (4H), 3.82 (8H), 3.76 (4H), 3.67 (4H), 3.64 (12H), 3.44-3.56 (12H), 3.0-3.3 (18H), 2.84-2.86 (8H), 2.7 (8H), 2.38 (4H), 2.03 (4H), 1.94 (2H); MS (MALDI-TOFMS) calcd 1579.88, obsd (M$^+$): 1579.6.

DPA 80:

$^1$HNMR (300 MHz, D$_2$O, 25° C.): 5.40 (br, 2H), 5.37 (2H), 5.11 (2H), 4.9 (2H), 4.23 (2H), 4.09 (4H), 3.82 (8H), 3.76 (4H), 3.67 (4H), 3.44-3.56 (12H), 3.34 (4H), 3.0-3.3 (18H), 2.84-2.86 (8H), 2.7 (8H), 2.38 (4H), 2.03 (4H), 1.94 (2H), 1.35 (8H), 1.15 (12H).

6. General Synthetic Procedure for Compounds DPA 51-DPA 65

To a solution of 5"-azide-1,3,2',6',2'",6'"-hexa-N-(tert-butoxycarbonyl)-5"-deoxy-neomycin B (62 mg, 0.05 mmol) in toluene (5 mL), 1,9-decadiyne (3.35 mg, 0.5 eq) was added followed by the addition of CuI (4.76 mg, 0.025 mmol) and DIPEA (6.46 mg, 0.05 mmol). The reaction mixture stirred at r.t. for 18 h. under the atmosphere of N$_2$. The volatiles were evaporated by roto-vap. Purification by column chromatography (0 to 10% ethanol in CH$_2$Cl$_2$) afforded the desired product (98 mg, 89%) as a white solid.

7. General Synthetic Procedure for Compounds DPA 71-DPA 80

To a solution of 4, 9-dioxa-1, 12-dodecadiisothiocyanate (9.0 mg, 0.031 mmol) in dry pyridine (5 ml), 5"-amine-1,3,2',6',2'",6'"-hexa-N-(tert-butoxycarbonyl)-5"-deoxy-neomycin B (75.28 mg, 0.062 mmol, 2 eq.) was added followed by 4-dimethyl-aminopyridine (DMAP, catalytic amount) and stirred overnight at room temperature under the atmosphere of N$_2$. The volatiles were evaporated by roto-vap and co-evaporated with toluene. Purification by column chromatography (R$_f$ 0.46, 10% Me-OH in CH$_2$Cl$_2$) afforded the desired product (50.53 mg, 60%) as a yellowish solid.

8. Percent Yield of DPA51-DPA80

Disclosed in Table 7 are the percent yields for each of the disclosed neomycin-neomycin conjugates. Synthesizing conjugates using click chemistry gave a higher percent yield compared to thio-coupling chemistry.

TABLE 7

% yield of the Neo Neo dimer's after deprotection

| Neo-Neo Dimer | Linker length | % yield |
|---|---|---|
| click chemistry | | |
| DPA51 | 11 | 89.5 |
| DPA52 | 11 | 88.2 |
| DPA53 | 12 | 87.0 |
| DPA54 | 12 | 88.5 |
| DPA55 | 14 | 82.0 |
| DPA56 | 14 | 88.8 |
| DPA58 | 20 | 83.5 |
| DPA60 | 24 | 82.8 |
| DPA65 | 11 | 83.0 |
| thio-coupling chemistry | | |
| DPA71 | 5 | 66.2 |
| DPA72 | 11 | 61.7 |
| DPA73 | 11 | 65.0 |
| DPA74 | 12 | 61.2 |
| DPA75 | 14 | 61.5 |
| DPA76 | 17 | 60.4 |
| DPA77 | 20 | 69.2 |
| DPA78 | 20 | 68.0 |
| DPA79 | 22 | 66.3 |
| DPA80 | 26 | 67.2 |

9. MALDI-TOF Data of Neomycin Conjugates

Disclosed in table 15 are the observed and calculated masses for some neomycin-neomycin conjugates.

TABLE 15

MALDI-TOF data of neomycin conjugates

| Name | m/z Calcd. | m/z observed |
|---|---|---|
| DPA 51 | 2572.84 | 2595.19 (+Na) |
| DPA 52 | 2574.81 | 2599.27 (Na + H) |
| DPA 53 | 2606.86 | 2619.17 |
| DPA 54 | 2586.87 | 2787.86 |
| DPA 55 | 2640.96 | 2664.20 (+Na) |
| DPA 56 | 2614.92 | 2631.66 (H2O) |
| DPA 58 | 2703.03 | |
| DPA 60 | 2759.05 | 2766.54 (+H2O) |
| DPA 65 | 2606.86 | 2618.46 |
| DPA 71 | 2470.77 | 2485.70 (H2O) |
| DPA 72 | 2620.97 | 2659.44 (H$_2$O + Na) |
| DPA 73 | 2586.95 | 2619.50 (H2O, Na) |
| DPA 74 | 2588.84 | 2604.10 (H2O + H) |
| DPA 75 | 2596.90 | 2627.14 |
| DPA 76 | 2661.03 | 2659.44 |
| DPA 77 | 2681.06 | 2710.96 |
| DPA 78 | 2717.14 | 2731.60 |
| DPA 79 | 2749.14 | 2775.79 (Na, H) |
| DPA 80 | 2801.30 | 2814.45 |

G. EXAMPLES

The following examples are put forth so as to provide those of ordinary skill in the art with a complete disclosure and description of how the compounds, compositions, articles, devices and/or methods claimed herein are made and evaluated, and are intended to be purely exemplary and are not intended to limit the disclosure. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

1. Example 1 B

Figure 8:
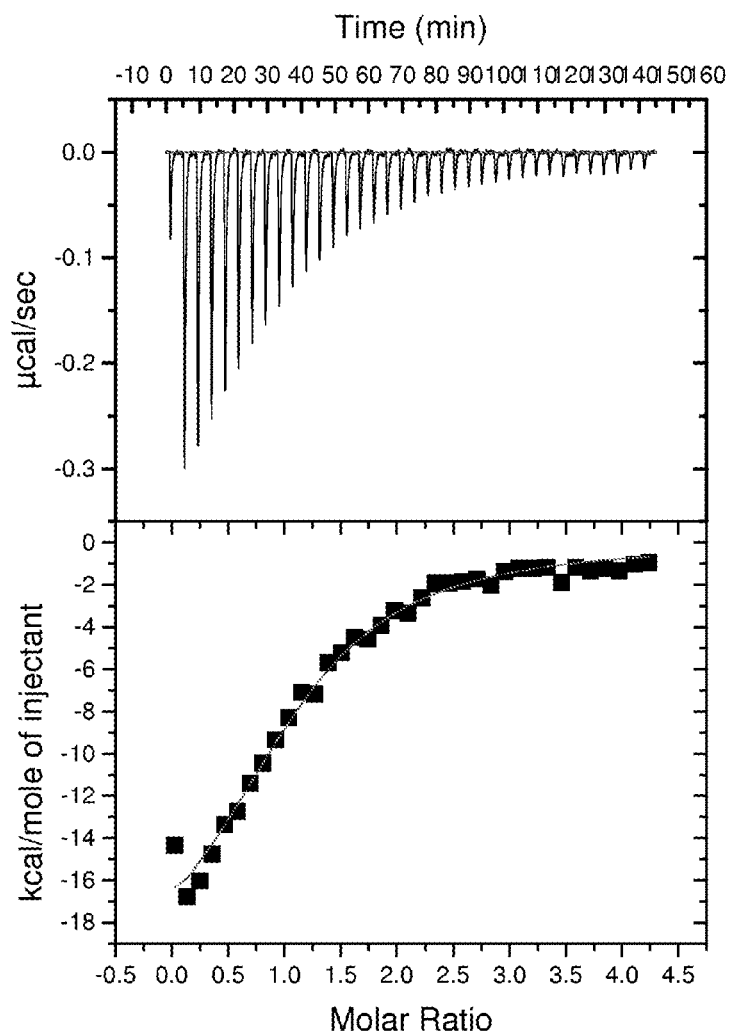
FIG. 8 shows the result from the ITC Titration of TAR RNA with Neomycin. Neomycin (80 µM) was serially injected to the TAR RNA (4 µM/molecule) solution at 20° C.
Figures 9A, 9B:
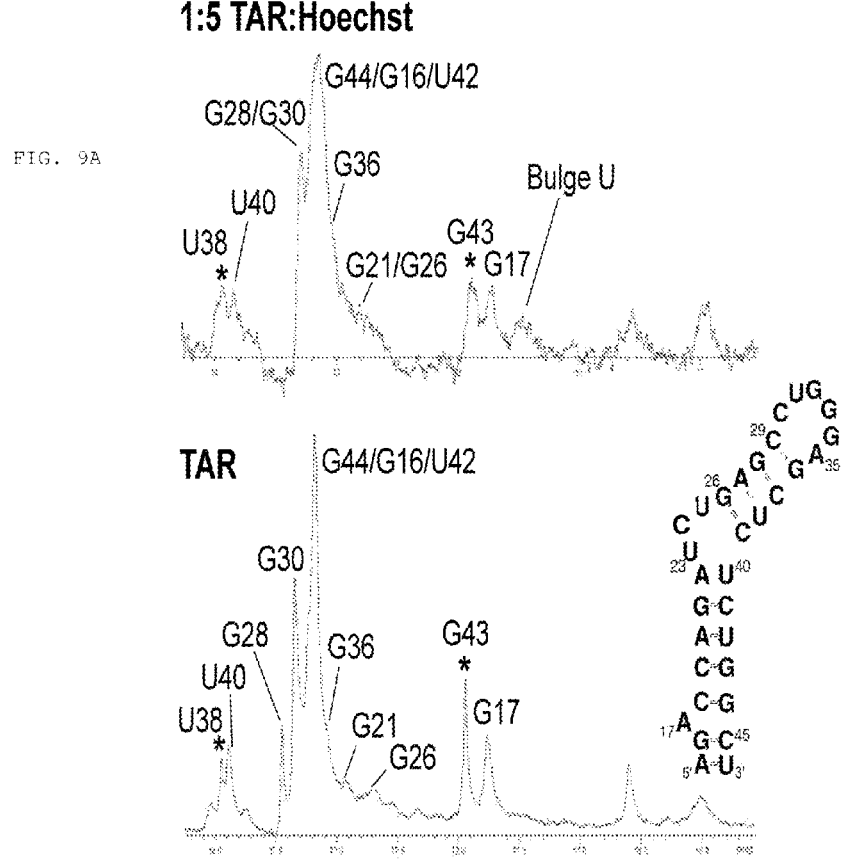
FIGS. 9A and 9B show the result from Hoechst-TAR NMR titrations. (A) Virtually all imino resonances shift slightly, indicating global conformational changes and/or non-specific binding of Hoechst at higher concentrations of the drug. Resonances near the bulge have a steeper titration curve (B), indicating specific binding of hoechst in the vicinity. A bulge U resonance emerges upon addition of >1 eq. concentrations of hoechst, indicating induced conformational change in the region upon binding, and/or protection by Hoechst.
Figure 10A:
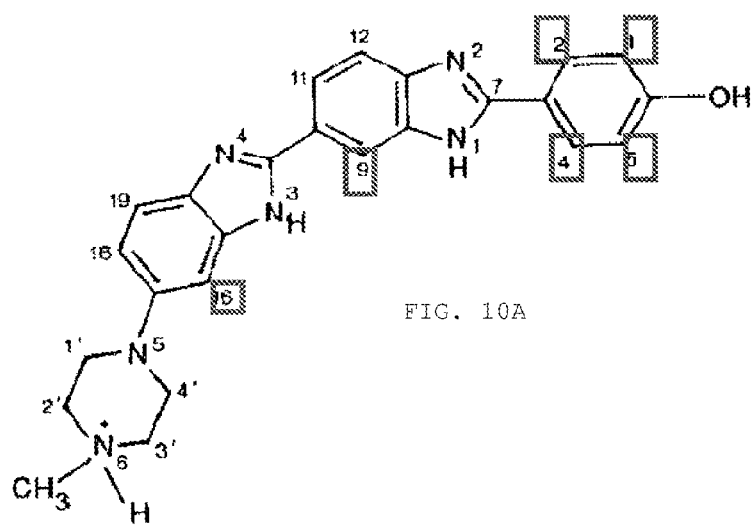
Figure 10B:
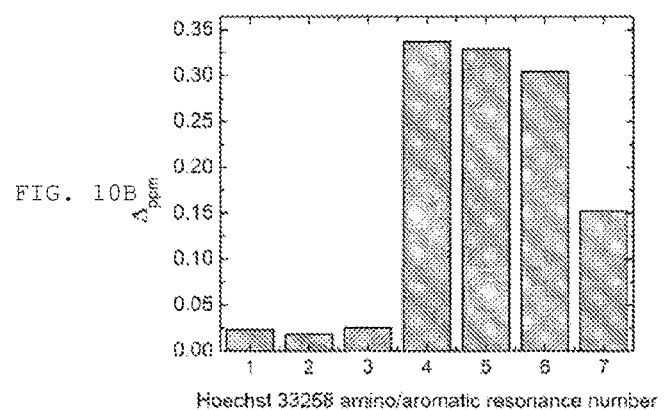
Figure 10C:
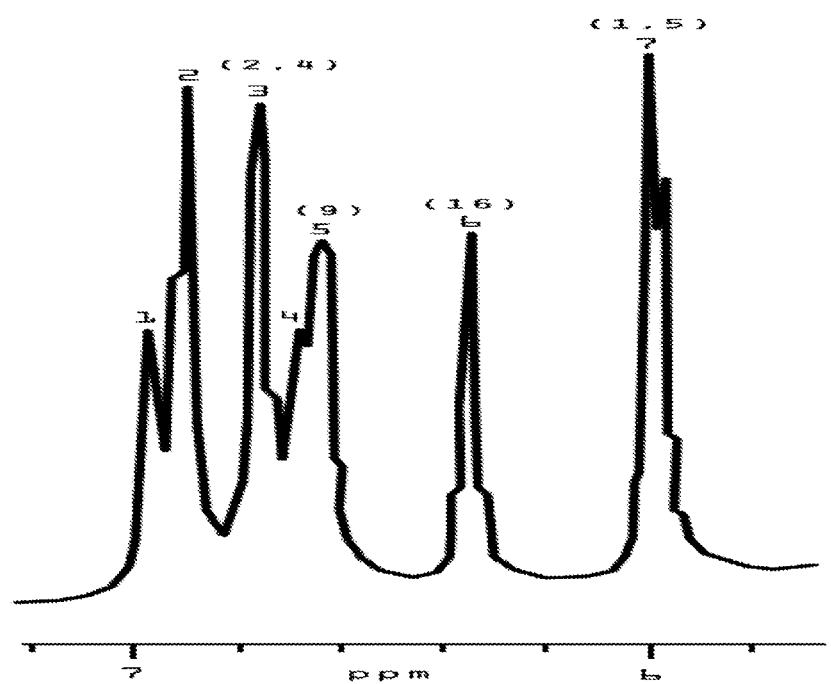

FIG. 8 shows the isothermal titration calorimetry (ITC) of TAR with neomycin. As shown in FIG. 8 and Table 8,

TABLE 8

Results from the thermodynamic data from ITC titration of TAR RNA with Neomycin

| N | K | ΔH | ΔS |
|---|---|---|---|
| 1.09 ± 0.04 | (6.61 ± 0.84) × $10^5$ | −22.1 ± 1.1 Kcal/mol | −48.74 |

NMR titrations were performed on TAR-Hoechst interactions. A 1:5 TAR:Hoechst ratio resulted in global conformational changes. FIGS. 9A and 9B FIGS. 10A-D show the results of NMR titration of Hoechst 33258 with TAR RNA. Shown highlighted are regions of the Hoechst 33258 that showed changes in chemical shift upon binding to TAR.

The Hoescht-TAR interactions is not perturbed significantly by neomycin-TAR interactions. FIG. 11 shows that in the absence of neomycin, the fluorescence titration of TAR in Hoescht produces a maximum fluorescence of about $5×10^4$ units. In the presence of neomycin, very little change in Hoechst fluorescence is seen, suggesting that neomycin binding does not mitigate Hoechst-TAR interaction.

Figure 12:
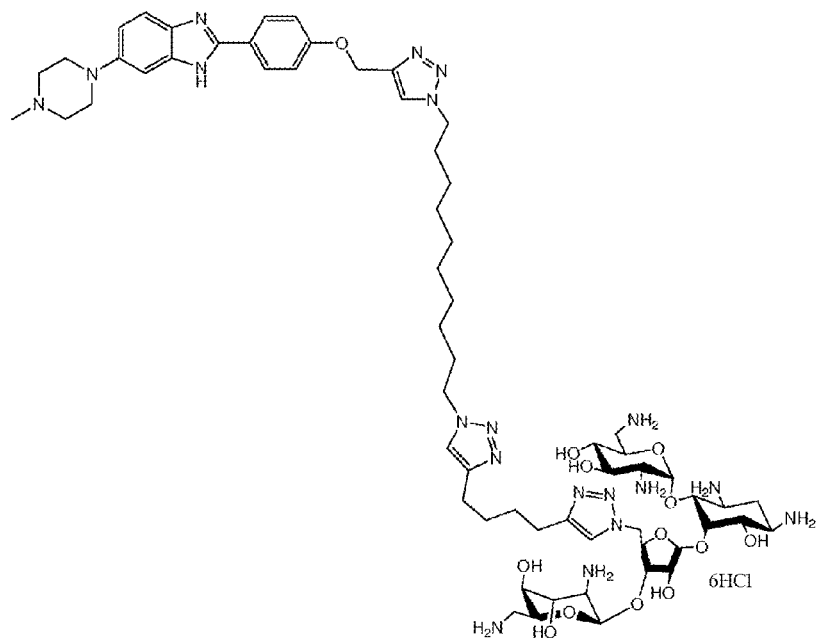
FIG. 12 shows the $^1$HNMR spectra of the deprotected Neomycin-Benzimidazole conjugate.
Figure 12:
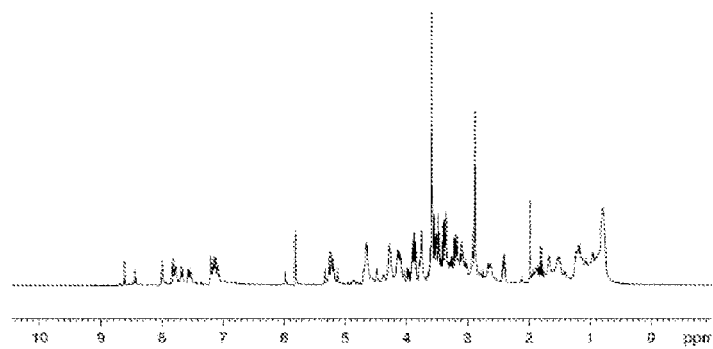

FIG. 12 shows the NMR spectra of the deprotected Neomycin-Benzimidazole conjugate.

Figure 13:
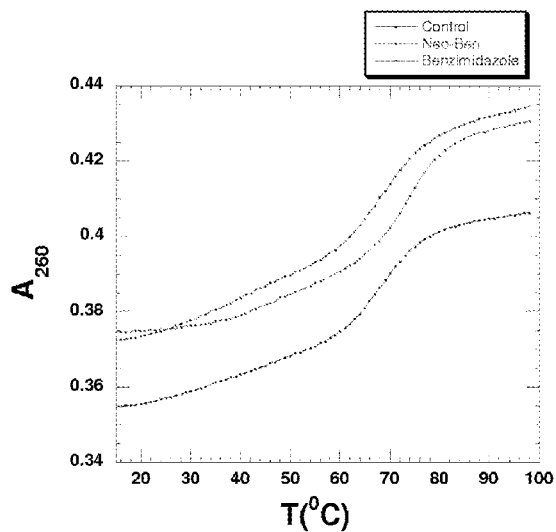
FIG. 13 shows the UV melting of TAR RNA in the presence and absence of various ligands. The bottom line represents the control which is TAR without any ligands. The middle line represents TAR in the presence of neomycin-benzimidazole conjugate. The top line represents TAR in the presence of benzimidazole. The reactions were done in the presence of 10 mM sodium cacodylate, 0.5 mM EDTA, 0.1 mM MgCl$_2$ pH 7.0. The heating rate was 0.3° C./min.

UV melting studies of TAR were performed in the presence and absence of various ligands (FIG. 13). The melting temperature was increased more in the Neomycin-Benzimidazole/TAR complex compared to Neomycin/TAR or TAR alone.

Table 9, below, shows the binding constants of the different ligands with TAR. Upon review of the UV melting studies, Neomycin-Benzimidazole was determined to have a higher binding constant compared to Neomycin, Hoescht 33258 or Benzimidazole alone.

TABLE 9

Binding constants of ligands to TAR

| Ligand | Binding Constant |
|---|---|
| Neomycin | $1.7 × 10^5 M^{-1}$ |
| Hoechst 33258 | $4.2 × 10^5 M^{-1}$ |
| Benzimidazole (Alkyne ended) | $5.2 × 10^5 M^{-1}$ |
| Neomycin-Benzimidazole | $4.4 × 10^7 M^{-1}$ |

Figure 14:
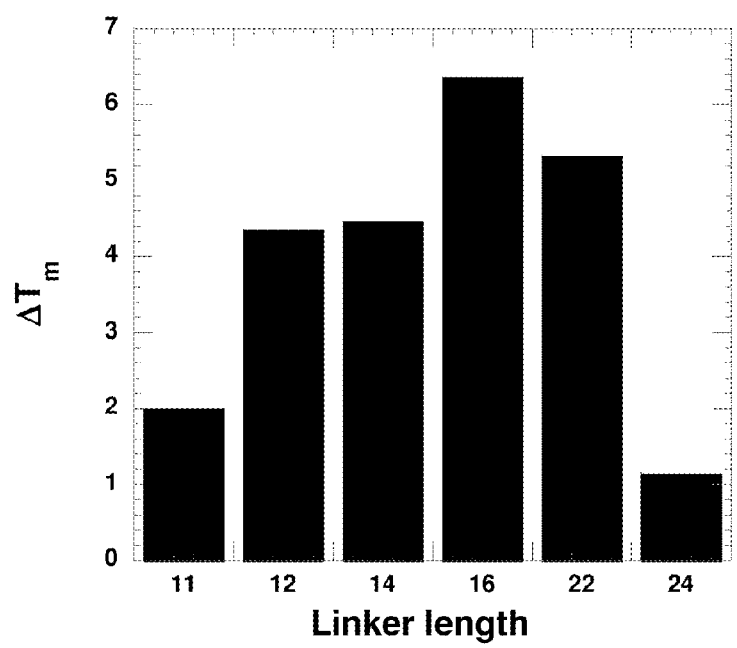
FIG. 14 shows the dependence of linker length as a function of melting temperature of TAR as the control.

As demonstrated in FIG. 14 and Table 10, the length of the linker can affect the change in melting temperature of the Neomycin-Benzimidazole conjugates. A linker length of 24 backbone atoms was shown to have the biggest change in melting temperature.

TABLE 10

Results for $ΔT_m$ TAR RNA with and without the presence of ligands.

| TAR with | $T_m$ (° C.) | $ΔT_m$ (° C.) |
|---|---|---|
| None (Control) | 69.3 | NA |
| DPA113 | 72.4 | 3.1 |
| DPA114 | 73.1 | 3.8 |
| DPA115 | 73.4 | 4.1 |
| DPA116 | 73.1 | 3.8 |
| DPA117 | 75.6 | 6.3 |
| DPA118 | 74.1 | 4.8 |
| DPA119 | 73.5 | 4.2 |
| DPA120 | 73.2 | 3.9 |
| DPA122 | 74.8 | 5.4 |

Figure 15:
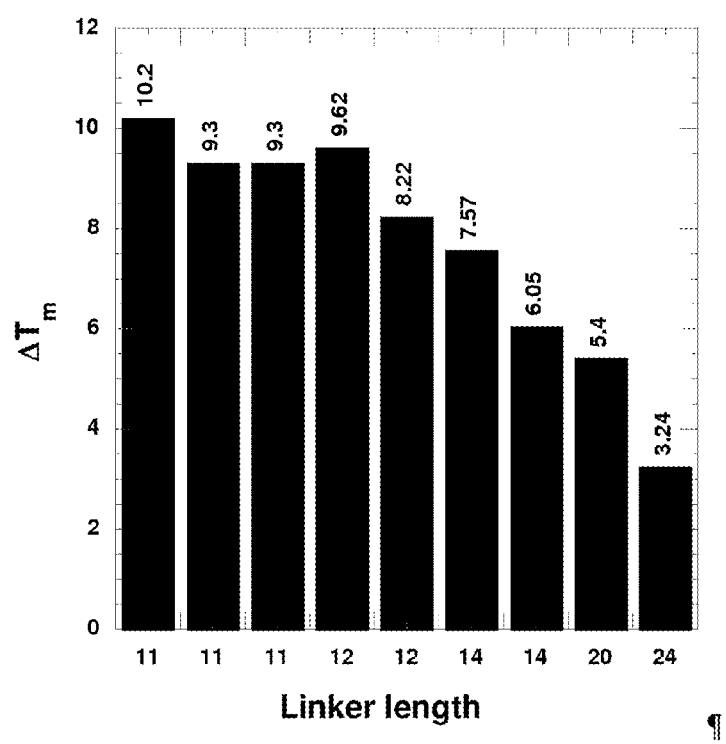
FIG. 15 shows that the linking length of the Neo-Neo dimer is directly correlated to melting point stabilization.

The linker length of the Neomycin Neomycin dimer appears to have a direct correlation to the ΔTm (FIG. 15 and Table 11). The shorter the linker length, the lower the ΔTm.

TABLE 11

Melting point stabilization of HIV-TAR RNA by Neo Neo dimer's

| Neo-Neo dimmer | Linker length | $ΔT_m$ |
|---|---|---|
| DPA51 | 11 | 10.19 |
| DPA51 | 11 | 9.30 |
| DPA65 | 11 | 9.30 |
| DPA53 | 12 | 9.62 |
| DPA54 | 12 | 8.22 |
| DPA55 | 14 | 7.57 |
| DPA56 | 14 | 6.05 |
| DPA58 | 20 | 5.40 |
| DPA60 | 24 | 3.24 |
| Neomycin | NA | 0.20 |

Figure 16A:
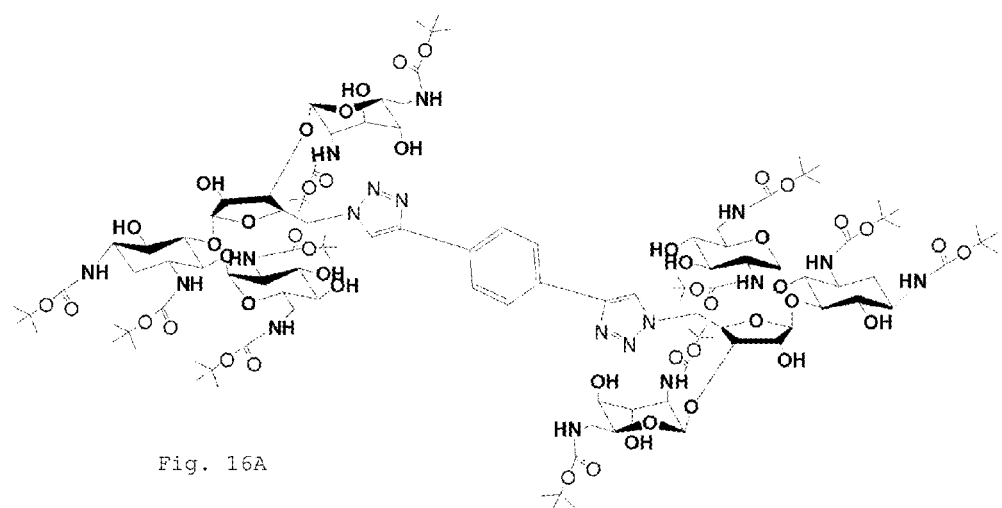
FIGS. 16A-16C show the characterization ($^1$H-NMR and MALDI-TOF) of Neo-Neo dimer by using 1,4-diethynylbenzene.
Figure 16B:
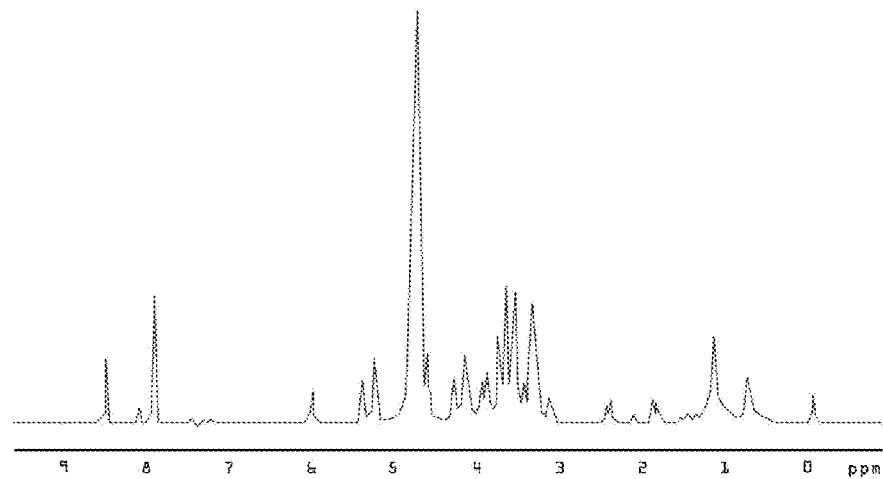
Figure 16C:
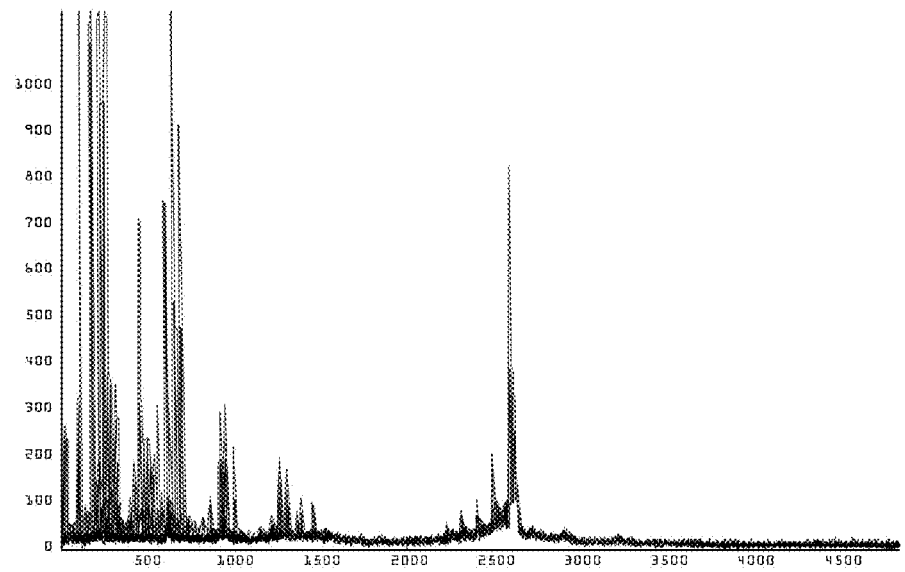

DPA53, a Neomycin Neomycin dimer, was characterized, via $^1$H-NMR and MALDI-TOF, by using 1, 4-diethynylbenzene (FIGS. 16A-C).

Figure 17A:
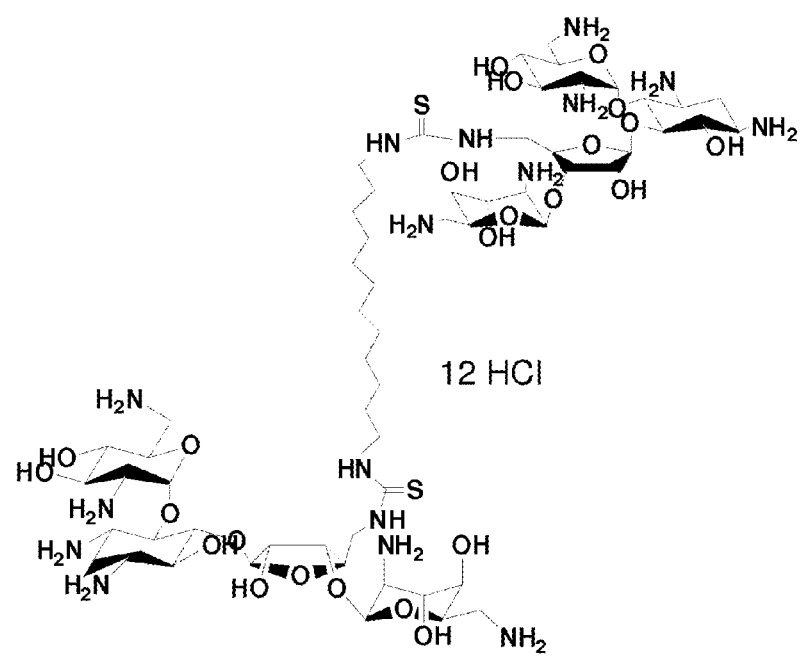
FIGS. 17A-17C show shows the characterization ($^1$H-NMR and MALDI-TOF) of Neo Neo dimer by 1,12-diisothiocyantododecane.
Figure 17B:
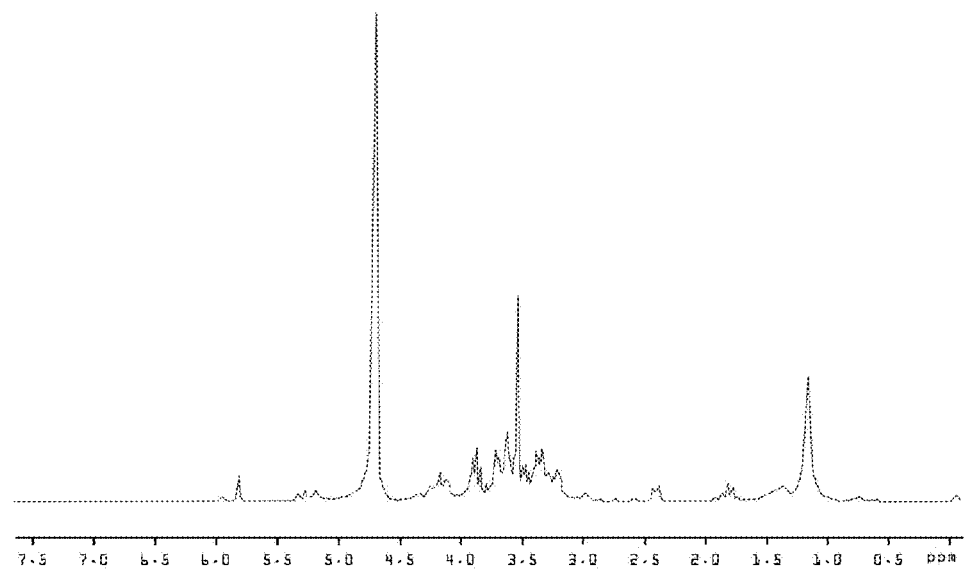
Figure 17C:
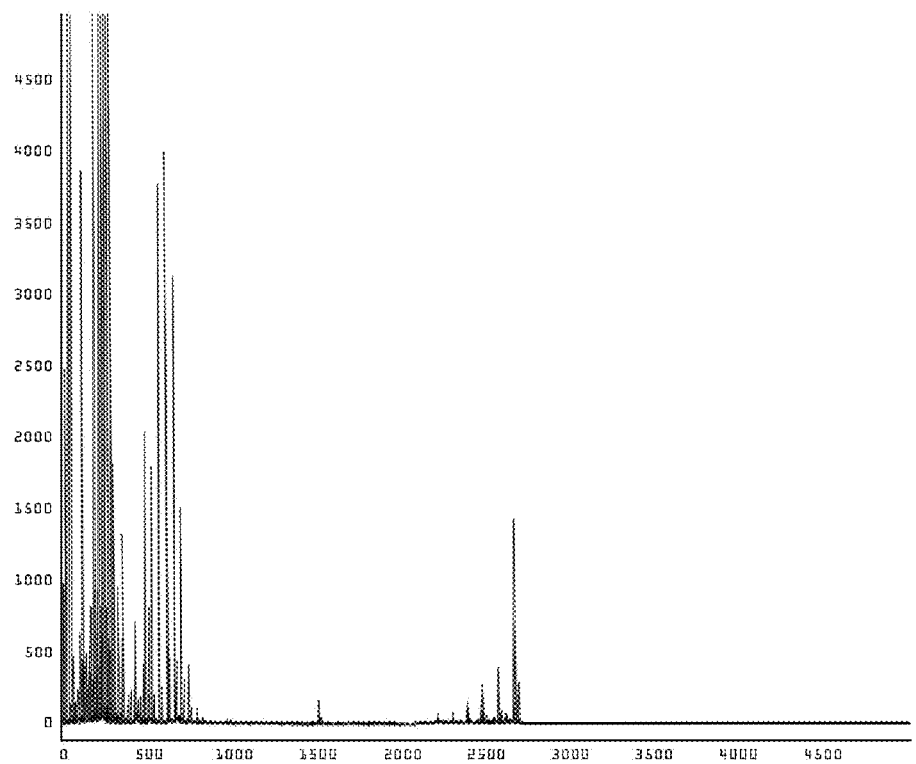
Figure 18A:
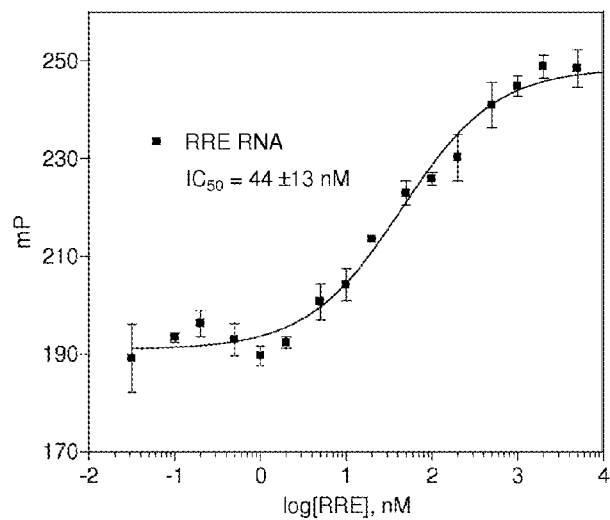
FIGS. 18A-18H show a saturation binding curve of fluorescein-labeled HIV-1 Rev peptide to HIV-1 RRE RNA in binding buffer at 25° C., as well as a number of competition curves of compositions disclosed herein. A) RRE, B) DPA 120, C) DPA 121, D) DPA 122, E) DPA 123, F) DPA 165, G) DPA 166, H) DPA 506.
Figure 18B:
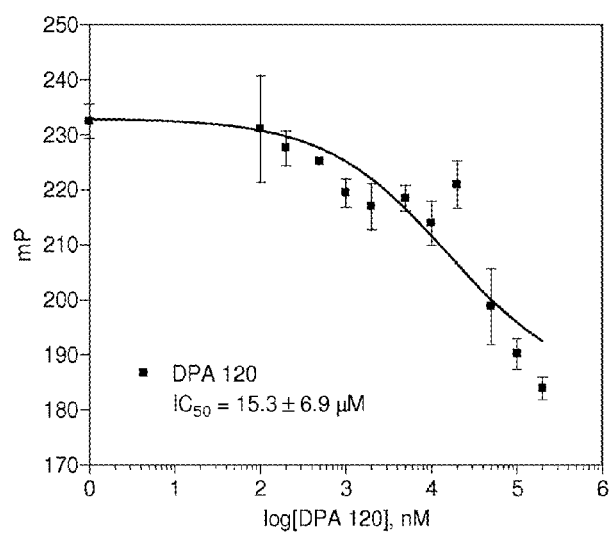
Figure 18C:
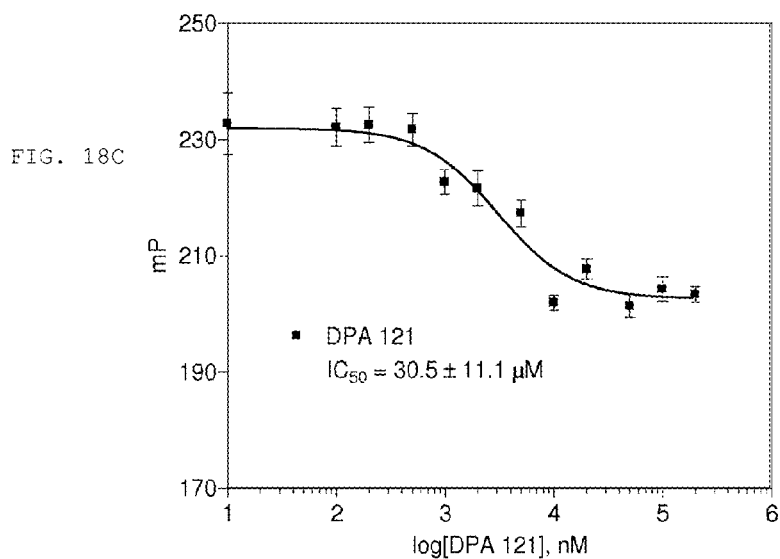
Figure 18D:
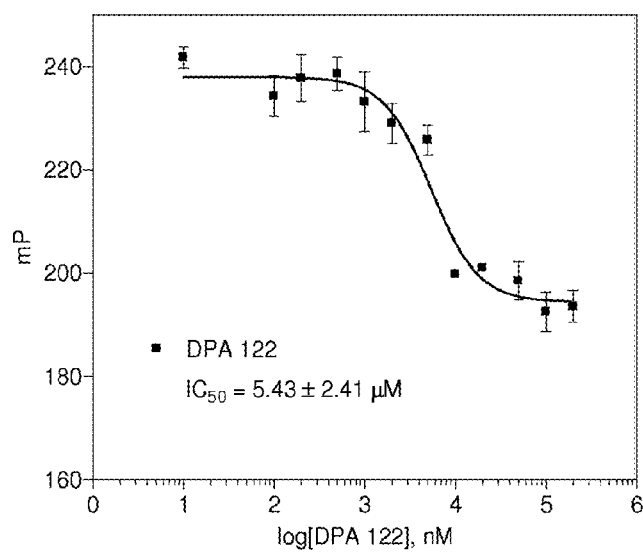
Figure 18E:
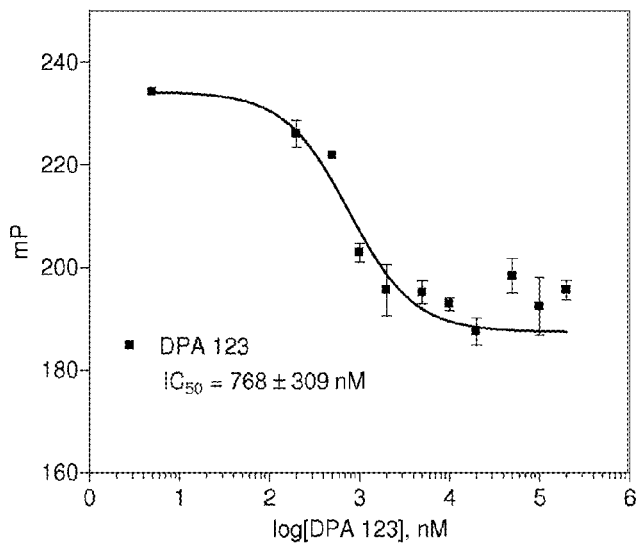
Figure 18F:
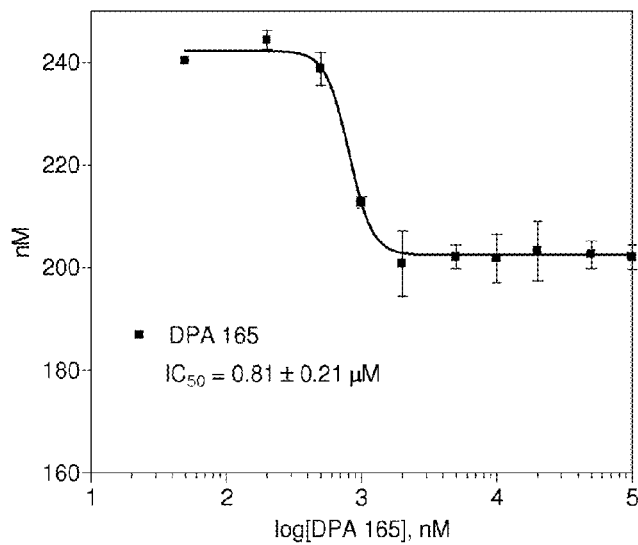
Figure 18G:
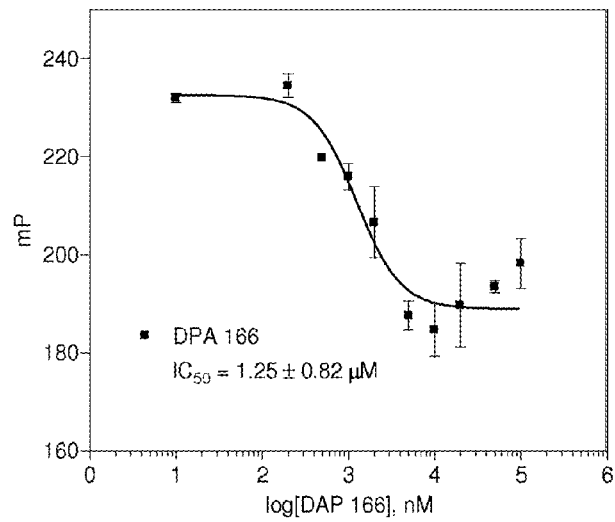
Figure 18H:
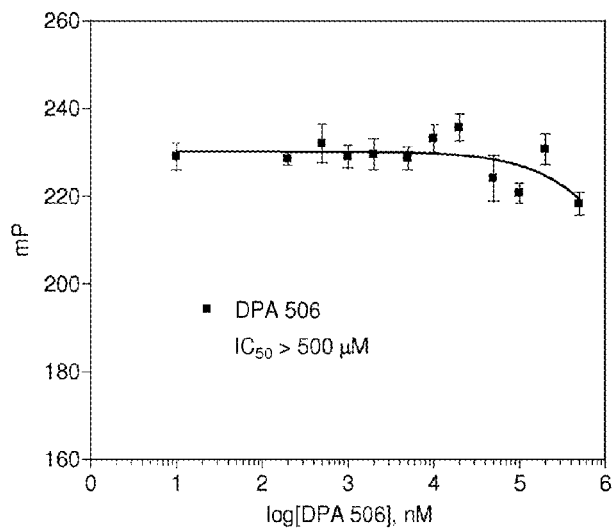
Figure 19C:
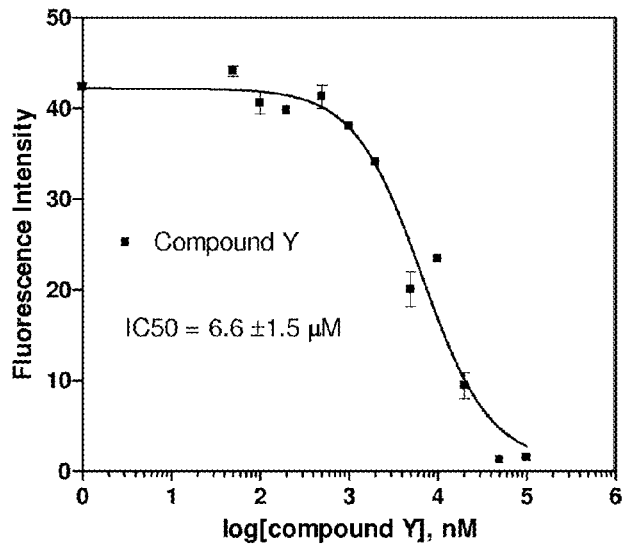
FIGS. 19A-19HH show a saturation binding curve of fluorescein-labeled HIV-1 Tat peptide (100 nM) with HIV-1 TAR RNA in TK buffer at 25° C., as well as a number of competition curves of compositions disclosed herein. A) TAR RNA, B) compound X, C) compound Y, D) DPA 51, E) DPA 52, F) DPA 53, G) DPA 54, H) DPA 55, I) DPA 56, J) DPA 58, K) DPA 60, L) DPA 65, M) DPA 66, N) DPA 101, O) DPA 113, P) DPA 114, Q) DPA 115, R) DPA 116, S) DPA 117, T) DPA 118, U) DPA 119, V) DPA 120, W) DPA 121, X) DPA 122, Y) DPA 165, Z) DPA 166, AA) DPA 123, BB) DPA 502, CC) DPA 503, DD) DPA 504, EE) DPA 505, FF) DPA 506, GG) DPA 507, HH) DPA 508.
Figure 19D:
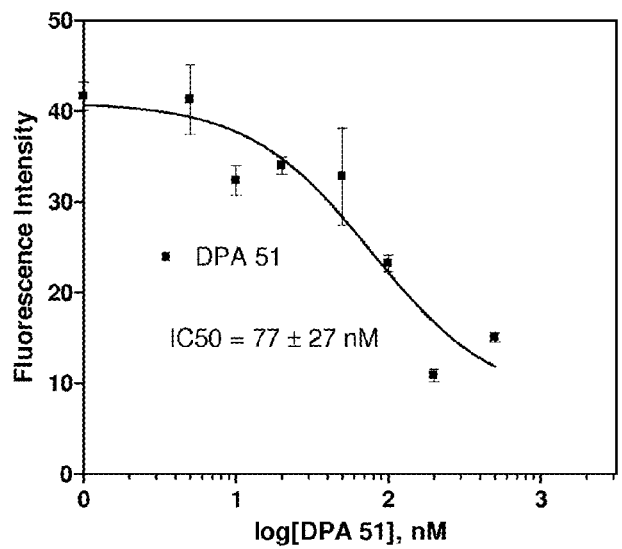
Figure 19O:
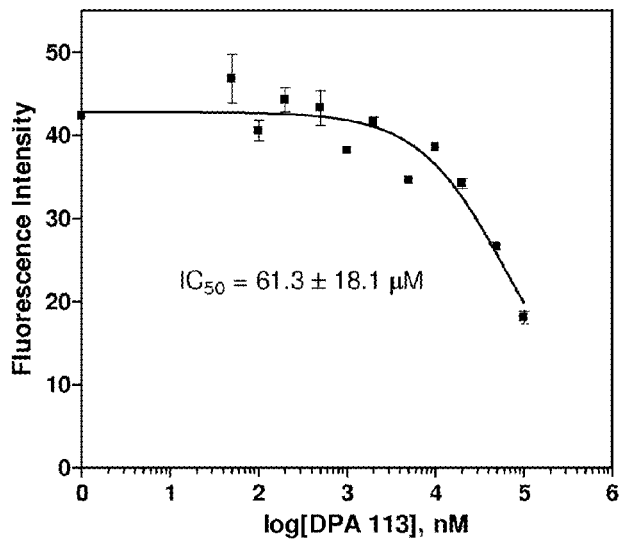
Figure 19P:
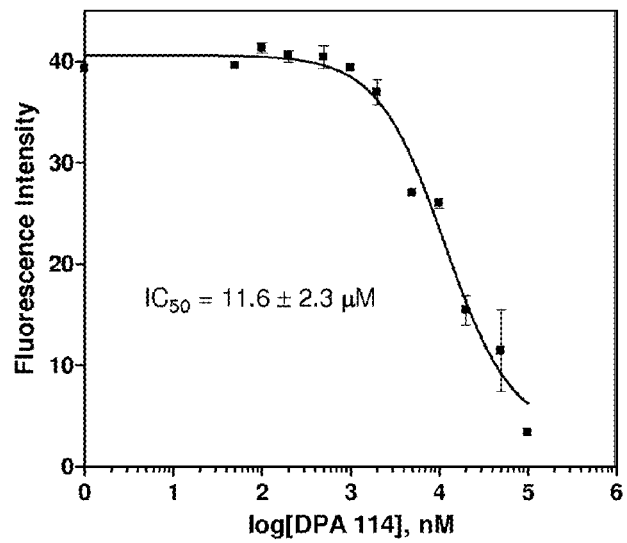
Figure 20:
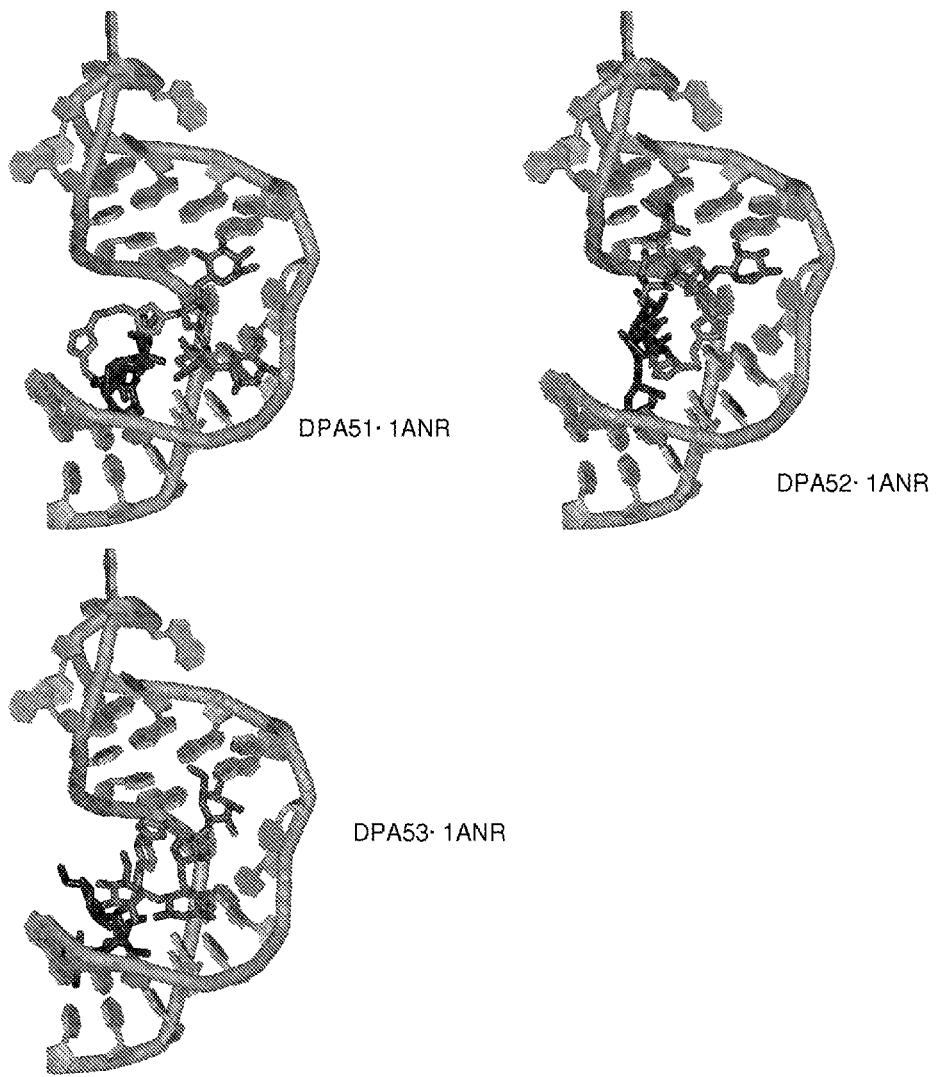
FIG. 20 shows schematics of molecules binding RNA.
Figure 20:
Figure 20:
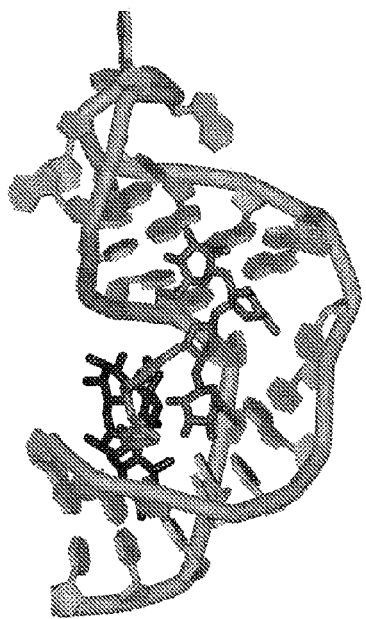
Figure 20:
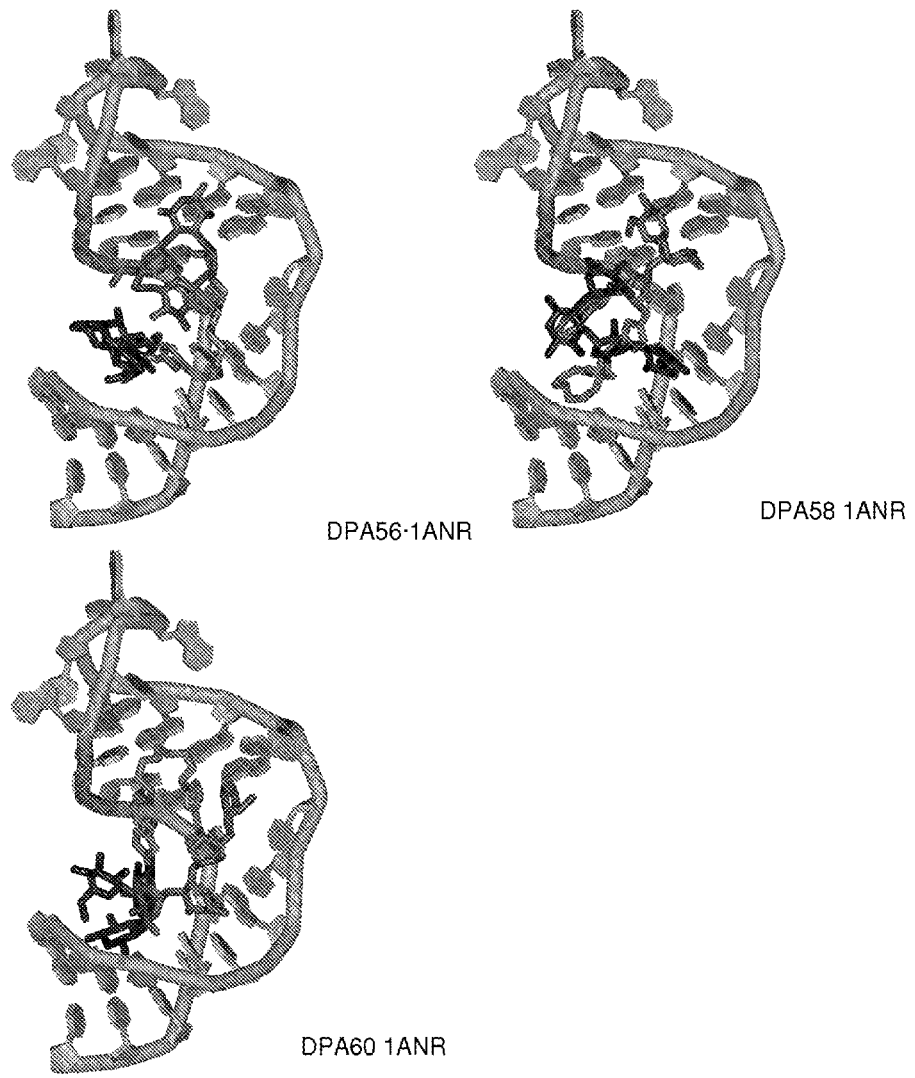
Figure 20:
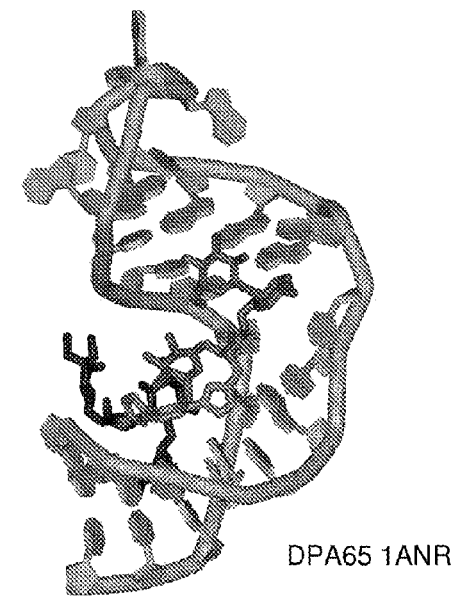
Figure 20:
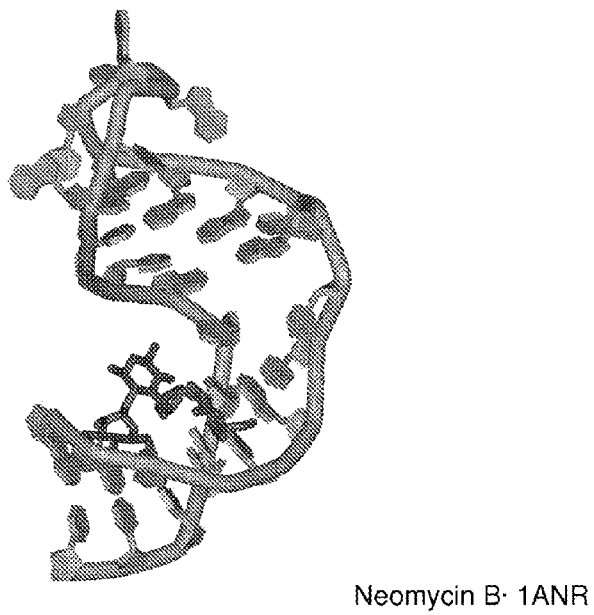
Figures 21A, 21B:
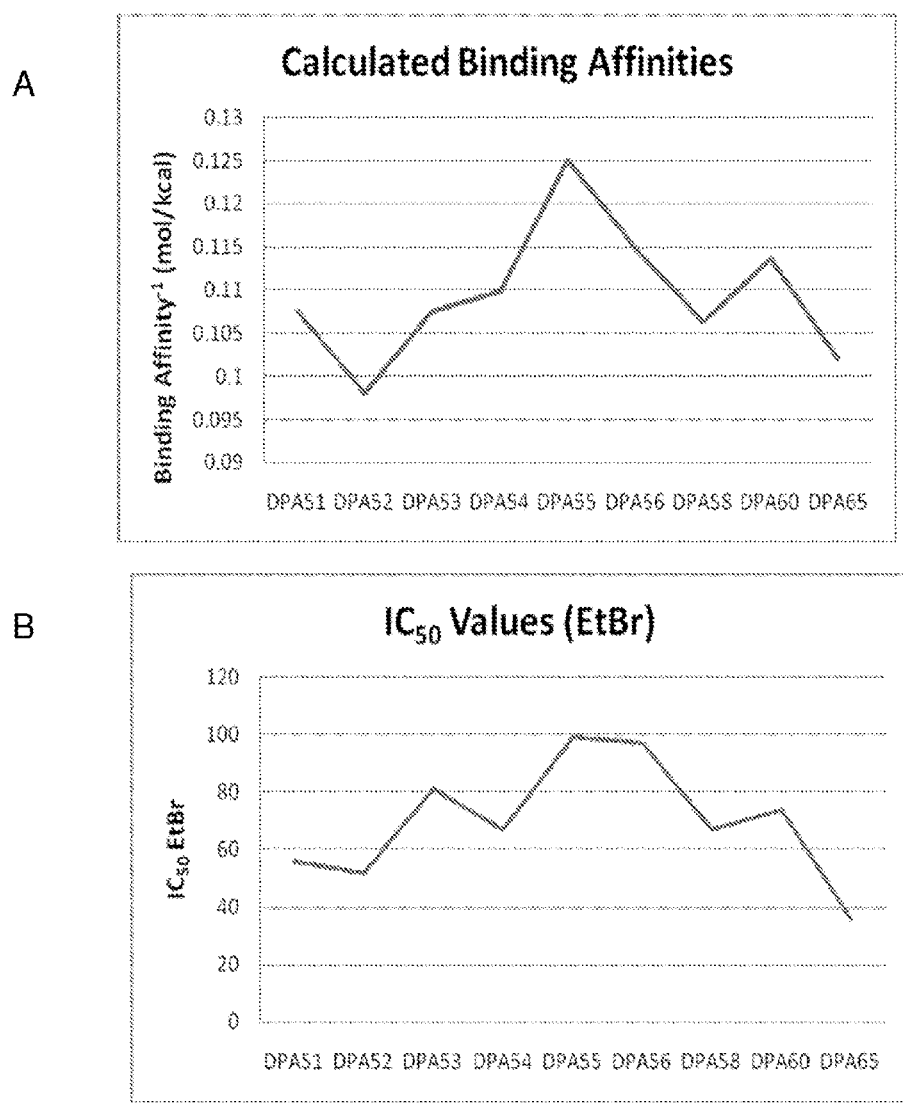
FIGS. 21A and 21B show graphs which depict (A) the inverse of the absolute value of the calculated binding affinities of the various dimers for TAR and (B) the IC$_{50}$ values obtained by FID of EtBr.

DPA, a Neomycin Neomycin dimer, was characterized, via $^1$H-NMR and MALDI-TOF, by 1,12-diisothiocyantododecane (FIGS. 17A-17C).

As shown in Tables 12 and 13, the disclosed neomycin conjugates provide protection from HIV cytopathic effects Table 12 shows the concentration of the conjugate in which 5% or less cell death is seen. Also shown is the percent of maximum protection from HIV cytopathic effects each conjugate achieves with the concentration at which the protection is seen shown in parentheses. Several conjugates provide good protection from HIV cytopathic effects below the concentration responsible for cellular toxicity.

TABLE 12

5% Toxicity concentrations and maximum protection from HIV cytopathic effects

| Compound | 5% Toxicity microM | Maximum protection (concentration achieved in microM) |
|---|---|---|
| DPA101 | 35 | 13% (17) |
| DPA113 | 176 | 6% (5) |
| DPA114 | 11 | 5% (10) |
| DPA116 | 83 | 3% (21) |
| DPA117 | 41 | 4% (20) |
| DPA118 | >184 | 17% (184) |
| DPA119 | 94 | 25% (188)-16% at 24 microM |
| DPA120 | 94 | 6% (188) |
| DPA121 | >186 | 0% (186) |
| DPA122 | 46 | 15% (83) |
| DPA165 | >189 | 44% (189) |
| DPA166 | 11 | 18% (6) |

TABLE 12-continued

5% Toxicity concentrations and maximum protection from HIV cytopathic effects

| Compound | 5% Toxicity microM | Maximum protection (concentration achieved in microM) |
|---|---|---|
| X (neomycin) | >206 | 9% (206) |
| Y (Hoechst 33258) | 18 | 2% (2) |
| DPA52 | >138 | 1% (9) |
| DPA53 | 17 | 33% (8) |
| DPA54 | 69 | 31% (17) |
| DPA55 | 8 | 20% (4) |
| DPA56 | 34 | 33% (17%) |
| Water | None | 2% |

The disclosed neomycin conjugates inhibit the synthesis of HIV antigens in treated cells. Table 13 shows the concentration of each compound used as well as the percentage of cells positive for HIV antigens. Several compounds inhibit HIV antigen synthesis compared to the virus control sample.

TABLE 13

Active compounds inhibit HIV antigen synthesis in treated cells

| Compound | Concentration (microM) | Day 2 | Day 4 | Day 6 |
|---|---|---|---|---|
| DPA119 | 24 | 5-7% | 90% | 100% |
| DPA52 | 25 | 15% | 100% | 100% |
| DPA53 | 9 | 2% | 40% | 100% |
| DPA54 | 17 | 3-5% | 80% | 100% |
| DPA55 | 4 | 3-5% | 30% | 100% |
| DPA56 | 8 | 5-7% | 40% | 100% |
| DPA121 | 25 | 15% | 100% | 100% |
| Virus Control | NA | 15% | 100% | 100% |

The disclosed conjugates also reduce the amount of reverse transcriptase (RT) released into the cell culture supernatant upon in vitro cell culture experiments (Table 14 below). Compared to the virus control, several of the compounds inhibit the release of RT from the cells. Although by Day 6, all cells showed HIV antigen synthesis even in the presence of different compounds, these same cells did not show similar amounts of RT release by Day 6. It is possible that even though the cells are positive for HIV, they are making much fewer unspliced transcripts, and thus the virion release into the media remains suppressed. Nonetheless, RT release is inhibited by several of the neomycin conjugates.

TABLE 14

Release of reverse transcriptase into the culture supernatant (cpm/ml)

| Compound (microM) | Concentration | Day 2 | Day 4 | Day 6 |
|---|---|---|---|---|
| DPA119 | 24 | 16,576 (3,815) | 241,955 (63,097) | 399,421 (71,668) |
| DPA52 | 25 | 21,485 (4,574) | 347,845 (10,680) | 268,357 (57,519) |
| DPA53 | 9 | 8,880 (1,373) | 45,539 (32,831)* | 221,445 (20,678) |
| DPA54 | 17 | 14,805 (1,309) | 165,301 (22,967) | 427,475 (49,583) |
| DPA55 | 4 | 20,072 (3,748) | 107,933 (17,963) | 305,277 (59,913) |
| DPA56 | 8 | 15,989 (2,523) | 105,704 (15,948) | 412,475 (19,612) |
| DPA121 | 25 | 26,499 (5,566) | 579,856 (1000,094) | 880,573 (130,520) |
| Virus Control | NA | 46,029 (6,651) | 928,112 (126,547) | 1,078,741 (188,673) |

Values are mean triplicate infections, values in parentheses are one standard deviation.
*Much higher than normal SD; two of three were much lower, one was high Anti-HIV activities can be routinely checked by measuring the percentage of cells positive for HIV antigens using immunofluorescence assay (IFA) and for the release of pelletable reverse transcriptase (RT) into the supernatant. For these assays, 500,000 MT-2 cells in 1 ml of media were added to the wells of a 24 well tissue culture plate. Next, 0.5 ml of 4× concentrated compound was added to triplicate wells of the plate. The cells and compounds were incubated for 1 hr at 37 C. Finally, 0.5 ml of HIVNL4-3, produced in H9 cells (a CD4+ lymphoblastoid cell line), 100,000 cpm of RT activity per well, was added to each well. Virus control wells contained no compounds. This inoculum is at a multiplicity of infection less than 1. On days 2, 4, and 6, 0.75 mls of supernatants were removed and placed into individual microfuge tubes for RT assay. Next, cells were resuspended in the media and 0.5 mls of the total remaining volume was removed for IFA. Cells were combined from their triplicate infections, pelleted, and the enriched cells were air-dried onto glass slides. The dried cells were fixed in acetonemethanol (50:50). After fixing, cells were stained with HIV immunoglobulin, washed in PBS, and counterstained with FITC-conjugated goat and human IgG. Slides were washed in PBS and the percentage of HIV-positive cells was determined by epifluorescence (Robinson et al. J Acquire Immune Defic Syndr 2:33-42, 1989).

The supernatants from each well were precipitated at 4 C overnight in a solution including 30% polyethylene glycol. After precipitation, precipitate was lysed in a solution containing Triton X100, Tris buffer, and DTT. RT activity of each aliquot was determined as incorporation of 3H-dTTP into a poly rA-oligo dT template. After a one hour assay at 37 C, the incorporated dTTP was precipitated onto a ZetaProbe (BioRad) membrane. Slots were excised and placed into liquid scintillation cocktail. After overnight incubation, counts per minute for each sample was determined on a beta counter. Results were calculated as cpm/ml of original culture supernatant (Robinson et al. J Acquire Immune Defic Syndr 2:33-42, 1989).

2. Example 2

HIV-1 RRE RNA Competition Binding Assay

Before used, HIV-1 RRE RNA (5'-GGU CUG GGC GCA GCG CAA GCU GAC GGU ACA GGC C-3', Thermo Scientific) in 10 μM batch in sterile water was heated to 95° C. for 3 min, and then cooled to ambient temperature over 1 hour.

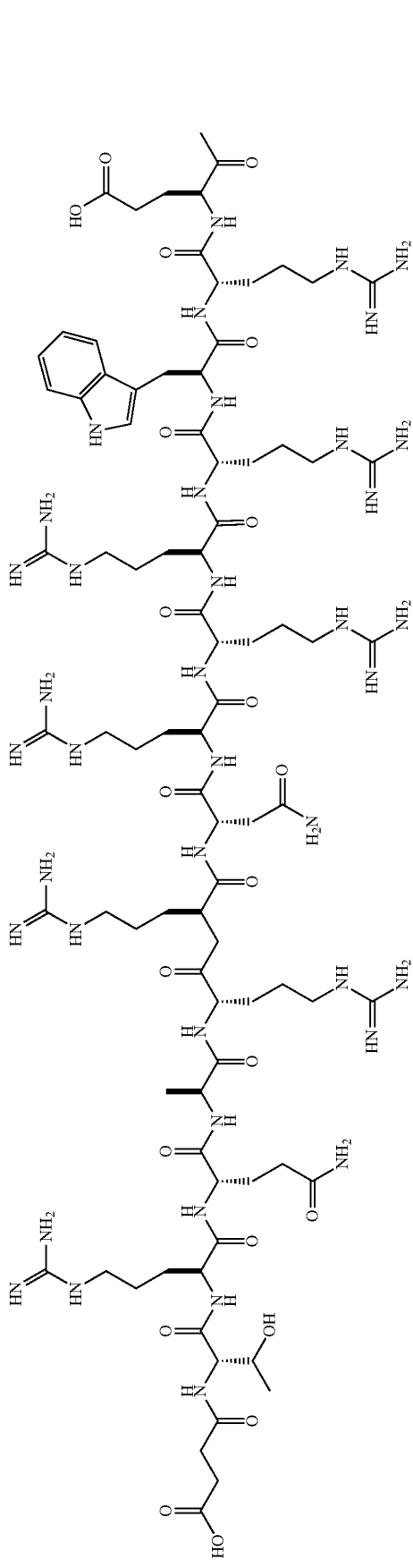
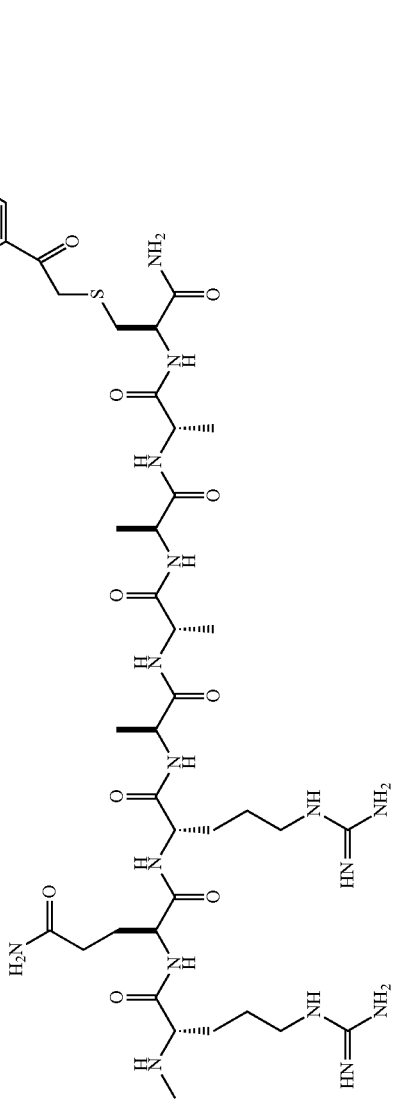

Fluorescein-Labeled HIV-1 Rev Peptide

The relative affinity of each compound for HIV-1 RRE RNA was determined using fluorescence polarization-based competitive binding assay with a fluorescein-labeled HIV-1 Rev peptide. The anisotropy experiments were performed with a Spectra Max Fluorimeter (Molecular Devices) at 25° C., with excitation and emission wavelengths of 485 and 525 nm, respectively. All samples were prepared in 96 well plates in binding buffer (30 mM Hepes, 100 mM KCl, 40 mM NaCl, 10 mM $NH_4OAc$, 10 mM Guanidinium Hydrochloride, 2 mM $MgCl_2$, 0.5 mM EDTA, pH 7.4) with 0.01% triton-X100 (Sigma). The binding data reported for each conjugate are the averages of 3~5 individual measurements.

Prior to the competition experiments, the affinity of fluorescein-labeled HIV-1 Rev peptide for HIV-1 RRE RNA was determined by monitoring polarization changes of the fluorescent probe upon addition of RRE RNA. Addition of an increasing concentration (0 nM to 5000 nM) of RRE RNA to a 10 nM solution of fluorescein-labeled HIV-1 Rev peptide in binding buffer at 25° C. afforded a saturation binding curve (FIGS. 18A-18H). The binding dose-response data were fitted to a sigmoidal nonlinear regression model on GraphPad Prism 4.0 to afford the $IC_{50}$ value (54 nM), which is in agreement with the previously reported value.

Competition Polarization Assay.

A solution of 100 nM RRE RNA and 10 nM fluorescein-labeled HIV-1 Rev peptide was incubated at 25° C. After 10 min, appropriate concentrations (0 nM to 500 μM) of the antagonists were added; total volume of the incubation solution was 80 pt. After 1 hour, the amount of the dissociated fluorescent probe was determined by the Spectra Max fluorescence plate reader. The experimental dose-response data for a given antagonist were fit to a sigmoidal dose-response nonlinear regression model on GraphPad Prism 4.0 to afford the $IC_{50}$ values for each conjugates (Table 16).

TABLE 16

Competition binding affinities of antagonists to HIV-1 RRE RNA.

| Neomycin conjugates | $IC_{50}$ |
|---|---|
| DPA 65 | 51 ± 24 nM |
| DPA 117 | 15.5 ± 6.3 μM |
| DPA 120 | 15.3 ± 6.9 μM |
| DPA 121 | 30.5 ± 11.1 μM |
| DPA 122 | 5.4 ± 2.4 nM |
| DPA 123 | 768 ± 309 nM |
| DPA 165 | 806 ± 210 nM |
| DPA 166 | 1.25 ± 0.86 μM |
| DPA 506 | >500 μM |

3. Example 3

HIV-1 TAR RNA Competition Binding Assay for Neomycin Conjugates

Before used, HIV-1 TAR RNA (5'-GGC AGA UCUGAG CCU GGG AGC UCU CUG CC-3', Thermo Scientific) in 10 μM batch in sterile water was heated to 95° C. for 4.5 min, and then cooled rapidly in ice bath for 5 min. This snap-cooling causes the RNA to adopt the kinetically favored hairpin rather than thermodynamically favored duplexes.

131 132
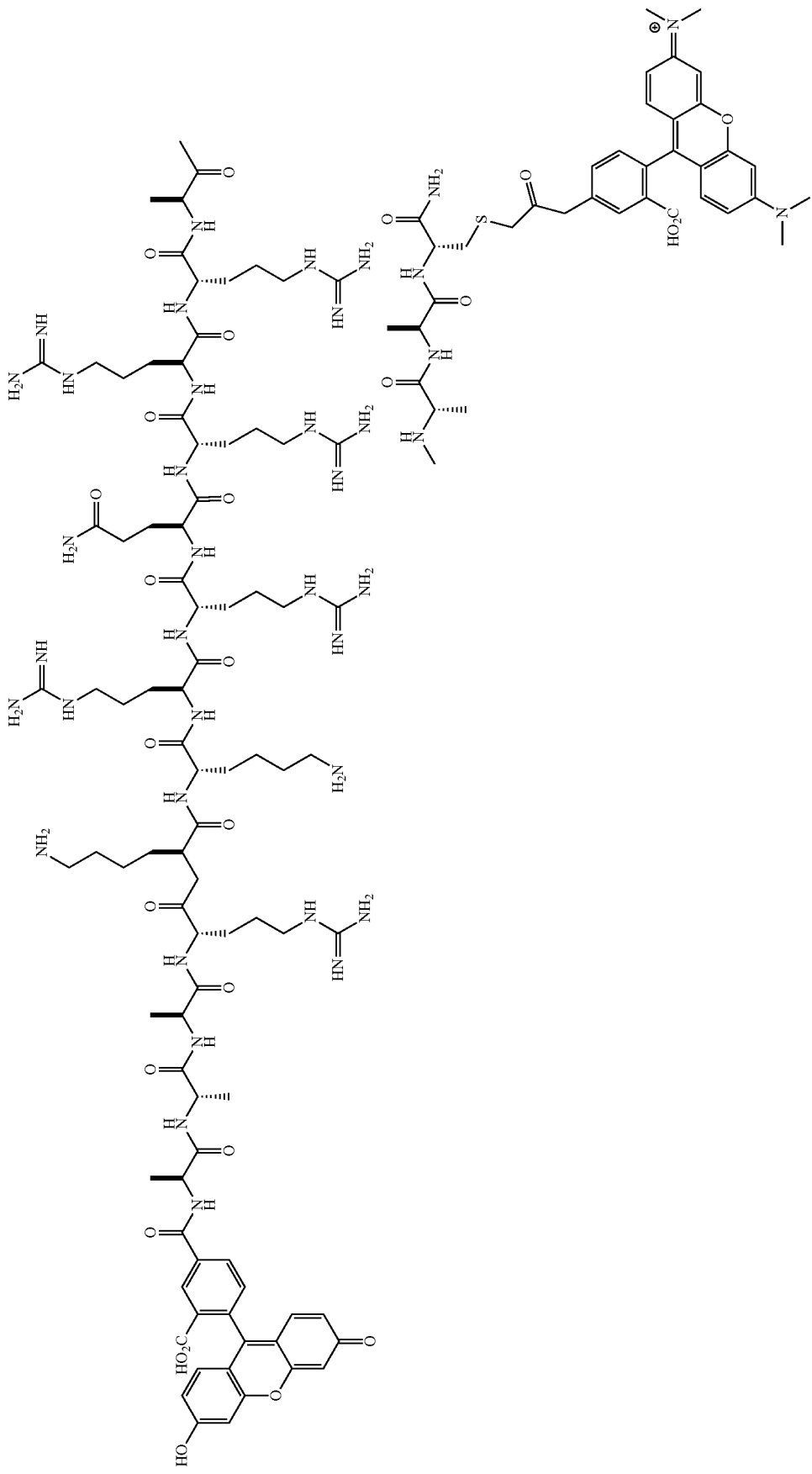

Fluorescein-Labeled HIV-1 Tat Peptide

The relative affinity of each polyamine for HIV-1 TAR RNA was determined using Fluorescence Resonance Energy Transfer (FRET)-based competitive binding assay with a fluorescein-labeled HIV-1 Tat peptide as described in the literature. The fluorescence experiments were performed with a Spectra Max Fluorimeter (Molecular Devices) at 25° C., with excitation and emission wavelengths of 495 and 570 nm, respectively. All samples were prepared in 96 well plates in 1×TK buffer (50 mM Tris, 20 mM KCl, pH=7.4) with 0.1% Trixton-100 (Sigma). The binding affinity ($IC_{50}$) values reported for each neomycin conjugates are the averages of 3~5 individual measurements, and were determined by fitting the experimental data to a sigmoidal dose-response nonlinear regression model on GraphPad Prism 4.0.

Prior to the competition experiments, the affinity of fluorescein-labeled Tat peptide for HIV-1 TAR RNA was determined by monitoring fluorescence intensity changes of the fluorescent probe upon addition of HIV-1 TAR RNA. Addition of an increasing concentration (0 nM to 1000 nM) of HIV-1 TAR RNA to a 100 nM solution of fluorescein-labeled Tat peptide in TK buffer at 25° C. afforded a saturation binding curve. The $IC_{50}$ value obtained from this binding curve was 86 nM (FIG. 19).

Competition FRET Assay.

To a solution of 100 nM HIV-1 TAR RNA and 100 nM fluorescein-labeled HIV-1 Tat peptide, appropriate concentrations (0 nM to 100 μM) of the antagonists were added at 25° C.; total volume of the incubation solution was 80 μL. After 60 min, fluorescence changes of the sample solution were determined by the Spectra Max Fluorimeter Detector. The experimental dose-response data for a given polyamine were fit to a sigmoidal dose-response nonlinear regression model on GraphPad Prism 4.0 to afford the $IC_{50}$ values for each neomycin conjugates (Table 17&18).

TABLE 17

Competition binding affinities of neomycin conjugates to HIV-1 TAR RNA.

| Neomycin conjugates | $IC_{50}$ |
|---|---|
| Compound X | 713 ± 165 nM |
| Compound Y | 6.6 ± 1.5 μM |
| DPA 51 | 77 ± 27 nM |
| DPA 52 | 60 ± 8 nM |
| DPA 53 | 56 ± 6 nM |
| DPA 54 | 128 ± 12 nM |
| DPA 55 | 80 ± 9 nM |
| DPA 56 | 59 ± 11 nM |
| DPA 58 | 61 ± 13 nM |
| DPA 60 | 67 ± 9 nM |
| DPA 65 | 47 ± 6 nM |
| DPA 66 | 58 ± 6 nM |
| DPA 101 | >100 μM |
| DPA 113 | 61.3 ± 18.1 μM |
| DPA 114 | 11.6 ± 2.3 μM |
| DPA 115 | 99.4 ± 21.0 μM |
| DPA 116 | 4.3 ± 0.6 μM |
| DPA 117 | 1.3 ± 0.2 μM |
| DPA 118 | 12.1 ± 5.4 μM |
| DPA 119 | 464 ± 146 nM |
| DPA 120 | 1.7 ± 0.3 μM |
| DPA 121 | 686 ± 110 nM |
| DPA 122 | 825 ± 145 nM |
| DPA 165 | 251 ± 46 nM |
| DPA 166 | 419 ± 115 nM |

TABLE 18

Competition binding affinites of antagonists to HIV-1 TAR RNA.

| Neomycin conjugates | $IC_{50}$ |
|---|---|
| DPA 123 | 155 ± 49 nM |
| DPA 502 | 11.4 ± 3.3 μM |
| DPA 503 | 95.4 ± 20.4 μM |
| DPA 504 | >500 μM |
| DPA 505 | 17.2 ± 4.0 μM |
| DPA 506 | 17.4 ± 4.3 μM |
| DPA 507 | 92.5 ± 21.9 μM |
| DPA 508 | 146 ± 38 μM |

TABLE 19 structures of tested molecules

| Name | Structure |
|---|---|
| DPA502 paromomycin | |
| DPA503 kanamycin | |
| DPA504 hygromycin | |

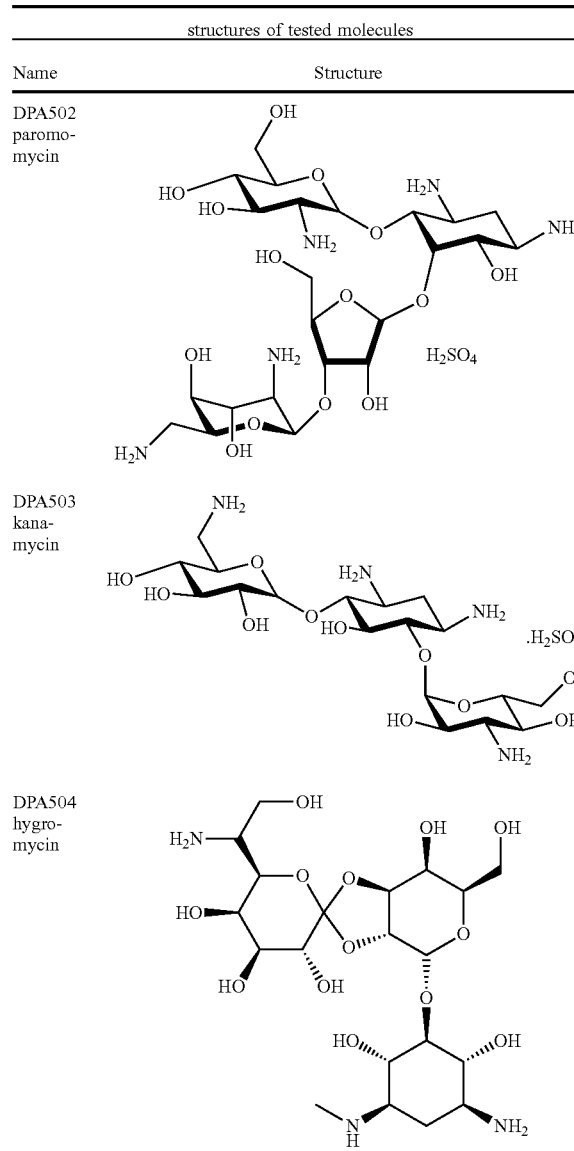

TABLE 19-continued structures of tested molecules

| Name | Structure |
|---|---|
| DPA505 gentamycin | (structure) |
| DPA506 streptomycin | (structure) |
| DPA507 lividomycin | (structure) |
| DPA508 ribostamycin | (structure) |

X = neomycin
Y = Hoechst 33258

4. Example 4 a) Results

Blind-Docking of each of the neomcyin dimers and the monomer to the NMR determined TAR RNA structure 1ANR[1] (Aboul-ela, F.; Kam, J.; Varani, G. *Nucleic Acids Res.* 1996, 24, 3974-3981) shown in table BLAH above resulted in high-affinity binding in the major groove with most ligand poses displaying significant interaction with the bulged region of the RNA. This region of HIV RNA provides excellent charge/shape complementarity to the dimers as well as presents large numbers of possible H-bond donors and acceptors.

The predicted lowest energy pose, bridging the upper and lower walls of the major groove below the bulge, of the monomer (neomycin) is consistent with the conformation predicted via Brownian dynamics simulations performed by Hermann and Westhof[2] (Hermann, T.; Westhof, E. *J. Med. Chem.* 1999, 42, 1250-1261.) in contrast to the minor groove pose proposed by Rösch et all.[3] (Faber, C.; Sticht, H.; Schweimer, K.; Rosch, P. *J. Biol. Chem.* 2000, 275, 20660-20666) In the pose suggested by Rösch et all no explanation is given for the failure of their model to accurately explain the RNAse footprinting data of Czarnik et all[4] (Mei, H. Y.; Cui, M.; Heldsinger, A.; Lemrow, S. M.; Loo, J. A.; Sannes-Lowery, K. A.; Sharmeen, L.; Czarnik, A. W. *Biochemistry* 1998, 37, 14204-14212), but the model described herein as well as that of Hermann and Westhof provides a clear explanation of the foot printing data of Czarnik et all.

The binding pocket of the neomycin dimers is likely the major groove, as predicted in this work, due to charge complementarity. The heavily negatively charged pocket of the major groove is a very attractive target to the ~10+ positive charges located on the dimer molecules. In addition, the fairly close relative agreement of the binding energy calculations to the experimentally determined binding constants (see Table 20 below) provides a strong indication that the mode of binding has been accurately predicted by autodock vina.

TABLE 20

| Ligand | HIV TAR Receptor (PDB ID) | Calculated Free Energy (kcal/mol) |
|---|---|---|
| DPA51 | 1ANR | −9.3 |
| DPA52 | 1ANR | −10.2 |
| DPA53 | 1ANR | −9.3 |
| DPA54 | 1ANR | −9.1 |
| DPA55 | 1ANR | −8.0 |
| DPA56 | 1ANR | −8.7 |
| DPA58 | 1ANR | −9.4 |
| DPA60 | 1ANR | −8.8 |
| DPA65 | 1ANR | −9.8 |
| Neomycin B | 1ANR | −9.0 |

The lowest energy binding poses for each of the dimers provides a possible explanation for the experimentally observed difference in $AC_{50}$ values. Those dimers which display the highest $AC_{50}$ values (those with the lowest predicted BEs) in general have the most flexible linkages which, as shown by images BLAH through BLAH, allow the two monomer units to fold back on themselves forming intramolecular hydrogen bonding and weakening the binding interaction of the drug with the receptor. The highest affinity binders are those dimers that have mostly rigid linkages that do not allow the drug to fold back on itself and force the drug to form intermolecular H-bonds. In addition the entropy lost in the binding of the drug to the receptor is reduced for those dimmers which have less flexible linker regions because less bond rotations are frozen.

The results of this work are suggestive of a general rule for a dimeric species whose monomers are capable of forming numerous hydrogen bonds and in which both monomer units are docking to the same groove or active site. When the above is the case increasing the flexibility of the linker will, in general, lead to decreased affinity of the drug for the receptor due to the increased ability of the dimer to form non-productive intramolecular hydrogen bonds as well as decreasing the $\Delta S_{Binding}$.

b) Docking Methods

All dockings were performed as blind dockings (blind-docking refers to the use of a search area which is large enough to encompass the entire receptor and therefore allow for any possible ligand-receptor complex) using newly introduced Autodock Vina 1.0.[5] (Trott, O.; Olson, A. J. *J. Comput. Chem.* 2009). AutoDock Vina was chosen because two factors make it superior to the previous Autodock program, Autodock 4.2. Firstly, its ability to take advantage of multiple core processors as well as its much more efficient search of the potential energy surface allows much faster docking. Secondly, its accuracy with ligands possessing more than 20 rotable bonds was very impressive compared to Autodock 4.2. Autodock Vina docking was performed using an "exhaustiveness" value of 12. This is the only customizable parameter and therefore all other parameters were defaults. All rotable bonds within the ligand were allowed to rotate freely and the receptor was considered rigid.

The Protein Data Bank file (PDB ID: 1ANR)[1] was used as the TAR RNA receptor for all dockings. The first structure of this file was used. All ligand structures were created using Discovery Studio® Visualizer 2.5 and then brought to their energetically minimized structures by the Vega ZZ program[6] (Pedretti, A.; Villa, L.; Vistoli, G. *J. Comput. Aided Mol. Des.* 2004, 18, 167-173) utilizing a conjugate gradient method with an SP4 forcefield. Autodock Tools version 1.5.4[77] (Sanner, M. F. *J. Mol. Graph. Model.* 1999, 17, 57-61) was used to convert the ligand and receptor molecules to the proper file formats for AutoDock Vina docking.

Validation that AutoDock Vina has the ability to identify the binding site and correctly score the receptor-ligand interactions with RNA was supported by its ability to accurately predict the differences among experimental binding constants for the series of dimers analyzed in this investigation.

H. REFERENCES

Alper et al. J Am Chem Soc 1998, 12:1965-1978
Andersen, E. S., S. A. Contera, et al. (2004). "Role of the trans-activation response element in dimerization of HIV-1 RNA." *J Biol Chem* 279(21): 22243-9.
Arya, D. P. (2005). Aminoglycoside-Nucleic Acid Interactions: The case for Neomycin. *Topics in Current Chemistry: DNA Binders*. J. B. Chaires and M. J. Waring. Heidelburg, Springer Verlag. 253: 149-178.
Arya, D. P. and R. L. Coffee Jr. (2000). "DNA Triple Helix Stabilization by Aminoglycoside Antibiotics." *Bioorganic and Medicinal Chemistry Letters* 10(17): 1897-1899.
Arya, D. P. and R. L. Coffee, Jr. (2000). "DNA triple helix stabilization by aminoglycoside antibiotics." *Bioorganic and Medicinal Chemistry Letters* 10(17): 1897-9.
Arya, D. P., R. L. Coffee, Jr., et al. (2001). "Neomycin-Induced Hybrid Triplex Formation." *Journal of the American Chemical Society* 123(44): 11093-11094.
Arya, D. P., R. L. Coffee, Jr., et al. (2001). "Aminoglycoside-Nucleic Acid Interactions: Remarkable Stabilization of DNA and RNA Triple Helices by Neomycin." *Journal of the American Chemical Society* 123(23): 5385-5395.
Arya, D. P., R. L. Coffee, et al. (2004). "From triplex to B-form duplex stabilization: reversal of target selectivity by aminoglycoside dimers." *Bioorganic & Medicinal Chemistry Letters* 14(18): 4643-4646.
Arya, D. P., L. Micovic, et al. (2003). "Neomycin Binding to DNA Triplex Watson-Hoogsteen (W-H) Groove: A Model." *Journal of the American Chemical Society* 125: 3733-3744.
Arya, D. P. and B. Willis (2003). "Reaching into the major groove of B-DNA; Synthesis and nucleic acid binding of a neomycin-Hoechst 33258 conjugate." *Journal of the American Chemical Society* 125(41): 12398-12399.
Arya, D. P., L. Xue, et al. (2003). "Combining the Best in Triplex Recognition: Synthesis and Nucleic Acid Binding of a BQQ-Neomycin Conjugate." *Journal of the American Chemical Society* 125(27): 8070-8071.
Arya, D. P., L. Xue, et al. (2003). "Aminoglycoside (neomycin) preference is for A-form nucleic acids, not just RNA: results from a competition dialysis study." *J Am Chem Soc* 125(34): 10148-9.
Bailly, C., P. Colson, et al. (1993). "The different binding modes of Hoechst 33258 to DNA studied by electric linear dichroism." *Nucleic Acids Res* 21(16): 3705-9.
Bailly, C., P. Colson, et al. (1996). "The binding mode of drugs to the TAR RNA of HIV-1 studied by electric linear dichroism." *Nucleic Acids Res* 24(8): 1460-4.
Bannwarth, S. and A. Gatignol (2005). "HIV-1 TAR RNA: the target of molecular interactions between the virus and its host." *Curr HIV Res* 3(1): 61-71.
Berkhout, B. (1992). "Structural features in TAR RNA of human and simian immunodeficiency viruses: a phylogenetic analysis." *Nucleic Acids Res* 20(1): 27-31.
Cho, J. and R. R. Rando (2000). "Specific binding of Hoechst 33258 to site 1 thymidylate synthase mRNA." *Nucleic Acids Res* 28(10): 2158-63.
Cordingley, M. G., R. L. LaFemina, et al. (1990). "Sequence-specific interaction of Tat protein and Tat peptides with the transactivation-responsive sequence element of human immunodeficiency virus type 1 in vitro." *Proc Natl Acad Sci USA* 87(22): 8985-9.
Dassonneville, L., F. Hamy, et al. (1997). "Binding of Hoechst 33258 to the TAR RNA of HIV-1. Recognition of a pyrimidine bulge-dependent structure." *Nucleic Acids Res* 25(22): 4487-92.
Ding et al. Angew Chem Int Ed 2003, 42: 3409-3412
Dingwall, C., I. Ernberg, et al. (1990). "HIV-1 tat protein stimulates transcription by binding to a U-rich bulge in the stem of the TAR RNA structure." *Embo J* 9(12): 4145-53.
Eftink, M. R. (1997). "Fluorescence methods for studying equilibrium macromolecule-ligand interactions." *Methods Enzymol* 278: 221-57.
Faber, C., H. Sticht, et al. (2000). "Structural rearrangements of HIV-1 Tat-responsive RNA upon binding of neomycin B." *J Biol Chem* 275(27): 20660-6.
Francois et al. Angew. Chem. Int. Ed. 2004, 43:6735-6738
Frankel, A. D. (1992). "Activation of HIV transcription by Tat." *Curr Opin Genet Dev* 2(2): 293-8.

Froeyen, M. and P. Herdewijn (2002). "RNA as a target for drug design, the example of Tat-TAR interaction." *Curr Top Med Chem* 2(10): 1123-45.

Greenberg et al. *J Am Chem Soc*, 121(28):6527-6541, 1999

Grzesiek, S. and A. Bax (1993). "Measurement of amide proton exchange rates and NOEs with water in 13C/15N-enriched calcineurin B." *J Biomol NMR* 3(6): 627-38.

Haddad et al. J Am Chem Soc, 124(13):3229-3237, 2002

Hamasaki, K. and R. R. Rando (1998). "A high-throughput fluorescence screen to monitor the specific binding of antagonists to RNA targets." *Anal Biochem* 261(2): 183-90.

Hamma, T. and P. S. Miller (2003). "Interactions of hairpin oligo-2'-O-methylribonucleotides containing methylphosphonate linkages with HIV TAR RNA." *Antisense Nucleic Acid Drug Dev* 13(1): 19-30.

Hamma, T., A. Saleh, et al. (2003) "Inhibition of HIV tat-TAR interactions by an antisense oligo-2'-O-methylribonucleoside methylphosphonate." *Bioorg Med Chem Lett* 13(11): 1845-8.

Haq, I., J. E. Ladbury, et al. (1997). "Specific binding of hoechst 33258 to the d(CGCAAATTTGCG)2 duplex: calorimetric and spectroscopic studies." *J Mol Biol* 271(2): 244-57.

Herbert, A., K. Lowenhaupt, et al. (1995). "Double-stranded RNA adenosine deaminase binds Z-DNA in vitro." *Nucleic Acids Symp Ser* 33: 16-9.

Hermann, T. (2000). "Strategies for the Design of Drugs Targeting RNA and RNA-Protein Complexes." *Angew Chem Int Ed Engl* 39(11): 1890-1904.

Hermann, T. and D. J. Patel (2000). "RNA bulges as architectural and recognition motifs." *Structure* 8(3): R47-54.

Hermann, T. and E. Westhof (1998). "RNA as a drug target: chemical, modelling, and evolutionary tools." *Curr Opin Biotechnol* 9(1): 66-73.

Hermann, T.; Westhof, E. *J. Med. Chem.* 1999, 42, 1250-1261.

Jin, E., V. Katritch, et al. (2000). "Aminoglycoside binding in the major groove of duplex RNA: the thermodynamic and electrostatic forces that govern recognition." *J Mol Biol* 298(1): 95-110.

Kamal A. et al., Medicinal Bioorganic & Chemistry Letters 14 (2004) 4791-4794; Synthetic Communications1, 39: 175-188, 2009, Helvetica Chimica Acta, 83, 2000, 2197-2213, Krebs, A., V. Ludwig, et al. (2003). "Targeting the HIV trans-activation responsive region—approaches towards RNA-binding drugs." *Chembiochem* 4(10): 972-8.

Lapidot, A., V. Vijayabaskar, et al. (2004). "Structure-activity relationships of aminoglycoside-arginine conjugates that bind HIV-1 RNAs as determined by fluorescence and NMR spectroscopy." *FEBS Lett* 577(3): 415-21.

Leng, F., W. Priebe, et al. (1998). "Ultratight DNA Binding of a New Bisintercalating Anthracycline Antibiotic." *Biochemistry* 37(7): 1743-1753.

Loontiens, F. G., L. W. McLaughlin, et al. (1991). "Binding of Hoechst 33258 and 4',6'-diamidino-2-phenylindole to self-complementary decadeoxynucleotides with modified exocyclic base substituents." *Biochemistry* 30(1): 182-9.

Loontiens, F. G., P. Regenfuss, et al. (1990). "Binding characteristics of Hoechst 33258 with calf thymus DNA, poly[d(A-T)], and d(CCGGAATTCCGG): multiple stoichiometries and determination of tight binding with a wide spectrum of site affinities." *Biochemistry* 29(38): 9029-39.

Loret, E. P., P. Georgel, et al. (1992). "Circular dichroism and molecular modeling yield a structure for the complex of human immunodeficiency virus type 1 trans-activation response RNA and the binding region of Tat, the trans-acting transcriptional activator." *Proc Natl Acad Sci USA* 89(20): 9734-8.

Luedtke, N. W. and Y. Tor (2003). "Fluorescence-based methods for evaluating the RNA affinity and specificity of HIV-1 Rev-RRE inhibitors." *Biopolymers* 70(1): 103-19.

Marciniak, R. A., B. J. Calnan, et al. (1990). "HIV-1 Tat protein trans-activates transcription in vitro." *Cell* 63(4): 791-802.

Matsumoto, C., K. Hamasaki, et al. (2000). "A high-throughput screening utilizing intramolecular fluorescence resonance energy transfer for the discovery of the molecules that bind HIV-1 TAR RNA specifically." *Bioorg Med Chem Lett* 10(16): 1857-61.

Mei, H.-Y. (1995). "Inhibition of an HIV-1 Tat-derived peptide binding to TAR RNA by aminoglycoside antibiotics." *Bioorganic and Medicinal Chemistry Letters* 5(22): 2755-2760.

Mei, H. Y.; Cui, M.; Heldsinger, A.; Lemrow, S. M.; Loo, J. A.; Sannes-Lowery, K. A.; Sharmeen, L.; Czarnik, A. W. *Biochemistry* 1998, 37, 14204-14212.

Michael et al. Bioorg Med Chem 1999, 7:1361-1371

Moazed, D. and H. F. Noller (1987). "Interaction of antibiotics with functional sites in 16S ribosomal RNA." *Nature* 327(6121): 389-94.

Nunns et al, Tetrahedron Letters, 40(52):9341-9345, 1999

Pedretti, A.; Villa, L.; Vistoli, G. *J. Comput. Aided Mol. Des.* 2004, 18, 167-173.

Pilch, D. S., M. A. Kirolos, et al. (1995). "Berenil Binding to Higher Ordered Nucleic Acid Structures: Complexation with a DNA and RNA Triple Helix." *Biochemistry* 34(49): 16107-16124.

Pilch, D. S., M. A. Kirolos, et al. (1995). "Berenil [1,3-bis (4'-amidinophenyl)triazene] Binding to DNA Duplexes and to a RNA Duplex: Evidence for Both Intercalative and Minor Groove Binding Properties." *Biochemistry* 34(31): 9962-76.

Piotto, M., V. Saudek, et al. (1992). "Gradient-tailored excitation for single-quantum NMR spectroscopy of aqueous solutions." *J Biomol NMR* 2(6): 661-5.

Quader et al. J. Org. Chem. 2007, 72:1962-1979

Rajur, S. B., J. Robles, et al. (1997). "Hoechst 33258 Tethered by a Hexa(ethyleneglycol) Linker to the 5'-Termini of Oligodeoxynucleotide 15-Mers: Duplex Stabilization and Fluorescence Properties." *J. Org. Chem.* 62(3): 523-529.

Ren, J. and J. B. Chaires (2000). "Preferential Binding of 3,3'-Diethyloxadicarbocyanine to Triplex DNA." *J Am Chem Soc* 122(2): 424-425.

Ren, J. and J. B. Chaires (2001). Rapid Screening of Structurally Selective Ligand Binding to Nucleic Acids. Methods in Enzymology. New York, Academic Press. 340: 99-108.

Rich, A. (1993). "DNA comes in many forms." *Gene* 135(1-2): 99-109.

Riguet, E. and C. Bailly (2004). "A Route for Preparing New Neamine Derivatives Targeting HIV-1 TAR RNA." *Tetrahedron* 60: 8053-8064.

Riguet, E., J. Desire, et al. (2005). "Neamine dimers targeting the HIV-1 TAR RNA." *Bioorg Med Chem Lett* 15(21): 4651-5.

Riguet, E., S. Tripathi, et al. (2004). "A peptide nucleic acid-neamine conjugate that targets and cleaves HIV-1 TAR RNA inhibits viral replication." *J Med Chem* 47(20): 4806-9.

Roy, S., U. Delling, et al. (1990). "A bulge structure in HIV-1 TAR RNA is required for Tat binding and Tat-mediated trans-activation." *Genes Dev* 4(8): 1365-73.

Sanner, M. F. *J. Mol. Graph. Model.* 1999, 17, 57-61.

Sehlstedt, U., P. Aich, et al. (1998). "Interactions of the Antiviral Quinoxaline Derivative 9-OH—B220 {2,3-dimethyl-6-(dimethylaminoethyl)-9-hydroxy-6H-indolo-[2,3-b]quinoxaline} with Duplex and Triplex Forms of Synthetic DNA and RNA." *J. Mol. Biol.* 278(1): 31-56.

Tanada, M., et al., J. Org. Chem., 2006, 71 (1), 125-134, Rajur S B, et al. J. Org. Chem., 1997, 62 (3), pp 523-529

Trott, O.; Olson, A. J. *J. Comput. Chem.* 2009.

Vicens, Q. and E. Westhof (2003). "RNA as a drug target: the case of aminoglycosides." *Chembiochem* 4(10): 1018-23.

Wang, S., P. W. Huber, et al. (1998). "Binding of neomycin to the TAR element of HIV-1 RNA induces dissociation of Tat protein by an allosteric mechanism." *Biochemistry* 37(16): 5549-57.

Wang, Y., K. Hamasaki, et al. (1997). "Specificity of aminoglycoside binding to RNA constructs derived from the 16S rRNA decoding region and the HIV-RRE activator region." *Biochemistry* 36(4): 768-79.

Wei, A. P., D. K. Blumenthal, et al. (1994). "Antibody-mediated fluorescence enhancement based on shifting the intramolecular dimer<->monomer equilibrium of fluorescent dyes." *Anal Chem* 66(9): 1500-6.

Willis, A., III and D. P. Arya (2006). An Expanding View of Aminoglycoside-Nucleic Acid Recognition. *Advances in Carbohydrate Chemistry and Biochemistry*. D. Horton, Elsevier. 60: 251-302.

Willis, A., III and D. P. Arya (2006). "Major Groove Recognition of DNA by Carbohydrates." *Current Organic Chemistry* 10(6): 663-673.

Willis, B. and D. P. Arya (2006). "Recognition of B-DNA by Neomycin-Hoechst 33258 Conjugates." *Biochemistry* 45(34): 10217-10232.

Xavier, K. A., P. S. Eder, et al. (2000). "RNA as a drug target: methods for biophysical characterization and screening." *Trends Biotechnol* 18(8): 349-56.

Xu, Y. Z. and E. T. Kool (1997). "A Novel 5'-iodonucleoside Allows Efficient Nonenzymatic Ligation of Single-stranded and Duplex DNAs." *Tetrahedron Letters* 38(32): 5595-5598.

Xu, Z. T., D. S. Pilch, et al. (1997). "Modulation of nucleic acid structure by ligand binding: Induction of a DNA center dot RNA center dot DNA hybrid triplex by DAPI intercalation." *Bioorganic and Medicinal Chemistry* 5(6): 1137-1147.

Yajima, S., H. Shionoya, et al. (2006). "Neamine derivatives having a nucleobase with a lysine or an arginine as a linker, their synthesis and evaluation as potential inhibitors for HIV TAR-Tat." *Bioorg Med Chem* 14(8): 2799-809.

Zaman, G. J., P. J. Michiels, et al. (2003). "Targeting RNA: new opportunities to address drugless targets." *Drug Discov Today* 8(7): 297-306.

We claim:

1. A method of inhibiting a viral life cycle, comprising incubating a virus with a composition wherein said composition comprises a compound comprising the structure

A-B-C or a pharmaceutically acceptable salt or acid form thereof,
wherein A is a glycoside, aminoglycoside, or sugar,
wherein B is a linker defined by -(L$_1$)$_v$-, wherein v is independently 1-20,
wherein each (L$_1$) is independently O, N, S, C$_1$-C$_8$ alkyl, C$_2$-C$_8$ alkenyl, C$_2$-C$_8$ alkoxy, aryl, heteroaryl, heterocyclyl,

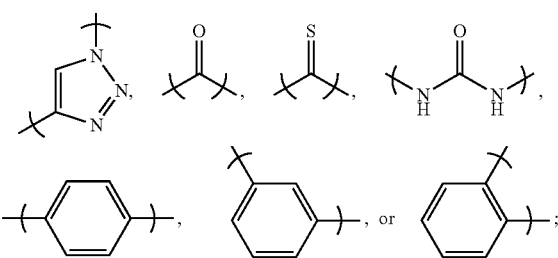

wherein each (L1) is the same or different, and
wherein C is a glycoside, aminoglycoside, sugar, Hoechst 33258, or a benzimidazole.

2. A method of treating a disease, comprising administering to a subject a composition comprising a compound comprising the structure

A-B-C or a pharmaceutically acceptable salt or acid form thereof,
wherein A is a glycoside, aminoglycoside, or sugar,
wherein B is a linker defined by -(L$_1$)$_v$-, wherein v is independently 1-20,
wherein each (L$_1$) is independently O, N, S, C$_1$-C$_8$ alkyl, C$_2$-C$_8$ alkenyl, C$_2$-C$_8$ alkoxy, aryl, heteroaryl, heterocyclyl,

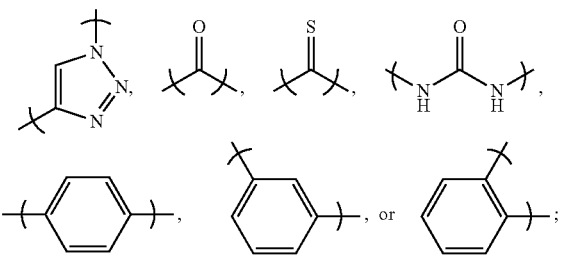

wherein each (L1) is the same or different, and wherein C is a glycoside, aminoglycoside, sugar, Hoechst 33258, or a benzimidazole.

3. The method of claim 2, wherein the disease is a viral disease.

4. A method of protecting cells from HIV cytopathic effects, comprising contacting a cell with a composition comprising a compound comprising the structure

A-B-C or a pharmaceutically acceptable salt or acid form thereof,
wherein A is a glycoside, aminoglycoside, or sugar, wherein B is a linker defined by -(L$_1$)$_v$-, wherein v is independently 1-20, wherein each (L$_1$) is independently O, N, S, C$_1$-C$_8$ alkyl, C$_2$-C$_8$ alkenyl, C$_2$-C$_8$ alkoxy, aryl, heteroaryl, heterocyclyl,

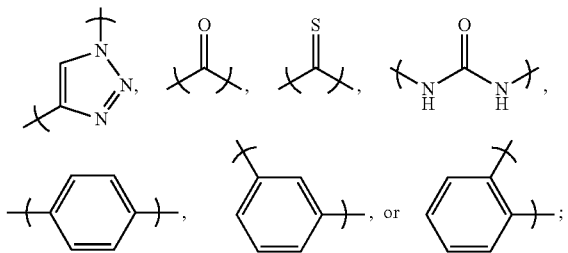

wherein each (L1) is the same or different, and wherein C is a glycoside, aminoglycoside, sugar, Hoechst 33258, or a benzimidazole.

5. The method of claim 4, wherein the cell is in vivo in a subject.

6. The method of inhibiting a viral life cycle of claim 1 wherein said A is an aminoglycoside.

7. The method of inhibiting a viral life cycle of claim 6 wherein said A comprises neomycin.

8. The method of inhibiting a viral life cycle of claim 1 wherein said B comprises a backbone of less than 50.

9. The method of inhibiting a viral life cycle of claim 1 wherein said benzimidazole is a Hoechst 33258 derived benzimidazole.

10. The method of treating a disease of claim 2 wherein said A is an aminoglycoside.

11. The method of treating a disease of claim 10 wherein said A comprises neomycin.

12. The method of treating a disease of claim 2 wherein said B comprises a backbone of less than 50.

13. The method of treating a disease of claim 2 wherein said benzimidazole is a Hoechst 33258 derived benzimidazole.

14. The method of protecting cells from HIV cytopathic effects of claim 4 wherein said A is an aminoglycoside.

15. The method of protecting cells from HIV cytopathic effects claim 14 wherein said A comprises neomycin.

16. The method of protecting cells from HIV cytopathic effects claim 4 wherein said B comprises a backbone of less than 50.

17. The method of protecting cells from HIV cytopathic effects claim 4 wherein said benzimidazole is a Hoechst 33258 derived benzimidazole.

* * * * *